(12) United States Patent
Westwell et al.

(10) Patent No.: US 10,273,218 B2
(45) Date of Patent: Apr. 30, 2019

(54) BCL-3 INHIBITORS

(71) Applicant: University College Cardiff Consultants Limited, Cardiff (GB)

(72) Inventors: Andrew David Westwell, Cardiff (GB); Andrea Brancale, Cardiff (GB); Richard William Ernest Clarkson, Dinas Powys (GB)

(73) Assignee: University College Cardiff Consultants Limited, Cardiff, Wales (GB)

( * ) Notice: Subject to any disclaimer, the term of this patent is extended or adjusted under 35 U.S.C. 154(b) by 0 days.

(21) Appl. No.: 15/500,016

(22) PCT Filed: Jul. 31, 2015

(86) PCT No.: PCT/IB2015/001807
§ 371 (c)(1),
(2) Date: Jan. 27, 2017

(87) PCT Pub. No.: WO2016/016728
PCT Pub. Date: Feb. 4, 2016

(65) Prior Publication Data
US 2017/0267653 A1    Sep. 21, 2017

Related U.S. Application Data

(60) Provisional application No. 62/031,774, filed on Jul. 31, 2014.

(51) Int. Cl.
| | |
|---|---|
| *C07D 295/13* | (2006.01) |
| *C07D 213/81* | (2006.01) |
| *C07D 213/82* | (2006.01) |
| *C07D 241/04* | (2006.01) |
| *C07C 237/42* | (2006.01) |
| *C07D 295/125* | (2006.01) |
| *C07C 237/44* | (2006.01) |

(52) U.S. Cl.
CPC .......... *C07D 295/13* (2013.01); *C07C 237/42* (2013.01); *C07C 237/44* (2013.01); *C07D 213/81* (2013.01); *C07D 213/82* (2013.01); *C07D 241/04* (2013.01); *C07D 295/125* (2013.01)

(58) Field of Classification Search
CPC ... C07D 295/13; C07D 213/81; C07D 213/82
See application file for complete search history.

(56) References Cited

U.S. PATENT DOCUMENTS

| | | | |
|---|---|---|---|
| 4,001,416 A | 1/1977 | Pommer et al. | |
| 5,397,798 A * | 3/1995 | Fitch | C07C 237/42 514/399 |
| 2007/0213321 A1 | 9/2007 | Chong et al. | |
| 2016/0185740 A1 | 6/2016 | Westwell et al. | |

FOREIGN PATENT DOCUMENTS

| | | |
|---|---|---|
| GB | 1 233 690 A | 5/1971 |
| WO | WO 01/55115 A1 | 8/2001 |
| WO | WO 2004/018414 A2 | 3/2004 |
| WO | WO 2004/022525 A1 | 3/2004 |
| WO | WO 2008/124838 A1 | 10/2008 |
| WO | WO 2009/026241 A1 | 2/2009 |
| WO | WO 2013/165606 A1 | 11/2013 |
| WO | WO 2014/077784 A | 5/2014 |
| WO | WO 2015/014972 * | 2/2015 |

OTHER PUBLICATIONS

Registry No. 433330-02-0, STN, File Registry, Jun. 25, 2002.*
Registry No. 694447-10-4, STN, File Registry, Jun. 17, 2004.*
Registry No. 693255-00-4, STN, Filre Registry, Jun. 15, 2004.*
Cheng Y. D. et al. "Anthranilic acid-based inhibitors of phosphodiesterase: design, synthesis and bioactive evaluation", *Organic & Biomolecular Chemistry*, vol. 9, 2011, pp. 7113-7125.
Ding C. et al. "Cytotoxic constituents of ethyl acetate fraction from Dianthus superbus", *Natural Product Research*, vol. 27, No. 18, 2013, pp. 1691-1694.
Heikkila T. et al. "The first de novo designed inhibitors of Plasmodium falciparum dihydroorotate dehydrogenase", *Bioorganic & Medicinal Chemistry Letters*, vol. 16, No. 1, 2006, pp. 88-92.
Hsieh P.W. et al. "New cytotoxic cyclic peptides and dianthramide from dianthus superbus", *Journal of Natural Products*, vol. 67, 2004, pp. 1522-1527.
Moffett R. B. et al. "Antiulcer Agents. P-Aminobenzamido Aromatic Compounds", *Journal of Medicinal Chemistry*, vol. 14, No. 10, 1971, pp. 963-968.
Shen Z. et al. "Palladium catalyzed intramolecular decarboxylative coupling of arene carboxylic acids/esters with aryl bromides", *Chem. Eur. J.*, vol. 18, 2012, pp. 4859-4865.

(Continued)

*Primary Examiner* — Rebecca L Anderson
(74) *Attorney, Agent, or Firm* — King & Schickli, PLLC

(57) ABSTRACT

The present application relates to compounds of any one of Formulae I, Ia, Ib, Ic, Id, Ie, and If. Compounds of Formula (I) have the structure:

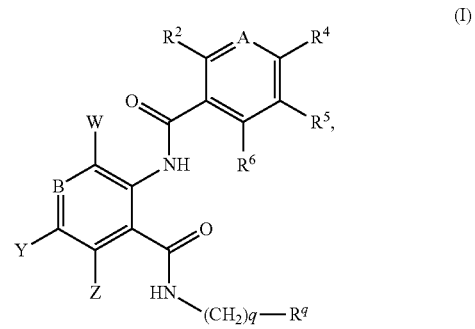

wherein A, B, W, Y, Z, $R^2$, $R^4$, $R^5$, $R^6$, $R^q$ and q are as defined herein. The compounds can be used as inhibitors of Bcl-3 and can be used for the treatment of cancer, particularly metastatic cancer.

2 Claims, 14 Drawing Sheets

(56) References Cited

OTHER PUBLICATIONS

Takasawa R. et al. "Discovery of a new type inhibitor of human glyoxalase I by myricetin-based 4-point pharmacophore", *Bioorganic & Medicinal Chemistry Letters*, vol. 21, No. 14, 2011, pp. 4337-4342.

* cited by examiner

Cell Titre Blue Assay

Cell Titre Blue Assay

Cell Titre Blue Assay

BCL-3 INHIBITORS

CROSS-REFERENCE TO RELATED APPLICATIONS

This application is a U.S. National Phase application, filed under 35 U.S.C. § 371, of International Application No. PCT/IB2015/001807, filed Jul. 31, 2015, which claims priority to, and the benefit of, U.S. Provisional Application No. 62/031,774, filed Jul. 31, 2014, the contents of each of which are incorporated herein by reference in their entireties.

BACKGROUND

Metastasis, or metastatic disease, is the spread of a cancer from an originating tissue or organ to another tissue or organ. The cells which constitute the primary cancerous tumour commonly undergo metaplasia, followed by dysplasia and then anaplasia, resulting in a malignant phenotype. This malignant phenotype allows for intravasation into the circulation, followed by extravasation to a second site for tumourigenesis. After the tumour cells have migrated to another site, they re-penetrate the vessel or walls and continue to multiply, eventually forming another clinically detectable tumour (secondary tumours). Whilst treatment regimens and therapies for primary tumours are much better understood, with improved efficacy and success rates, and whilst some types of metastatic cancer can be cured with such current treatments, most metastatic cancers show poor response. Treatments for metastatic disease do exist, such as systemic therapy (chemotherapy, biological therapy, targeted therapy, hormonal therapy), local therapy (surgery, radiation therapy), or a combination of these treatments. However, most often the primary goal of these treatments is to control the growth of the cancer or to relieve symptoms caused by same. It is therefore generally considered that most people who die of cancer die of metastatic disease.

Therefore, improved understanding of cancer progression towards aggressive metastatic forms and tumour cell-specific molecular pathways is necessary to improve and lead to new therapies.

NF-κB (nuclear factor kappa-light-chain-enhancer of activated B cells) is a protein complex that controls the transcription of DNA, and is involved in cellular responses to stimuli such as stress, cytokines, free radicals, ultraviolet irradiation, oxidized LDL, and bacterial or viral antigens. Members of the NF-κB family can both induce and repress gene expression through binding to DNA sequences, and regulate numerous genes that control programmed cell death, cell adhesion, proliferation, immunity and inflammation.

It is known that NF-κB provides a link between inflammation and cancer progression. Further, NF-κB is widely used by eukaryotic cells as a regulator of genes that control cell proliferation and cell survival. As such, many different types of human tumours have deregulated NF-κB: that is, NF-κB is constitutively active. Deregulated NF-κB has been documented in many cancers, including solid cancers such as breast, melanoma, lung, colon, pancreatic, oesophageal, and also haematological malignancies. For example, it has been shown that increased NF-κB activation was evident in 86% of HER2+/ER− breast cancers and in 33% of basal like cancers, which are associated with a shortened disease-free interval, poor survival and resistance to cancer therapy. Moreover, NF-κB activation in tumour cells, tumour-associated stromal and endothelial cells is thought to play a role in tumour progression and invasion.

B-cell Lymphoma 3 (Bcl-3) is a proto-oncogene modulating NF-κB signaling, which was first identified as a chromosome translocation in B-cell chronic lymphocytic leukaemia. Deregulated Bcl-3 over-expression has been reported in numerous tumours including several leukaemias and lymphomas, such as anaplastic large cell lymphomas (ALCLs), classic Hodgkin lymphomas (cHL) and non-Hodgkin's lymphoma. Additionally, deregulated expression has also been observed in solid tumour cancers, such as breast cancer, nasopharyngeal carcinoma, and hepatocarcinomas.

A role for NF-κB and Bcl-3 in metastatic colorectal cancer has also been shown, where it was observed that NF-κB activation occurs prior to metastatic spread. Notably, Bcl-3 expression was also observed in normal and tumour tissue, but a correlation between nuclear Bcl-3 and patient survival was observed. Bcl-3 expression has also been found to be increased in breast cancer cell lines and patient breast cancer samples versus non-tumorigenic cell lines and normal adjacent tissue, respectively. Cells overexpressing Bcl-3 also resulted in a significantly higher number of tumours which supports the role for Bcl-3 in breast cancer progression.

The underlying oncogenic function of Bcl-3 has never been fully elucidated. However, established thinking based on experiments performed on cancer cell lines in vitro is that it has a role in increased cellular proliferation and cell survival. It was previously shown that Bcl-3 specifically promotes the formation of metastasis of ErbB2 breast cancer driven tumours. Although primary tumour growth in the Bcl-3 deficient ErbB2 (MMTV/neu) murine model was not affected, it was shown that the occurrence of developed lung metastasis from a primary breast tumour was significantly reduced by 40%. Moreover, a significant reduction in mitotic index and apoptosis was observed in secondary tumour lesions but not in primary tumours. Furthermore, through gene expression knock down studies, it was shown that deletion of Bcl-3 resulted in an 80% decrease in lung metastases, which was attributed to loss of cell migration but importantly with no effect upon normal mammary function or overall systemic viability. The implication from these observations is that specific targeting of individual NF-κB subunits or their co-activators may be a more beneficial therapeutic strategy than suppressing their upstream regulators which appear to exhibit detrimental systemic toxicity. This therefore suggests Bcl-3 may represent a suitable therapeutic target for preventing cancer metastasis and secondary tumour formation.

Thus, there is a need to develop modulators of Bcl-3 for treating or preventing diseases or disorders in which Bcl-3 and/or NF-κB play a role.

SUMMARY

The present application relates to compounds which modulate Bcl-3 activity and may suppress Bcl-3-NF-κB protein interactions, inhibit NF-κB signaling and attenuate the cellular characteristics contributing to the metastatic phenotype observed in vivo. Therefore the compounds are suitable for the treatment of cancer, especially for the treatment or prevention of metastatic cancer or secondary tumours. The present application also relates to compounds that modulate Bcl-3 for treatment or prevention of a disease or disorder in which NF-κB plays a role.

According to a first aspect of the application there is provided a compound of Formula (I):

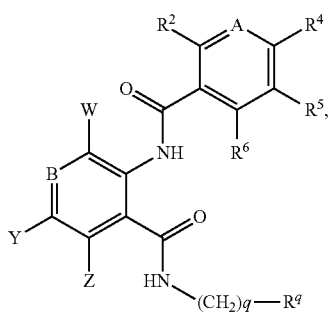

(I)

or a pharmaceutically acceptable salt thereof, wherein:
A is $CR^3$ or N
B is $CR^7$ or N
$R^2$, $R^3$, $R^4$, $R^5$ and $R^6$ are each, independently, hydrogen, halogen, $C_1$-$C_6$ haloalkyl, $NO_2$, $NR^aR^b$, OH, $O(C_1$-$C_6$ alkyl), or $O(C_1$-$C_6$ haloalkyl); or $R^3$ and $R^4$ together form a $C_6$ aryl ring, or $R^4$ and $R^5$ together form a $C_6$ aryl ring;
$R^7$ is hydrogen, fluorine, OH, or $O(C_1$-$C_6$ alkyl);
$R^a$ and $R^b$ are each, independently, hydrogen or $C_1$-$C_6$ alkyl;
W, Y, and Z are each, independently hydrogen, fluorine, OH, or $O(C_1$-$C_6$ alkyl);
q is 2 or 3;
$R^q$ is 1-piperazinyl, 1-(4-N—$(R^N)$)piperazinyl, N-morpholinyl or phenyl;
$R^N$ is $C_1$-$C_5$ straight chain or $C_1$-$C_5$ branched alkyl;
wherein, when A is $CR^3$ and $R^2$ is fluorine or chlorine, then $R^q$ is phenyl or 1-(4-N—$(R^N)$)piperazinyl, or when A is $CR^3$, $R^2$ is fluorine or chlorine, q is 2 and $R^q$ is N-morpholinyl, then at least one of W, $R^7$, Y and Z is not hydrogen but W is not $OCH_3$; or when A is $CR^3$, $R^2$ is fluorine or chlorine, q is 2 and $R^q$ is N-morpholinyl at least one of $R^3$, $R^4$, $R^5$ and $R^6$ is not hydrogen or halogen.

According to a second aspect of the application there is provided a compound of Formula (Ia):

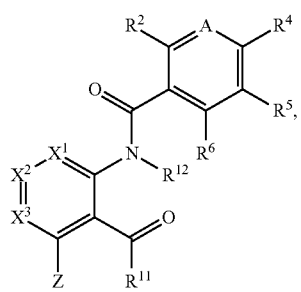

(Ia)

or a pharmaceutically acceptable salt thereof, wherein:
A is $CR^3$ or N;
$X^1$ is $CR^8$ or N;
$X^2$ is $CR^9$ or N;
$X^3$ is $CR^{10}$ or N;
wherein zero or one of $X^1$, $X^2$, or $X^3$ is N;
$R^2$, $R^3$, $R^4$, $R^5$ and $R^6$ are each, independently, hydrogen, halogen, $C_1$-$C_6$ haloalkyl, $NO_2$, $NR^aR^b$, OH, $O(C_1$-$C_6$ alkyl), $S(C_1$-$C_6$ alkyl), $O(C_1$-$C_6$ haloalkyl), or $S(C_1$-$C_6$ haloalkyl);

or $R^2$ and $R^3$ together with the carbon atoms to which they attach form a $C_6$ aryl ring, or $R^5$ and $R^6$ together with the carbon atoms to which they attach form a $C_6$ aryl ring, or $R^3$ and $R^4$ together with the carbon atoms to which they attach form a $C_6$ aryl ring, or $R^4$ and $R^5$ together with the carbon atoms to which they attach form a $C_6$ aryl ring;
$R^a$ and $R^b$ are each, independently, hydrogen or $C_1$-$C_6$ alkyl;
$R^8$, $R^9$, $R^{10}$, and Z are each, independently, hydrogen, halogen, OH, or $O(C_1$-$C_6$ alkyl);
$R^{11}$ is OH, $O(C_1$-$C_6$ alkyl), or —NH—$(CH_2)_q$—$R^q$, wherein:
q is 2 or 3;
$R^q$ is 1-piperazinyl, 1-(4-N—$(R^N)$)piperazinyl, N-morpholino or phenyl; and
$R^N$ is $C_1$-$C_5$ alkyl; and
$R^{12}$ is hydrogen or $C_1$-$C_6$ alkyl;
wherein: when A is $CR^3$ and $R^2$ is fluorine or chlorine, then $R^q$ is phenyl or 1-(4-N—$(R^N)$)piperazinyl; or when A is $CR^3$, $R^2$ is fluorine or chlorine, q is 2 and $R^q$ is N-morpholino, then at least one of $R^8$, $R^9$, $R^{10}$, and Z is not hydrogen and $R^8$ is not $OCH_3$; or when A is $CR^3$, $R^2$ is fluorine or chlorine, q is 2 and $R^q$ is N-morpholino, then at least one of $R^3$, $R^4$, $R^5$ and $R^6$ is not hydrogen or halogen; and at least three of $R^2$, $R^3$, $R^4$, $R^5$ and $R^6$ are hydrogen.

A further aspect of the application relates to a compound of Formula (Ia) which has the Formula (Ib).

A further aspect of the application relates to a compound of Formula (Ia) which has the Formula (Ic).

A further aspect of the application relates to a compound of Formula (Ia) which has the Formula (Id).

A further aspect of the application relates to a compound of Formula (Ia) which has the Formula (Ie).

A further aspect of the application relates to a compound of Formula (Ia) which has the Formula (If).

In another aspect of the application relates to a compound of Formula (I) or Formula (Ia) for use in medicine.

In another aspect of the application relates to a compound of Formula (I) or Formula (Ia) for use in the treatment of cancer.

In another aspect, the application relates to a compound of Formula (I) or Formula (Ia) for use in the treatment of leukaemia or lymphoma.

In another aspect of the application relates to a compound of Formula (I) or Formula (Ia) for use in the treatment of anaplastic large cell lymphomas (ALCLs), classic Hodgkin lymphomas (cHL), non-Hodgkin's lymphoma; or solid tumour cancers. In one embodiment, the solid tumour cancer is breast cancer, melanoma, lung cancer, pancreatic cancer, oesophageal cancer, colorectal cancer, nasopharyngeal carcinoma, or hepatocarcinoma.

In another aspect, the application relates to a compound of Formula (I) or Formula (Ia) for use in the preparation of an agent for the treatment of cancer.

A aspect of the application relates to a compound of Formula (I) or Formula (Ia) for use in the preparation of an agent for the treatment of leukaemia or lymphoma.

In another aspect, the application relates to a compound of Formula (I) or Formula (Ia) for use in the preparation of an agent for the treatment of anaplastic large cell lymphomas (ALCLs), classic Hodgkin lymphomas (cHL), non-Hodgkin's lymphoma; or solid tumour cancers. In one embodiment, the solid tumour cancer is breast cancer, melanoma, lung cancer, pancreatic cancer, oesophageal cancer, colorectal cancer, nasopharyngeal carcinoma, or hepatocarcinoma.

In another aspect of the application relates to a method for the treatment of cancer, the method comprising administering to a patient in need of such treatment an effective amount of a compound of Formula (I) or Formula (Ia). In one embodiment, the cancer is leukaemia or lymphoma. In another embodiment, the cancer is anaplastic large cell lymphoma (ALCLs), classic Hodgkin lymphoma (cHL), non-Hodgkin's lymphoma; or solid tumour cancer.

In another aspect, the application relates to any of the uses or methods defined above wherein the treatment comprises the treatment or prevention of metastasis in cancers.

In another aspect of the application relates to any of the uses or methods defined above wherein a compound of Formula (I) or Formula (Ia) is used in combination with one or more additional active agents which are useful in the treatment of cancer.

In another aspect, the application relates to a pharmaceutical composition comprising a compound of Formula (I) or Formula (Ia) together with a pharmaceutically or veterinarily acceptable excipient or carrier.

Unless otherwise defined, all technical and scientific terms used herein have the same meaning as commonly understood by one of ordinary skill in the art to which this application belongs. In the specification, the singular forms also include the plural unless the context clearly dictates otherwise. Although methods and materials similar or equivalent to those described herein can be used in the practice or testing of the present application, suitable methods and materials are described below. All publications, patent applications, patents, and other references mentioned herein are incorporated by reference. The references cited herein are not admitted to be prior art to the application. In the case of conflict, the present specification, including definitions, will control. In addition, the materials, methods, and examples are illustrative only and are not intended to be limiting.

Other features and advantages of the application will be apparent from the following detailed description and claims.

DETAILED DESCRIPTION

1. Compounds

Figure 1A:
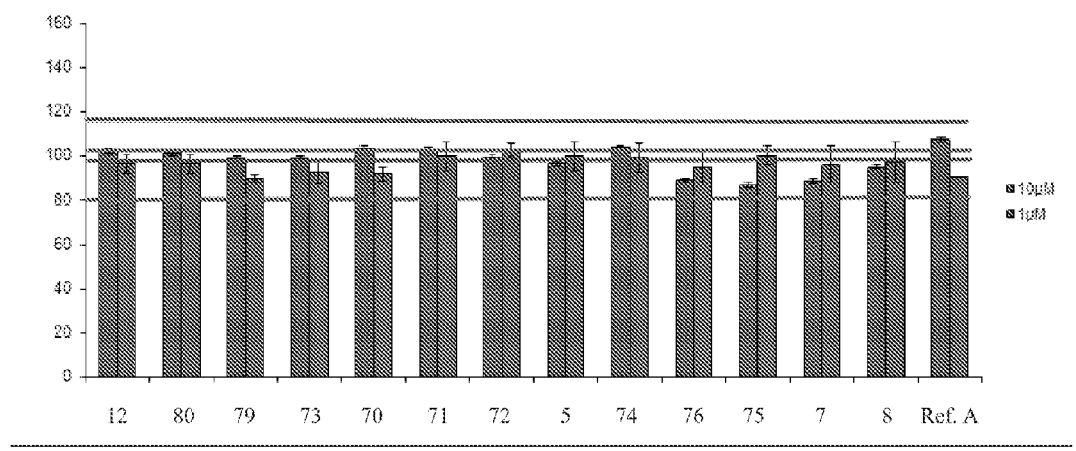
FIGS. 1a-1h are bar graphs showing the results of cell titer blue assays performed on cells treated with various compounds of the application (dark bars (10 μM), grey bars (1 μM)) to determine cell viability.
Figure 1B:
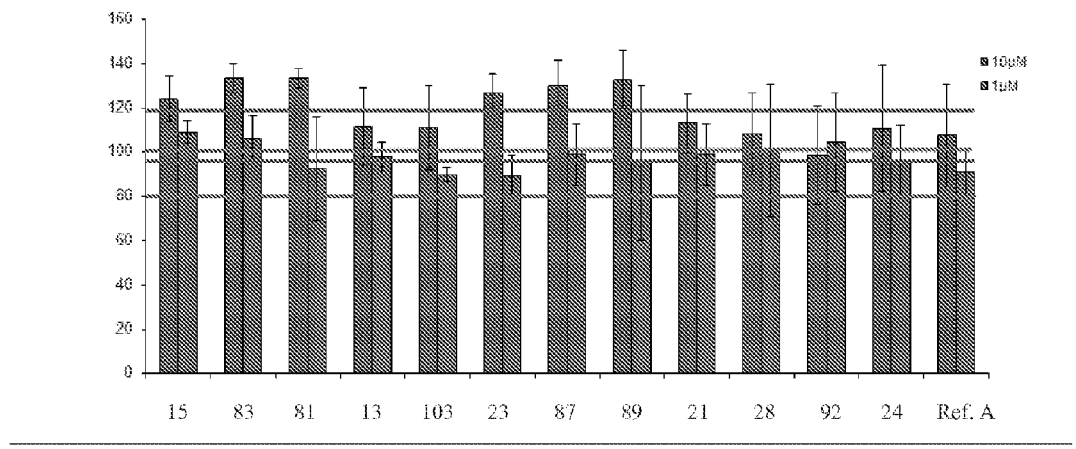
Figure 1C:
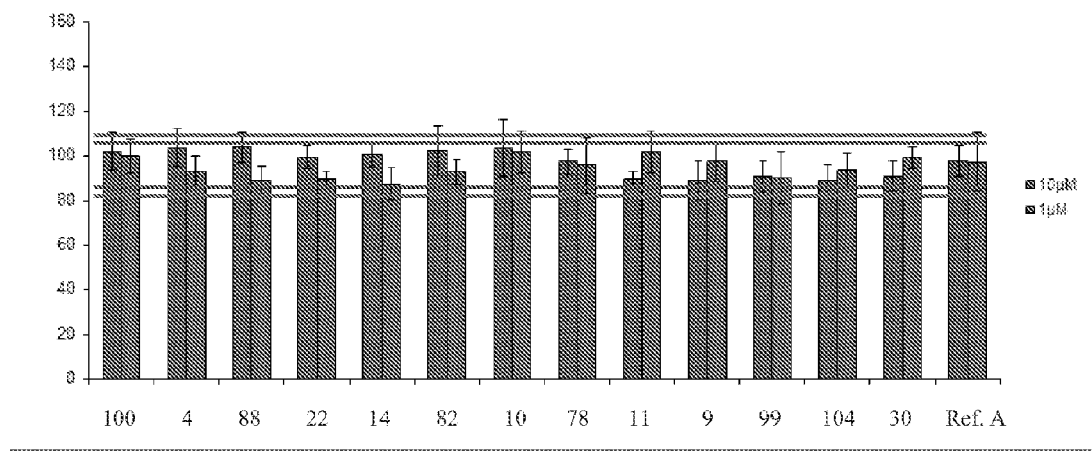
Figure 1D:
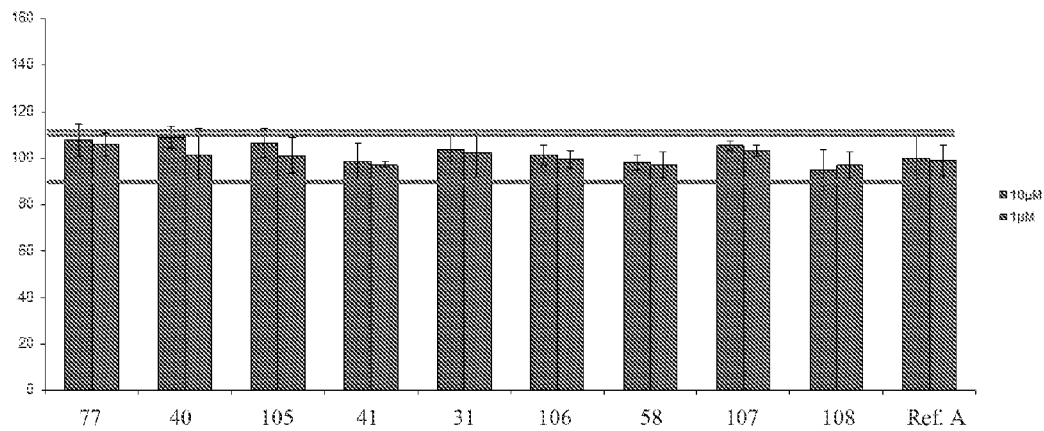
Figure 1E:
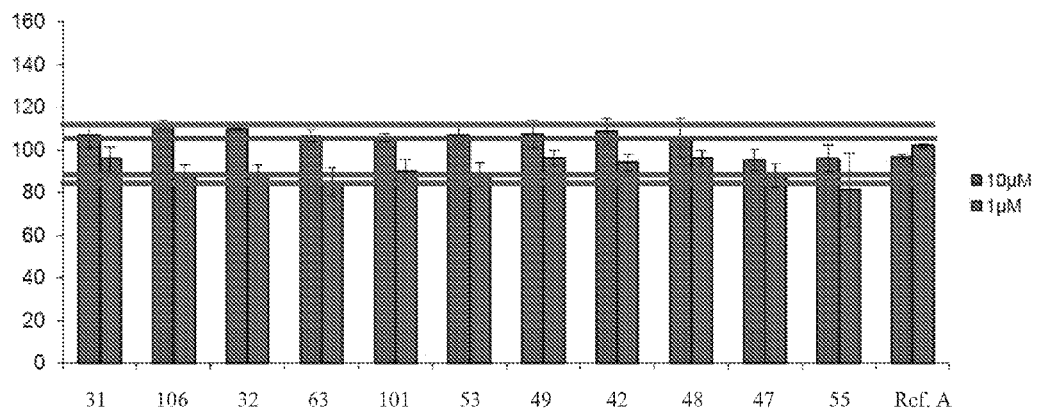
Figure 1F:
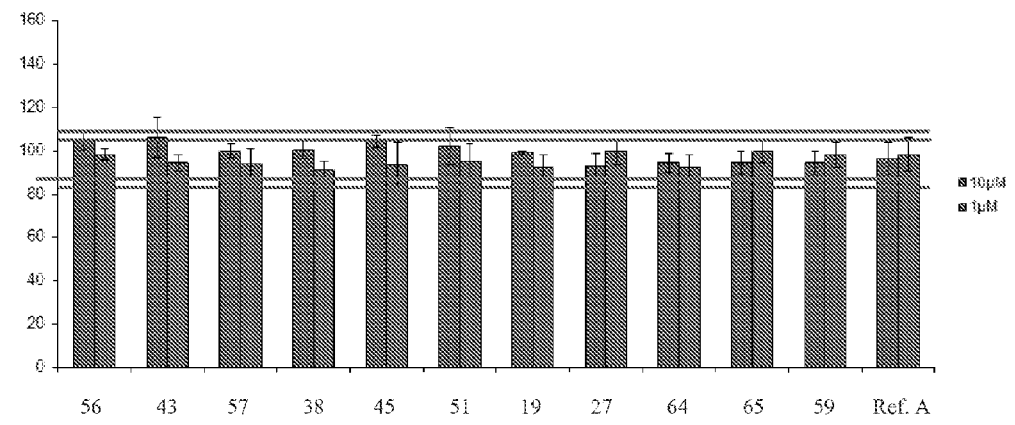
Figure 1G:
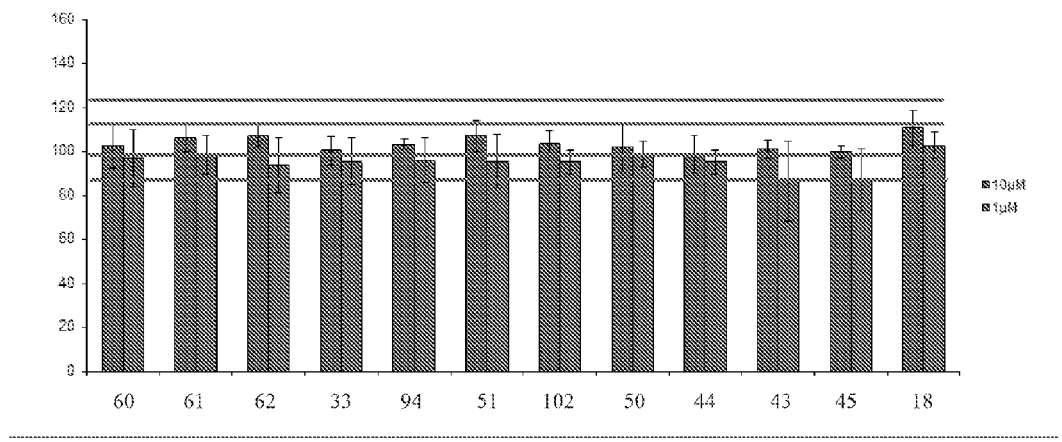
Figure 1H:
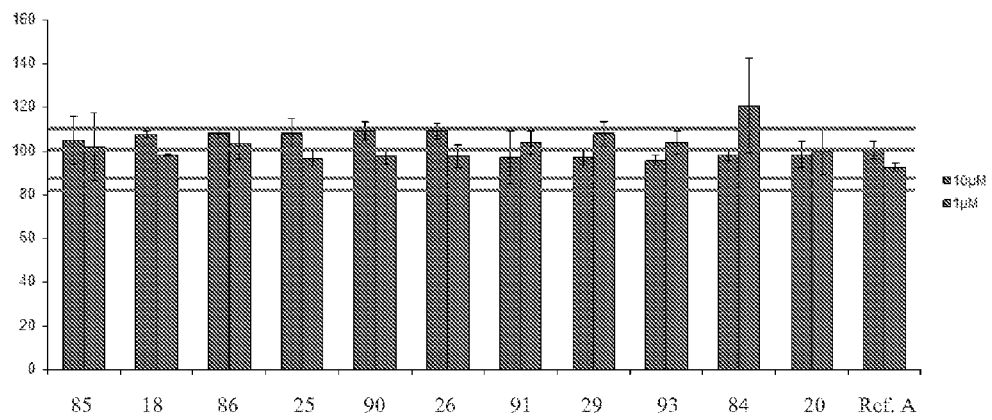

The present application provides compounds of Formula (I), Formula (Ia), Formula (Ib), Formula (Ic), Formula (Id), Formula (Ie), and Formula (If), i.e., the compounds of the application. The present application also provides pharmaceutical compositions containing the compounds of the application and various uses of the disclosed compounds. The compounds of the application may be used in treating a disease or disorder in which Bcl-3 plays a role (e.g., cancer).

The present application provides a compound of Formula (I):

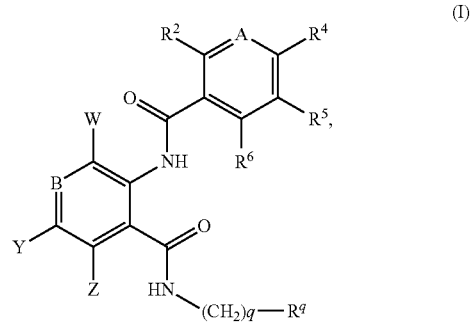

wherein:
A is $CR^3$ or N
B is $CR^7$ or N
$R^2$, $R^3$, $R^4$, $R^5$ and $R^6$ are each, independently, hydrogen, halogen, $C_1$-$C_6$ haloalkyl, $NO_2$, $NR^aR^b$, OH, $O(C_1$-$C_6$ alkyl), or $O(C_1$-$C_6$ haloalkyl); or $R^3$ and $R^4$ together form a $C_6$ aryl ring, or $R^4$ and $R^5$ together form a $C_6$ aryl ring;
$R^7$ is hydrogen, fluorine, OH, or $O(C_1$-$C_6$ alkyl);
$R^a$ and $R^b$ are each, independently, hydrogen or $C_1$-$C_6$ alkyl;
W, Y and Z are each, independently hydrogen, fluorine, OH, or $O(C_1$-$C_6$ alkyl);
q is 2 or 3;
$R^q$ is 1-piperazinyl, 1-(4-N—($R^N$))piperazinyl, N-morpholinyl or phenyl;
$R^N$ is $C_1$-$C_5$ straight chain or $C_1$-$C_5$ branched alkyl;
wherein,
when A is $CR^3$ and $R^2$ is fluorine or chlorine, then $R^q$ is phenyl or 1-(4-N—($R^N$))piperazinyl, or when A is $CR^3$, $R^2$ is fluorine or chlorine, q is 2 and $R^q$ is N-morpholinyl, then at least one of W, $R^7$, Y and Z is not hydrogen but W is not $OCH_3$; or when A is $CR^3$, $R^2$ is fluorine or chlorine, q is 2 and $R^q$ is N-morpholinyl at least one of $R^3$, $R^4$, $R^5$ and $R^6$ is not hydrogen or halogen.

In one embodiment, q is 2. In another embodiment, q is 3.

In another embodiment, A is N. In a further embodiment, A is $CR^3$.

In one embodiment, $R^q$ is 1-piperazinyl. In another embodiment, $R^q$ is 1-(4-N—($R^N$))piperazinyl. In yet another embodiment, $R^q$ is N-morpholinyl. In a further embodiment, $R^q$ is phenyl.

In one embodiment, $R^N$ is $C_1$-$C_5$ straight chain or $C_1$-$C_5$ branched alkyl. In another embodiment, $R^N$ is methyl, ethyl, propyl, isopropyl, n-butyl or n-pentyl. In a preferred embodiment, $R^N$ is methyl or ethyl. In a more preferred embodiment, $R^N$ is methyl.

In one embodiment, at least one of $R^2$, $R^3$, $R^4$, $R^5$ and $R^6$ is $NR^aR^b$.

In another embodiment, at least one of $R^2$, $R^3$, $R^4$, $R^5$ and $R^6$ is $C_1$-$C_6$ haloalkyl. In a preferred embodiment, $C_1$-$C_6$ haloalkyl is $CF_3$.

In another embodiment, at least one of $R^2$, $R^3$, $R^4$, $R^5$ and $R^6$ is halogen. In a preferred embodiment, at least one of $R^2$, $R^3$, $R^4$, $R^5$ and $R^6$ is —Cl or —F.

In another embodiment, at least one of $R^2$, $R^3$, $R^4$, $R^5$ and $R^6$ is —$NO_2$.

In yet another embodiment, $R^2$ is fluorine and at least one of $R^3$, $R^4$, $R^5$ and $R^6$ is $O(C_1$-$C_6$ alkyl).

In another embodiment, $R^2$ is fluorine and $R^4$ is $O(C_1$-$C_6$ alkyl). In a preferred embodiment, $R^2$ is fluorine and $R^4$ is $OCH_3$.

In a further embodiment, at least one of $R^3$, $R^4$, $R^5$ and $R^6$ is $OCH_3$. In another embodiment, at least one of W, $R^7$, Y and Z is not hydrogen. In another embodiment, at least one of W, $R^7$, Y and Z is $O(C_1$-$C_6$ alkyl). In a preferred embodiment, at least one of W, $R^7$, Y and Z is $OCH_3$. In another embodiment, at least one of W, $R^7$, Y and Z is halogen. In a preferred embodiment at least one of W, $R^7$, Y and Z is fluorine.

In one embodiment, $R^2$ is $OCH_3$.

In another embodiment, at least two of $R^2$, $R^3$, $R^4$, $R^5$ and $R^6$ are not hydrogen and are not the same.

In another embodiment, at least three of $R^2$, $R^3$, $R^4$, $R^5$ and $R^6$ are not hydrogen and at least two of $R^2$, $R^3$, $R^4$, $R^5$ and $R^6$ are not the same.

In one embodiment, A is $CR^3$ and one of $R^2$, $R^3$, $R^4$, $R^5$ and $R^6$ are not hydrogen. In another embodiment, A is $CR^3$ and two of $R^2$, $R^3$, $R^4$, $R^5$ and $R^6$ are not hydrogen. In yet another embodiment, A is $CR^3$ and three of $R^2$, $R^3$, $R^4$, $R^5$ and $R^6$ are not hydrogen. In a further embodiment, A is $CR^3$ and four of $R^2$, $R^3$, $R^4$, $R^5$ and $R^6$ are not hydrogen.

In one embodiment, $R^q$ is N-morpholinyl, A is $CR^3$, and B is $CR^7$. In a further embodiment, $R^q$ is N-morpholinyl, A is CH, and B is CH. In another embodiment, $R^q$ is N-morpholinyl, A is CH, B is CH and q is 2.

In one embodiment, $R^q$ is N-morpholinyl, A is $CR^3$, and B is $CR^7$. In a further embodiment, $R^q$ is N-morpholinyl, A is CH, and B is CH. In another embodiment, $R^q$ is N-morpholinyl, A is CH, B is CH and q is 3.

In one embodiment, $R^q$ is 1-piperazinyl, A is $CR^3$, and B is $CR^7$. In a further embodiment, $R^q$ is 1-piperazinyl, A is CH, and B is CH. In another embodiment, $R^q$ is 1-piperazinyl, A is CH, B is CH and q is 2.

In one embodiment, $R^q$ is 1-piperazinyl, A is $CR^3$, and B is $CR^7$. In a further embodiment, $R^q$ is 1-piperazinyl, A is CH, and B is CH. In another embodiment, $R^q$ is 1-piperazinyl, A is CH, B is CH and q is 3.

In one embodiment, $R^q$ is phenyl, A is $CR^3$, and B is $CR^7$. In a further embodiment, $R^q$ is phenyl, A is CH, and B is CH. In another embodiment, $R^q$ is phenyl, A is CH, B is CH and q is 2.

In one embodiment, $R^q$ is phenyl, A is $CR^3$, and B is $CR^7$. In a further embodiment, $R^q$ is phenyl, A is CH, and B is CH. In another embodiment, $R^q$ is phenyl, A is CH, B is CH and q is 3.

In one embodiment, $R^q$ is 1-(4-N—($R^N$))piperazinyl, A is $CR^3$, and B is $CR^7$. In a further embodiment, $R^q$ is 1-(4-N—($R^N$))piperazinyl, A is CH, and B is CH. In another embodiment, $R^q$ is 1-(4-N—($R^N$))piperazinyl, A is CH, B is CH and q is 2.

In one embodiment, $R^q$ is 1-(4-N—($R^N$))piperazinyl, A is $CR^3$, and B is $CR^7$. In a further embodiment, $R^q$ is 1-(4-N—($R^N$))piperazinyl, A is CH, and B is CH. In another embodiment, $R^q$ is 1-(4-N—($R^N$))piperazinyl, A is CH, B is CH and q is 3.

In one embodiment, $R^q$ is N-morpholinyl, A is $CR^3$, and B is $CR^7$. In a further embodiment, $R^q$ is N-morpholinyl, A is $CR^3$, B is $CR^7$ and q is 2. In another embodiment, $R^q$ is N-morpholinyl, A is $CR^3$, B is $CR^7$ and q is 3.

In one embodiment, $R^q$ is 1-piperazinyl, A is $CR^3$, and B is $CR^7$. In a further embodiment, $R^q$ is 1-piperazinyl, A is $CR^3$, B is $CR^7$ and q is 2. In another embodiment, $R^q$ is 1-piperazinyl, A is $CR^3$, B is $CR^7$ and q is 3.

In one embodiment, $R^q$ is phenyl, A is $CR^3$, and B is $CR^7$. In a further embodiment, $R^q$ is phenyl, A is $CR^3$, B is $CR^7$ and q is 2. In another embodiment, $R^q$ is phenyl, A is $CR^3$, B is $CR^7$ and q is 3.

In one embodiment, $R^q$ is 1-(4-N—($R^N$))piperazinyl, A is $CR^3$, and B is $CR^7$. In a further embodiment, $R^q$ is 1-(4-N—($R^N$))piperazinyl, A is $CR^3$, B is $CR^7$ and q is 2. In another embodiment, $R^q$ is 1-(4-N—($R^N$))piperazinyl, A is $CR^3$, B is $CR^7$ and q is 3.

In one embodiment, $R^q$ is N-morpholinyl, A is N, and B is $CR^7$. In a further embodiment, $R^q$ is N-morpholinyl, A is N, B is $CR^7$ and q is 2. In another embodiment, $R^q$ is N-morpholinyl, A is N, B is $CR^7$ and q is 3.

In one embodiment, $R^q$ is 1-piperazinyl, A is N, and B is $CR^7$. In a further embodiment, $R^q$ is 1-piperazinyl, A is N, B is $CR^7$ and q is 2. In another embodiment, $R^q$ is 1-piperazinyl, A is N, B is $CR^7$ and q is 3.

In one embodiment, $R^q$ is phenyl, A is N, and B is $CR^7$. In a further embodiment, $R^q$ is phenyl, A is N, B is $CR^7$ and q is 2. In another embodiment, $R^q$ is phenyl, A is N, B is $CR^7$ and q is 3.

In one embodiment, $R^q$ is 1-(4-N—($R^N$))piperazinyl, A is N, and B is $CR^7$. In a further embodiment, $R^q$ is 1-(4-N—($R^N$))piperazinyl, A is N, B is $CR^7$ and q is 2. In another embodiment, $R^q$ is 1-(4-N—($R^N$))piperazinyl, A is N, B is $CR^7$ and q is 3.

The present application provides a compound of Formula (Ia):

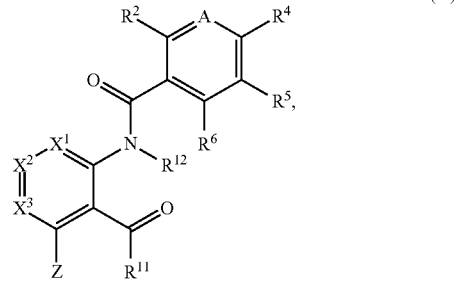

or a pharmaceutically acceptable salt thereof,
wherein:
A is $CR^3$ or N;
$X^1$ is $CR^8$ or N;

$X^2$ is $CR^9$ or N;

$X^3$ is $CR^{10}$ or N;

wherein zero or one of $X^1$, $X^2$, or $X^3$ is N;

$R^2$, $R^3$, $R^4$, $R^5$ and $R^6$ are each, independently, hydrogen, halogen, $C_1$-$C_6$ haloalkyl, $NO_2$, $NR^aR^b$, OH, $O(C_1$-$C_6$ alkyl), $S(C_1$-$C_6$ alkyl), $O(C_1$-$C_6$ haloalkyl), or $S(C_1$-$C_6$ haloalkyl);

or $R^2$ and $R^3$ together with the carbon atoms to which they attach form a $C_6$ aryl ring, or $R^5$ and $R^6$ together with the carbon atoms to which they attach form a $C_6$ aryl ring, or $R^3$ and $R^4$ together with the carbon atoms to which they attach form a $C_6$ aryl ring, or $R^4$ and $R^5$ together with the carbon atoms to which they attach form a $C_6$ aryl ring;

$R^a$ and $R^b$ are each, independently, hydrogen or $C_1$-$C_6$ alkyl;

$R^8$, $R^9$, $R^{10}$, and Z are each, independently, hydrogen, halogen, OH, or $O(C_1$-$C_6$ alkyl);

$R^{11}$ is OH, $O(C_1$-$C_6$ alkyl), or —NH—$(CH_2)_q$—$R^q$, wherein:

q is 2 or 3;

$R^q$ is 1-piperazinyl, 1-(4-N—$(R^N)$)piperazinyl, N-morpholino or phenyl; and $R^N$ is $C_1$-$C_5$ alkyl; and $R^{12}$ is hydrogen or $C_1$-$C_6$ alkyl;

wherein, when A is $CR^3$ and $R^2$ is fluorine or chlorine, then $R^q$ is phenyl or 1-(4-N—$(R^N)$)piperazinyl; or when A is $CR^3$, $R^2$ is fluorine or chlorine, q is 2 and $R^q$ is N-morpholino, then at least one of $R^8$, $R^9$, $R^{10}$, and Z is not hydrogen and $R^8$ is not $OCH_3$; or when A is $CR^3$, $R^2$ is fluorine or chlorine, q is 2 and $R^q$ is N-morpholino, then at least one of $R^3$, $R^4$, $R^5$ and $R^6$ is not hydrogen or halogen; and at least three of $R^2$, $R^3$, $R^4$, $R^5$ and $R^6$ are hydrogen.

In one embodiment, q is 2. In another embodiment, q is 3.

In another embodiment, A is N. In a further embodiment, A is $CR^3$.

In one embodiment, one of $X^1$, $X^2$, or $X^3$ is N. In a further embodiment, none of $X^1$, $X^2$, or $X^3$ is N.

In one embodiment, $X^1$ is N, $X^2$ is $CR^9$, $X^3$ is $CR^{10}$, and A is N.

In one embodiment, $X^2$ is N, $X^1$ is $CR^8$, $X^3$ is $CR^{10}$, and A is N.

In one embodiment, $X^3$ is N, $X^1$ is $CR^8$, $X^2$ is $CR^9$, and A is N.

In one embodiment, $X^1$ is N, $X^2$ is $CR^9$, $X^3$ is $CR^{10}$, and A is $CR^3$.

In one embodiment, $X^2$ is N, $X^1$ is $CR^8$, $X^3$ is $CR^{10}$, and A is $CR^3$.

In one embodiment, $X^3$ is N, $X^1$ is $CR^8$, $X^2$ is $CR^9$, and A is $CR^3$.

In one embodiment, $R^q$ is 1-piperazinyl. In another embodiment, $R^q$ is 1-(4-N—$(R^N)$)piperazinyl. In yet another embodiment, $R^q$ is N-morpholinyl. In a further embodiment, $R^q$ is phenyl.

In one embodiment, $R^N$ is $C_1$-$C_5$ straight chain or $C_1$-$C_5$ branched alkyl. In another embodiment, $R^N$ is methyl, ethyl, propyl, isopropyl, n-butyl or n-pentyl. In a preferred embodiment, $R^N$ is methyl or ethyl. In a more preferred embodiment, $R^N$ is methyl.

In one embodiment, $R^2$, $R^3$, $R^4$, $R^5$ and $R^6$ are each, independently, hydrogen, halogen, $C_1$-$C_6$ haloalkyl, $NO_2$, $NR^aR^b$, OH, $O(C_1$-$C_6$ alkyl), or $O(C_1$-$C_6$ haloalkyl).

In one embodiment, $R^8$, $R^9$, $R^{10}$, and Z are each, independently, hydrogen, flourine, OH, or $O(C_1$-$C_6$ alkyl).

In one embodiment, $R^2$, $R^3$, $R^4$, $R^5$ and $R^6$ are each, independently, hydrogen, halogen, $C_1$-$C_6$ haloalkyl, $NO_2$, $NR^aR^b$, OH, $O(C_1$-$C_6$ alkyl), or $O(C_1$-$C_6$ haloalkyl).

In one embodiment, $R^2$ and $R^3$ together with the carbon atoms to which they attach form a $C_6$ aryl ring, and $R^4$, $R^5$ and $R^6$ are each, independently, hydrogen, halogen, $C_1$-$C_6$ haloalkyl, $NO_2$, $NR^aR^b$, OH, $O(C_1$-$C_6$ alkyl), or $O(C_1$-$C_6$ haloalkyl).

In one embodiment, $R^3$ and $R^4$ together with the carbon atoms to which they attach form a $C_6$ aryl ring, and $R^2$, $R^5$ and $R^6$ are each, independently, hydrogen, halogen, $C_1$-$C_6$ haloalkyl, $NO_2$, $NR^aR^b$, OH, $O(C_1$-$C_6$ alkyl), or $O(C_1$-$C_6$ haloalkyl).

In one embodiment, $R^4$ and $R^5$ together with the carbon atoms to which they attach form a $C_6$ aryl ring, and $R^2$, $R^3$, and $R^6$ are each, independently, hydrogen, halogen, $C_1$-$C_6$ haloalkyl, $NO_2$, $NR^aR^b$, OH, $O(C_1$-$C_6$ alkyl), or $O(C_1$-$C_6$ haloalkyl).

In one embodiment, $R^5$ and $R^6$ together with the carbon atoms to which they attach form a $C_6$ aryl ring, and $R^2$, $R^3$, and $R^4$ are each, independently, hydrogen, halogen, $C_1$-$C_6$ haloalkyl, $NO_2$, $NR^aR^b$, OH, $O(C_1$-$C_6$ alkyl), or $O(C_1$-$C_6$ haloalkyl).

In one embodiment, at least one of $R^2$, $R^3$, $R^4$, $R^5$ and $R^6$ is $NR^aR^b$.

In another embodiment, at least one of $R^2$, $R^3$, $R^4$, $R^5$ and $R^6$ is $C_1$-$C_6$ haloalkyl. In a preferred embodiment, $C_1$-$C_6$ haloalkyl is $CF_3$.

In another embodiment, at least one of $R^2$, $R^3$, $R^4$, $R^5$ and $R^6$ is halogen. In a preferred embodiment, at least one of $R^2$, $R^3$, $R^4$, $R^5$ and $R^6$ is —Cl or —F.

In another embodiment, at least one of $R^2$, $R^3$, $R^4$, $R^5$ and $R^6$ is —$NO_2$.

In yet another embodiment, $R^2$ is fluorine and at least one of $R^3$, $R^4$, $R^5$ and $R^6$ is $O(C_1$-$C_6$ alkyl).

In another embodiment, $R^2$ is fluorine and $R^4$ is $O(C_1$-$C_6$ alkyl). In a preferred embodiment, $R^2$ is fluorine and $R^4$ is $OCH_3$.

In a further embodiment, at least one of $R^3$, $R^4$, $R^5$ and $R^6$ is $OCH_3$. In another embodiment, at least one of $R^8$, $R^9$, $R^{10}$, and Z is not hydrogen. In another embodiment, at least one of $R^8$, $R^9$, $R^{10}$, and Z is $O(C_1$-$C_6$ alkyl). In a preferred embodiment, at least one of $R^8$, $R^9$, $R^{10}$, and Z is $OCH_3$. In another embodiment, at least one of $R^8$, $R^9$, $R^{10}$, and Z is halogen. In a preferred embodiment at least one of $R^8$, $R^9$, $R^{10}$, and Z is fluorine.

In one embodiment, $R^2$ is $OCH_3$.

In another embodiment, at least two of $R^2$, $R^3$, $R^4$, $R^5$ and $R^6$ are not hydrogen and are not the same.

In another embodiment, at least three of $R^2$, $R^3$, $R^4$, $R^5$ and $R^6$ are not hydrogen and at least two of $R^2$, $R^3$, $R^4$, $R^5$ and $R^6$ are not the same.

In one embodiment, A is $CR^3$ and one of $R^2$, $R^3$, $R^4$, $R^5$ and $R^6$ are not hydrogen. In another embodiment, A is $CR^3$ and two of $R^2$, $R^3$, $R^4$, $R^5$ and $R^6$ are not hydrogen. In yet another embodiment, A is $CR^3$ and three of $R^2$, $R^3$, $R^4$, $R^5$ and $R^6$ are not hydrogen. In a further embodiment, A is $CR^3$ and four of $R^2$, $R^3$, $R^4$, $R^5$ and $R^6$ are not hydrogen.

In one embodiment, $R^q$ is N-morpholinyl, A is $CR^3$, and $X^2$ is $CR^9$. In a further embodiment, $R^q$ is N-morpholinyl, A is CH, and $X^2$ is CH. In another embodiment, $R^q$ is N-morpholinyl, A is CH, $X^2$ is CH and q is 2.

In one embodiment, $R^q$ is N-morpholinyl, A is $CR^3$, and $X^2$ is $CR^9$. In a further embodiment, $R^q$ is N-morpholinyl, A is CH, and $X^2$ is CH. In another embodiment, $R^q$ is N-morpholinyl, A is CH, $X^2$ is CH and q is 3.

In one embodiment, $R^q$ is 1-piperazinyl, A is $CR^3$, and $X^2$ is $CR^9$. In a further embodiment, $R^q$ is 1-piperazinyl, A is CH, and $X^2$ is CH. In another embodiment, $R^q$ is 1-piperazinyl, A is CH, $X^2$ is CH and q is 2.

In one embodiment, $R^q$ is 1-piperazinyl, A is $CR^3$, and $X^2$ is $CR^9$. In a further embodiment, $R^q$ is 1-piperazinyl, A is CH, and $X^2$ is CH. In another embodiment, $R^q$ is 1-piperazinyl, A is CH, $X^2$ is CH and q is 3.

In one embodiment, $R^q$ is phenyl, A is $CR^3$, and $X^2$ is $CR^9$. In a further embodiment, $R^q$ is phenyl, A is CH, and $X^2$ is CH. In another embodiment, $R^q$ is phenyl, A is CH, $X^2$ is CH and q is 2.

In one embodiment, $R^q$ is phenyl, A is $CR^3$, and $X^2$ is $CR^9$. In a further embodiment, $R^q$ is phenyl, A is CH, and $X^2$ is CH. In another embodiment, $R^q$ is phenyl, A is CH, $X^2$ is CH and q is 3.

In one embodiment, $R^q$ is 1-(4-N—($R^N$))piperazinyl, A is $CR^3$, and $X^2$ is $CR^9$. In a further embodiment, $R^q$ is 1-(4-N—($R^N$))piperazinyl, A is CH, and $X^2$ is CH. In another embodiment, $R^q$ is 1-(4-N—($R^N$))piperazinyl, A is CH, $X^2$ is CH and q is 2.

In one embodiment, $R^q$ is 1-(4-N—($R^N$))piperazinyl, A is $CR^3$, and $X^2$ is $CR^9$. In a further embodiment, $R^q$ is 1-(4-N—($R^N$))piperazinyl, A is $CH_2$, and $X^2$ is CH. In another embodiment, $R^q$ is 1-(4-N—($R^N$))piperazinyl, A is CH, $X^2$ is CH and q is 3.

In one embodiment, $R^q$ is N-morpholinyl, A is $CR^3$, and $X^2$ is $CR^9$. In a further embodiment, $R^q$ is N-morpholinyl, A is $CR^3$, $X^2$ is $CR^9$ and q is 2. In another embodiment, $R^q$ is N-morpholinyl, A is $CR^3$, $X^2$ is $CR^9$ and q is 3.

In one embodiment, $R^q$ is 1-piperazinyl, A is $CR^3$, and $X^2$ is $CR^9$. In a further embodiment, $R^q$ is 1-piperazinyl, A is $CR^3$, $X^2$ is $CR^9$ and q is 2. In another embodiment, $R^q$ is 1-piperazinyl, A is $CR^3$, $X^2$ is $CR^9$ and q is 3.

In one embodiment, $R^q$ is phenyl, A is $CR^3$, and $X^2$ is $CR^9$. In a further embodiment, $R^q$ is phenyl, A is $CR^3$, $X^2$ is $CR^9$ and q is 2. In another embodiment, $R^q$ is phenyl, A is $CR^3$, $X^2$ is $CR^9$ and q is 3.

In one embodiment, $R^q$ is 1-(4-N—($R^N$))piperazinyl, A is $CR^3$, and $X^2$ is $CR^9$. In a further embodiment, $R^q$ is 1-(4-N—($R^N$))piperazinyl, A is $CR^3$, $X^2$ is $CR^9$ and q is 2. In another embodiment, $R^q$ is 1-(4-N—($R^N$))piperazinyl, A is $CR^3$, $X^2$ is $CR^9$ and q is 3.

In one embodiment, $R^q$ is N-morpholinyl, A is N, and $X^2$ is $CR^9$. In a further embodiment, $R^q$ is N-morpholinyl, A is N, $X^2$ is $CR^9$ and q is 2. In another embodiment, $R^q$ is N-morpholinyl, A is N, $X^2$ is $CR^9$ and q is 3.

In one embodiment, $R^q$ is 1-piperazinyl, A is N, and $X^2$ is $CR^9$. In a further embodiment, $R^q$ is 1-piperazinyl, A is N, $X^2$ is $CR^9$ and q is 2. In another embodiment, $R^q$ is 1-piperazinyl, A is N, $X^2$ is $CR^9$ and q is 3.

In one embodiment, $R^q$ is phenyl, A is N, and $X^2$ is $CR^9$. In a further embodiment, $R^q$ is phenyl, A is N, $X^2$ is $CR^9$ and q is 2. In another embodiment, $R^q$ is phenyl, A is N, $X^2$ is $CR^9$ and q is 3.

In one embodiment, $R^q$ is 1-(4-N—($R^N$))piperazinyl, A is N, and $X^2$ is $CR^9$. In a further embodiment, $R^q$ is 1-(4-N—($R^N$))piperazinyl, A is N, $X^2$ is $CR^9$ and q is 2. In another embodiment, $R^q$ is 1-(4-N—($R^N$))piperazinyl, A is N, $X^2$ is $CR^9$ and q is 3.

A further aspect of the application relates to any compound of Formula (Ia).

A further aspect of the application relates to any compound of Formula (Ia), wherein the compound has the Formula (Ib).

A further aspect of the application relates to a compound being of Formula (Ib),

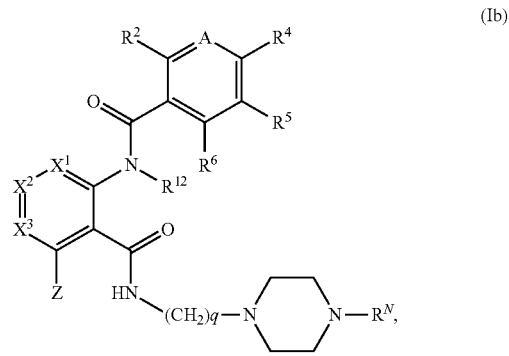

or a pharmaceutically acceptable salt thereof,
wherein:
A is $CR^3$ or N;
$X^1$ is $CR^8$ or N;
$X^2$ is $CR^9$ or N;
$X^3$ is $CR^{10}$ or N;
wherein zero or one of $X^1$, $X^2$, or $X^3$ is N;
$R^2$, $R^3$, $R^4$, $R^5$ and $R^6$ are each, independently, hydrogen, halogen, $C_1$-$C_6$ haloalkyl, $NO_2$, $NR^aR^b$, OH, $O(C_1$-$C_6$ alkyl), or $O(C_1$-$C_6$ haloalkyl);
$R^a$ and $R^b$ are each, independently, hydrogen or $C_1$-$C_6$ alkyl;
$R^8$, $R^9$, $R^{10}$, and Z are each, independently, hydrogen, fluorine, OH, or $O(C_1$-$C_6$ alkyl);
q is 2 or 3;
$R^N$ is $C_1$-$C_5$ alkyl; and
$R^{12}$ is hydrogen or $C_1$-$C_6$ alkyl.

In one embodiment, $R^N$ is methyl.

In one embodiment, q is 2. In another embodiment, q is 3.

In one embodiment, $X^2$ is $CR^9$.

In one embodiment, at least one of $R^8$, $R^9$, $R^{10}$ and Z is not hydrogen.

In one embodiment, at least one of $R^8$, $R^9$, $R^{10}$ and Z is $O(C_1$-$C_6$ alkyl).

In one embodiment, at least one of $R^8$, $R^9$, $R^{10}$ and Z is $OCH_3$.

In one embodiment, at least one of $R^8$, $R^9$, $R^{10}$ and Z is fluorine.

In one embodiment, at least one of $R^2$, $R^3$, $R^4$, $R^5$ and $R^6$ is not hydrogen.

In one embodiment, at least one of $R^2$, $R^3$, $R^4$, $R^5$ and $R^6$ is $O(C_1$-$C_6$ alkyl).

In one embodiment, at least one of $R^2$, $R^3$, $R^4$, $R^5$ and $R^6$ is $OCH_3$.

In one embodiment, at least one of $R^2$, $R^3$, $R^4$, $R^5$ and $R^6$ is fluorine.

In one embodiment, $R^{12}$ is hydrogen.

In one embodiment, A is N. In a further embodiment, A is $CR^3$.

In one embodiment, one of $X^1$, $X^2$, or $X^3$ is N. In a further embodiment, none of $X^1$, $X^2$, or $X^3$ is N.

In one embodiment, $X^1$ is N, $X^2$ is $CR^9$, $X^3$ is $CR^{10}$, and A is N.

In one embodiment, $X^2$ is N, $X^1$ is $CR^8$, $X^3$ is $CR^{10}$, and A is N.

In one embodiment, $X^3$ is N, $X^1$ is $CR^8$, $X^2$ is $CR^9$, and A is N.

In one embodiment, $X^1$ is N, $X^2$ is $CR^9$, $X^3$ is $CR^{10}$, and A is $CR^3$.

In one embodiment, $X^2$ is N, $X^1$ is $CR^8$, $X^3$ is $CR^{10}$, and A is $CR^3$.

In one embodiment, $X^3$ is N, $X^1$ is $CR^8$, $X^2$ is $CR^9$, and A is $CR^3$.

In one embodiment, A is $CR^3$, and $X^2$ is $CR^9$. In a further embodiment, A is CH, and $X^2$ is CH. In another embodiment, A is CH, $X^2$ is CH and q is 2. In another embodiment, A is CH, $X^2$ is CH and q is 3.

In one embodiment, A is N, and $X^2$ is $CR^9$. In a further embodiment, A is N, $X^2$ is $CR^9$ and q is 2. In another embodiment, A is N, $X^2$ is $CR^9$ and q is 3.

A further aspect of the application relates to any compound of Formula (Ia), wherein the compound has the Formula (Ic).

A further aspect of the application relates to a compound being of Formula (Ic),

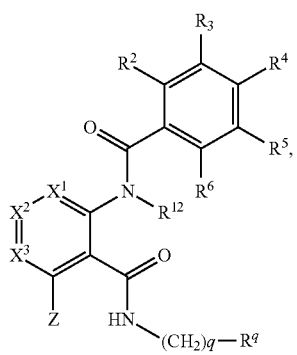

or a pharmaceutically acceptable salt thereof,
wherein:
$X^1$ is $CR^8$ or N;
$X^2$ is $CR^9$ or N;
$X^3$ is $CR^{10}$ or N;
wherein zero or one of $X^1$, $X^2$, or $X^3$ are N;
$R^2$ and $R^3$ together with the carbon atoms to which they attach form a $C_6$ aryl ring, or $R^5$ and $R^6$ together with the carbon atoms to which they attach form a $C_6$ aryl ring, and the remaining of $R^2$, $R^3$, $R^4$, $R^5$ and $R^6$ are each, independently, hydrogen, halogen, $C_1$-$C_6$ haloalkyl, $NO_2$, $NR^aR^b$, OH, $O(C_1$-$C_6$ alkyl), or $O(C_1$-$C_6$ haloalkyl);
$R^a$ and $R^b$ are each, independently, hydrogen or $C_1$-$C_6$ alkyl; $R^8$, $R^9$, $R^{10}$, and Z are each, independently, hydrogen, halogen, OH, or $O(C_1$-$C_6$ alkyl);
q is 2 or 3;
$R^q$ is 1-piperazinyl, 1-(4-N—($R^N$))piperazinyl, N-morpholino or phenyl;
$R^N$ is $C_1$-$C_5$ alkyl; and
$R^{12}$ is hydrogen or $C_1$-$C_6$ alkyl;
wherein,
when A is $CR^3$ and $R^2$ is fluorine or chlorine, then $R^q$ is phenyl or 1-(4-N—($R^N$))piperazinyl, or when A is $CR^3$, $R^2$ is fluorine or chlorine, q is 2 and $R^q$ is N-morpholino, then at least one of $R^8$, $R^9$, $R^{10}$, and Z is not hydrogen and $R^8$ is not $OCH_3$.

In one embodiment, $R^2$ and $R^3$ together with the carbon atoms to which they attach form a $C_6$ aryl ring; and $R^4$, $R^5$ and $R^6$ are each, independently, hydrogen, halogen, $C_1$-$C_6$ haloalkyl, $NO_2$, $NR^aR^b$, OH, $O(C_1$-$C_6$ alkyl), or $O(C_1$-$C_6$ haloalkyl).

In one embodiment, $R^5$ and $R^6$ together with the carbon atoms to which they attach form a $C_6$ aryl ring; and $R^2$, $R^3$ and $R^4$ are each, independently, hydrogen, halogen, $C_1$-$C_6$ haloalkyl, $NO_2$, $NR^aR^b$, OH, $O(C_1$-$C_6$ alkyl), or $O(C_1$-$C_6$ haloalkyl).

In one embodiment, $X^2$ is $CR^9$.

In one embodiment, $X^1$ is $CR^8$. In another embodiment, $X^1$ is $CR^8$ and $R^8$ is hydrogen.

In one embodiment, $X^1$ is $CR^8$. In another embodiment, $X^1$ is $CR^8$ and $R^8$ is $OCH_3$.

In one embodiment, q is 2. In another embodiment, q is 3.

In one embodiment, $R^q$ is 1-piperazinyl. In one embodiment, $R^q$ is 1-(4-N—($R^N$))piperazinyl. In one embodiment, $R^q$ is N-morpholino. In one embodiment, $R^q$ is phenyl.

In one embodiment, $R^q$ is 1-(4-N—($R^N$))piperazinyl and $R^N$ is methyl, ethyl, propyl, isopropyl, n-butyl or n-pentyl. In one embodiment, $R^q$ is 1-(4-N—($R^N$))piperazinyl and $R^N$ is methyl or ethyl. In one embodiment, $R^q$ is 1-(4-N—($R^N$))piperazinyl and $R^N$ is methyl.

In one embodiment, at least one of $R^8$, $R^9$, $R^{10}$, and Z is halogen.

In one embodiment, at least one of $R^8$, $R^9$, $R^{10}$, and Z is chlorine or fluorine.

In one embodiment, $R^{12}$ is hydrogen.

A further aspect of the application relates to a compound being of Formula (Ic),

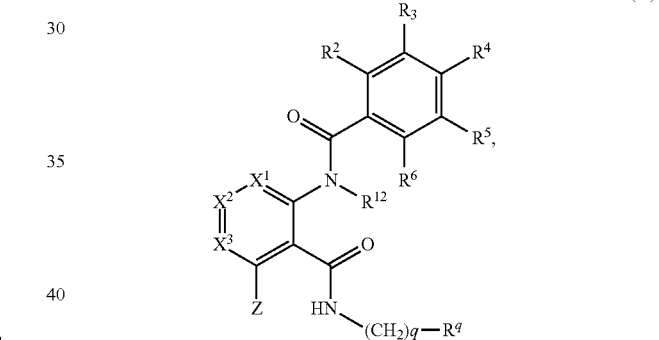

or a pharmaceutically acceptable salt thereof,
wherein:
$X^1$ is $CR^8$ or N;
$X^2$ is $CR^9$ or N;
$X^3$ is $CR^{10}$ or N;
wherein zero or one of $X^1$, $X^2$, or $X^3$ are N;
$R^3$ and $R^4$ together with the carbon atoms to which they attach form a $C_6$ aryl ring, or $R^4$ and $R^5$ together with the carbon atoms to which they attach form a $C_6$ aryl ring, and $R^2$, $R^6$ and the remaining of $R^3$ and $R^5$ are each, independently, hydrogen, halogen, $C_1$-$C_6$ haloalkyl, $NO_2$, $NR^aR^b$, OH, $O(C_1$-$C_6$ alkyl), or $O(C_1$-$C_6$ haloalkyl);
$R^a$ and $R^b$ are each, independently, hydrogen or $C_1$-$C_6$ alkyl;
$R^8$, $R^9$, $R^{10}$, and Z are each, independently, hydrogen, halogen, OH, or $O(C_1$-$C_6$ alkyl);
q is 2 or 3;
$R^q$ is 1-piperazinyl, 1-(4-N—($R^N$))piperazinyl, N-morpholino, or phenyl;
$R^N$ is $C_1$-$C_5$ alkyl; and
$R^{12}$ is hydrogen or $C_1$-$C_6$ alkyl;
wherein,
when A is $CR^3$ and $R^2$ is fluorine or chlorine, then $R^q$ is phenyl or 1-(4-N—($R^N$))piperazinyl, or when A is $CR^3$, $R^2$ is fluorine or chlorine, q is 2 and $R^q$ is N-morpholino, then at least one of $R^8$, $R^9$, $R^{10}$, and Z is not hydrogen and $R^8$ is not $OCH_3$.

In one embodiment, $R^3$ and $R^4$ together with the carbon atoms to which they attach form a $C_6$ aryl ring; and $R^2$, $R^5$ and $R^6$ are each, independently, hydrogen, halogen, $C_1$-$C_6$ haloalkyl, $NO_2$, $NR^aR^b$, OH, $O(C_1$-$C_6$ alkyl), or $O(C_1$-$C_6$ haloalkyl).

In one embodiment, $R^4$ and $R^5$ together with the carbon atoms to which they attach form a $C_6$ aryl ring; and $R^2$, $R^3$, and $R^6$ are each, independently, hydrogen, halogen, $C_1$-$C_6$ haloalkyl, $NO_2$, $NR^aR^b$, OH, $O(C_1$-$C_6$ alkyl), or $O(C_1$-$C_6$ haloalkyl).

In one embodiment, $X^2$ is $CR^9$.

In one embodiment, $X^1$ is $CR^8$, $X^2$ is $CR^9$, and $X^3$ is $CR^{10}$.

In one embodiment, q is 2. In another embodiment, q is 3.

In one embodiment, $R^q$ is 1-piperazinyl. In one embodiment, $R^q$ is 1-(4-N—($R^N$))piperazinyl. In one embodiment, $R^q$ is N-morpholino. In one embodiment, $R^q$ is phenyl.

In one embodiment, $R^q$ is 1-(4-N—($R^N$))piperazinyl and $R^N$ is methyl, ethyl, propyl, isopropyl, n-butyl or n-pentyl. In one embodiment, $R^q$ is 1-(4-N—($R^N$))piperazinyl and $R^N$ is methyl or ethyl. In one embodiment, $R^q$ is 1-(4-N—($R^N$))piperazinyl and $R^N$ is methyl.

In one embodiment, at least one of $R^8$, $R^9$, $R^{10}$, and Z is halogen.

In one embodiment, at least one of $R^8$, $R^9$, $R^{10}$, and Z is chlorine of fluorine.

In one embodiment, $R^{12}$ is hydrogen.

In one embodiment, $R^3$ and $R^4$ together form a $C_6$ aryl ring.

In one embodiment, $R^2$, $R^5$ and $R^6$ are each hydrogen.

In one embodiment, $R^8$, $R^9$, $R^{10}$, and Z are each hydrogen.

In one embodiment, $R^3$ and $R^4$ together with the carbon atoms to which they attach form a $C_6$ aryl ring, and $R^2$, $R^5$, $R^6$, $R^8$, $R^9$, $R^{10}$, and Z are each hydrogen.

In one embodiment, $R^3$ and $R^4$ together with the carbon atoms to which they attach form a $C_6$ aryl ring, and $R^2$, $R^5$, $R^6$, $R^8$, $R^9$, $R^{10}$, and Z are each hydrogen, and q is 2.

In one embodiment, $R^3$ and $R^4$ together with the carbon atoms to which they attach form a $C_6$ aryl ring, and $R^2$, $R^5$, $R^6$, $R^8$, $R^9$, $R^{10}$, and Z are each hydrogen, and $R^q$ is N-morpholino.

A further aspect of the application relates to any compound of Formula (Ic).

A further aspect of the application relates to any compound of Formula (Ia), wherein the compound has the Formula (Id).

A further aspect of the application relates to a compound being of Formula (Id),

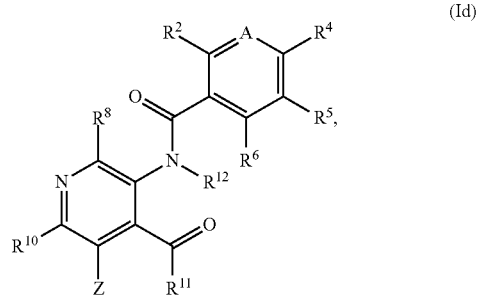

(Id)

or a pharmaceutically acceptable salt thereof,
wherein:
A is $CR^3$ or N;
$R^2$, $R^3$, $R^4$, $R^5$ and $R^6$ are each, independently, hydrogen, halogen, $C_1$-$C_6$ haloalkyl, $NO_2$, $NR^aR^b$, OH, $O(C_1$-$C_6$ alkyl), or $O(C_1$-$C_6$ haloalkyl);
$R^a$ and $R^b$ are each, independently, hydrogen or $C_1$-$C_6$ alkyl;
$R^8$, $R^{10}$, and Z are each, independently, hydrogen, fluorine, OH, or $O(C_1$-$C_6$ alkyl);
$R^{11}$ is OH, $O(C_1$-$C_6$ alkyl), or —NH—$(CH_2)_q$—$R^q$, wherein:
q is 2 or 3;
$R^q$ is 1-piperazinyl, 1-(4-N—($R^N$))piperazinyl, N-morpholino or phenyl; and
$R^N$ is $C_1$-$C_5$ alkyl; and
$R^{12}$ is hydrogen or $C_1$-$C_6$ alkyl;
wherein:
when A is $CR^3$ and $R^2$ is fluorine or chlorine, then $R^q$ is phenyl or 1-(4-N—($R^N$))piperazinyl; or when A is $CR^3$, $R^2$ is fluorine or chlorine, q is 2 and $R^q$ is N-morpholino, then at least one of $R^8$, $R^{10}$, and Z is not hydrogen and $R^8$ is not $OCH_3$; or
when A is $CR^3$, $R^2$ is fluorine or chlorine, q is 2 and $R^q$ is N-morpholino at least one of $R^3$, $R^4$, $R^5$ and $R^6$ is not hydrogen or halogen; and at least three of $R^2$, $R^3$, $R^4$, $R^5$ and $R^6$ are hydrogen.

In one embodiment, $R^{11}$ is —NH—$(CH_2)_q$—$R^q$.

In one embodiment, q is 2. In another embodiment, q is 3.

In one embodiment, $R^q$ is 1-piperazinyl. In one embodiment, $R^q$ is 1-(4-N—($R^N$))piperazinyl. In one embodiment, $R^q$ is N-morpholino. In one embodiment, $R^q$ is phenyl.

In one embodiment, $R^4$ is $OCH_3$.

In one embodiment, A is $CR^3$.

In one embodiment, $R^2$, $R^3$, $R^5$ and $R^6$ are each hydrogen.

In one embodiment, $R^8$, $R^{10}$, and Z are each hydrogen.

In one embodiment, $R^{12}$ is hydrogen.

A further aspect of the application relates to any compound of Formula (Id).

A further aspect of the application relates to any compound of Formula (Ia), wherein the compound has the Formula (Ie).

A further aspect of the application relates to a compound being of Formula (Ie),

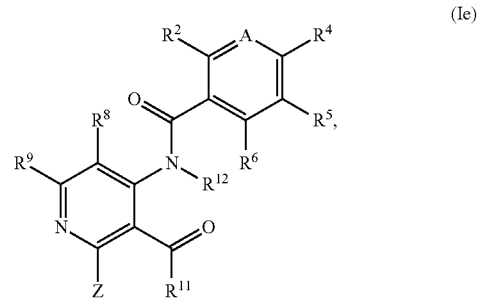

(Ie)

or a pharmaceutically acceptable salt thereof,
wherein:
A is $CR^3$ or N;
$R^2$, $R^3$, $R^4$, $R^5$ and $R^6$ are each, independently, hydrogen, halogen, $C_1$-$C_6$ haloalkyl, $NO_2$, $NR^aR^b$, OH, $O(C_1$-$C_6$ alkyl), or $O(C_1$-$C_6$ haloalkyl);
$R^a$ and $R^b$ are each, independently, hydrogen or $C_1$-$C_6$ alkyl;
$R^8$, $R^9$, and Z are each, independently, hydrogen, fluorine, OH, or $O(C_1$-$C_6$ alkyl);
$R^{11}$ is OH, $O(C_1$-$C_6$ alkyl), or —NH—$(CH_2)_q$—$R^q$, wherein:

q is 2 or 3;

$R^q$ is 1-piperazinyl, 1-(4-N—($R^N$))piperazinyl, N-morpholino or phenyl;

$R^N$ is $C_1$-$C_5$ alkyl; and $R^{12}$ is hydrogen or $C_1$-$C_6$ alkyl;

wherein:

when A is $CR^3$ and $R^2$ is fluorine or chlorine, then $R^q$ is phenyl or 1-(4-N—($R^N$))piperazinyl; or when A is $CR^3$, $R^2$ is fluorine or chlorine, q is 2 and $R^q$ is N-morpholino, then at least one of $R^8$, $R^9$, and Z is not hydrogen and $R^8$ is not $OCH_3$; or when A is $CR^3$, $R^2$ is fluorine or chlorine, q is 2 and $R^q$ is N-morpholino at least one of $R^3$, $R^4$, $R^5$ and $R^6$ is not hydrogen or halogen; and at least three of $R^2$, $R^3$, $R^4$, $R^5$ and $R^6$ are hydrogen.

In one embodiment, $R^{11}$ is —NH—$(CH_2)_q$—$R^q$.

In one embodiment, $R^q$ is 1-(4-N—($R^N$))piperazinyl.

In one embodiment, q is 2.

In one embodiment, $R^4$ is $OCH_3$.

In one embodiment, $R^2$, $R^3$, $R^5$, $R^6$, $R^8$, $R^9$, and Z are each hydrogen.

In one embodiment, $R^{12}$ is hydrogen.

A further aspect of the application relates to any compound of Formula (Ie).

A further aspect of the application relates to any compound of Formula (Ia), wherein the compound has the Formula (If).

A further aspect of the application relates to a compound being of formula (If),

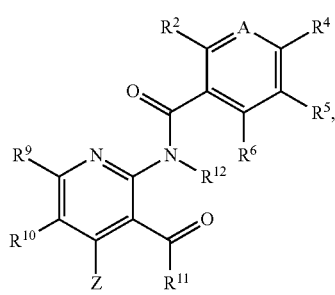

(If)

or a pharmaceutically acceptable salt thereof, wherein:

A is $CR^3$ or N;

$R^2$, $R^3$, $R^4$, $R^5$ and $R^6$ are each, independently, hydrogen, halogen, $C_1$-$C_6$ haloalkyl, $NO_2$, $NR^aR^b$, OH, O($C_1$-$C_6$ alkyl), or O($C_1$-$C_6$ haloalkyl);

$R^a$ and $R^b$ are each, independently, hydrogen or $C_1$-$C_6$ alkyl;

$R^9$, $R^{10}$, and Z are each, independently, hydrogen, fluorine, OH, or O($C_1$-$C_6$ alkyl);

$R^{11}$ is OH, O($C_1$-$C_6$ alkyl), or —NH—$(CH_2)_q$—$R^q$, wherein:

q is 2 or 3;

$R^q$ is 1-piperazinyl, 1-(4-N—($R^N$))piperazinyl, N-morpholino or phenyl; and $R^N$ is $C_1$-$C_5$ alkyl; and $R^{12}$ is hydrogen or $C_1$-$C_6$ alkyl;

wherein, when A is $CR^3$ and $R^2$ is fluorine or chlorine, then $R^q$ is phenyl or 1-(4-N—($R^N$))piperazinyl; or when A is $CR^3$, $R^2$ is fluorine or chlorine, q is 2 and $R^q$ is N-morpholino, then at least one of $R^9$, $R^{10}$, and Z is not hydrogen and $R^8$ is not $OCH_3$; or when A is $CR^3$, $R^2$ is fluorine or chlorine, q is 2 and $R^q$ is N-morpholino at least one of $R^3$, $R^4$, $R^5$ and $R^6$ is not hydrogen or halogen; and at least three of $R^2$, $R^3$, $R^4$, $R^5$ and $R^6$ are hydrogen.

In one embodiment, A is $CR^3$.

In one embodiment, $R^2$, $R^3$, $R^4$, $R^5$, $R^6$, $R^9$, $R^{10}$ and Z are each, independently, hydrogen or fluorine.

In one embodiment, $R^2$ is fluorine.

In one embodiment, $R^{11}$ is OH or O($C_1$-$C_6$ alkyl).

In one embodiment, $R^{11}$ is OH or $OCH_3$.

In one embodiment, $R^{11}$ is OH.

In one embodiment, $R^{12}$ is hydrogen or methyl.

In one embodiment, $R^{12}$ is hydrogen.

In one embodiment, $R^{12}$ is methyl.

A further aspect of the application relates to any compound of Formula (If).

A skilled person in the art would understand that any embodiment described within can be combined with any other embodiments.

In a further embodiment, the compound of Formula (I) or Formula (Ia) is selected from a compounds listed in Table 1:

TABLE 1

| Cmpd | Structure | Chemical Name |
|---|---|---|
| 4 | $NH_2$ (structure shown) | 2-(3-aminobenzamido)-N-(2-morpholinoethyl)benzamide |

TABLE 1-continued
| Cmpd | Structure | Chemical Name |
|---|---|---|
| 5 | 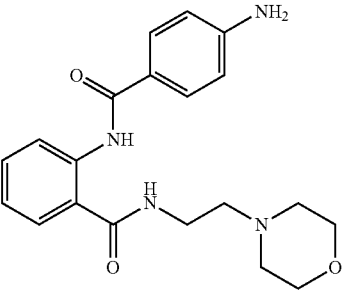 | 2-(4-aminobenzamido)-N-(2-morpholinoethyl)benzamide |
| 7 | 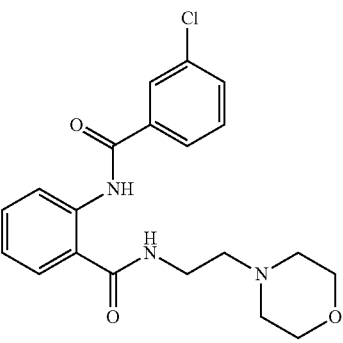 [SMILES: O=C(Nc1ccccc1C(=O)NCCN1CCOCC1)c1cccc(Cl)c1] | 2-(3-chlorobenzamido)-N-(2-morpholinoethyl)benzamide |
| 8 | 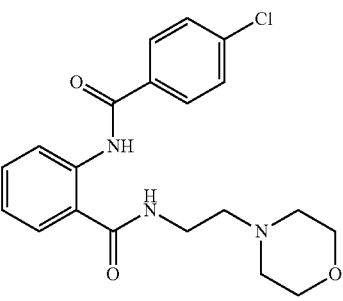 [SMILES: O=C(Nc1ccccc1C(=O)NCCN1CCOCC1)c1ccc(Cl)cc1] | 2-(4-chlorobenzamido)-N-(2-morpholinoethyl)benzamide |
| 9 | 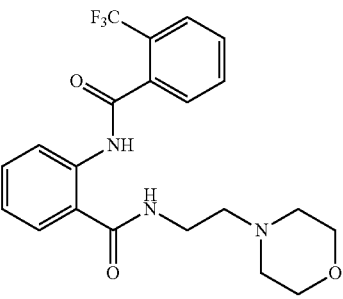 | N-(2-morpholinoethyl)-2-(2-(trifluoromethyl)benzamido)benzamide |
| 10 | 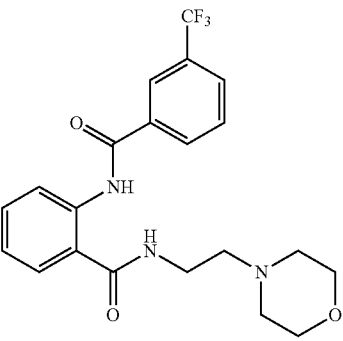 | N-(2-morpholinoethyl)-2-(3-(trifluoromethyl)benzamido)benzamide |

TABLE 1-continued

| Cmpd | Structure | Chemical Name |
|---|---|---|
| 11 | 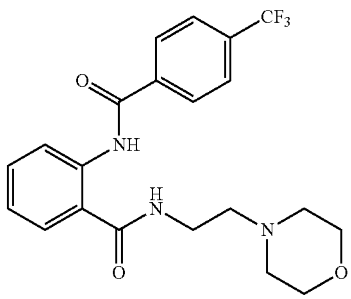 [SMILES: O=C(Nc1ccccc1C(=O)NCCN1CCOCC1)c1ccc(C(F)(F)F)cc1] | N-(2-morpholinoethyl)-2-(4-(trifluoromethyl)benzamido)benzamide |
| 12 | 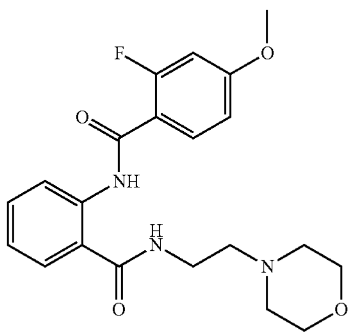 [SMILES: COc1ccc(C(=O)Nc2ccccc2C(=O)NCCN2CCOCC2)c(F)c1] | 2-fluoro-4-methoxy-N-(2-((2-morpholinoethyl)carbamoyl)phenyl)benzamide |
| 13 | 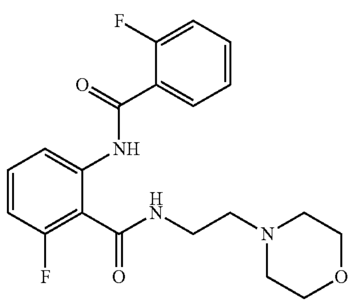 [SMILES: O=C(Nc1cccc(F)c1C(=O)NCCN1CCOCC1)c1ccccc1F] | 2-fluoro-6-(2-fluorobenzamido)-N-(2-morpholinoethyl)benzamide |
| 14 | 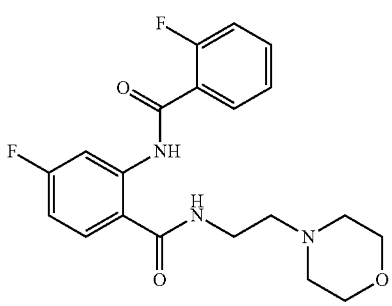 [SMILES: O=C(Nc1cc(F)ccc1C(=O)NCCN1CCOCC1)c1ccccc1F] | 4-fluoro-2-(2-fluorobenzamido)-N-(2-morpholinoethyl)benzamide |
| 15 | 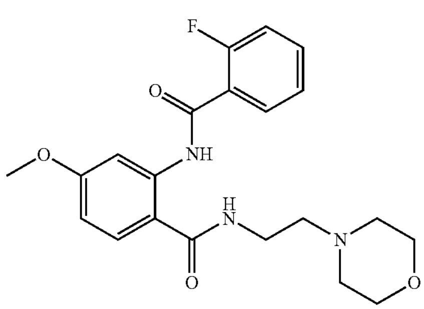 [SMILES: COc1ccc(C(=O)NCCN2CCOCC2)c(NC(=O)c2ccccc2F)c1] | 2-(2-fluorobenzamido)-4-methoxy-N-(2-morpholinoethyl)benzamide |

TABLE 1-continued

| Cmpd | Structure | Chemical Name |
|---|---|---|
| 17 | 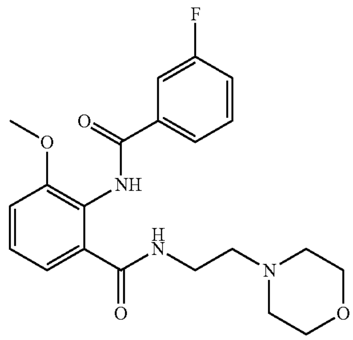 [SMILES: COc1cccc(C(=O)NCCN2CCOCC2)c1NC(=O)c1cccc(F)c1] | 2-(3-fluorobenzamido)-3-methoxy-N-(2-morpholinoethyl)benzamide |
| 18 | 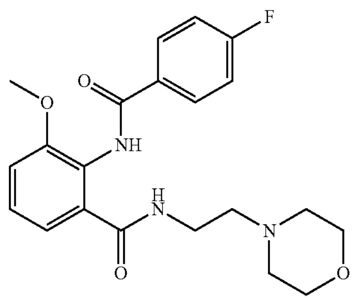 [SMILES: COc1cccc(C(=O)NCCN2CCOCC2)c1NC(=O)c1ccc(F)cc1] | 2-(4-fluorobenzamido)-3-methoxy-N-(2-morpholinoethyl)benzamide |
| 19 | 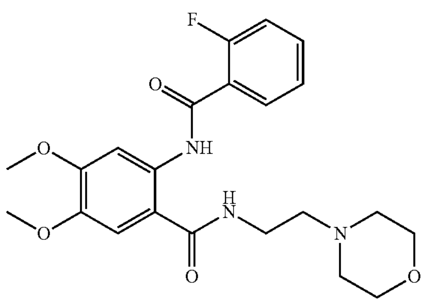 [SMILES: COc1cc(NC(=O)c2ccccc2F)c(C(=O)NCCN2CCOCC2)cc1OC] | 2-(2-fluorobenzamido)-4,5-dimethoxy-N-(2-morpholinoethyl)benzamide |
| 20 | 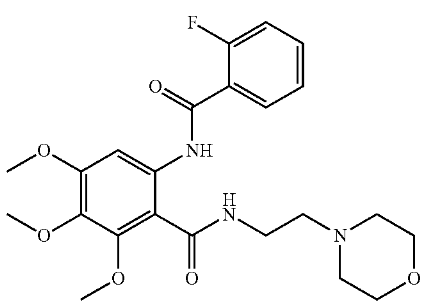 [SMILES: COc1cc(NC(=O)c2ccccc2F)c(C(=O)NCCN2CCOCC2)c(OC)c1OC] | 6-(2-fluorobenzamido)-2,3,4-trimethoxy-N-(2-morpholinoethyl)benzamide |
| 21 | 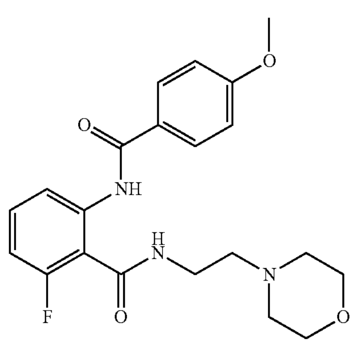 [SMILES: COc1ccc(C(=O)Nc2cccc(F)c2C(=O)NCCN2CCOCC2)cc1] | 2-fluoro-6-(4-methoxybenzamido)-N-(2-morpholinoethyl)benzamide |

TABLE 1-continued

| Cmpd | Structure | Chemical Name |
|------|-----------|---------------|
| 22 | 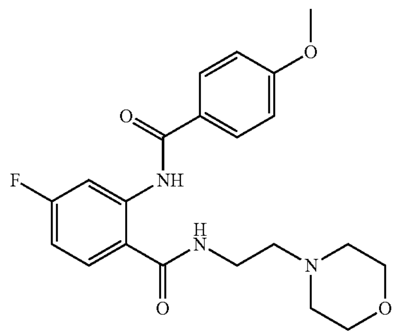 [SMILES: COc1ccc(C(=O)Nc2cc(F)ccc2C(=O)NCCN2CCOCC2)cc1] | 4-fluoro-2-(4-methoxybenzamido)-N-(2-morpholinoethyl)benzamide |
| 23 | 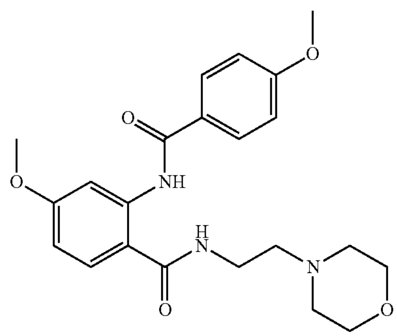 [SMILES: COc1ccc(C(=O)Nc2cc(OC)ccc2C(=O)NCCN2CCOCC2)cc1] | 4-methoxy-2-(4-methoxybenzamido)-N-(2-morpholinoethyl)benzamide |
| 24 | 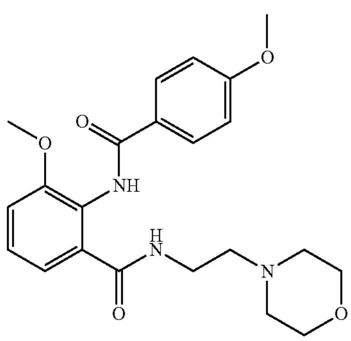 [SMILES: COc1ccc(C(=O)Nc2c(OC)cccc2C(=O)NCCN2CCOCC2)cc1] | 3-methoxy-2-(4-methoxybenzamido)-N-(2-morpholinoethyl)benzamide |
| 25 | 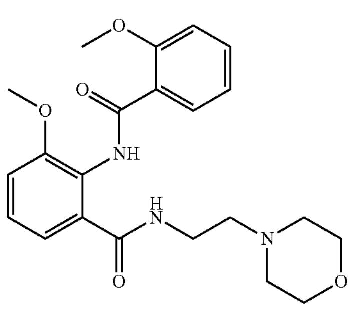 [SMILES: COc1ccccc1C(=O)Nc1c(OC)cccc1C(=O)NCCN1CCOCC1] | 3-methoxy-2-(2-methoxybenzamido)-N-(2-morpholinoethyl)benzamide |

TABLE 1-continued

| Cmpd | Structure | Chemical Name |
|------|-----------|---------------|
| 26 | 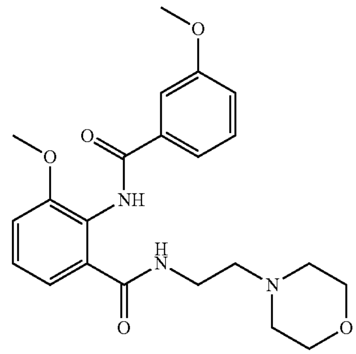 [SMILES: COc1cccc(C(=O)Nc2c(OC)cccc2C(=O)NCCN2CCOCC2)c1] | 3-methoxy-2-(3-methoxybenzamido)-N-(2-morpholinoethyl)benzamide |
| 27 | 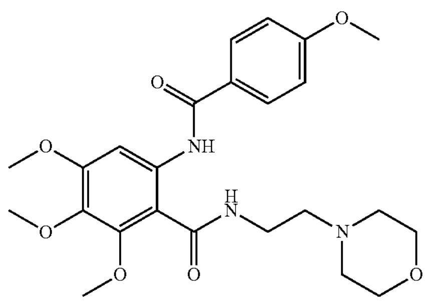 [SMILES: COc1ccc(C(=O)Nc2cc(OC)c(OC)c(OC)c2C(=O)NCCN2CCOCC2)cc1] | 2,3,4-trimethoxy-6-(4-methoxybenzamido)-N-(2-morpholinoethyl)benzamide |
| 28 | 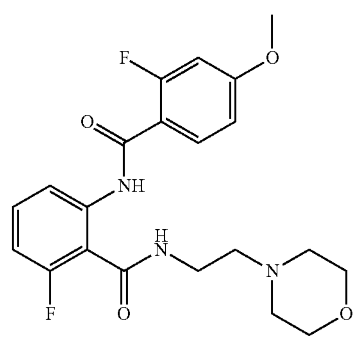 [SMILES: COc1ccc(C(=O)Nc2cccc(F)c2C(=O)NCCN2CCOCC2)c(F)c1] | 2-fluoro-N-(3-fluoro-2-((2-morpholinoethyl)carbamoyl)phenyl)-4-methoxybenzamide |
| 29 | 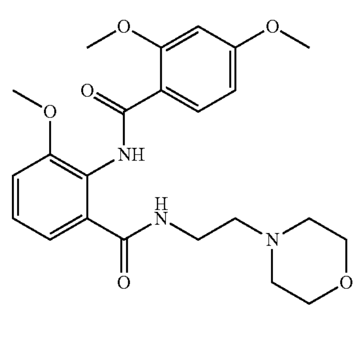 [SMILES: COc1ccc(C(=O)Nc2c(OC)cccc2C(=O)NCCN2CCOCC2)c(OC)c1] | 2-(2,4-dimethoxybenzamido)-3-methoxy-N-(2-morpholinoethyl)benzamide |

TABLE 1-continued

| Cmpd | Structure | Chemical Name |
|---|---|---|
| 30 | 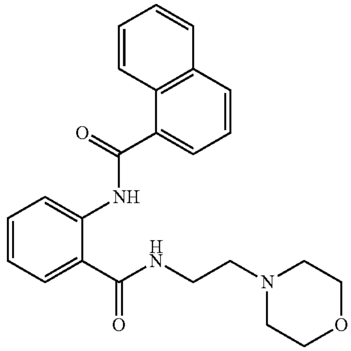 [SMILES: O=C(NCCN1CCOCC1)c1ccccc1NC(=O)c1cccc2ccccc12] | N-(2-((2-morpholinoethyl)carbamoyl)phenyl)-1-naphthamide |
| 31 | 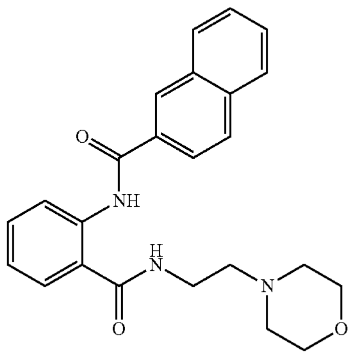 [SMILES: O=C(Nc1ccccc1C(=O)NCCN1CCOCC1)c1ccc2ccccc2c1] | N-(2-((2-morpholinoethyl)carbamoyl)phenyl)-2-naphthamide |
| 32 | 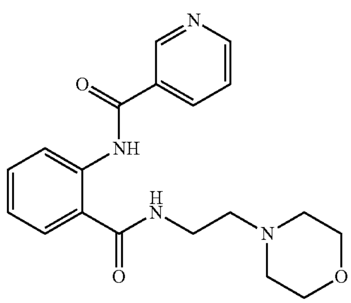 [SMILES: O=C(Nc1ccccc1C(=O)NCCN1CCOCC1)c1cccnc1] | N-(2-((2-morpholinoethyl)carbamoyl)phenyl)nicotinamide |
| 33 | 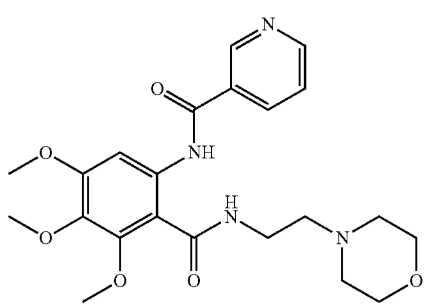 [SMILES: COc1cc(NC(=O)c2cccnc2)c(C(=O)NCCN2CCOCC2)c(OC)c1OC] | N-(3,4,5-trimethoxy-2-((2-morpholinoethyl)carbamoyl)phenyl)nicotinamide |
| 34 | 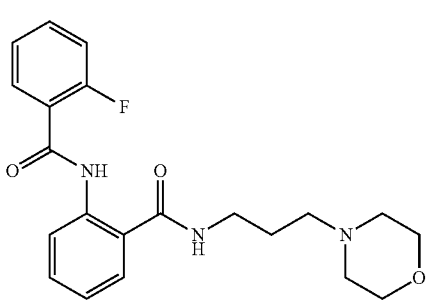 [SMILES: O=C(Nc1ccccc1C(=O)NCCCN1CCOCC1)c1ccccc1F] | 2-fluoro-N-(2-((3-morpholinopropyl)carbamoyl)phenyl)benzamide |

TABLE 1-continued
| Cmpd | Structure | Chemical Name |
|---|---|---|
| 35 | 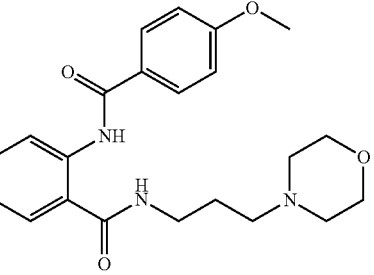 | 2-(4-methoxybenzamido)-N-(3-morpholinopropyl)benzamide |
| 36 | 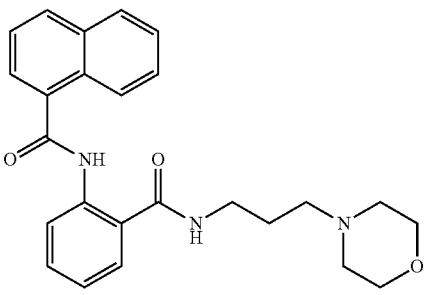 [SMILES: O=C(NCCCN1CCOCC1)c1ccccc1NC(=O)c1cccc2ccccc12] | N-(2-((3-morpholinopropyl)carbamoyl)phenyl)-1-naphthamide |
| 37 | 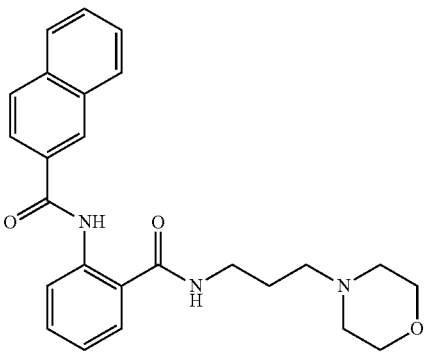 [SMILES: O=C(Nc1ccccc1C(=O)NCCCN1CCOCC1)c1ccc2ccccc2c1] | N-(2-((3-morpholinopropyl)carbamoyl)phenyl)-2-naphthamide |
| 38 | 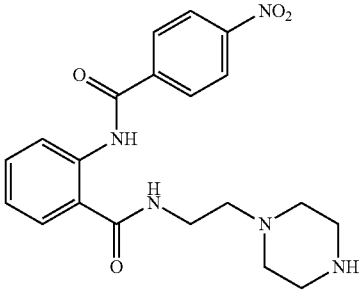 [SMILES: O=C(Nc1ccccc1C(=O)NCCN1CCNCC1)c1ccc([N+](=O)[O-])cc1] | 2-(4-nitrobenzamido)-N-(2-(piperazin-1-yl)ethyl)benzamide |
| 39 | 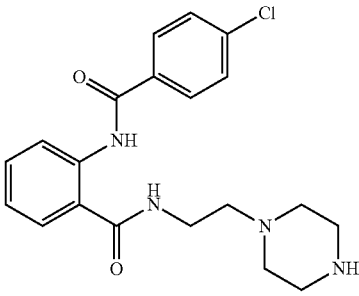 [SMILES: O=C(Nc1ccccc1C(=O)NCCN1CCNCC1)c1ccc(Cl)cc1] | 2-(4-chlorobenzamido)-N-(2-(piperazin-1-yl)ethyl)benzamide |

TABLE 1-continued

| Cmpd | Structure | Chemical Name |
|---|---|---|
| 40 | 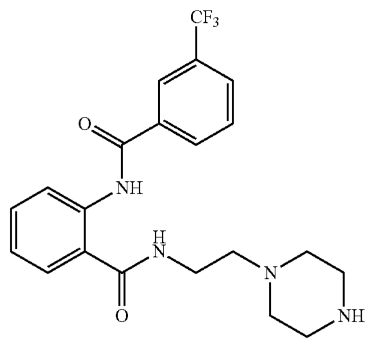 | N-(2-(piperazin-1-yl)ethyl)-2-(3-(trifluoromethyl)benzamido)benzamide |
| 41 | 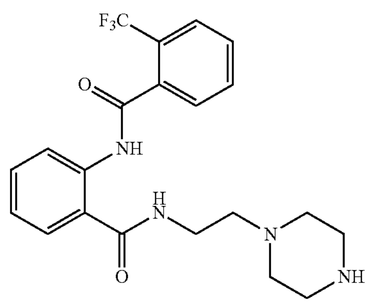 [SMILES: O=C(NCCN1CCNCC1)c1ccccc1NC(=O)c1ccccc1C(F)(F)F] | N-(2-(piperazin-1-yl)ethyl)-2-(2-(trifluoromethyl)benzamido)benzamide |
| 42 | 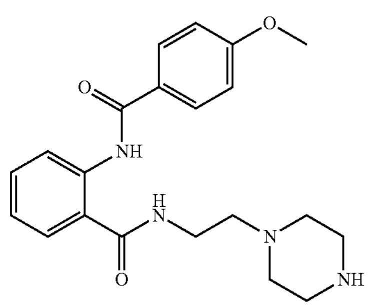 [SMILES: COc1ccc(C(=O)Nc2ccccc2C(=O)NCCN2CCNCC2)cc1] | 2-(4-methoxybenzamido)-N-(2-(piperazin-1-yl)ethyl)benzamide |
| 43 | 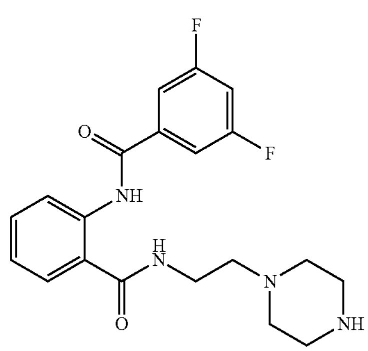 [SMILES: O=C(Nc1ccccc1C(=O)NCCN1CCNCC1)c1cc(F)cc(F)c1] | 3,5-difluoro-N-(2-((2-(piperazin-1-yl)ethyl)carbamoyl)phenyl)benzamide |
| 44 | 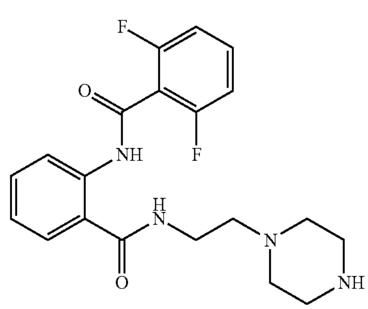 [SMILES: O=C(NCCN1CCNCC1)c1ccccc1NC(=O)c1c(F)cccc1F] | 2,6-difluoro-N-(2-((2-(piperazin-1-yl)ethyl)carbamoyl)phenyl)benzamide |

TABLE 1-continued
| Cmpd | Structure | Chemical Name |
|---|---|---|
| 45 | 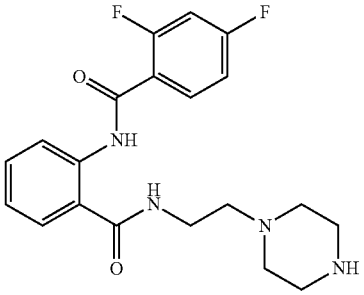 [SMILES: O=C(Nc1ccccc1C(=O)NCCN1CCNCC1)c1ccc(F)cc1F] | 2,4-difluoro-N-(2-((2-(piperazin-1-yl)ethyl)carbamoyl)phenyl)benzamide |
| 46 | 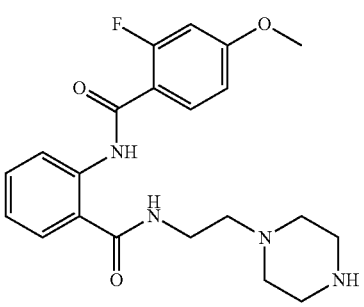 [SMILES: COc1ccc(C(=O)Nc2ccccc2C(=O)NCCN2CCNCC2)c(F)c1] | 2-fluoro-4-methoxy-N-(2-((2-(piperazin-1-yl)ethyl)carbamoyl)phenyl)benzamide |
| 47 | 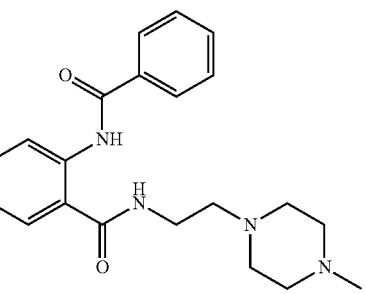 | 2-benzamido-N-(2-(4-methylpiperazin-1-yl)ethyl)benzamide |
| 48 | 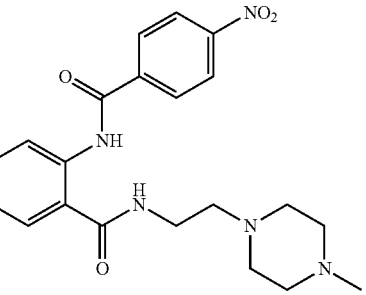 | N-(2-(4-methylpiperazin-1-yl)ethyl)-2-(4-nitrobenzamido)benzamide |
| 49 | 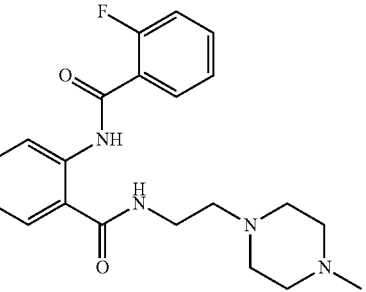 | 2-fluoro-N-(2-((2-(4-methylpiperazin-1-yl)ethyl)carbamoyl)phenyl)benzamide |

TABLE 1-continued

| Cmpd | Structure | Chemical Name |
| --- | --- | --- |
| 50 | 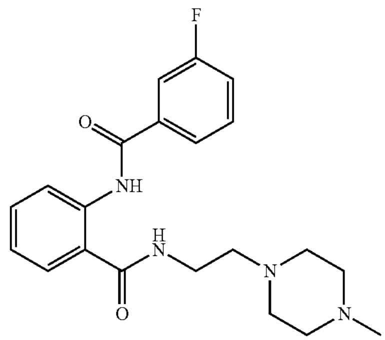 [SMILES: CN1CCN(CCNC(=O)c2ccccc2NC(=O)c2cccc(F)c2)CC1] | 2-(3-fluorobenzamido)-N-(2-(4-methylpiperazin-1-yl)ethyl)benzamide |
| 51 | 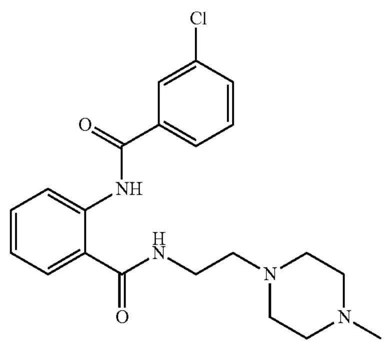 | 2-(3-chlorobenzamido)-N-(2-(4-methylpiperazin-1-yl)ethyl)benzamide |
| 52 | 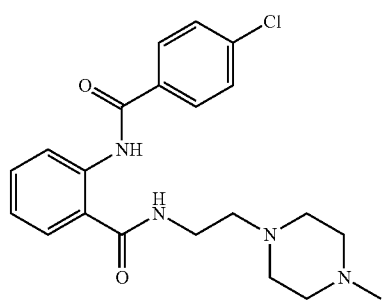 [SMILES: CN1CCN(CCNC(=O)c2ccccc2NC(=O)c2ccc(Cl)cc2)CC1] | 2-(4-chlorobenzamido)-N-(2-(4-methylpiperazin-1-yl)ethyl)benzamide |
| 53 | 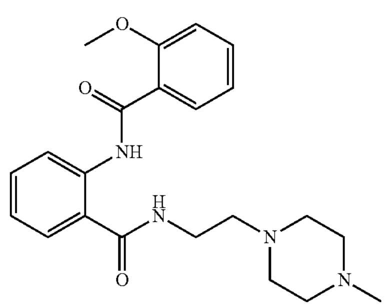 [SMILES: COc1ccccc1C(=O)Nc1ccccc1C(=O)NCCN1CCN(C)CC1] | 2-methoxy-N-(2-((2-(4-methylpiperazin-1-yl)ethyl)carbamoyl)phenyl)benzamide |
| 54 | 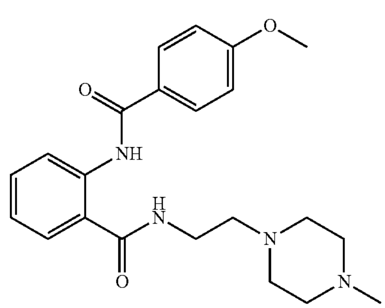 [SMILES: COc1ccc(C(=O)Nc2ccccc2C(=O)NCCN2CCN(C)CC2)cc1] | 2-(4-methoxybenzamido)-N-(2-(4-methylpiperazin-1-yl)ethyl)benzamide |

TABLE 1-continued

| Cmpd | Structure | Chemical Name |
|---|---|---|
| 55 | 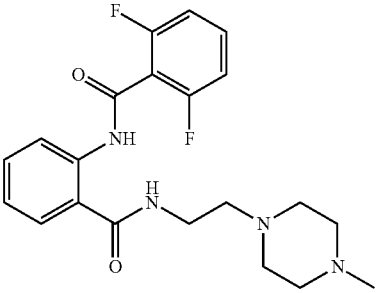 [SMILES: CN1CCN(CCNC(=O)c2ccccc2NC(=O)c2c(F)cccc2F)CC1] | 2,6-difluoro-N-(2-((2-(4-methylpiperazin-1-yl)ethyl)carbamoyl)phenyl)benzamide |
| 56 | 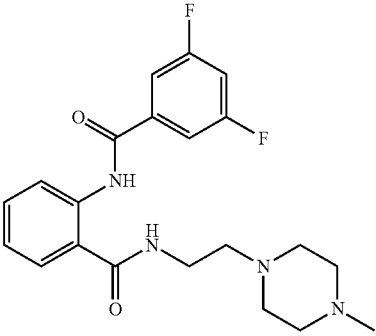 [SMILES: CN1CCN(CCNC(=O)c2ccccc2NC(=O)c2cc(F)cc(F)c2)CC1] | 3,5-difluoro-N-(2-((2-(4-methylpiperazin-1-yl)ethyl)carbamoyl)phenyl)benzamide |
| 57 | 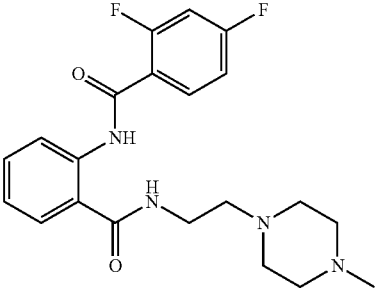 [SMILES: CN1CCN(CCNC(=O)c2ccccc2NC(=O)c2ccc(F)cc2F)CC1] | 2,4-difluoro-N-(2-((2-(4-methylpiperazin-1-yl)ethyl)carbamoyl)phenyl)benzamide |
| 58 | 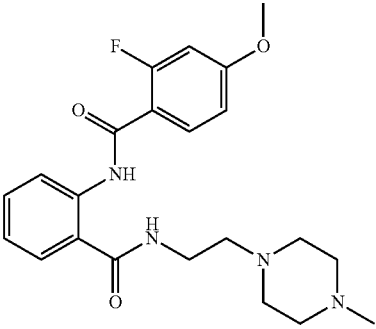 [SMILES: COc1ccc(C(=O)Nc2ccccc2C(=O)NCCN2CCN(C)CC2)c(F)c1] | 2-fluoro-4-methoxy-N-(2-((2-(4-methylpiperazin-1-yl)ethyl)carbamoyl)phenyl)benzamide |
| 59 | 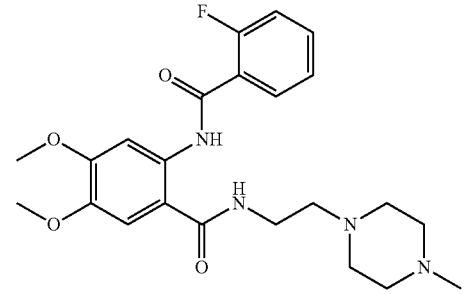 | 2-(2-fluorobenzamido)-4,5-dimethoxy-N-(2-(4-methylpiperazin-1-yl)ethyl)benzamide |

TABLE 1-continued

| Cmpd | Structure | Chemical Name |
|---|---|---|
| 60 | 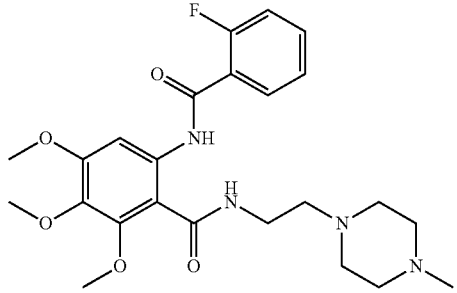 | 6-(2-fluorobenzamido)-2,3,4-trimethoxy-N-(2-(4-methylpiperazin-1-yl)ethyl)benzamide |
| 61 | 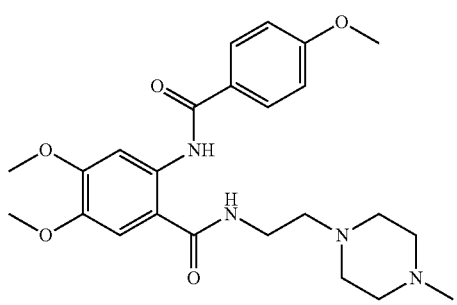 | 4,5-dimethoxy-2-(4-methoxybenzamido)-N-(2-(4-methylpiperazin-1-yl)ethyl)benzamide |
| 62 | 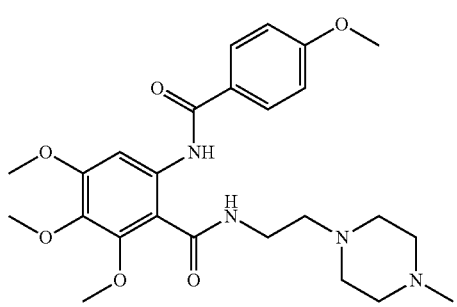 | 2,3,4-trimethoxy-6-(4-methoxybenzamido)-N-(2-(4-methylpiperazin-1-yl)ethyl)benzamide |
| 63 | 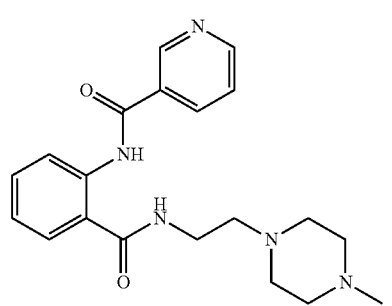 [SMILES: CN1CCN(CCNC(=O)c2ccccc2NC(=O)c2cccnc2)CC1] | N-(2-((2-(4-methylpiperazin-1-yl)ethyl)carbamoyl)phenyl)nicotinamide |
| 64 | 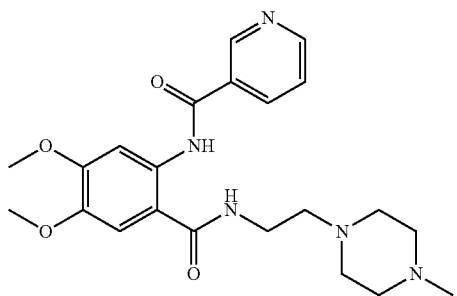 | N-(4,5-dimethoxy-2-((2-(4-methylpiperazin-1-yl)ethyl)carbamoyl)phenyl)nicotinamide |

TABLE 1-continued

| Cmpd | Structure | Chemical Name |
|---|---|---|
| 65 | 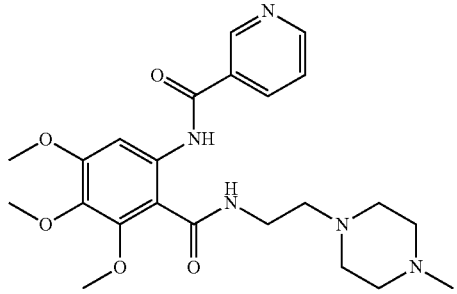 | N-(3,4,5-trimethoxy-2-((2-(4-methylpiperazin-1-yl)ethyl)carbamoyl)phenyl)nicotinamide |
| 66 | 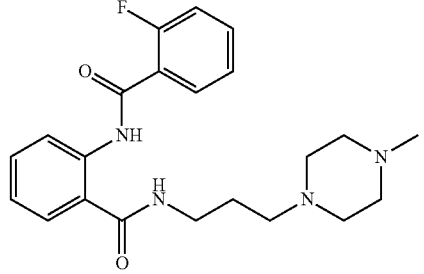 [SMILES: CN1CCN(CCCNC(=O)c2ccccc2NC(=O)c2ccccc2F)CC1] | 2-fluoro-N-(2-((3-(4-methylpiperazin-1-yl)propyl)carbamoyl)phenyl)benzamide |
| 67 | 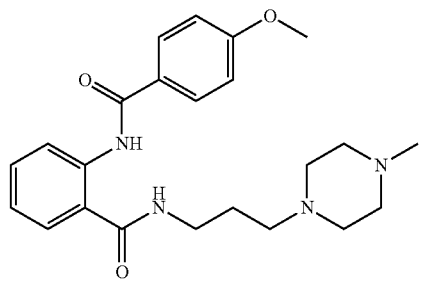 [SMILES: COc1ccc(C(=O)Nc2ccccc2C(=O)NCCCN2CCN(C)CC2)cc1] | 2-(4-methoxybenzamido)-N-(3-(4-methylpiperazin-1-yl)propyl)benzamide |
| 68 | 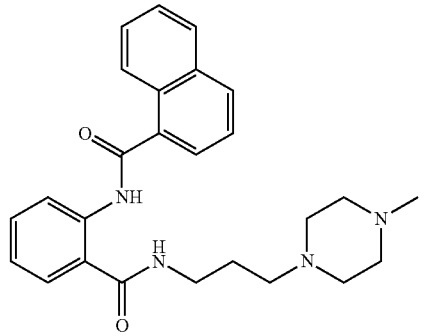 [SMILES: CN1CCN(CCCNC(=O)c2ccccc2NC(=O)c2cccc3ccccc23)CC1] | N-(2-((3-(4-methylpiperazin-1-yl)propyl)carbamoyl)phenyl)-1-naphthamide |
| 69 | 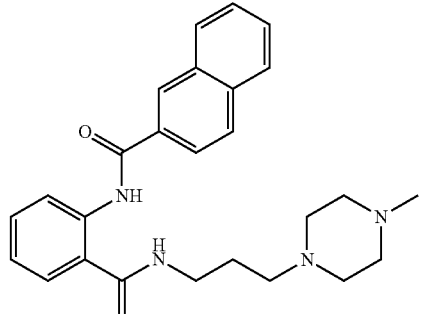 | N-(2-((3-(4-methylpiperazin-1-yl)propyl)carbamoyl)phenyl)-2-naphthamide |

TABLE 1-continued

| Cmpd | Structure | Chemical Name |
|---|---|---|
| 70 | 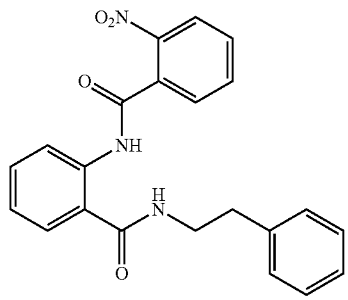 [SMILES: O=C(NCCc1ccccc1)c1ccccc1NC(=O)c1ccccc1[N+](=O)[O-]] | 2-nitro-N-(2-(phenethylcarbamoyl)phenyl)benzamide |
| 71 | 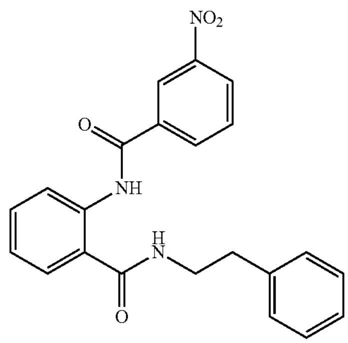 [SMILES: O=C(Nc1ccccc1C(=O)NCCc1ccccc1)c1cccc([N+](=O)[O-])c1] | 2-(3-nitrobenzamido)-N-phenethylbenzamide |
| 72 | 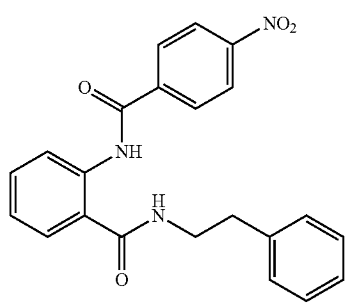 [SMILES: O=C(Nc1ccccc1C(=O)NCCc1ccccc1)c1ccc([N+](=O)[O-])cc1] | 2-(4-nitrobenzamido)-N-phenethylbenzamide |
| 73 | 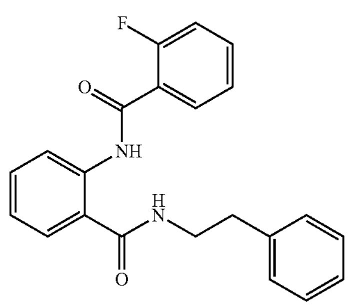 [SMILES: O=C(Nc1ccccc1C(=O)NCCc1ccccc1)c1ccccc1F] | 2-fluoro-N-(2-(phenethylcarbamoyl)phenyl)benzamide |
| 74 | 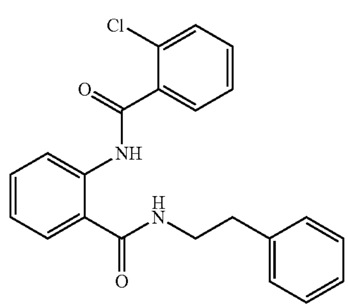 [SMILES: O=C(Nc1ccccc1C(=O)NCCc1ccccc1)c1ccccc1Cl] | 2-chloro-N-(2-(phenethylcarbamoyl)phenyl)benzamide |

TABLE 1-continued
| Cmpd | Structure | Chemical Name |
|---|---|---|
| 75 | 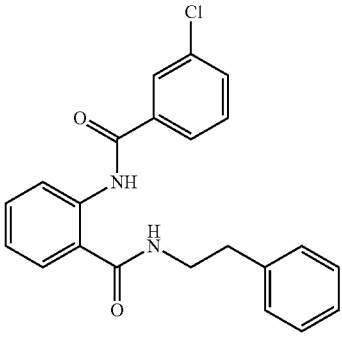 [SMILES: O=C(Nc1ccccc1C(=O)NCCc1ccccc1)c1cccc(Cl)c1] | 2-(3-chlorobenzamido)-N-phenethylbenzamide |
| 76 | 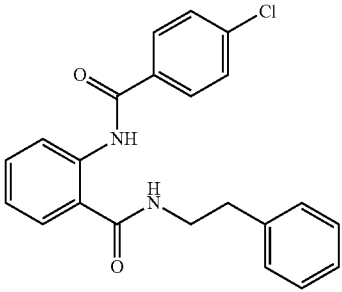 [SMILES: O=C(Nc1ccccc1C(=O)NCCc1ccccc1)c1ccc(Cl)cc1] | 2-(4-chlorobenzamido)-N-phenethylbenzamide |
| 77 | 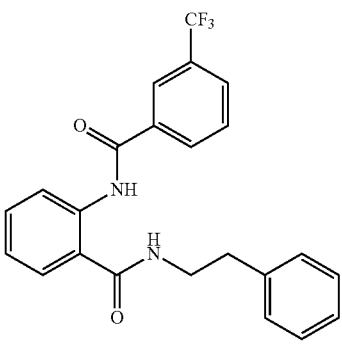 [SMILES: O=C(Nc1ccccc1C(=O)NCCc1ccccc1)c1cccc(C(F)(F)F)c1] | N-phenethyl-2-(3-(trifluoromethyl)benzamido)benzamide |
| 78 | 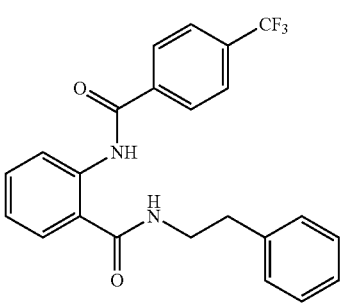 [SMILES: O=C(Nc1ccccc1C(=O)NCCc1ccccc1)c1ccc(C(F)(F)F)cc1] | N-phenethyl-2-(4-(trifluoromethyl)benzamido)benzamide |

TABLE 1-continued

| Cmpd | Structure | Chemical Name |
|---|---|---|
| 79 | 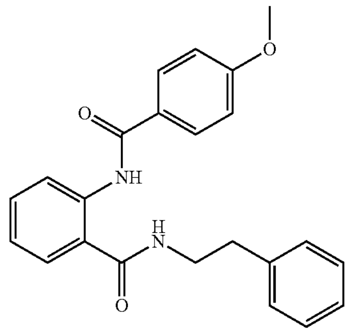 [SMILES: COc1ccc(C(=O)Nc2ccccc2C(=O)NCCc2ccccc2)cc1] | 2-(4-methoxybenzamido)-N-phenethylbenzamide |
| 80 | 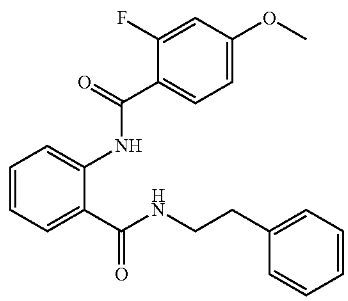 [SMILES: COc1ccc(C(=O)Nc2ccccc2C(=O)NCCc2ccccc2)c(F)c1] | 2-fluoro-4-methoxy-N-(2-(phenethylcarbamoyl)phenyl)benzamide |
| 81 | 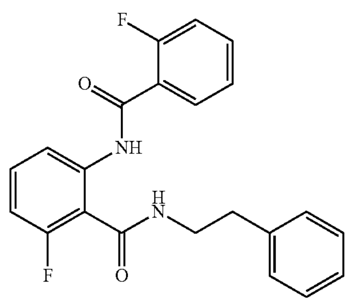 [SMILES: O=C(Nc1cccc(F)c1C(=O)NCCc1ccccc1)c1ccccc1F] | 2-fluoro-6-(2-fluorobenzamido)-N-phenethylbenzamide |
| 82 | 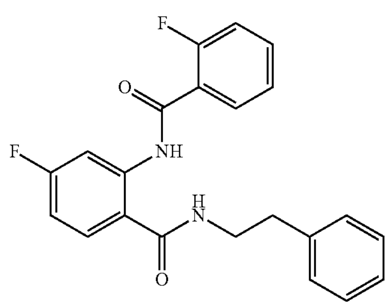 [SMILES: O=C(Nc1cc(F)ccc1C(=O)NCCc1ccccc1)c1ccccc1F] | 4-fluoro-2-(2-fluorobenzamido)-N-phenethylbenzamide |
| 83 | 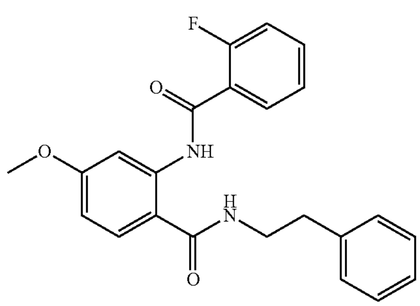 [SMILES: COc1ccc(C(=O)NCCc2ccccc2)c(NC(=O)c2ccccc2F)c1] | 2-(2-fluorobenzamido)-4-methoxy-N-phenethylbenzamide |

TABLE 1-continued
| Cmpd | Structure | Chemical Name |
|---|---|---|
| 84 | 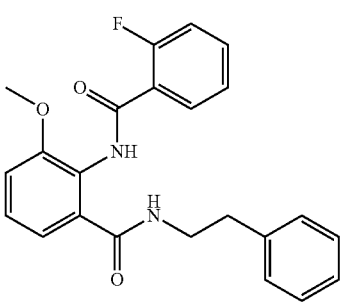 [SMILES: COc1cccc(C(=O)NCCc2ccccc2)c1NC(=O)c1ccccc1F] | 2-(2-fluorobenzamido)-3-methoxy-N-phenethylbenzamide |
| 85 | 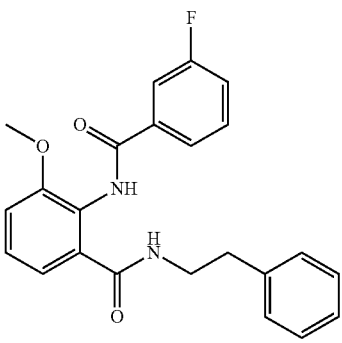 [SMILES: COc1cccc(C(=O)NCCc2ccccc2)c1NC(=O)c1cccc(F)c1] | 2-(3-fluorobenzamido)-3-methoxy-N-phenethylbenzamide |
| 86 | 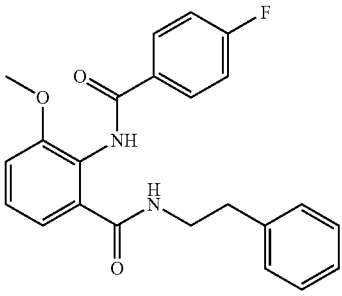 [SMILES: COc1cccc(C(=O)NCCc2ccccc2)c1NC(=O)c1ccc(F)cc1] | 2-(4-fluorobenzamido)-3-methoxy-N-phenethylbenzamide |
| 87 | 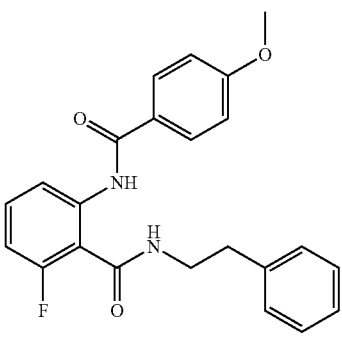 [SMILES: COc1ccc(C(=O)Nc2cccc(F)c2C(=O)NCCc2ccccc2)cc1] | 2-fluoro-6-(4-methoxybenzamido)-N-phenethylbenzamide |

TABLE 1-continued

| Cmpd | Structure | Chemical Name |
|---|---|---|
| 88 | 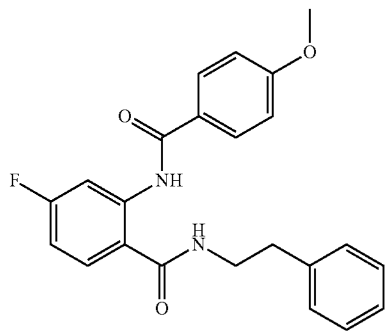 [SMILES: COc1ccc(C(=O)Nc2cc(F)ccc2C(=O)NCCc2ccccc2)cc1] | 4-fluoro-2-(4-methoxybenzamido)-N-phenethylbenzamide |
| 89 | 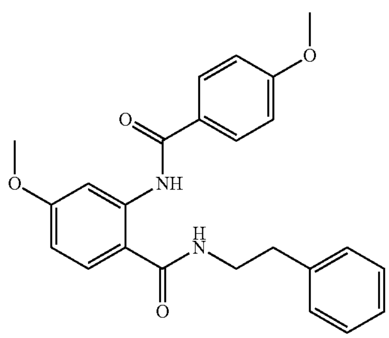 [SMILES: COc1ccc(C(=O)Nc2cc(OC)ccc2C(=O)NCCc2ccccc2)cc1] | 4-methoxy-2-(4-methoxybenzamido)-N-phenethylbenzamide |
| 90 | 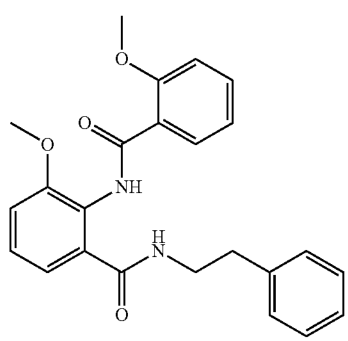 [SMILES: COc1ccccc1C(=O)Nc1c(OC)cccc1C(=O)NCCc1ccccc1] | 3-methoxy-2-(2-methoxybenzamido)-N-phenethylbenzamide |
| 91 | 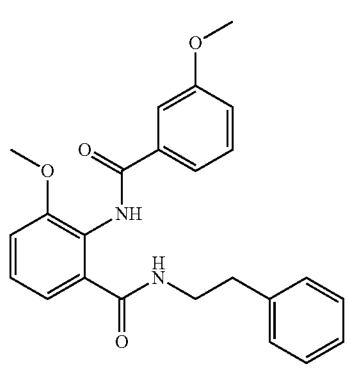 [SMILES: COc1cccc(C(=O)Nc2c(OC)cccc2C(=O)NCCc2ccccc2)c1] | 3-methoxy-2-(3-methoxybenzamido)-N-phenethylbenzamide |

TABLE 1-continued

| Cmpd | Structure | Chemical Name |
|---|---|---|
| 92 | 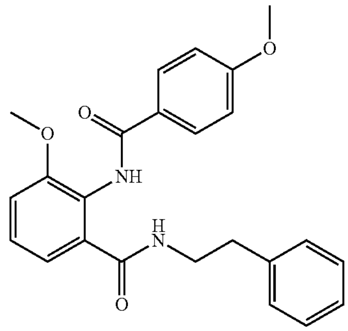 [SMILES: COc1ccc(C(=O)Nc2c(OC)cccc2C(=O)NCCc2ccccc2)cc1] | 3-methoxy-2-(4-methoxybenzamido)-N-phenethylbenzamide |
| 93 | 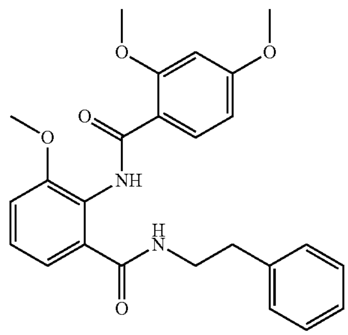 [SMILES: COc1ccc(C(=O)Nc2c(OC)cccc2C(=O)NCCc2ccccc2)c(OC)c1] | 2-(2,4-dimethoxybenzamido)-3-methoxy-N-phenethylbenzamide |
| 94 | 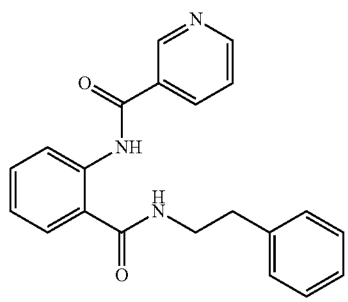 [SMILES: O=C(Nc1ccccc1C(=O)NCCc1ccccc1)c1cccnc1] | N-(2-(phenethylcarbamoyl)phenyl)nicotinamide |
| 95 | 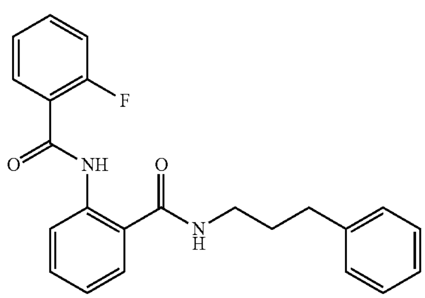 [SMILES: O=C(Nc1ccccc1C(=O)NCCCc1ccccc1)c1ccccc1F] | 2-fluoro-N-(2-((3-phenylpropyl)carbamoyl)phenyl)benzamide |
| 96 | 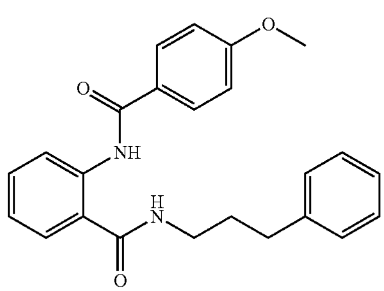 [SMILES: COc1ccc(C(=O)Nc2ccccc2C(=O)NCCCc2ccccc2)cc1] | 2-(4-methoxybenzamido)-N-(3-phenylpropyl)benzamide |

TABLE 1-continued
| Cmpd | Structure | Chemical Name |
|---|---|---|
| 97 | 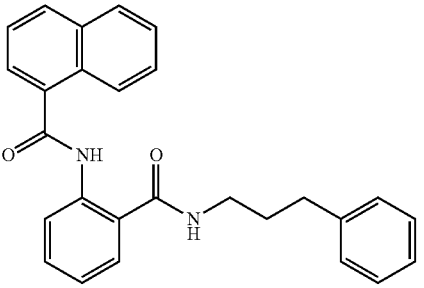 [SMILES: O=C(NCCCc1ccccc1)c1ccccc1NC(=O)c1cccc2ccccc12] | N-(2-((3-phenylpropyl)carbamoyl)phenyl)-1-naphthamide |
| 98 | 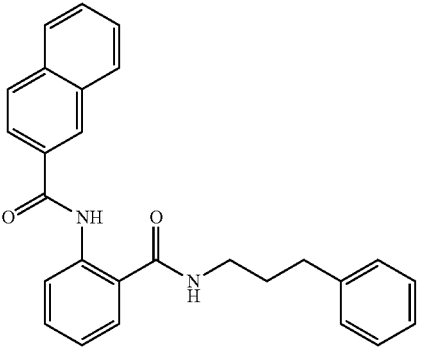 [SMILES: O=C(Nc1ccccc1C(=O)NCCCc1ccccc1)c1ccc2ccccc2c1] | N-(2-((3-phenylpropyl)carbamoyl)phenyl)-2-naphthamide |
| 99 | 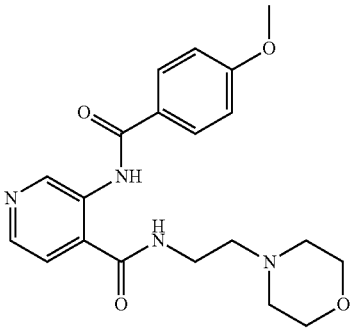 [SMILES: COc1ccc(C(=O)Nc2cnccc2C(=O)NCCN2CCOCC2)cc1] | 3-(4-methoxybenzamido)-N-(2-morpholinoethyl)isonicotinamide |
| 100 | 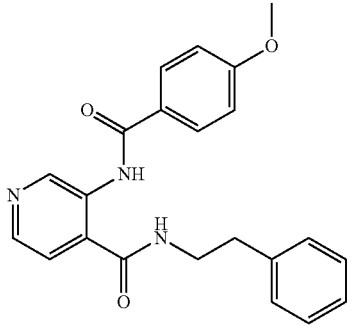 [SMILES: COc1ccc(C(=O)Nc2cnccc2C(=O)NCCc2ccccc2)cc1] | 3-(4-methoxybenzamido)-N-phenethylisonicotinamide |

TABLE 1-continued
| Cmpd | Structure | Chemical Name |
| --- | --- | --- |
| 101 | 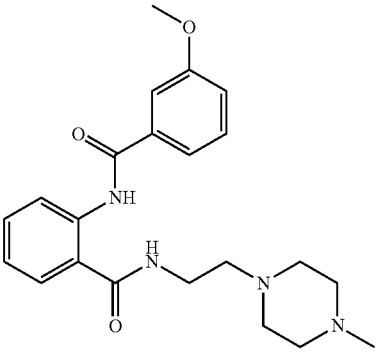 [SMILES: COc1cccc(C(=O)Nc2ccccc2C(=O)NCCN2CCN(C)CC2)c1] | 2-(3-methoxybenzamido)-N-(2-(4-methylpiperazin-1-yl)ethyl)benzamide |
| 102 | 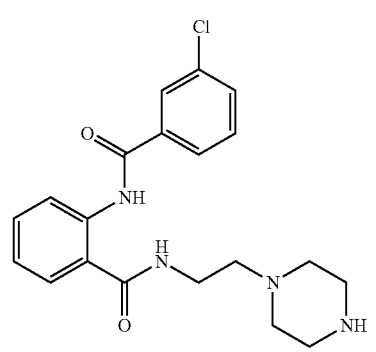 [SMILES: O=C(Nc1ccccc1C(=O)NCCN1CCNCC1)c1cccc(Cl)c1] | 2-(3-chlorobenzamido)-N-(2-(piperazin-1-yl)ethyl)benzamide |
| 103 | 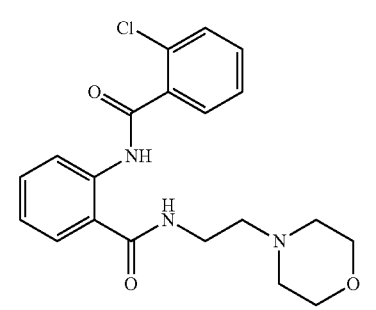 [SMILES: O=C(Nc1ccccc1C(=O)NCCN1CCOCC1)c1ccccc1Cl] | 2-chloro-N-(2-((2-morpholinoethyl)carbamoyl)phenyl)benzamide |
| 104 | 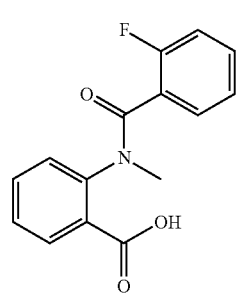 [SMILES: CN(C(=O)c1ccccc1F)c1ccccc1C(=O)O] | 2-(2-fluoro-N-methylbenzamido)benzoic acid |
| 105 | 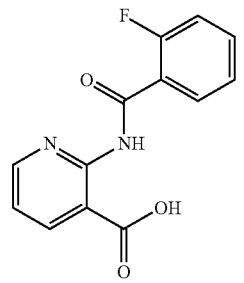 [SMILES: O=C(Nc1ncccc1C(=O)O)c1ccccc1F] | 2-(2-fluorobenzamido)nicotinic acid |

TABLE 1-continued

| Cmpd | Structure | Chemical Name |
|---|---|---|
| 106 | 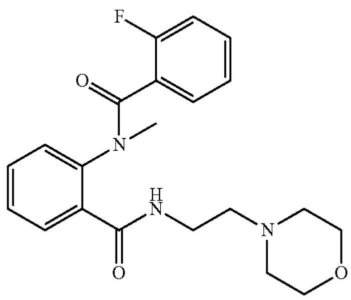 [SMILES: CN(C(=O)c1ccccc1F)c1ccccc1C(=O)NCCN1CCOCC1] | 2-fluoro-N-methyl-N-(2-((2-morpholinoethyl)carbamoyl)phenyl)benzamide |
| 107 | 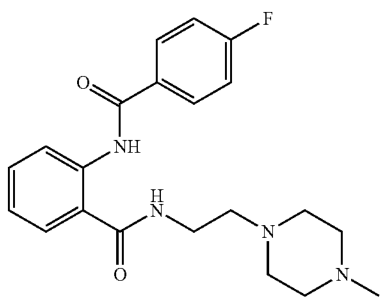 [SMILES: CN1CCN(CCNC(=O)c2ccccc2NC(=O)c2ccc(F)cc2)CC1] | 2-(4-fluorobenzamido)-N-(2-(4-methylpiperazin-1-yl)ethyl)benzamide |
| 108 | 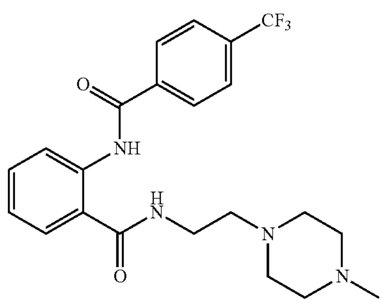 | N-(2-(4-methylpiperazin-1-yl)ethyl)-2-(4-(trifluoromethyl)benzamido)benzamide |
| 109 | 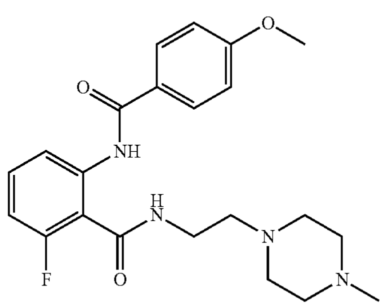 [SMILES: COc1ccc(C(=O)Nc2cccc(F)c2C(=O)NCCN2CCN(C)CC2)cc1] | 2-fluoro-6-(4-methoxybenzamido)-N-(2-(4-methylpiperazin-1-yl)ethyl)benzamide |
| 110 | 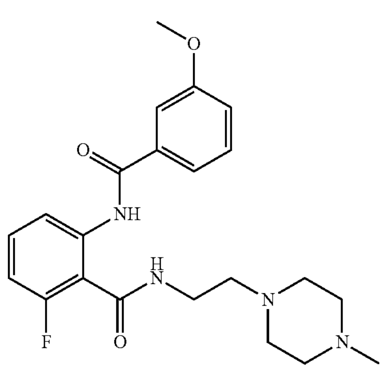 [SMILES: COc1cccc(C(=O)Nc2cccc(F)c2C(=O)NCCN2CCN(C)CC2)c1] | 2-fluoro-6-(3-methoxybenzamido)-N-(2-(4-methylpiperazin-1-yl)ethyl)benzamide |

TABLE 1-continued

| Cmpd | Structure | Chemical Name |
|---|---|---|
| 111 | 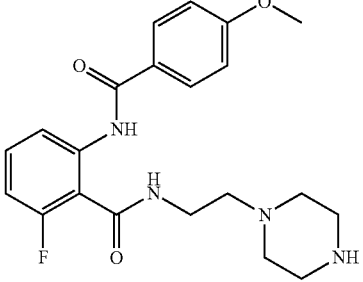 | 2-fluoro-6-(4-methoxybenzamido)-N-(2-(piperazin-1-yl)ethyl)benzamide |
| 112 | 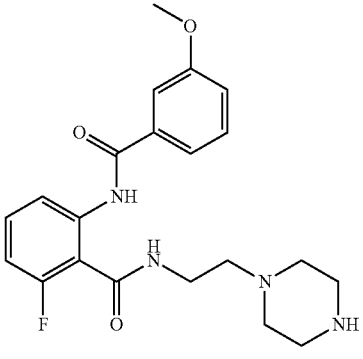 [SMILES: COc1cccc(C(=O)Nc2cccc(F)c2C(=O)NCCN2CCNCC2)c1] | 2-fluoro-6-(3-methoxybenzamido)-N-(2-(piperazin-1-yl)ethyl)benzamide |
| 113 | 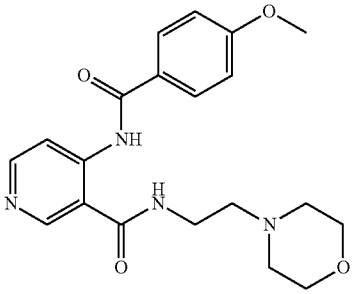 | 4-(4-methoxybenzamido)-N-(2-morpholinoethyl)nicotinamide |
| 114 | 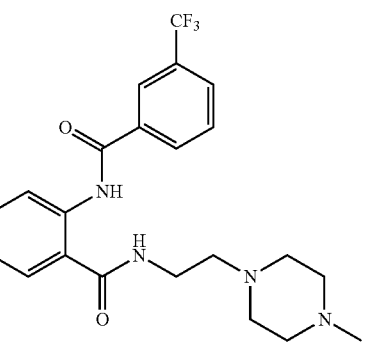 | N-(2-(4-methylpiperazin-1-yl)ethyl)-2-(3-(trifluoromethyl)benzamido)benzamide |
| 115 | 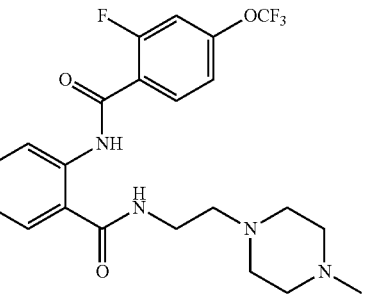 | 2-fluoro-N-(2-((2-(4-methylpiperazin-1-yl)ethyl)carbamoyl)phenyl)-4-(trifluoromethoxy)benzamide |

TABLE 1-continued

| Cmpd | Structure | Chemical Name |
|---|---|---|
| 116 | 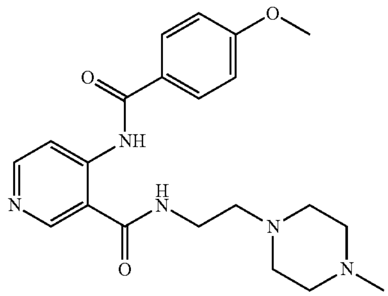 [SMILES: COc1ccc(C(=O)Nc2ccncc2C(=O)NCCN2CCN(C)CC2)cc1] | 4-(4-methoxybenzamido)-N-(2-(4-methylpiperazin-1-yl)ethyl)nicotinamide |
| 117 | 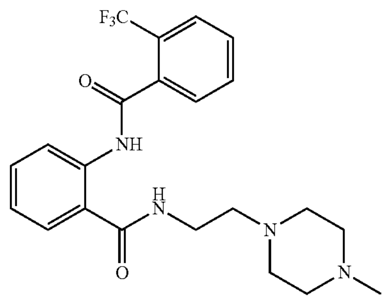 [SMILES: CN1CCN(CCNC(=O)c2ccccc2NC(=O)c2ccccc2C(F)(F)F)CC1] | N-(2-(4-methylpiperazin-1-yl)ethyl)-2-(2-(trifluoromethyl)benzamido)benzamide |
| 118 | 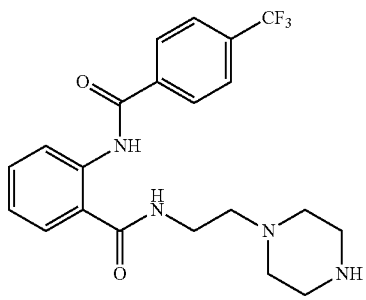 [SMILES: O=C(Nc1ccccc1C(=O)NCCN1CCNCC1)c1ccc(C(F)(F)F)cc1] | N-(2-(piperazin-1-yl)ethyl)-2-(4-(trifluoromethyl)benzamido)benzamide |
| 119 | 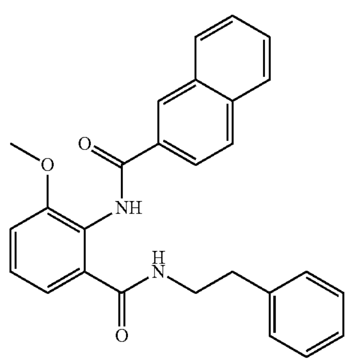 [SMILES: COc1cccc(C(=O)NCCc2ccccc2)c1NC(=O)c1ccc2ccccc2c1] | N-(2-methoxy-6-(phenethylcarbamoyl)phenyl)-2-naphthamide |
| 120 | 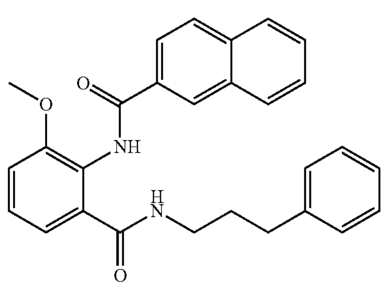 [SMILES: COc1cccc(C(=O)NCCCc2ccccc2)c1NC(=O)c1ccc2ccccc2c1] | N-(2-methoxy-6-((3-phenylpropyl)carbamoyl)phenyl)-2-naphthamide |

TABLE 1-continued

| Cmpd | Structure | Chemical Name |
|---|---|---|
| 121 | 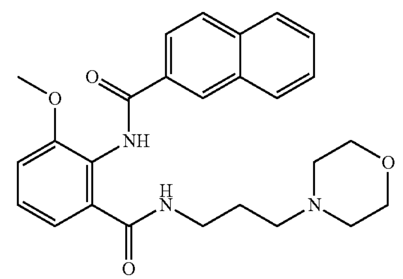 [SMILES: COc1cccc(C(=O)NCCCN2CCOCC2)c1NC(=O)c1ccc2ccccc2c1] | N-(2-methoxy-6-(3-morpholinopropylcarbamoyl)phenyl)-2-naphthamide |
| 122 | 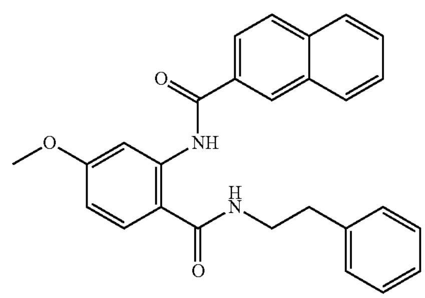 [SMILES: COc1ccc(C(=O)NCCc2ccccc2)c(NC(=O)c2ccc3ccccc3c2)c1] | N-(5-methoxy-2-(phenethylcarbamoyl)phenyl)-2-naphthamide |
| 123 | 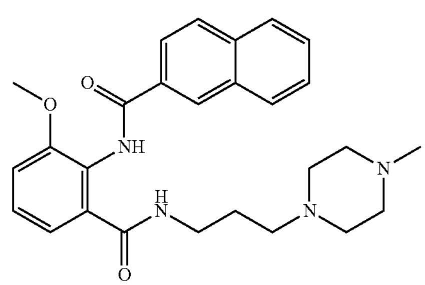 [SMILES: COc1cccc(C(=O)NCCCN2CCN(C)CC2)c1NC(=O)c1ccc2ccccc2c1] | N-(2-methoxy-6-((3-(4-methylpiperazin-1-yl)propyl)carbamoyl)phenyl)-2-naphthamide |
| 124 | 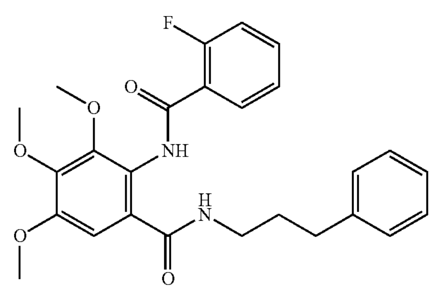 [SMILES: COc1cc(C(=O)NCCCc2ccccc2)c(NC(=O)c2ccccc2F)c(OC)c1OC] | 2-(2-fluorobenzamido)-3,4,5-trimethoxy-N-(3-phenylpropyl)benzamide |
| 125 | 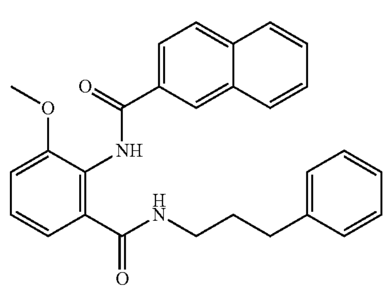 [SMILES: COc1cccc(C(=O)NCCCc2ccccc2)c1NC(=O)c1ccc2ccccc2c1] | N-(2-methoxy-6-((3-phenylpropyl)carbamoyl)phenyl)-1-naphthamide |

TABLE 1-continued

| Cmpd | Structure | Chemical Name |
|---|---|---|
| 126 | 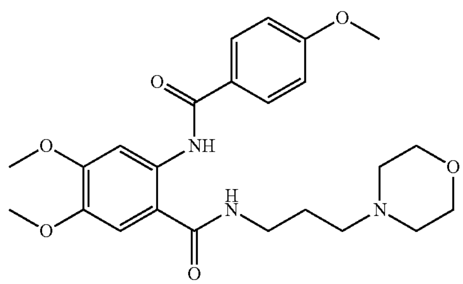 [SMILES: COc1ccc(C(=O)Nc2cc(OC)c(OC)cc2C(=O)NCCCN2CCOCC2)cc1] | 4,5-dimethoxy-2-(4-methoxybenzamido)-N-(3-morpholinopropyl)benzamide |
| 127 | 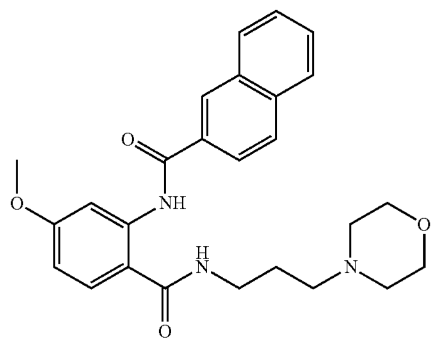 [SMILES: COc1ccc(C(=O)NCCCN2CCOCC2)c(NC(=O)c2ccc3ccccc3c2)c1] | N-(5-methoxy-2-(3-morpholinepropylcarbamoyl)phenyl)-2-naphthamide |
| 128 | 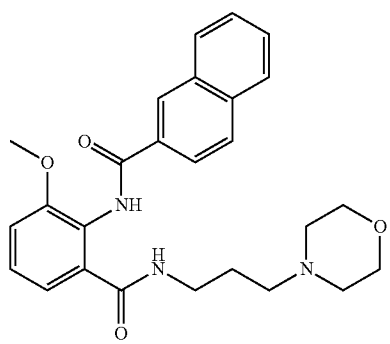 [SMILES: COc1cccc(C(=O)NCCCN2CCOCC2)c1NC(=O)c1ccc2ccccc2c1] | N-(2-methoxy-6-(3-morpholinopropylcarbamoyl)phenyl)-1-naphtamide |
| 129 | 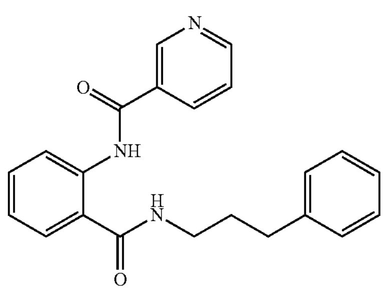 [SMILES: O=C(Nc1ccccc1C(=O)NCCCc1ccccc1)c1cccnc1] | N-(2-((3-phenylpropyl)carbamoyl)phenyl)nicotinamide |
| 130 | 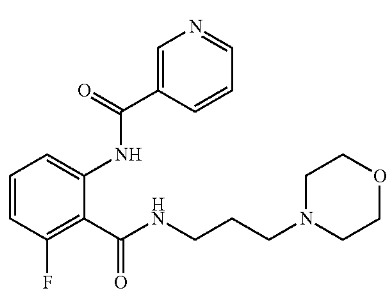 [SMILES: O=C(Nc1cccc(F)c1C(=O)NCCCN1CCOCC1)c1cccnc1] | N-(3-fluoro-2-((3-morpholinopropyl)carbamoyl)phenyl)nicotinamide |

TABLE 1-continued

| Cmpd | Structure | Chemical Name |
| --- | --- | --- |
| 131 | 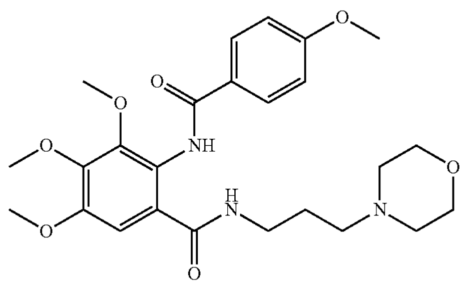 [SMILES: COc1ccc(C(=O)Nc2c(C(=O)NCCCN3CCOCC3)cc(OC)c(OC)c2OC)cc1] | 3,4,5-trimethoxy-2-(4-methoxybenzamido)-N-(3-morpholinopropyl)benzamide |
| 132 | 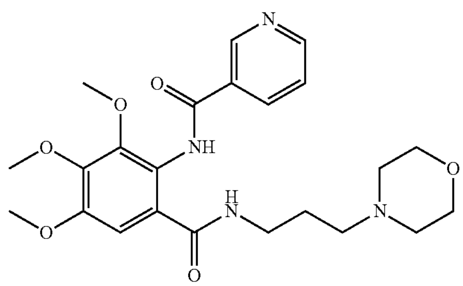 [SMILES: COc1cc(C(=O)NCCCN2CCOCC2)c(NC(=O)c2cccnc2)c(OC)c1OC] | N-(2,3,4-trimethoxy-6-((3-morpholinopropyl)carbamoyl)phenyl) nicotinamide |
| 133 | 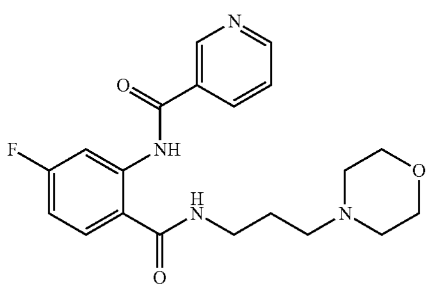 [SMILES: O=C(Nc1cc(F)ccc1C(=O)NCCCN1CCOCC1)c1cccnc1] | N-(5-fluoro-2-(3-morpholinopropylcarbamoyl)phenyl)nicotinamide |
| 134 | 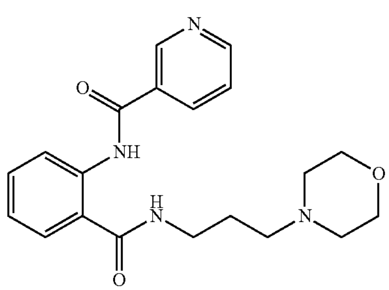 [SMILES: O=C(Nc1ccccc1C(=O)NCCCN1CCOCC1)c1cccnc1] | N-(2-(3-morpholinopropylcarbamoyl)phenyl)nicotinamide |
| 135 | 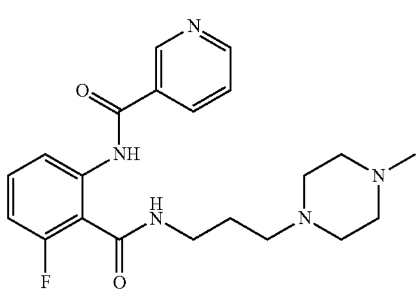 [SMILES: CN1CCN(CCCNC(=O)c2c(F)cccc2NC(=O)c2cccnc2)CC1] | N-(3-fluoro-2-((3-(4-methylpiperazin-1-yl)propyl)carbamoyl)phenyl)nicotinamide |

TABLE 1-continued

| Cmpd | Structure | Chemical Name |
|---|---|---|
| 136 | 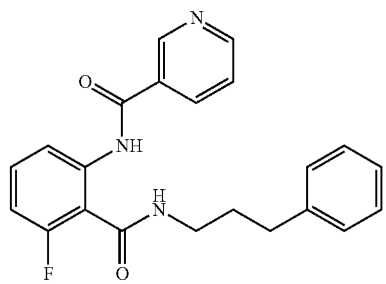 [SMILES: O=C(Nc1cccc(F)c1C(=O)NCCCc1ccccc1)c1cccnc1] | N-(3-fluoro-2-((3-phenylpropyl)carbamoyl)phenyl) nicotinamide |
| 137 | 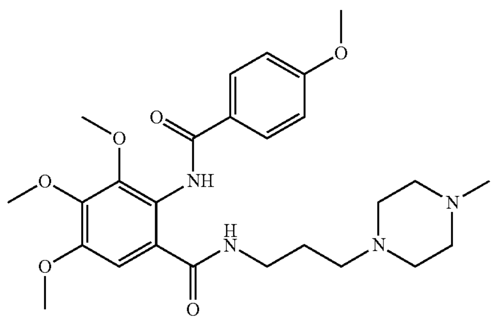 | 3,4,5-trimethoxy-2-(4-methoxybenzamido)-N-(3-(4-methylpiperazin-1-yl)propyl)benzamide |
| 138 | 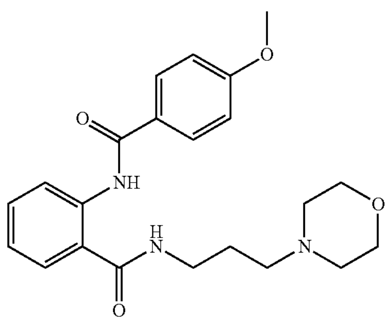 [SMILES: COc1ccc(C(=O)Nc2ccccc2C(=O)NCCCN2CCOCC2)cc1] | 2-(4-methoxybenzamido)-N-(3-morpholinopropyl)benzamide |
| 139 | 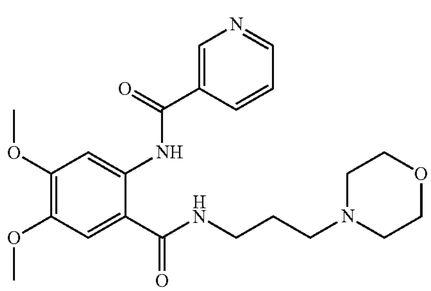 [SMILES: COc1cc(NC(=O)c2cccnc2)c(C(=O)NCCCN2CCOCC2)cc1OC] | N-(4,5-dimethoxy-2-(3-morpholinopropylcarbamoyl) phenyl) nicotinamide |
| 140 | 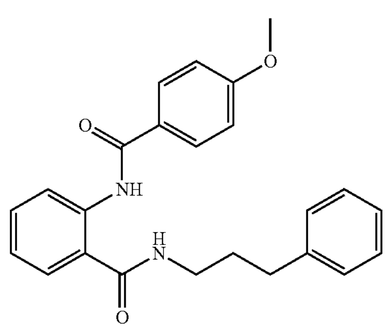 [SMILES: COc1ccc(C(=O)Nc2ccccc2C(=O)NCCCc2ccccc2)cc1] | 2-(4-methoxybenzamido)-N-(3-phenylpropyl)benzamide |

TABLE 1-continued
| Cmpd | Structure | Chemical Name |
|---|---|---|
| 141 | 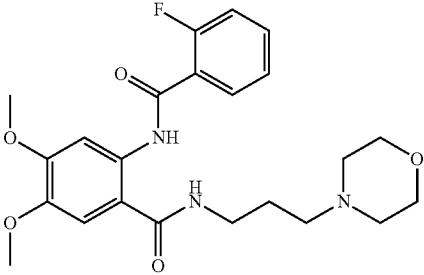 [SMILES: COc1cc(NC(=O)c2ccccc2F)c(C(=O)NCCCN2CCOCC2)cc1OC] | 2-(2-fluorobenzamido)-4,5-dimethoxy-N-(3-morpholinopropyl)benzamide |
| 142 | 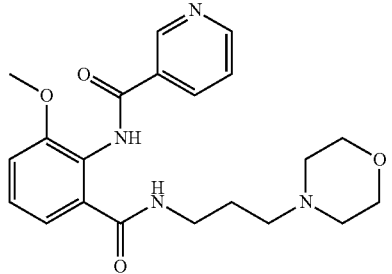 [SMILES: COc1cccc(C(=O)NCCCN2CCOCC2)c1NC(=O)c1cccnc1] | N-(2-methoxy-6-((3-morpholinopropyl)carbamoyl)phenyl) nicotinamide |
| 143 | 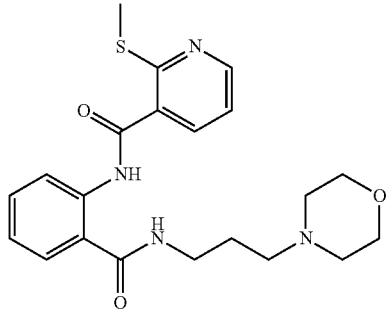 [SMILES: CSc1ncccc1C(=O)Nc1ccccc1C(=O)NCCCN1CCOCC1] | 2-(methylthio)-N-(2-((3-morpholinopropyl)carbamoyl)phenyl) nicotinamide |
| 144 | 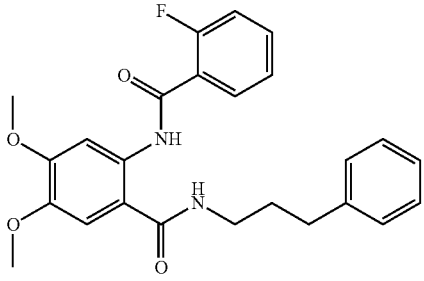 [SMILES: COc1cc(NC(=O)c2ccccc2F)c(C(=O)NCCCc2ccccc2)cc1OC] | 2-(2-fluorobenzamido)-4,5-dimethoxy-N-(3-phenylpropyl)benzamide |
| 145 | 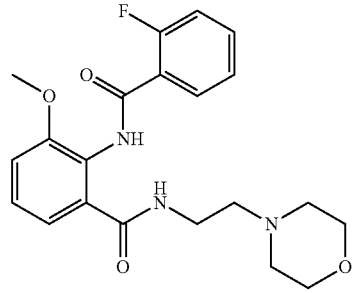 [SMILES: COc1cccc(C(=O)NCCN2CCOCC2)c1NC(=O)c1ccccc1F] | 2-(2-fluorobenzamido)-3-methoxy-N-(2-morpholinoethyl)benzamide |

TABLE 1-continued

| Cmpd | Structure | Chemical Name |
|---|---|---|
| 146 | 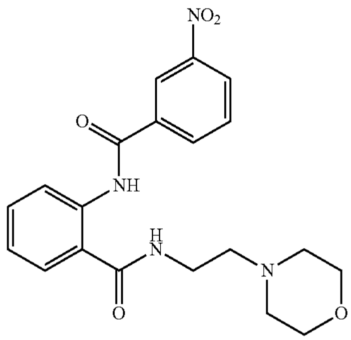 | N-(2-morpholinoethyl)-2-(3-nitrobenzamido)benzamide |
| 147 | 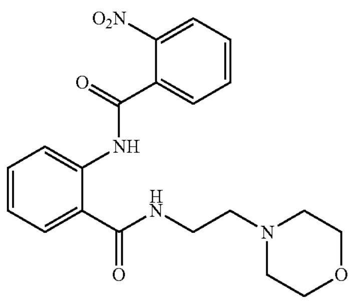 | N-(2-morpholinoethyl)-2-(2-nitrobenzamido)benzamide |
| 148 | 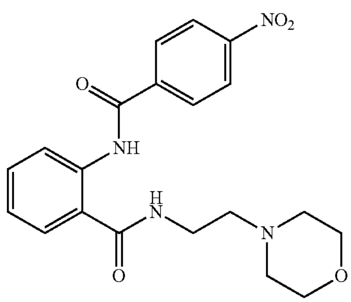 | N-(2-morpholinoethyl)-2-(4-nitrobenzamido)benzamide |

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

"Heteroalkyl" groups are alkyl groups, as defined above, that have an oxygen, nitrogen, sulfur or phosphorous atom replacing one or more hydrocarbon backbone carbon atoms.

As used herein, the term "cycloalkyl", "$C_3$, $C_4$, $C_5$, $C_6$, $C_7$ or $C_8$ cycloalkyl" or "$C_3$-$C_8$ cycloalkyl" is intended to include hydrocarbon rings having from three to eight carbon atoms in their ring structure. In one embodiment, a cycloalkyl group has five or six carbons in the ring structure.

The term "substituted alkyl" refers to alkyl moieties having substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)).

Unless the number of carbons is otherwise specified, "lower alkyl" includes an alkyl group, as defined above, having from one to six, or in another embodiment from one to four, carbon atoms in its backbone structure. "Lower alkenyl" and "lower alkynyl" have chain lengths of, for example, two to six or of two to four carbon atoms.

As used herein, "alkyl linker" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl linker is intended to include $C_1$, $C_2$, $C_3$, $C_4$, $C_5$ and $C_6$ alkyl linker groups. Examples of alkyl linker include, moieties having from one to six carbon atoms, such as, but not limited to, methyl (—$CH_2$—), ethyl (—$CH_2CH_2$—), n-propyl (—$CH_2CH_2CH_2$—), i-propyl (—$CHCH_3CH_2$—), n-butyl (—$CH_2CH_2CH_2CH_2$—), s-butyl (—$CHCH_3CH_2CH_2$—), i-butyl (—$C(CH_3)_2CH_2$—), n-pentyl (—$CH_2CH_2CH_2CH_2CH_2$—), s-pentyl (—$CHCH_3CH_2CH_2CH_2$—) or n-hexyl (—$CH_2CH_2CH_2CH_2CH_2CH_2$—).

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), branched alkenyl groups, cycloalkenyl (e.g., alicyclic) groups (e.g., cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. In certain embodiments, a straight chain or branched alkenyl group has six or fewer carbon atoms in its backbone (e.g., $C_2$-$C_6$ for straight chain, $C_3$-$C_6$ for branched chain). Likewise, cycloalkenyl groups may have from five to eight carbon atoms in their ring structure, and in one embodiment, cycloalkenyl groups have five or six carbons in the ring structure. The term "$C_2$-$C_6$" includes alkenyl groups containing two to six carbon atoms. The term "$C_3$-$C_6$" includes alkenyl groups containing three to six carbon atoms.

"Heteroalkenyl" includes alkenyl groups, as defined herein, having an oxygen, nitrogen, sulfur or phosphorous atom replacing one or more hydrocarbon backbone carbons.

The term "substituted alkenyl" refers to alkenyl moieties having substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), branched alkynyl groups, and cycloalkyl or cycloalkenyl substituted alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

"Heteroalkynyl" includes alkynyl groups, as defined herein, having an oxygen, nitrogen, sulfur or phosphorous atom replacing one or more hydrocarbon backbone carbons.

The term "substituted alkynyl" refers to alkynyl moieties having substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aryl" includes groups with aromaticity, including "conjugated", or multicyclic, systems with at least one aromatic ring. Examples include phenyl, benzyl, etc.

"Heteroaryl" groups are aryl groups, as defined above, having from one to four heteroatoms in the ring structure, and may also be referred to as "aryl heterocycles" or "heteroaromatics". As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthridine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The aryl or heteroaryl aromatic ring can be substituted at one or more ring positions with such substituents as described above, for example, alkyl, alkenyl, akynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

As used herein, "carbocycle" or "carbocyclic ring" is intended to include any stable monocyclic, bicyclic or tricyclic ring having the specified number of carbons, any of which may be saturated, unsaturated, or aromatic. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, [4.4.0]bicyclodecane and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" includes any ring structure (saturated or partially unsaturated) which contains at least one ring heteroatom (e.g., N, O or S). Examples of heterocycles include, but are not limited to, morpholine, pyrrolidine, tetrahydrothiophene, piperidine, piperazine and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted", as used herein, means that any one or more hydrogen atoms on the designated atom is replaced with a selection from the indicated groups, provided that the designated atom's normal valency is not exceeded, and that the substitution results in a stable compound. When a substituent is keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

The term "hydroxy" or "hydroxyl" includes groups with an —OH or —O⁻.

As used herein, "halo" or "halogen" refers to fluoro, chloro, bromo and iodo. The term "perhalogenated" generally refers to a moiety wherein all hydrogen atoms are replaced by halogen atoms.

The term "carbonyl" or "carboxy" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

"Acyl" includes moieties that contain the acyl radical (—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aroyl" includes moieties with an aryl or heteroaromatic moiety bound to a carbonyl group. Examples of aroyl groups include phenylcarboxy, naphthyl carboxy, etc.

"Alkoxyalkyl", "alkylaminoalkyl" and "thioalkoxyalkyl" include alkyl groups, as described above, wherein oxygen, nitrogen or sulfur atoms replace one or more hydrocarbon backbone carbon atoms.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "ether" or "alkoxy" includes compounds or moieties which contain an oxygen bonded to two carbon atoms or heteroatoms. For example, the term includes "alkoxyalkyl", which refers to an alkyl, alkenyl, or alkynyl group covalently bonded to an oxygen atom which is covalently bonded to an alkyl group.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "haloalkyl" includes compounds or moieties which contain alkyl group substituted with one or more halogen atoms. As used herein, "haloalkyl", "$C_1$, $C_2$, $C_3$, $C_4$, $C_5$ or $C_6$ haloalkyl" or "$C_1$-$C_6$ haloalkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups substituted with one or more halogen atoms. Examples of haloalkyl groups include, but are not limited to, —$CF_3$, —$CF_2CF_3$, and —$CF_2CF_2CF_3$.

As used herein, "amine" or "amino" includes moieties where a nitrogen atom is covalently bonded to at least one carbon or heteroatom. "Alkylamino" includes groups of compounds wherein nitrogen is bound to at least one alkyl group. Examples of alkylamino groups include benzylamino, methylamino, ethylamino, phenethylamino, etc. "Dialkylamino" includes groups wherein the nitrogen atom is bound to at least two additional alkyl groups. Examples of dialkylamino groups include, but are not limited to, dimethylamino and diethylamine. "Arylamino" and "diarylamino" include groups wherein the nitrogen is bound to at least one or two aryl groups, respectively. "Alkylarylamino", "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

Compounds of the present application that contain nitrogens can be converted to N-oxides by treatment with an oxidizing agent (e.g., 3-chloroperoxybenzoic acid (m-CPBA) and/or hydrogen peroxides) to afford other compounds of the present application. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present application can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

In the present specification, the structural formula of the compound represents a certain isomer for convenience in some cases, but the present application includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present application. Furthermore, so-called metabolite which is produced by degradation of the present compound in vivo is included in the scope of the present application.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four nonidentical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this application include all atropic isomers thereof "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine.

It is to be understood that the compounds of the present application may be depicted as different tautomers. It should also be understood that when compounds have tautomeric forms, all tautomeric forms are intended to be included in the scope of the present application, and the naming of the compounds does not exclude any tautomer form.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Additionally, the compounds of the present application, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds represented by formula I are imidazopyridinyl-aminopyridine derivatives, and have formula I as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physico-chemically or topologically based. Examples of carboxylic acid bioisosteres include, but are not limited to, acyl sulfonimides, tetrazoles, sulfonates and phosphonates. See, e.g., Patani and LaVoie, *Chem. Rev.* 96, 3147-3176, 1996.

The present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

As discussed above, these compounds are capable of suppressing Bcl-3-NF-κB protein interactions, inhibiting NF-κB signalling and attenuating the cellular characteristics contributing to the metastatic phenotype observed in vivo and therefore the compounds are suitable for the treatment of cancer, especially for the treatment or prevention of metastatic cancer or secondary tumours.

Throughout the description and claims of this specification, the words "comprise" and "contain" and variations of the words, for example "comprising" and "comprises", mean "including but not limited to" and do not exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the application may be as described in connection with any of the other aspects.

In the present specification, references to compounds of Formula (I) or Formula (Ia) includes amorphous and crystalline forms, including all polymorphs, as well as isotopic variants, for example compounds of Formula (I) or Formula (Ia) in which one or more hydrogen atoms is replaced by deuterium, one or more carbon atoms is replaced by $^{14}C$ or one or more nitrogen atoms is replaced by $^{15}N$.

2. Synthesis of Compounds of Formula (I) and Formula (Ia)

Compounds of Formula (I) and Formula (Ia) may be prepared by any suitable route. Compounds of Formula (Ia) include the compounds of Formula (Ib), Formula (Ic), Formula (Id), Formula (Ie), and Formula (If). The synthetic processes apply to all compounds of the application. The synthetic processes of the application can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, ester or prodrug thereof.

Compounds of the present application can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, 5$^{th}$ edition, John Wiley & Sons: New York, 2001; and Greene, T. W., Wuts, P. G. M., *Protective Groups in Organic Synthesis*, 3$^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present application.

Compounds of the present application can be conveniently prepared by a variety of methods familiar to those skilled in the art. The compounds each of the formulae described herein may be prepared according to the following procedures from commercially available starting materials or starting materials which can be prepared using literature procedures. These procedures show the preparation of representative compounds of this application.

All the abbreviations used in this application are found in "Protective Groups in Organic Synthesis" by John Wiley & Sons, Inc, or the MERCK INDEX by MERCK & Co., Inc, or other chemistry books or chemicals catalogs by chemicals vendor such as Aldrich, or according to usage know in the art.

For example, compounds of Formula (I) and Formula (Ia) may be prepared from a compound of general formula (II) and general formula (II'). respectively:

(II)

(II')

wherein A, B, W, Y, Z, $R^2$, $R^4$, $R^5$, and $R^6$ are as defined for Formula (I);
wherein A, Z, $X^1$, $X^2$, $X^3$, $R^2$, $R^4$, $R^5$, and $R^6$ are as defined for Formula (Ia);
by reaction with a compound of general formula (III):

(III)

wherein R is H or an amine protecting group and q and $R^q$ are as defined for Formula (I) and Formula (Ia).

The reaction is carried out in the presence of a base, typically a non-nucleophilic base, for example a tertiary amine such as N,N-diisopropylethylamine. The reaction may be conducted in an organic solvent such as N,N-dimethylformamide and at a temperature of about 15° C. to about 30° C., more typically at about 18 to about 25° C. (room temperature).

Amines of general formula (III) are well known and are readily available or may be prepared by literature methods well known to those of skill in the art.

Compounds of general formula (II) and general formula (II') may be prepared from compounds of general formula (IIa) or general formula (IIa'), respectively:

(IIa)

(IIa')

wherein B, W, Y, and Z are as defined for Formula (I);
by reaction with compounds of general formula (IIb):

(IIb)

wherein A, $R^2$, $R^4$, $R^5$, and $R^6$ are as defined for Formula (I) and Formula (Ia) and X is a leaving group, typically a halo group such as chloro.

The reaction may be carried out in an organic solvent such as pyridine and at a temperature of about 15 to about 30° C., more typically at about 18 to about 25° C. (room temperature).

Compounds of general formulae (IIa), (IIa'), and (IIb) are well known and are readily available or may be prepared by literature methods well known to those of skill in the art.

An example of a general procedure for the synthesis of a compound of general formula (II) is described below in Scheme A.

Scheme A: Representative Synthesis of a compound of formula (II) from compounds of formulas (IIa) and (IIb)

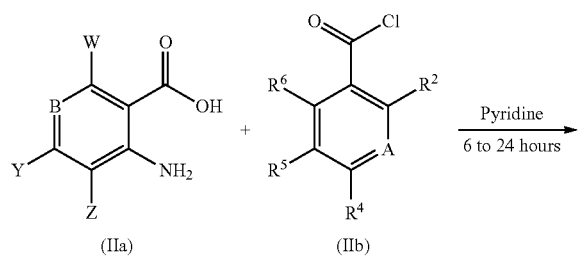

An example of a general procedure for the synthesis of a compound of Formula (I) is described below in Scheme B.

Scheme B: Representative Synthesis of a compound of Formula (I)

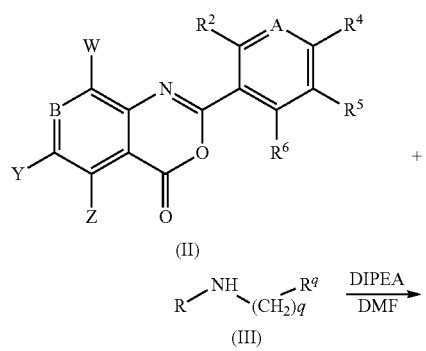

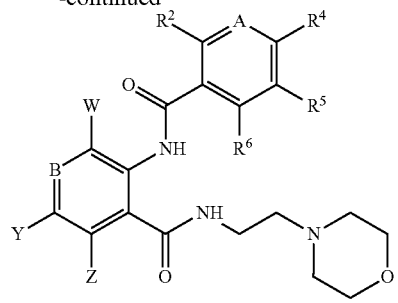

3. Biological Assays

Cell Titre Blue Viability Cell Based Assay

The viability of cells at experimental endpoints for particular assays is determined using the Cell Titre Blue reagent (Promega, Southampton, UK). This reagent measures the cellular metabolic activity using resazurin as an indicator dye. Viable cells, therefore metabolically active, will reduce resazurin into highly fluorescent resofurin. The resulting fluorescence levels are measured and indicate cell viability.

Cells are plated at low confluency into 96 well plates in 100 µl of complete growth media in triplicates and are incubated at 37° C. in 5% $CO_2$ for the desired test exposure period. For each 100 µl of media in 96 well plates, 20 µl Cell Titre Blue reagent is added followed by incubation for an hour at 37° C. in 5% $CO_2$. Fluorescence is then measured by setting excitation/emission wavelengths to 560/590 nm on a Fluorostar Optima plate reader (BMG tabtech, Bucks, UK).

Cell Count

To establish cell viability over time period of three days, respective cells are seeded at low confluency into 96 well plates in 100 µl of complete growth media in triplicates and are incubated at 37° C. in 5% $CO_2$. After 24 hrs, cells from triplicate wells are detached for the first time point using 0.25% Trypsin/EDTA (Invitrogen) and resuspended in complete growth media and individually counted. The same is done for each cell line at 48 hrs and 72 hrs post-seeding.

Determination of the Migration of Cells in Scratch Assay

The migration of cells in the presence of a compound of Formula (I) or Formula (Ia) is determined using a Scratch assay.

For the Scratch Assay, 1 micromolar solutions of the compounds are prepared. In six well plates, the complete growth media of the seeded cells (density $11*10E^{-6}$ in 20 mL) is removed and replaced by 3 mL of a fresh one containing compounds of Formula (I) or Formula (Ia). Media is used as a negative compound.

After a 24 h incubation period at 5% $CO_2$ and 37° C., the media is removed and a scratch is performed in each well. 1 mL of fresh complete growth media is used to wash the well. After its removal, 3 mL of a solution containing a compound of Formula (I) or Formula (Ia) is added in each well in triplicate. Pictures of the wells are then taken. After 24 h, pictures of the wells are again taken. The comparison between the two images provides a measure of the migration of the cells.

Determination of NF-kB Activity in Cells

MDA-MB-231 is a highly metastatic, human basal epithelial cell line isolated from the pleural effusion of an adenocarcinoma. The cells are 'triple negative' as they lack estrogen, progesterone and ERBB2 receptor and they strongly over-express EGFR. The expression of receptors in this line has been confirmed by the host laboratory.

For NF-κB luciferase assays, cells are seeded into clear bottom black 96-well plates (Corning Inc., Lowell, US) in antibiotic free culture media in appropriate density. After about 20-24 hrs, cells are transfected with 10 ng of 3×κB luciferase plasmid and 10 ng of pcDNA3.1-Lacl plasmid per well. Empty pcDNA3.1 plasmid is also included to normalize the total weight of DNA transfected to 100 ng. For positive and negative controls respectively, 10 ng of pGL3control or pGL3basic are transfected in place of 3×KB luciferase plasmid. Transfection is carried out using Lipofectamine LTX reagents (Invitrogen, Paisley, UK).

After 48 hrs post-transfection with luciferase reporter plasmid, the media is aspirated and cells are lyzed using 50 µl/well of Glo-lysis buffer (Promega, Southampton, UK). The plate is left on a rocker for 20 min to facilitate complete cell lysis. Then, 20 µl of lysate from each well is removed and transferred into a new clear bottom black well plate for measuring LacZ activity as a transfection efficiency control and is followed by addition of 20 µl/well of Beta-Glo substrate (Promega, Southampton, UK) and cultivation at room temperature for at least 20 min. Subsequently, 30 µl/well of Bright-Glo luciferase substrate (Promega, Southampton, UK) is added to the original plate and is assayed immediately for luminescence activity. The luminescence produced from either reaction is read using a Fluorostar Optima plate reader (BMG tabtech, Bucks, UK). The resulting luciferase activity is then normalized against lacZ activity obtained from Beta-glo measurement and is displayed as relative light units (R.t.U).

In Vivo Metastasis Mouse Models

Nude mice are injected i.v. with 200,000 highly metastatic human breast cancer cells expressing luciferase (MDA-MB-231-Luc) then are given a compound of Formula (I) or Formula (Ia) once daily for about 10 days and are monitored for tumours by total body scan using Xenogen-IVIS. Mice with a luciferase signal above background in repeated scans in any part of their torso are scored as having metastatic disease. Total light emission in the abdominal region is quantified at time points up to 49 days post surgery and plotted as mean total light yield.

Tumour efficacy of the compounds of the application was determined using murine xenograft models of breast and colorectal cancers, each model demonstrating different aspects of tumour biology. In all experiments, each compound was administered by intraperitoneally at 3.5 mg/kg.

One model (Model 1) studied the effect of the compound's ability to inhibit the seeding and early colonization of circulating tumour cells at distal sites, most commonly in the lungs and liver. Human tumour cell lines were injected into the bloodstream of recipient mice, followed by single daily intraperitoneal injections of the compound (3.5 mg/kg in 1% DMSO) for 10 consecutive days. Tumour burden was monitored longitudinally for up to 8 weeks in vivo by live luminescence imaging, and subsequently histology performed on affected organs at the end of the experiment.

Another model (Model 2) tested the effect of the compound's ability to inhibit the colonization and subsequent growth and spread of secondary lesions at distal sites. Human tumour cell lines were injected into the bloodstream of recipient mice, followed 2 days later by single daily intraperitoneal injections of the compound (3.5 mg/kg in 1% DMSO) for the entire course of the experiment. Tumour burden was monitored longitudinally for up to 8 weeks in vivo by live luminescence imaging, and subsequently histology performed on affected organs at the end of the experiment.

Another model (Model 4) studied the effect of the compound's ability to inhibit the growth of tumour cells at the transplantation site. Human tumour cell lines were injected subcutaneously into recipient mice, followed 2 days later by single daily intraperitoneal injections of a compound (3.5 mg/kg in 1% DMSO) for the entire course of the experiment. Tumour burden was monitored longitudinally for up to 12 weeks in vivo by palpation and caliper measurements of tumour volume, and subsequently histology performed on tumours at the end of the experiment.

4. Methods of Treatment

As discussed above, the compounds of the present application are Bcl-3 inhibitors and are therefore of use in the treatment of cancer, for example leukaemias and lymphomas, such as anaplastic large cell lymphomas (ALCLs), classic Hodgkin lymphomas (cHL) and non-Hodgkin's lymphoma; and solid tumour cancers, such as breast cancer, melanoma, lung cancer, pancreatic cancer, oesophageal cancer, colorectal cancer, nasopharyngeal carcinoma, ovarian, prostate and hepatocarcinomas.

In another aspect, the present application provides a compound Formula (I) or Formula (Ia) for use in medicine.

Therefore, in a further aspect of the application there is provided a compound of Formula (I) or Formula (Ia) for use in medicine. In particular, there is provided a compound of Formula (I) or Formula (Ia) for use in the treatment of cancer, for example leukaemias and lymphomas, such as anaplastic large cell lymphomas (ALCLs), classic Hodgkin lymphomas (cHL) and non-Hodgkin's lymphoma; and solid tumour cancers, such as breast cancer, melanoma, lung cancer, pancreatic cancer, oesophageal cancer, colorectal cancer, ovarian cancer, prostate cancer, nasopharyngeal carcinoma, and hepatocarcinomas.

In a further aspect of the application, there is provided the use of a compound of Formula (I) or Formula (Ia) in the preparation of an agent for the treatment of cancer, for example leukaemias and lymphomas, such as anaplastic large cell lymphomas (ALCLs), classic Hodgkin lymphomas (cHL) and non-Hodgkin's lymphoma; and solid tumour cancers, such as breast cancer, melanoma, lung cancer, pancreatic cancer, oesophageal cancer, colorectal cancer, ovarian cancer, prostate cancer, nasopharyngeal carcinoma and hepatocarcinomas.

The compounds may be used either in human or in veterinary medicine and the patient may be any mammal but especially a human.

The application also provides a method for the treatment of cancer, for example leukaemias and lymphomas, such as anaplastic large cell lymphomas (ALCLs), classic Hodgkin lymphomas (cHL) and non-Hodgkin's lymphoma; and solid tumour cancers, such as breast cancer, melanoma, lung cancer, pancreatic cancer, oesophageal cancer, colorectal cancer, ovarian cancer, prostate cancer, nasopharyngeal carcinoma, and hepatocarcinomas, the method comprising administering to a patient in need of such treatment an effective amount of a compound of Formula (I) or Formula (Ia).

The compounds are particularly useful for the treatment or prevention of metastasis in cancers.

Suitably, the cancer is breast cancer, more particularly triple negative breast cancer or HER2 enriched breast cancer. The compounds of Formula (I) or Formula (Ia) have been shown to be particularly effective in preventing or treating metastasis in models of these breast cancer subtypes. However this does not preclude its relevance or efficacy in metastatic disease in other tumour types. Moreover, our experimental evidence in human cancer cell lines indicates that there may also be beneficial therapeutic effects of Bcl-3 suppression on tumour cell viability, as both genetic suppression of Bcl-3 and use of compounds of Formula (I) or Formula (Ia) partially but significantly reduce tumour cell numbers in vitro.

In yet another aspect, the present application provides a compound Formula (I) or Formula (Ia) for use in the preparation of an agent for the treatment of cancer.

In a further aspect, the present application provides a compound Formula (I) or Formula (Ia) for use in the preparation of an agent for the treatment of leukaemia or lymphoma.

In another aspect, the present application provides a compound Formula (I) or Formula (Ia) for use in the treatment or prevention of metastasis in cancers.

The compounds of the application will generally be formulated for administration by a desired route.

As used herein, a "subject in need thereof" is a subject having a cell proliferative disorder, or a subject having an increased risk of developing a cell proliferative disorder relative to the population at large. A subject in need thereof can have a precancerous condition. Preferably, a subject in need thereof has cancer. A "subject" includes a mammal. The mammal can be e.g., any mammal, e.g., a human, primate, bird, mouse, rat, fowl, dog, cat, cow, horse, goat, camel, sheep or a pig. Preferably, the mammal is a human.

As used herein, "contacting a cell" refers to a condition in which a compound or other composition of matter is in direct contact with a cell, or is close enough to induce a desired biological effect in a cell.

As used herein, "monotherapy" refers to the administration of a single active or therapeutic compound to a subject in need thereof. Preferably, monotherapy will involve administration of a therapeutically effective amount of an active compound. For example, cancer monotherapy with one of the compound of the present application, or a pharmaceutically acceptable salt, prodrug, metabolite, analog or derivative thereof, to a subject in need of treatment of cancer. Monotherapy may be contrasted with combination therapy, in which a combination of multiple active compounds is administered, preferably with each component of the combination present in a therapeutically effective amount. In one aspect, monotherapy with a compound of the present application, or a pharmaceutically acceptable salt, prodrug, metabolite, polymorph or solvate thereof, is more effective than combination therapy in inducing a desired biological effect.

As used herein, "treating" or "treat" describes the management and care of a patient for the purpose of combating a disease, condition, or disorder and includes the administration of a compound of the present application, or a pharmaceutically acceptable salt, prodrug, metabolite, polymorph or solvate thereof, to alleviate the symptoms or complications of a disease, condition or disorder, or to eliminate the disease, condition or disorder.

A compound of the present application, or a pharmaceutically acceptable salt, prodrug, metabolite, polymorph or solvate thereof, can also be used to prevent a disease, condition or disorder. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the application leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute). Furthermore, severity describes a nuclear grade, which refers to the size and shape of the nucleus in tumor cells and the percentage of tumor cells that are dividing (see, National Cancer Institute).

In another aspect of the application, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein, the term "selectively" means tending to occur at a higher frequency in one population than in another population. The compared populations can be cell populations. Preferably, a compound of the present application, or a pharmaceutically acceptable salt, prodrug, metabolite, polymorph or solvate thereof, acts selectively on a cancer or precancerous cell but not on a normal cell. Preferably, a compound of the present application, or a pharmaceutically acceptable salt, prodrug, metabolite, polymorph or solvate thereof, acts selectively to modulate one molecular target (e.g., Bcl-3) but does not significantly modulate another molecular target.

A compound of the present application, or a pharmaceutically acceptable salt, prodrug, metabolite, polymorph or solvate thereof, can modulate the activity of a molecular target (e.g., a Bcl-3). Modulating refers to stimulating or inhibiting an activity of a molecular target. Preferably, a compound of the present application, or a pharmaceutically acceptable salt, prodrug, metabolite, polymorph or solvate thereof, modulates the activity of a molecular target if it stimulates or inhibits the activity of the molecular target by at least 2-fold relative to the activity of the molecular target under the same conditions but lacking only the presence of said compound. More preferably, a compound of the present application, or a pharmaceutically acceptable salt, prodrug, metabolite, polymorph or solvate thereof, modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

In another aspect, the present application provides a compound Formula (I) or Formula (Ia) for use in combination with one or more additional active agents which are useful in the treatment of cancer. The additional active agent include, but are not limited to, anti-HER2 agents such as trastuzumab and pertuzumab; standard adjuvant therapy regimens such as 5-fluorouracil, doxorubicin, and cyclophosphamide (FAC); 5-fluorouracil, epirubicin, and cyclophosphamide (FEC); and doxorubicin and cyclophosphamide (AC); cyclophosphamide, methotrexate, and 5-fluorouracil (CMF); and docetaxel, doxorubicin, cyclophosphamide (TAC); and anti-angiogenic/antimetastatic agents such as bevacizumab (Avastin).

As used herein, "combination therapy" or "co-therapy" includes the administration of a compound of the present application, or a pharmaceutically acceptable salt, prodrug, metabolite, polymorph or solvate thereof, and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations of the present application.

"Combination therapy" is intended to embrace administration of these therapeutic agents in a sequential manner, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

5. Pharmaceutical Compositions

The present application also provides pharmaceutical compositions comprising a compound of each of the formulae described herein in combination with at least one pharmaceutically acceptable excipient or carrier. The carrier, or, if more than one be present, each of the carriers, must be acceptable in the sense of being compatible with the other ingredients of the formulation and not deleterious to the recipient.

In one aspect, the application relates to a pharmaceutical composition comprising a compound of Formula (I) or Formula (Ia) together with a pharmaceutically or veterinarily acceptable excipient or carrier. In one embodiment, formulated for parenteral administration.

In another aspect, the present application relates to a process for the preparation of a pharmaceutical composition the process comprising bringing into association the compound of Formula (I) or Formula (Ia) into association with a pharmaceutically or veterinarily acceptable excipient or carrier.

A "pharmaceutical composition" is a formulation containing the compounds of the present application in a form suitable for administration to a subject.

The formulations include those suitable for oral, rectal, nasal, topical (including eye drops, buccal and sublingual), vaginal or parenteral (including subcutaneous, intramuscular, intravenous and intradermal) administration and may be prepared by any methods well known in the art of pharmacy.

The route of administration will depend upon the condition to be treated but preferred compositions are formulated for parenteral administration. Parenteral formulations will generally be sterile.

The composition may be prepared by bringing into association the above defined active agent with the carrier. In general, the formulations are prepared by uniformly and intimately bringing into association the active agent with liquid carriers or finely divided solid carriers or both, and then if necessary shaping the product. The application extends to methods for preparing a pharmaceutical composition comprising bringing a compound of Formula (I) or Formula (Ia) into association with a pharmaceutically or veterinarily acceptable excipient or carrier.

In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this application include powders, sprays, ointments, pastes, creams, lotions, gels, solutions, patches and inhalants. In one embodiment, the active compound is mixed under sterile conditions with a pharmaceutically acceptable carrier, and with any preservatives, buffers or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the application is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the application can be administered to a subject in many of the well-known methods currently used for chemotherapeutic treatment. For example, for treatment of cancers, a compound of the application may be injected directly into tumors, injected into the blood stream or body cavities or taken orally or applied through the skin with patches. The dose chosen should be sufficient to constitute effective treatment but not as high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present application may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the application are dictated by and directly dependent on the unique characteristics of the active compound and the particular therapeutic effect to be achieved.

In therapeutic applications, the dosages of the pharmaceutical compositions used in accordance with the application vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. In preferred aspects, dosages can range from about 0.01 mg/kg per day to about 1000 mg/kg per day; so as to maintain the concentration of drug in the plasma at a concentration effective to inhibit Bcl-3. The precise amount of a compound of Formula (I) or Formula (Ia) which is therapeutically effective, and the route by which such compound is best administered, is readily determined by one of ordinary skill in the art by comparing the blood level of the agent to the concentration required to have a therapeutic effect.

An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The compounds of the present application are capable of further forming salts. All of these forms are also contemplated within the scope of the claimed application.

As used herein, "pharmaceutically acceptable salts" refer to derivatives of the compounds of the present application wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. In certain embodiments pharmaceutically acceptable salts include veterinarily acceptable salts.

Salts of the compounds of the present application include salts of organic acids, especially carboxylic acids, including but not limited to acetate, trifluoroacetate, lactate, gluconate, malonate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, pamoate, pectinate, 3-phenylpropionate, picrate, pivalate, proprionate, tartrate, lactobionate, pivolate, camphorate, undecanoate and succinate, organic sulfonic acids such as methanesulfonate, ethanesulfonate, 2-hydroxyethane sulfonate, camphorsulfonate, 2-naphthalenesulfonate, benzenesulfonate, p-chlorobenzenesulfonate and p-toluenesulfonate; and inorganic acids such as hydrochloride, hydrobromide, hydroiodide, sulfate, bisulfate, hemisulfate, thiocyanate, persulfate, phosphoric and sulfonic acids.

Where appropriate, pharmaceutically or veterinarily acceptable salts of the compounds of Formula (I) or Formula (Ia) may also include basic addition salts such as sodium, potassium, calcium, aluminium, zinc, magnesium and other metal salts as well as choline, diethanolamine, ethanolamine, ethyl diamine and other well-known basic addition salts.

Salts will preferably be pharmaceutically or veterinarily acceptable but other salts may still be valuable as intermediates.

It should be understood that all references to pharmaceutically acceptable salts include solvent addition forms (solvates) or crystal forms (polymorphs) as defined herein, of the same salt.

The compounds of the present application can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., an acetate, propionate or other ester.

The compounds of the present application can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compounds of the present application can be delivered in prodrug form. Thus, the present application is intended to cover prodrugs of the presently claimed compounds, methods of delivering the same and compositions containing the same. "Prodrugs" are intended to include any covalently bonded carriers that release an active parent drug of the present application in vivo when such prodrug is administered to a subject. Prodrugs in the present application are prepared by modifying functional groups present in the compound in such a way that the modifications are cleaved, either in routine manipulation or in vivo, to the parent compound. Prodrugs include compounds of the present application wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the application, and the like, See Bundegaard, H., *Design of Prodrugs*, p 1-92, Elesevier, New York-Oxford (1985).

The compounds, or pharmaceutically acceptable salts, esters or prodrugs thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Techniques for formulation and administration of the disclosed compounds of the application can be found in *Remington: the Science and Practice of Pharmacy*, $19^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present application will become apparent from the different examples. The provided examples illustrate different components and methodology useful in practicing the present application. Generally speaking, the application extends to any novel one, or any novel combination, of the features disclosed in this specification (including the accompanying claims and drawings). The examples do not limit the claimed application. Thus, features, integers, characteristics, compounds or chemical moieties described in conjunction with a particular aspect, embodiment or example of the application are to be understood to be applicable to any other aspect, embodiment or example described herein, unless incompatible therewith. Based on the present disclosure the skilled artisan can identify and employ other components and methodology useful for practicing the present application. Moreover, unless stated otherwise, any feature disclosed herein may be replaced by an alternative feature serving the same or a similar purpose.

The Application will now be described by way of example only with reference to the Examples below:

6. Examples

All the chemicals, reagents and solvents were purchased from SIGMA Aldrich or Alpha Aesar without further purification or purified by standard techniques. Acid chlorides can be prepared directly from the corresponding carboxylic acid using known synthetic methods, e.g., reaction of the corresponding carboxylic acid in thionyl chloride and catalytic N,N-dimethyl formamide for 8-24 hours at refluxing temperatures. Silica gel plates (Merck Kieselgel 60F$_{254}$) were used and were developed by the ascending method. After solvent evaporation, compounds were visualized by irradiation with UV light at 254 nm and 366 nm. Purification was performed by silica gel chromatography using silica gel 40-60 µm from Merck and the appropriate eluent mixture. Melting points were determined using Griffin Melting Point Apparatus. $^1$H-NMR, $^{13}$C-NMR, $^{19}$F-NMR spectra were recorded using a Bruker AVANCE (500 MHz and 75 MHz) spectrometer auto-calibrated to the deuterated solvent reference peak (used the applied solvent simultaneously as internal standard).
Chemical shifts (δ) are given in ppm (parts per million) relative to tetramethylsilane (used as internal standard, δ=0 ppm) together with the relative assignment, the coupling constant (J$_{(H-H)}$/Hz) and the multiplicity: singlet (s), doublet (d), triplet (t), quartet (q), multiplet (m), broad multiplet (bm). MestReNova version: 6.0.2-5475 software program was used for the assignment of peaks and for the calculation of the coupling constant. Mass spectrometry was carried out in Electrospray mode on a Bruker MicroTOF instrument.

General Procedure 1

The compounds of general formula (II) can be prepared according to the synthetic scheme shown in Scheme 1.

Scheme 1

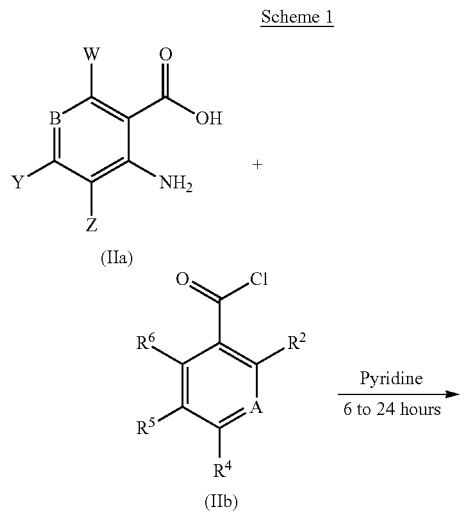

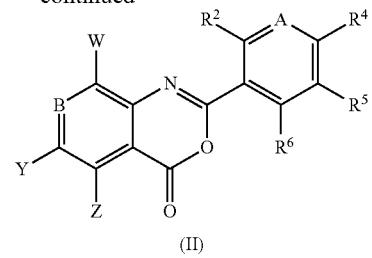

To a suspension containing 1 equivalent of anthranilic acid (IIa) in the minimum amount of pyridine is added 2.2 equivalents of the appropriate benzoyl-chloride (IIb). The reaction mixture is stirred at room temperature over a period between about 2 hours and 12 hours. The reaction is monitored by TLC and is stopped after the complete disappearance of the anthranilic acid (IIa). The reaction is poured into a 10% aqueous solution of sodium carbonate. The formed precipitate is collected by filtration under reduced pressure as a powder and washed three times with n-hexane in order to obtain the title compound (II).

Compounds 160-206 were prepared of general procedure 1 substituting (IIa) with the appropriate substituted anthranilic acid and substituting (IIb) with the appropriate benzoyl chloride.

Example 1

Synthesis of 2-(2-chlorophenyl)-4H-benzo[d][1,3]oxazin-4-one (160)

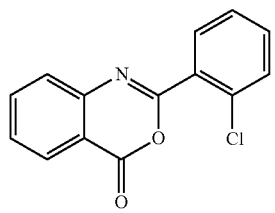

Compound 160 was obtained as a white powder in 89% yield. $^1$H-NMR (CDCl3): δ 7.57 (td, J=7.6, 1.3 Hz, 1H), 7.62-7.74 (m, 3H), 7.76 (d, J=7.8 Hz, 1H), 7.95 (dd, J=7.7, 1.5 Hz, 1H), 7.98-8.04 (m, 1H), 8.22 (dd, J=1.2, 7.9 Hz, 1H) ppm. $^{13}$C-NMR (CDCl$_3$): δ 116.82 (C,C-aromatic), 127.11 (CH,C-aromatic), 127.49 (CH,C-aromatic), 128.05 (CH,C-aromatic), 129.38 (CH,C-aromatic), 130.20 (C,C-aromatic), 130.64 (CH,C-aromatic), 131.67 (C,C-aromatic), 131.76 (CH,C-aromatic), 132.85 (CH,C-aromatic), 137.05 (CH,C-aromatic), 145.80 (C,C-aromatic), 155.78 (C,C-aromatic), 158.72 (C,C-aromatic) ppm.

Example 2

Synthesis of 2-(3-chlorophenyl)-4H-benzo[d][1,3]oxazin-4-one (161)

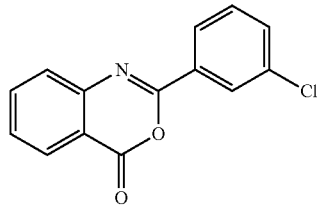
(161)

Compound 161 was obtained as a white powder in 39% yield. $^1$H-NMR (CDCl$_3$): δ 7.63-7.67 (m, 2H), 7.74-7.79 (m, 2H), 7.96-8.01 (m, 1H), 8.14-8.17 (m, 3H) ppm. $^{13}$C-NMR (CDCl$_3$): δ 117.10 (C, C-aromatic), 126.42 (CH, C-aromatic), 127.05 (CH, C-aromatic), 127.20 (CH, C-aromatic), 128.11 (CH, C-aromatic), 128.96 (CH, C-aromatic), 131.06 (CH, C-aromatic), 132.23 (C, C-aromatic), 132.42 (CH, C-aromatic), 136.94 (CH, C-aromatic), 145.97 (C, C-aromatic), 155.33 (C, C-aromatic), 158.68 (C, C-aromatic), 159.1 (C, C-aromatic) ppm.

Example 3

Synthesis of 2-(4-chlorophenyl)-4H-benzo[d][1,3]oxazin-4-one (162)

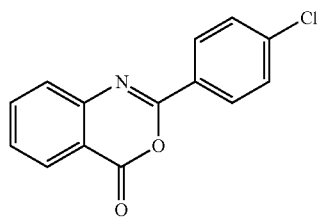
(162)

Compound 162 was obtained as a white powder in 45% yield. $^1$H-NMR (CDCl3): δ 7.54 (m, 3H), 7.71 (d, J=5 Hz, 1H), 7.86 (m, 1H), 8.28 (m, 3H) ppm. $^{13}$C-NMR (CDCl3): δ 116.8 (C, C-aromatic), 124.1 (CH, C-aromatic), 126.5 (CH, C-aromatic), 127.9 (C, C-aromatic), 128.9 (CH, C-aromatic), 128.2 (CH, C-aromatic), 129.1 (CH, C-aromatic), 135.2 (CH, C-aromatic), 136.6 (C, C-aromatic), 146.1 (C, C-aromatic), 156.2 (C, C-aromatic), 159.4 (C, C-aromatic) ppm.

Example 4

Synthesis of 2-(2-nitrophenyl)-4H-benzo[d][1,3]oxazin-4-one (163)

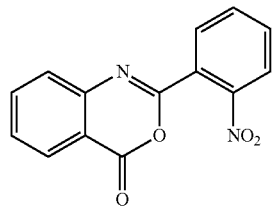
(163)

Compound 163 was obtained as a white powder in 71% yield. $^1$H-NMR (CDCl$_3$): δ 7.65-7.61 (m, 1H). 7.72-7.69 (m, 1H), 7.70-7.78 (m, 2H), 7.84-7.93 (m, 1H), 8.01-8.04 (m, 1H), 8.08 (dd, J=1.0, 8.1 Hz, 1H), 8.29 (dd, J=1.2, 7.9 Hz, 1H) ppm. $^{13}$C-NMR (CDCl$_3$): δ 116.68 (C, C-aromatic), 124.57 (CH, C-aromatic), 124.98 (C, C-aromatic), 127.04 (CH, C-aromatic), 128.22 (CH, C-aromatic), 129.61 (CH, C-aromatic), 131.16 (CH, C-aromatic), 132.97 (CH, C-aromatic), 133.60 (CH, C-aromatic), 137.26 (CH, C-aromatic), 145.58 (C, C-aromatic), 148.15 (C, C-aromatic), 154.50 (C, C-aromatic), 158.20 (C, C-aromatic) ppm.

Example 5

Synthesis of 2-(3-nitrophenyl)-4H-benzo[d][1,3]oxazin-4-one (164)

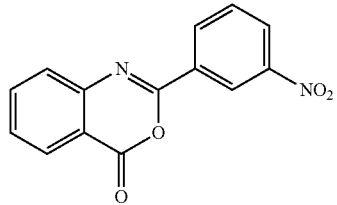
(164)

Compound 164 was obtained as a white powder in 61% yield. $^1$H-NMR (CDCl$_3$): δ 7.62 (s, 1H), 7.77 (m, 2H), 7.96-7.89 (m, 1H), 8.30 (d, J=1.2 Hz, 1H), 8.51-8.44 (m, 1H), 8.70-8.56 (m, 1H), 9.22 (s, 1H) ppm. $^{13}$C-NMR (CDCl$_3$): δ 117.11 (C, C-aromatic), 123.39 (CH, C-aromatic), 126.88 (CH, C-aromatic), 128.87 (CH, C-aromatic), 129.17 (CH, C-aromatic), 129.98 (CH, C-aromatic), 132.19 (CH, C-aromatic), 131.65 (C, C-aromatic), 133.68 (CH, C-aromatic), 136.95 (CH, C-aromatic), 145.99 (C, C-aromatic), 158.36 (C, C-aromatic), 167.99 (C, C-aromatic), 173.58 (C, C-aromatic) ppm.

Example 6

Synthesis of 2-(4-nitrophenyl)-4H-benzo[d][1,3]oxazin-4-one (165)

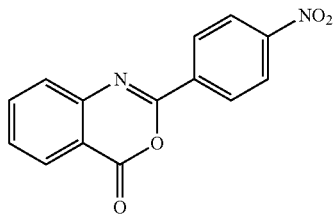

(165)

Compound 165 was obtained as a white powder in 95% yield. $^1$H-NMR (CDCl$_3$): δ 7.69 (t, J=7.6 Hz, 2H), 7.79 (d, J=8.1 Hz, 2H), 8.00 (t, J=7.8 Hz, 2H), 8.19 (t, J=7.8 Hz, 2H) ppm. $^{13}$C-NMR (CDCl$_3$): δ 117.20 (C, C-aromatic), 124.08 (CH, C-aromatic), 127.24 (CH, C-aromatic), 128.13 (CH, C-aromatic), 129.13 (CH, C-aromatic), 129.37 (CH, C-aromatic), 135.81 (C, C-aromatic), 136.98 (CH, C-aromatic), 145.77 (C, C-aromatic), 149.62 (C, C-aromatic), 154.74 (C, C-aromatic), 158.43 (C, C-aromatic) ppm.

Example 7

Synthesis of 2-(4-methoxyphenyl)-4H-benzo[d][1,3]oxazin-4-one (166)

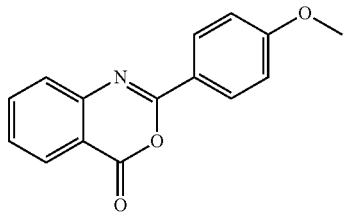

(166)

Compound 166 was obtained as a white powder in 95.31% yield. $^1$H-NMR (CDCl$_3$): δ 3.92 (s, 7H), 7.01-7.05 (m, 4H), 7.47-7.53 (m, 2H), 7.67 (d, J=8.0 Hz, 2H), 7.80-7.85 (m, 2H), 8.25 (dd, J=1.3, 7.9 Hz, 2H), 8.27-8.31 (m, 4H) ppm. $^{13}$C-NMR (CDCl$_3$): δ 55.57 (CH$_3$, C-aliphatic), 114.16 (CH, C-aromatic), 116.73 (C, C-aromatic), 122.56 (C, C-aromatic), 126.93 (CH, C-aromatic), 127.72 (CH, C-aromatic), 128.57 (CH, C-aromatic), 130.30 (CH, C-aromatic), 132.85 (CH, C-aromatic), 136.52 (CH, C-aromatic), 147.37 (C, C-aromatic), 157.14 (C, C-aromatic), 159.82 (C, C-aromatic), 163.29 (C, C-aromatic) ppm.

Example 8

Synthesis of 2-(2-fluorophenyl)-4H-benzo[d][1,3]oxazin-4-one (167)

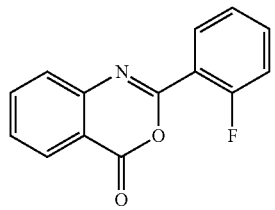

(167)

Compound 167 was obtained as a yellow powder in 89.4% yield. $^1$H-NMR (500 MHz, CDCl$_3$): δ 7.29 (2H, s), 7.59 (2H, s), 7.76 (1H, s), 7.88 (1H, s), 8.16 (1H, s), 8.29 (1H, d, J=7.88 Hz) ppm. $^{13}$C-NMR (CDCl$_3$): δ 117.02 (C, C-aromatic), 117.20 (CH, C-aromatic), 117.38 (CH, C-aromatic), 119.10 (C, C-aromatic), 124.33 (CH, C-aromatic), 127.46 (CH, C-aromatic), 128.60 (CH, C-aromatic), 128.80 (CH, C-aromatic), 131.16 (CH, C-aromatic), 133.99 (CH, C-aromatic), 134.06 (CH, C-aromatic), 136.65 (CH, C-aromatic), 146.71 (C, C-aromatic), 159.24 (C, C-aromatic), 160.37 (C, C-aromatic), 162.44 (C, C-aromatic) ppm. $^{19}$F-NMR (CDCl$_3$): δ −105.99 ppm.

Example 9

Synthesis of 2-(2-fluoro-4-methoxyphenyl)-4H-benzo[d][1,3]oxazin-4-one (168)

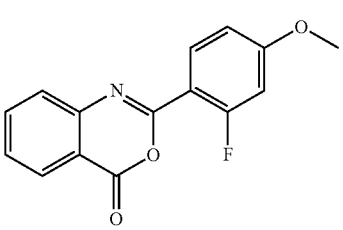

(168)

Compound 168 was obtained as a white powder in 25% yield. $^1$H-NMR (CDCl$_3$): δ 6.76 (dd, J=2.4, 12.9 Hz, 1H), 6.84 (dd, J=2.4, 8.9 Hz, 1H), 7.52-7.56 (m, 1H), 7.71 (d, J=8.1 Hz, 1H), 7.82-7.88 (m, 1H), 8.13 (t, J=8.7 Hz, 1H), 8.26 (dd, J=1.2, 7.9 Hz, 1H) ppm. $^{13}$C-NMR (CDCl$_3$): δ 55.87 (CH$_3$, C-aliphatic), 102.66 (CH, C-aromatic), 110.68 (C, C-aromatic), 116.82 (C, C-aromatic), 127.19 (CH,C-aromatic), 128.21 (CH, C-aromatic), 128.52 (CH, C-aromatic), 132.17 (CH,C-aromatic), 132.19 (CH,C-aromatic), 136.51 (CH, C-aromatic), 147.08 (C, C-aromatic), 159.41 (C, C-aromatic), 161.80 (C, C-aromatic), 163.87 (C, C-aromatic), 164.34 (C, C-aromatic) ppm.

Example 10

Synthesis of 5-fluoro-2-(4-methoxyphenyl)-4H-benzo[d][1,3]oxazin-4-one (169)

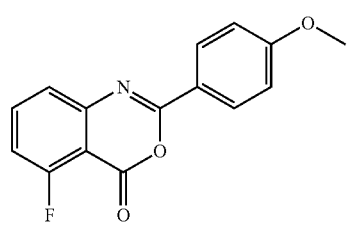
(169)

Compound 169 was obtained as a white powder in 56% yield. $^1$H-NMR (CDCl$_3$): δ 3.93 (s, 3H), 7.00-7.05 (m, 2H), 7.14-7.21 (m, 1H), 7.48 (d, J=8.1 Hz, 1H), 7.72-7.78 (m, 1H), 8.25-8.32 (m, 2H) ppm. $^{13}$C-NMR (CDCl$_3$): δ 55.57 (CH$_3$, C-aliphatic), 114.14 (CH, C-aromatic), 114.66 (CH, C-aromatic), 122.02 (C, C-aromatic), 122.79 (CH, C-aromatic), 130.53 (CH, C-aromatic), 132.85 (CH, C-aromatic), 134.99 (C, C-aromatic), 137.18 (CH, C-aromatic), 149.21 (C, C-aromatic), 160.89 (C, C-aromatic), 163.02 (C, C-aromatic), 163.6 (C, C-aromatic) ppm. $^{19}$F-NMR (CDCl$_3$): δ −106.84 ppm.

Example 11

Synthesis of 7-methoxy-2-(4-methoxyphenyl)-4H-benzo[d][1,3]oxazin-4-one (170)

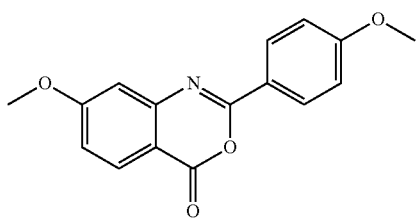
(170)

Compound 170 was obtained as a white powder in 90% yield. $^1$H-NMR (CDCl$_3$): δ 3.92 (s, 3H), 3.97 (s, 3H), 6.99-7.05 (m, 3H), 7.08 (d, J=2.4 Hz, 1H), 8.12-8.16 (m, 1H), 8.25-8.30 (m, 2H) ppm. $^{13}$C-NMR (CDCl$_3$): δ 55.61 (CH$_3$, C-aliphatic), 55.88 (CH$_3$, C-aliphatic), 108.57 (CH, C-aromatic), 109.56 (C, C-aromatic), 114.14 (CH, C-aromatic), 116.91 (CH, C-aromatic), 122.63 (C, C-aromatic), 130.31 (CH, C-aromatic), 132.85 (CH, C-aromatic), 149.82 (C, C-aromatic), 155.00 (C, C-aromatic), 159.47 (C, C-aromatic), 163.30 (C, C-aromatic), 166.29 (C, C-aromatic) ppm.

Example 12

Synthesis of 5-fluoro-2-(2-fluorophenyl)-4H-benzo[d][1,3]oxazin-4-one (171)

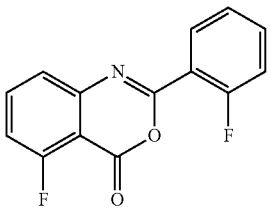
(171)

Compound 171 was obtained as a beige powder in 26% yield. $^1$H-NMR (CDCl$_3$): δ 7.23-7.35 (m, 3H), 7.55-7.62 (m, 2H), 7.79-7.83 (m, 1H), 8.10-8.15 (m, 1H) ppm. $^{13}$C-NMR (CDCl$_3$): δ 115.72 (CH, C-aromatic), 117.35 (CH, C-aromatic), 123.35 (CH, C-aromatic), 123.38 (CH, C-aromatic), 124.37 (C, C-aromatic), 124.40 (CH, C-aromatic), 131.20 (CH, C-aromatic), 134.36 (CH, C-aromatic), 134.44 (CH, C-aromatic), 137.32 (CH, C-aromatic), 137.40 (CH, C-aromatic), 148.42 (C, C-aromatic), 154.69 (CH, C-aromatic), 160.47 (CH, C-aromatic), 162.55 (C, C-aromatic), 162.89 (C, C-aromatic) ppm.

Example 13

Synthesis of 5-fluoro-2-(2-fluoro-4-methoxyphenyl)-4H-benzo[d][1,3]oxazin-4-one (172)

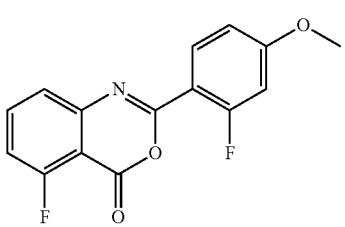
(172)

Compound 172 was obtained as a white powder in 31% yield. $^1$H-NMR (CDCl$_3$): δ 3.92 (s, 3H), 6.76 (dd, J=2.4, 12.9 Hz, 1H), 6.82-6.85 (m, 1H), 7.21 (t, J=8.7 Hz, 1H), 7.51 (t, J=7.5 Hz, 1H), 7.72-7.80 (m, 1H), 8.13 (t, J=8.7 Hz, 1H) ppm. $^{13}$C-NMR (CDCl$_3$): δ 55.94 (CH$_3$, C-aliphatic), 102.82 (CH, C-aromatic), 110.76 (CH, C-aromatic), 115.10 (C, C-aromatic), 123.08 (CH, C-aromatic), 132.27 (CH, C-aromatic), 137.18 (CH, C-aromatic), 137.26 (CH, C-aromatic), 148.84 (C, C-aromatic), 153.80 (C, C-aromatic), 160.78 (C, C-aromatic), 161.05 (C, C-aromatic), 161.97 (C, C-aromatic), 162.91 (C, C-aromatic) ppm. $^{19}$F-NMR (CDCl$_3$): δ −104.71, −106.43 ppm.

Example 14

Synthesis of 2-(2-fluoro-4-methoxyphenyl)-7-methoxy-4H-benzo[d][1,3]oxazin-4-one (173)

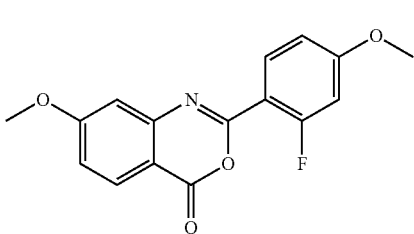

(173)

Compound 173 was obtained as a white powder in 17% yield. $^1$H-NMR (CDCl$_3$): δ 3.91 (s, 3H), 3.97 (s, 3H), 6.76 (dd, J=2.2, 12.9 Hz, 1H), 6.84 (dd, J=2.2, 8.9 Hz, 1H), 7.03-7.13 (m, 2H), 8.07-8.18 (m, 2H) ppm. $^{13}$C-NMR (126 MHz, CDCl$_3$): δ 55.92 (CH$_3$, C-aliphatic), 102.88 (CH, C-aromatic), 106.3 (C, C-aromatic), 108.82 (CH, C-aromatic), 110.5 (C, C-aromatic), 110.63 (CH, C-aromatic), 117.49 (CH, C-aromatic), 130.16 (CH, C-aromatic), 132.19 (CH, C-aromatic), 154.9 (C, C-aromatic), 156.3 (C, C-aromatic), 159.4 (C, C-aromatic), 160.6 (C, C-aromatic), 162.1 (C, C-aromatic), 167.1 (C, C-aromatic) ppm. $^{19}$F-NMR (471 MHz, CDCl$_3$): δ −110.94 ppm.

Example 15

Synthesis of 2-(2-fluorophenyl)-7-methoxy-4H-benzo[d][1,3]oxazin-4-one (174)

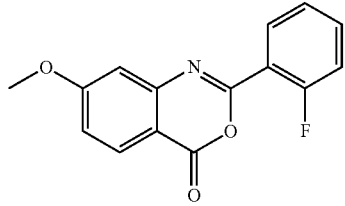

(174)

Compound 174 was obtained as a beige powder in 54% yield. $^1$H-NMR (CDCl$_3$): δ 3.98 (s, 3H), 7.12 (dd, J=2.5, 8.8 Hz, 1H), 7.16 (d, J=2.4 Hz, 1H), 7.26 (dd, J=8.4, 11.1 Hz, 1H), 7.32 (t, J=7.6 Hz, 1H), 7.55-7.61 (m, 1H), 8.10-8.15 (m, 2H) ppm. $^{13}$C-NMR (CDCl$_3$): δ 55.98 (CH$_3$, C-aliphatic), 106.3 (C, C-aromatic), 109.15 (CH, C-aromatic), 117.37 (CH, C-aromatic), 117.94 (CH, C-aromatic), 118.6 (C, C-aromatic), 124.32 (CH, C-aromatic), 130.23 (CH, C-aromatic), 131.14 (CH, C-aromatic), 133.97 (CH, C-aromatic), 154.9 (C, C-aromatic), 156.3 (C, C-aromatic), 159.1 (C, C-aromatic), 159.8 (C, C-aromatic), 167.6 (C, C-aromatic) ppm.

Example 16

Synthesis of 2-(4-methoxyphenyl)-4H-pyrido[3,4-d][1,3]oxazin-4-one (175)

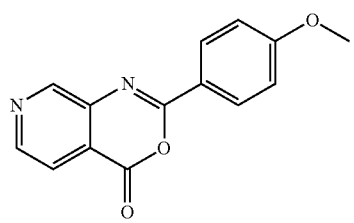

(175)

Compound 175 was obtained as a white powder in 75% yield. $^1$H-NMR (CDCl$_3$): δ 3.93 (s, 3H), 7.02-7.08 (m, 2H), 8.00 (dd, J=0.7, 5.1 Hz, 1H), 8.21-8.35 (m, 2H), 8.76 (d, J=5.1 Hz, 1H), 9.11 (s, 1H) ppm. $^{13}$C-NMR (126 MHz, CDCl$_3$): δ 55.60 (CH$_3$, C-aromatic), 114.14 (CH, C-aromatic), 114.36 (CH, C-aromatic), 119.96 (C, C-aromatic), 121.81 (C, C-aromatic), 122.33 (CH, C-aromatic), 130.61 (C, C-aromatic), 132.86 (C, C-aromatic), 147.82 (CH, C-aromatic), 150.24 (CH, C-aromatic), 158.06 (C, C-aromatic), 158.95 (C, C-aromatic), 163.84 (C, C-aromatic) ppm.

Example 17

Synthesis of 7-fluoro-2-(4-methoxyphenyl)-4H-benzo[d][1,3]oxazin-4-one (176)

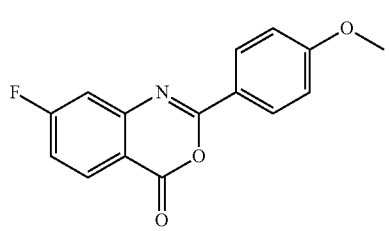

(176)

Compound 176 was obtained as a white powder in 93% yield. $^1$H-NMR (CDCl$_3$): δ 3.92 (s, 3H), 7.01-7.04 (m, 2H), 7.16-7.20 (m, 1H), 7.32 (dd, J=2.4, 9.4 Hz, 1H), 8.23-8.26 (m, 1H), 8.26-8.29 (m, 2H) ppm. $^{13}$C-NMR (126 MHz, CDCl$_3$): δ 55.56 (CH$_3$, C-aromatic), 112.83 (CH, C-aromatic), 113.01 (CH, C-aromatic), 114.24 (CH, C-aromatic), 116.04 (C, C-aromatic), 116.23 (CH, C-aromatic), 122.12 (CH, C-aromatic), 130.54 (C, C-aromatic), 131.35 (C, C-aromatic), 158.35 (C, C-aromatic), 158.88 (C, C-aromatic), 163.61 (C, C-aromatic), 168.84 (C, C-aromatic) ppm.

Example 18

Synthesis of 7-fluoro-2-(2-fluorophenyl)-4H-benzo[d][1,3]oxazin-4-one (177)

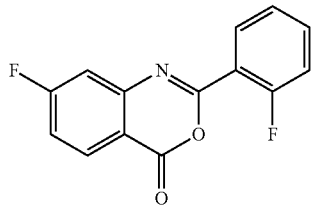
(177)

Compound 177 was obtained as a white powder in 94% yield. ¹H-NMR (CDCl₃): δ 7.23-7.27 (m, 1H), 7.31-7.37 (m, 2H), 7.42 (dd, J=1.24, 9.1 Hz, 1H), 7.57-7.63 (m, 1H), 8.11-8.16 (m, 1H), 8.31 (dd, J=5.9, 8.8 Hz, 1H) ppm. ¹³C-NMR (126 MHz, CDCl₃): δ 113.50 (CH, C-aromatic), 113.61 (C, C-aromatic), 117.30 (CH, C-aromatic), 117.47 (CH, C-aromatic), 124.41 (CH, C-aromatic), 131.40 (CH, C-aromatic), 134.41 (CH, C-aromatic), 134.48 (CH, C-aromatic), 149.03 (C, C-aromatic), 158.29 (C, C-aromatic), 160.48 (C, C-aromatic), 162.56 (C, C-aromatic), 166.63 (C, C-aromatic), 168.87 (C, C-aromatic) ppm. ¹⁹F-NMR (CDCl₃): δ −104.11, −112.36 ppm.

Example 19

Synthesis of 2-(2-(trifluoromethyl)phenyl)-4H-benzo[d][1,3]oxazin-4-one (178)

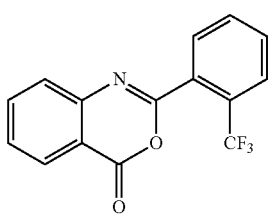
(178)

Compound 178 was obtained as a white powder in 53% yield. ¹H-NMR (CDCl₃): δ 7.65-7.60 (m, 1H), 7.69-7.75 (m, 3H), 7.85-7.89 (m, 2H), 7.95-7.99 (m, 1H), 8.31 (dd, J=1.4, 7.9 Hz, 1H) ppm. ¹³C NMR (126 MHz, CDCl₃): 116.91 (C, C-aromatic), 122.04 (C, C-aromatic), 127.46 (CH, C-aromatic), 128.69 (CH, C-aromatic), 129.12 (CH, C-aromatic), 129.21 (CH, C-aromatic), 130.09 (C, C-aromatic), 131.08 (CH, C-aromatic), 131.28 (CH, C-aromatic), 131.89 (CH, C-aromatic), 136.72 (CH, C-aromatic), 146.32 (C, C-aromatic), 156.80 (C, C-aromatic), 158.66 (C, C-aromatic) ppm. ¹⁹F-NMR: δ −58.79 ppm.

Example 20

Synthesis of 2-(3-(trifluoromethyl)phenyl)-4H-benzo[d][1,3]oxazin-4-one (179)

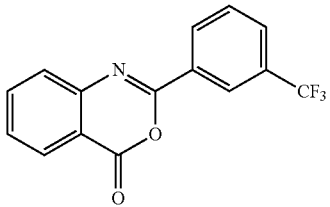
(179)

Compound 179 was obtained as a white powder in 41% yield. ¹H-NMR (CDCl₃): δ 7.60 (t, J=7.6 Hz, 1H), 7.69 (t, J=7.8 Hz, 1H), 7.76 (d, J=8.1 Hz, 1H), 7.84-7.93 (m, 2H), 8.30 (d, J=7.9 Hz, 1H), 8.53 (d, J=7.9 Hz, 1H), 8.63 (s, 1H) ppm. ¹³C NMR (126 MHz, CDCl₃): δ117.12 (C, C-aromatic), 125.29 (CH, C-aromatic), 127.44 (CH, C-aromatic), 128.82 (CH, C-aromatic), 129.80 (CH, C-aromatic), 131.23 (CH, C-aromatic), 131.34 (C, C-aromatic), 133.68 (CH, C-aromatic), 136.78 (CH, C-aromatic), (CH, C-aromatic), 146.57 (C, C-aromatic), 155.60 (C, C-aromatic), 155.92 (C, C-aromatic), 159.05 (C, C-aromatic) ppm. ¹⁹F-NMR: δ −62.75 ppm.

Example 21

Synthesis of 2-(4-(trifluoromethyl)phenyl)-4H-benzo[d][1,3]oxazin-4-one (180)

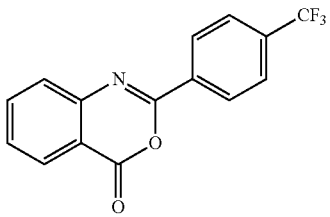
(180)

Compound 180 was obtained as a white powder in 73% yield. ¹H-NMR (CDCl₃): δ 7.58-7.62 (m, 1H), 7.74-7.87 (m, 3H), 7.88-7.92 (m, 1H), 8.30 (dd, J=1.4, 7.9 Hz, 1H), 8.47 (d, J=8.2 Hz, 2H). ¹³C-NMR (126 MHz, CDCl₃): δ 117.11 (C, C-aromatic), 125.47 (CH, C-aromatic), 127.64 (CH, C-aromatic), 128.65 (CH, C-aromatic), 128.77 (CH, C-aromatic), 128.95 (CH, C-aromatic), 136.64 (CH, C-aromatic), 133.43 (C, C-aromatic), 133.83 (C, C-aromatic), 134.14 (C, C-aromatic), 134.41 (C, C-aromatic), 146.58 (C, C-aromatic), 158.95 (C, C-aromatic) ppm. ¹⁹F-NMR: −63.59 ppm.

Example 22

Synthesis of 2-(4-methoxyphenyl)-4H-pyrido[2,3-d][1,3]oxazin-4-one (181)

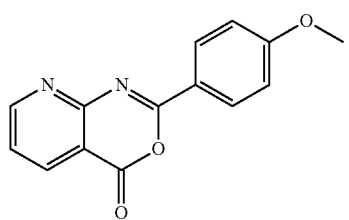

Compound 181 was obtained as a white powder in 43% yield. ¹H-NMR (CDCl₃): δ 3.93 (s, 3H), 7.05 (d, J=8.9 Hz, 2H), 7.29 (s, 1H), 8.40 (d, J=8.9 Hz, 2H), 8.56 (dd, J=1.9, 7.8 Hz, 1H), 9.01 (dd, J=4.6, 1.9 Hz, 1H) ppm. ¹³C-NMR (126 MHz, CDCl₃): δ 55.59 (CH₃, C-aromatic), 112.45 (C, C-aromatic), 114.34 (CH, C-aromatic), 121.68 (C, C-aromatic), 123.02 (CH, C-aromatic), 131.20 (CH, C-aromatic), 137.83 (CH, C-aromatic), 157.53 (CH, C-aromatic), 158.22 (C, C-aromatic), 159.64 (C, C-aromatic), 164.17 (C, C-aromatic) ppm.

Example 23

Synthesis of 2-(4-methoxyphenyl)-4H-pyrido[4,3-d][1,3]oxazin-4-one (182)

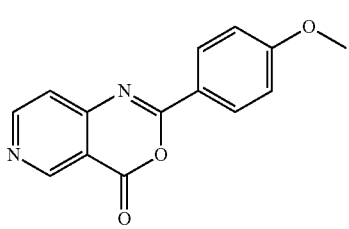

Compound 182 was obtained as a white powder in 76% yield. ¹H-NMR (CDCl₃): δ 3.94 (s, 3H), 6.97-7.10 (m, 2H), 7.29 (s, 1H), 8.28-8.43 (m, 2H), 8.93 (d, J=5.6 Hz, 1H), 9.43 (d, J=0.6 Hz, 1H) ppm. ¹³C-NMR (126 MHz, CDCl₃): δ 55.65 (CH₃, C-aromatic), 112.55 (C, C-aromatic), 114.41 (CH, C-aromatic), 120.14 (C, C-aromatic), 121.62 (CH, C-aromatic), 131.19 (CH, C-aromatic), 151.59 (CH, C-aromatic), 153.22 (CH, C-aromatic), 156.12 (C, C-aromatic), 158.15 (C, C-aromatic), 164.30 (C, C-aromatic) ppm.

Example 24

Synthesis of 2-(naphthalen-1-yl)-4H-benzo[d][1,3]oxazin-4-one (183)

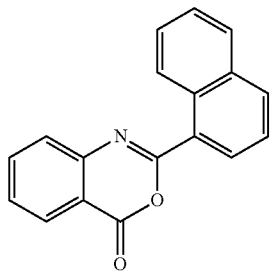

Compound 183 was obtained as a white powder in 89% yield. ¹H-NMR (CDCl₃): δ 7.58-7.64 (m, 3H), 7.68-7.72 (m, 1H), 7.84 (dd, J=0.6, 8.1 Hz, 1H), 7.89-7.94 (m, 1H), 7.97 (t, J=6.3 Hz, 1H), 8.09 (d, J=8.2 Hz, 1H), 8.32-8.38 (m, 2H), 9.17 (dd, J=4.9, 8.3 Hz, 1H) ppm. ¹³C-NMR (126 MHz, CDCl₃): δ 117.03 (C, C-aromatic), 124.82 (CH, C-aromatic), 125.79 (CH, C-aromatic), 126.42 (CH, C-aromatic), 126.79 (C, C-aromatic), 127.44 (CH, C-aromatic), 127.88 (CH, C-aromatic), 128.57 (CH, C-aromatic), 128.63 (CH, C-aromatic), 128.85 (CH, C-aromatic), 130.04 (CH, C-aromatic), 130.78 (C, C-aromatic), 133.19 (CH, C-aromatic), 134.09 (C, C-aromatic), 136.31 (CH, C-aromatic), 146.85 (C, C-aromatic), 157.71 (C, C-aromatic), 159.77 (C, C-aromatic) ppm.

Example 25

Synthesis of 2-(naphthalen-2-yl)-4H-benzo[d][1,3]oxazin-4-one (184)

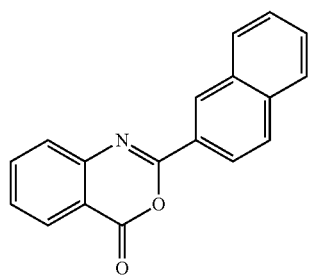

Compound 184 was obtained as a white powder in 91% yield. ¹H-NMR (CDCl₃): δ 7.60 (dd, J=1.2, 7.6 Hz, 3H), 7.77 (dd, J=0.5, 8.1 Hz, 1H), 7.88 (ddd, J=1.5, 7.3, 8.2, Hz, 1H), 7.93 (d, J=8.0 Hz, 1H), 7.98 (d, J=8.7 Hz, 1H), 8.03 (d, J=7.9 Hz, 1H), 8.30 (dd, J=1.1, 7.9 Hz, 1H), 8.40 (dd, J=1.7, 8.7 Hz, 1H), 8.88 (s, 1H) ppm. ¹³C-NMR (126 MHz, CDCl₃): δ 117.09 (C, C-aromatic), 124.18 (CH, C-aromatic), 126.89 (CH, C-aromatic), 127.29 (C, C-aromatic), 127.45 (C, C-aromatic), 127.83 (CH, C-aromatic), 128.28 (CH, C-aromatic), 128.33 (CH, C-aromatic), 128.58 (CH, C-aromatic), 128.67 (CH, C-aromatic), 129.39 (CH, C-aromatic), 129.55 (CH, C-aromatic), 132.80 (C, C-aromatic), 135.37 (CH, C-aromatic), 136.61 (CH, C-aromatic), 147.13 (C, C-aromatic), 157.24 (C, C-aromatic), 159.68 (C, C-aromatic) ppm.

Example 26

Synthesis of 2-(2-fluorophenyl)-4H-pyrido[2,3-d][1,3]oxazin-4-one (185)

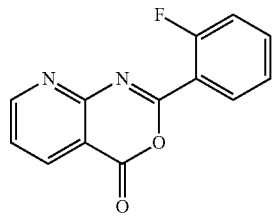

185

Compound 185 was obtained as a white powder in 27.52% yield. $^1$H-NMR (CDCl$_3$): δ 7.23-7.28 (m, 1H), 7.31-7.37 (m, 1H), 7.56 (dd, J=4.7, 4.7 Hz, 1H), 7.59-7.66 (m, 1H), 8.31 (td, J=1.8, 7.7 Hz, 1H), 8.61 (dd, J=2.0, 7.8 Hz, 1H), 9.07 (dd, J=2.0, 4.7 Hz, 1H) ppm. $^{13}$C-NMR (126 MHz, CDCl$_3$): δ 112.89 (C, C-aromatic), 117.39 (CH, C-aromatic), 117.57 (CH, C-aromatic), 124.06 (CH, C-aromatic), 124.43 (CH, C-aromatic), 131.79 (CH, C-aromatic), 135.07 (CH, C-aromatic), 135.15 (C, C-aromatic), 137.90 (CH, C-aromatic), 157.53 (C, C-aromatic), 157.66 (CH, C-aromatic), 159.11 (C, C-aromatic), 160.78 (C, C-aromatic), 162.87 (C, C-aromatic) ppm. $^{19}$F-NMR: δ −107.15 ppm.

Example 27

Synthesis of 5-fluoro-2-(2-methoxyphenyl)-4H-benzo[d][1,3]oxazin-4-one (186)

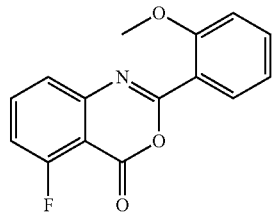

186

Compound 186 was obtained as a white powder in 98% yield. $^{13}$C-NMR (126 MHz, CDCl$_3$): δ 56.13 (CH$_3$, C-aliphatic), 112.22 (CH, C-aromatic), 115.15 (CH, C-aromatic, J=26.25 MHz), 120.09 (CH, C-aromatic), 120.61 (C, C-aromatic), 123.11 (CH, C-aromatic), 123.15 (CH, C-aromatic), 131.39 (CH, C-aromatic), 133.54 (CH, C-aromatic), 137.08 (CH, C-aromatic), 148.87 (C, C-aromatic), 155.35 (C, C-aromatic), 158.71 (C, C-aromatic), 158.80 (C, C-aromatic), 160.76 (C, C-aromatic), 162.89 (C, C-aromatic) ppm. $^{19}$F-NMR: δ −106.66 ppm.

Example 28

Synthesis of 5-fluoro-2-(3-methoxyphenyl)-4H-benzo[d][1,3]oxazin-4-one (187)

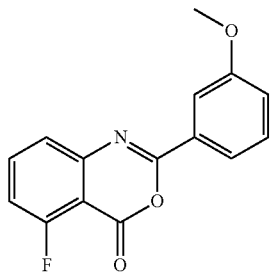

187

Compound 187 was obtained as a white powder in 94% yield. $^1$H-NMR (CDCl$_3$): δ 3.94 (s, 3H), 7.16 (ddd, J=0.9, 2.6, 8.2 Hz, 1H), 7.21 (ddd, J=0.9, 8.4, 9.5 Hz, 1H), 7.44 (t, J=8.0 Hz, 1H), 7.53 (d, J=8.1 Hz, 1H), 7.77-7.81 (m, 1H), 7.82 (dt, J=2.8, 5.4 Hz, 1H), 7.92 (ddd, J=1.0, 1.4, 7.8 Hz, 1H) ppm. $^{13}$C-NMR (126 MHz, CDCl$_3$): δ 55.59 (CH$_3$, C-aliphatic), 112.75 (CH, C-aromatic), 115.11 (CH, C-aromatic), 119.71 (CH, C-aromatic), 121.06 (CH, C-aromatic), 123.12 (CH, C-aromatic), 129.83 (CH, C-aromatic), 131.09 (CH, C-aromatic), 137.18 (C, C-aromatic), 137.26 (CH, C-aromatic), 148.77 (C, C-aromatic), 155.22 (C, C-aromatic), 157.75 (C, C-aromatic), 159.93 (C, C-aromatic), 160.87 (C, C-aromatic), 163.00 (C, C-aromatic) ppm. $^{19}$F-NMR: δ −106.52 ppm.

Example 29

Synthesis of 2-(2-fluoro-4-(trifluoromethoxy)phenyl)-4H-benzo[d][1,3]oxazin-4-one (188)

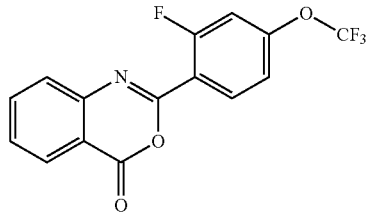

188

Compound 188 was obtained as a white powder in 95% yield. $^1$H-NMR (CDCl$_3$): δ 7.11-7.21 (m, 2H), 7.58-7.63 (m, 1H), 7.75 (d, J=8.1 Hz, 1H), 7.86-7.92 (m, 1H), 8.24 (t, J=8.5 Hz, 1H), 8.29 (dd, J=7.9, 1.2 Hz, 1H) ppm. $^{13}$C-NMR (126 MHz, CDCl$_3$): δ 109.97 (CH, C-aromatic), 116.14 (CH, C-aromatic), 117.03 (C, C-aromatic), 119.00 (C, C-aromatic), 117.2 (C, C-aromatic), 127.51 (CH, C-aromatic), 128.68 (CH, C-aromatic), 129.01 (CH, C-aromatic), 132.47 (CH, C-aromatic), 136.72 (CH, C-aromatic), 146.27 (C, C-aromatic), 152.46 (C, C-aromatic), 158.85 (C, C-aromatic), 160.68 (C, C-aromatic) ppm. $^{19}$F-NMR: δ −57.99, −103.77 ppm.

Example 30

Synthesis of 6,7-dimethoxy-2-(4-methoxyphenyl)-4H-benzo[d][1,3]oxazin-4-one (189)

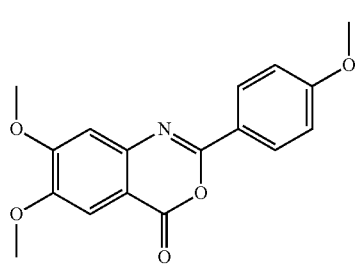

189

Compound 189 was obtained as a white powder in 72% yield. $^1$H-NMR (CDCl$_3$): δ 3.83 (s, 3H), 3.93 (s, 3H), 3.96 (s, 3H), 6.89-6.97 (m, 2H), 7.01 (s, 1H), 7.19 (s, 1H), 7.48 (s, 1H), 8.14-8.18 (m, 1H) ppm. $^{13}$C-NMR (126 MHz, CDCl$_3$): δ 55.51 (—CH3, C-aliphatic), 56.44 (—CH3, C-aliphatic), 56.50 (—CH3, C-aliphatic), 107.71 (CH, C-aromatic), 107.85 (CH, C-aromatic), 107.56 (CH, C-aromatic), 109.26 (C, C-aromatic), 114.15 (CH, C-aromatic), 122.80 (C, C-aromatic), 129.93 (CH, C-aromatic), 132.85 (CH, C-aromatic), 143.76 (C, C-aromatic), 149.37 (C, C-aromatic), 156.49 (C, C-aromatic) 156.72 (C, C-aromatic), 159.74 (C, C-aromatic), 163.05 (C, C-aromatic) ppm.

Example 31

Synthesis of 6,7,8-trimethoxy-2-(4-methoxyphenyl)-4H-benzo[d][1,3]oxazin-4-one (190)

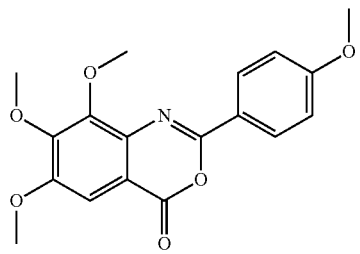

190

Compound 190 was obtained as a white powder in 79% yield. $^1$H-NMR (CDCl$_3$): δ 3.92 (s, 3H), 3.99 (s, 3H), 4.09 (s, 3H), 4.18 (s, 3H), 6.96-7.06 (m, 2H), 7.45 (s, 1H), 8.09-8.15 (m, 1H), 8.26-8.33 (m, 2H) ppm. $^{13}$C-NMR (126 MHz, CDCl$_3$): δ 55.51 (CH3, C-aliphatic), 56.40 (CH3, C-aliphatic), 61.51 (CH3, C-aliphatic), 62.71 (CH3, C-aliphatic), 104.02 (CH, C-aromatic), 112.06 (C, C-aromatic), 114.11 (CH, C-aromatic), 122.83 (C, C-aromatic), 129.99 (CH, C-aromatic), 136.92 (C, C-aromatic), 147.64 (C, C-aromatic), 149.45 (C, C-aromatic), 152.99 (C, C-aromatic), 155.26 (C, C-aromatic), 159.76 (C, C-aromatic), 163.05 (C, C-aromatic) ppm.

Example 32

Synthesis of 8-methoxy-2-(naphthalene-2-yl)-4H-benzo[d][1,3]oxazin-4-one (191)

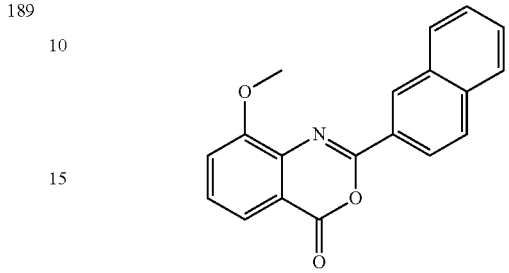

191

Compound 191 was obtained as a white powder in 89% yield. $^1$H-NMR (CDCl$_3$): δ 4.11 (s, 3H), 7.34-7.39 (m, 1H), 7.51 (t, J=7.9 Hz, 1H), 7.57-7.69 (m, 2H), 7.87-7.94 (m, 2H), 7.97 (d, J=8.2 Hz, 1H), 8.03 (d, J=7.9 Hz, 1H), 8.44 (dd, J=1.7, 8.7 Hz, 1H), 8.89 (s, 1H) ppm. $^{13}$C-NMR (126 MHz, CDCl$_3$): δ 56.64 (CH$_3$, C-aliphatic), 117.31 (CH, C-aromatic), 118.03 (C, C-aromatic), 119.91 (CH, C-aromatic), 124.36 (CH, C-aromatic), 126.85 (CH, C-aromatic), 127.46 (CH, C-aromatic), 127.83 (CH, C-aromatic), 128.3 (CH, C-aromatic), 128.54 (C, C-aromatic), 128.7 (CH, C-aromatic), 129.42 (CH, C-aromatic), 129.57 (CH, C-aromatic) 132.76 (C, C-aromatic), 135.35 (C, C-aromatic), 137.09 (C, C-aromatic), 154.37 (C, C-aromatic), 156.65 (C, C-aromatic), 159.63 (C, C-aromatic) ppm.

Example 33

Synthesis of 7-methoxy-2-(naphthalene-2-yl)-4H-benzo[d][1,3]oxazin-4-one (192)

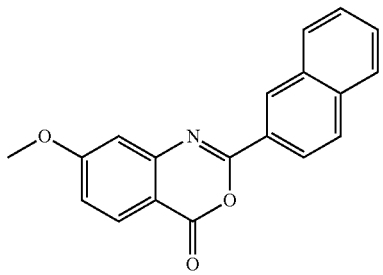

192

Compound 192 was obtained as a white powder in 87% yield. $^1$H-NMR (CDCl$_3$): δ 4.01 (s, 3H), 7.10 (dt, J=4.6, 9.3 Hz, 1H), 7.54-7.65 (m, 1H), 7.68-7.73 (m, 1H), 7.93 (d, J=8.0 Hz, 1H), 7.96-8.02 (m, 1H), 8.04 (dd, J=8.0, 11.2 Hz, 1H), 8.19-8.26 (m, 1H), 8.39 (dd, J=1.7, 8.7 Hz, 1H), 8.81 (s, 1H), 8.87 (s, 1H) ppm. $^{13}$C-NMR (126 MHz, CDCl$_3$): δ 55.96 (CH$_3$, C-aliphatic), 108.96 (CH, C-aromatic), 109.86 (C, C-aromatic), 117.43 (CH, C-aromatic), 124.16 (CH, C-aromatic), 126.91 (CH, C-aromatic), 127.84 (CH, C-aromatic), 127.96 (C, C-aromatic), 128.36 (CH, C-aromatic), 128.59 (CH, C-aromatic), 129.41 (CH, C-aromatic), 129.62 (CH, C-aromatic), 130.33 (CH, C-aromatic), 132.85 (C, C-aromatic), 135.36 (C, C-aromatic), 149.57 (C, C-aromatic), 158.08 (C, C-aromatic), 159.39 (C, C-aromatic), 166.37 (C, C-aromatic) ppm.

Example 34

Synthesis of 2-(2-fluorophenyl)-6,7,8-trimethoxy-4H-benzo[d][1,3]oxazin-4-one (193)

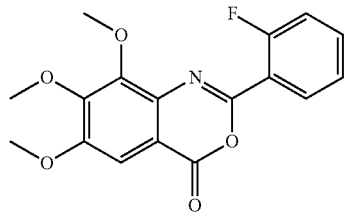

193

Compound 193 was obtained as a white powder in 79% yield. $^1$H-NMR (CDCl$_3$): δ 4.01 (3H, s), 4.09 (3H, s), 4.21 (3H, s), 7.22-7.26 (1H, m), 7.30-7.32 (1H, m), 7.48 (1H, s), 7.54-7.56 (1H, m), 8.15-8.18 (1H, m) ppm. $^{13}$C-NMR (126 MHz, CDCl$_3$): δ 56.47 (CH$_3$, C-aliphatic), 61.55 (CH$_3$, C-aliphatic), 62.77 (CH$_3$, C-aliphatic), 103.89 (CH, C-aromatic), 112.39 (C, C-aromatic), 117.26 (CH, C-aromatic), 124.24 (CH, C-aromatic), 130.87 (CH, C-aromatic), 133.65 (CH, C-aromatic), 136.08 (C, C-aromatic), 148.06 (C, C-aromatic), 149.33 (C, C-aromatic), 152.28 (C, C-aromatic), 153.77 (C, C-aromatic), 159.25 (C, C-aromatic), 160.44 (C, C-aromatic), 162.51 (C, C-aromatic) ppm.

Example 35

Synthesis of 8-methoxy-(2-naphthalen-1-yl)-4H-benzo[d][1,3]oxazin-4-one (194)

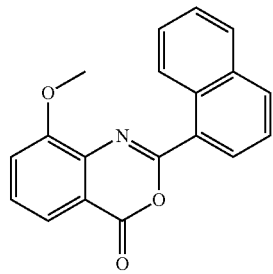

194

Compound 194 was obtained as a yellow powder in 82% yield. $^1$H-NMR (CDCl$_3$): δ 4.09 (s, 3H), 7.38 (dd, J=1.1, 8.2 Hz, 1H), 7.55 (t, J=8.0 Hz, 1H), 7.57-7.63 (m, 2H), 7.68-7.76 (m, 1H), 7.87-7.96 (m, 2H), 8.06 (d, J=8.2 Hz, 1H), 8.35 (dd, J=1.2, 7.3 Hz, 1H), 9.20 (t, J=9.8 Hz, 1H) ppm. $^{13}$C-NMR (126 MHz, CDCl$_3$): δ 56.59 (CH$_3$, C-aliphatic), 117.26 (CH, C-aromatic), 117.97 (C, C-aromatic), 119.62 (CH, C-aromatic), 124.76 (CH, C-aromatic), 125.70 (CH, C-aromatic), 126.34 (CH, C-aromatic), 127.28 (C, C-aromatic), 128.03 (CH, C-aromatic), 128.79 (CH, C-aromatic), 128.95 (CH, C-aromatic), 130.00 (CH, C-aromatic), 130.97 (C, C-aromatic), 133.06 (CH, C-aromatic), 135.54 (C, C-aromatic), 136.89 (C, C-aromatic), 154.65 (C, C-aromatic), 156.95 (C, C-aromatic), 159.76 (C, C-aromatic) ppm.

Example 36

Synthesis of 6,7-dimethoxy-2-(4-methoxyphenyl)-4H-benzo[d][1,3]oxazin-4-one (195)

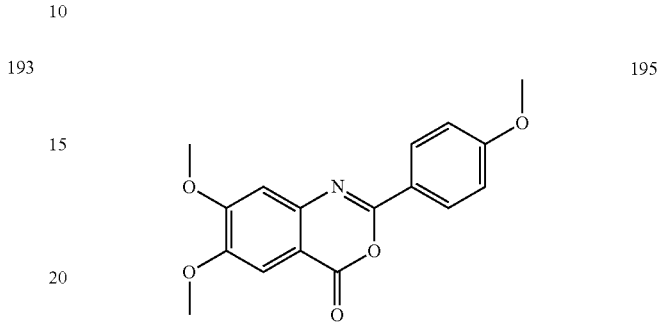

195

Compound 195 was obtained as a white powder in 91% yield. $^1$H-NMR (CDCl$_3$): δ 3.83 (s, 3H), 3.93 (s, 3H), 3.96 (s, 3H), 6.87-6.95 (m, 2H), 7.01 (s, 1H), 7.48 (s, 1H), 8.13-8.21 (m, 2H) ppm. $^{13}$C-NMR (126 MHz, CDCl$_3$): δ 55.51 (CH$_3$, C-aliphatic), 56.44 (CH$_3$, C-aliphatic), 56.50 (CH$_3$, C-aliphatic), 107.71 (CH, C-aromatic), 107.85 (CH, C-aromatic), 107.56 (CH, C-aromatic), 109.26 (C, C-aromatic), 114.15 (CH, C-aromatic), 122.80 (C, C-aromatic), 129.93 (CH, C-aromatic), 132.85 (CH, C-aromatic), 143.76 (C, C-aromatic), 149.37 (C, C-aromatic), 156.49 (C, C-aromatic) 156.72 (C, C-aromatic), 159.74 (C, C-aromatic), 163.05 (C, C-aromatic) ppm.

Example 37

Synthesis of 6,7,8-trimethoxy-2-(4-methoxyphenyl) 4H-benzo[d][1,3]oxazin-4-one (196)

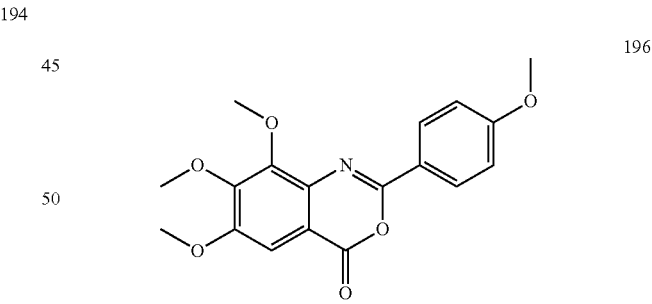

196

Compound 196 was obtained as a white powder in 85% yield. $^1$H-NMR (CDCl$_3$): δ 3.83 (s, 3H), 3.90 (s, 3H), 3.99 (s, 3H), 4.09 (s, 3H), 6.99-6.84 (m, 2H), 7.19 (s, 1H), 8.27-8.14 (m, 2H) ppm. $^{13}$C-NMR (126 MHz, CDCl$_3$): δ 55.51 (CH$_3$, C-aliphatic), 56.40 (CH$_3$, C-aliphatic), 61.51 (—CH$_3$, C-aliphatic), 62.71 (CH$_3$, C-aliphatic), 104.02 (CH, C-aromatic), 112.06 (C, C-aromatic), 114.11 (CH, C-aromatic), 122.83 (C, C-aromatic), 129.99 (CH, C-aromatic), 136.92 (C, C-aromatic), 147.64 (C, C-aromatic), 149.45 (C, C-aromatic), 152.99 (C, C-aromatic), 155.26 (C, C-aromatic), 159.76 (C, C-aromatic), 163.05 (C, C-aromatic) ppm.

Example 38

Synthesis of 2-(pyridin-3-yl)-4H-benzo[d][1,3]oxazin-4-one (197)

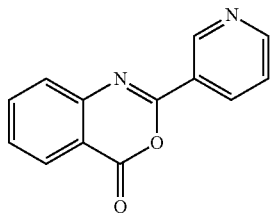

197

Compound 197 was obtained as a white powder in 81% yield. ¹H-NMR (CDCl₃): δ 7.49 (ddd, J=0.8, 4.8, 8.0 Hz, 1H), 7.60 (td, J=1.1, 7.9 Hz, 1H), 7.76 (dd, J=0.6, 8.1 Hz, 1H), 7.90 (ddd, J=1.5, 7.4, 8.1 Hz, 1H), 8.30 (dd, J=1.3, 7.9 Hz, 1H), 8.46-8.63 (m, 1H), 8.83 (dd, J=1.7, 4.8 Hz, 1H), 9.55 (dd, J=0.7, 2.2 Hz, 1H) ppm. ¹³C-NMR (126 MHz, CDCl₃): δ 117.20 (C, C-aromatic), 123.48 (C, C-aromatic), 126.42 (CH, C-aromatic), 127.42 (C, C-aromatic), 128.78 (CH, C-aromatic), 128.86 (CH, C-aromatic), 135.49 (CH, C-aromatic), 136.81 (CH, C-aromatic), 146.52 (C, C-aromatic), 149.73 (C, C-aromatic), 152.99 (C, C-aromatic), 155.60 (C, C-aromatic), 158.98 (C, C-aromatic) ppm.

Example 39

Synthesis of 5-fluoro-2-(pyridin-3-yl)-4H-benzo[d][1,3]oxazin-4-one (198)

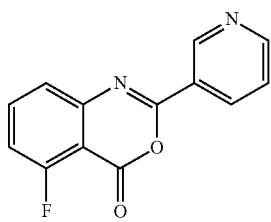

198

Compound 198 was obtained as a white powder in 62% yield. ¹H-NMR (CDCl₃): δ 7.22-7.29 (m, 2H), 7.50 (ddd, J=0.7, 4.8, 8.0 Hz, 1H), 7.57 (d, J=8.1 Hz, 1H), 7.85 (td, J=5.5, 8.2 Hz, 1H), 8.36-8.65 (m, 1H), 8.84 (dd, J=1.7, 4.8 Hz, 1H), 9.45-9.52 (m, 1H) ppm. ¹³C-NMR (126 MHz, CDCl₃): δ 115.75-115.92 (CH, C-aromatic), 123.30 (CH, C-aromatic), 123.33 (CH, C-aromatic), 125.97 (C, C-aromatic), 135.62 (CH, C-aromatic), 137.51-137.59 (CH, C-aromatic), 148.21 (C, C-aromatic), 149.86 (CH, C-aromatic), 153.30 (CH, C-aromatic), 154.46 (C, C-aromatic), 156.36 (C, C-aromatic), 160.87 (C, C-aromatic), 163.01 (C, C-aromatic) ppm. ¹⁹F-NMR: δ -105.84 ppm.

Example 40

Synthesis of 6,7,8-trimethoxy-2-(pyridin-3-yl)-4H-benzo[d][1,3]oxazin-4-one (199)

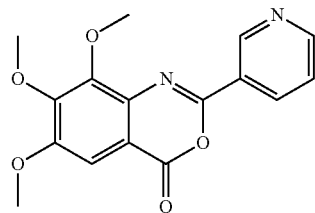

199

Compound 199 was obtained as a white powder in 75% yield. ¹H-NMR (CDCl₃): δ 4.02 (s, 3H), 4.10 (s, 3H), 4.20 (s, 3H), 7.29 (s, 1H), 7.37-7.59 (m, 1H), 8.50-8.65 (m, 1H), 8.81 (dd, J=1.7, 4.8 Hz, 1H), 9.55 (dd, J=0.7, 2.2 Hz, 1H) ppm. ¹³C-NMR (126 MHz, CDCl₃): δ 56.49 (CH₃, C-aromatic), 61.56 (CH₃, C-aromatic), 62.87 (CH₃, C-aromatic), 104.24 (CH, C-aromatic), 112.54 (C, C-aromatic), 123.45 (CH, C-aromatic), 126.60 (C, C-aromatic), 135.14 (CH, C-aromatic), 135.95 (C, C-aromatic), 148.21 (C, C-aromatic), 148.52 (C, C-aromatic), 149.47 (CH, C-aromatic), 149.62 (C, C-aromatic), 152.68 (CH, C-aromatic), 153.88 (C, C-aromatic), 158.94 (C, C-aromatic) ppm.

Example 41

Synthesis of 7-fluoro-2-(pyridin-3-yl)-4H-benzo[d][1,3]oxazin-4-one (200)

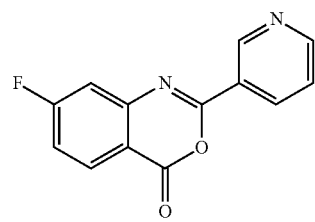

200

Compound 200 was obtained as a white powder in 58% yield. ¹H-NMR (CDCl₃): δ 7.27-7.35 (m, 1H), 7.42 (dd, J=2.4, 9.1 Hz, 1H), 7.50 (ddd, J=0.7, 4.8, 8.0 Hz, 1H), 8.31 (dd, J=5.9, 8.7 Hz, 1H), 8.55-8.60 (m, 1H), 8.85 (dd, J=1.7, 4.8 Hz, 1H), 9.54 (d, J=1.5 Hz, 1H) ppm. ¹³C-NMR (126 MHz, CDCl₃): δ 113.57 (CH, C-aromatic), 113.73 (C, C-aromatic), 117.27 (CH, C-aromatic), 123.52 (CH, C-aromatic), 126.07 (C, C-aromatic), 131.59 (CH, C-aromatic), 135.66 (CH, C-aromatic), 149.88 (CH, C-aromatic), 153.34 (CH, C-aromatic), 156.73 (C, C-aromatic), 158.00 (C, C-aromatic), 166.86 (C, C-aromatic), 168.91 (C, C-aromatic) ppm. ¹⁹F-NMR: δ -98.26 ppm.

Example 42

Synthesis of 6,7-dimethoxy-2-(pyridin-3-yl)-4H-benzo[d][1,3]oxazin-4-one (201)

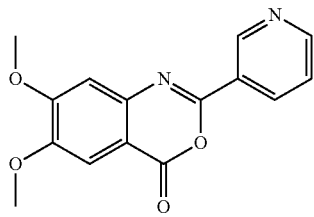

201

Compound 201 was obtained as a white powder in 58% yield. $^1$H-NMR (CDCl$_3$): δ 4.04 (s, 3H), 4.08 (s, 3H), 7.04 (bs, 1H), 7.37-7.64 (m, 1H), 7.55 (d, J=56.3 Hz, 1H), 8.31-8.61 (m, 1H), 8.81 (dd, J=1.7, 4.8, Hz, 1H), 9.52 (d, J=1.6 Hz, 1H) ppm. $^{13}$C-NMR (126 MHz, CDCl$_3$): δ 56.52 (CH$_3$, C-aliphatic), 56.60 (CH$_3$, C-aliphatic), 107.72 (CH, C-aromatic), 108.26 (CH, C-aromatic), 109.84 (C, C-aromatic), 123.45 (CH, C-aromatic), 126.60 (C, C-aromatic), 135.12 (CH, C-aromatic), 142.88 (C, C-aromatic), 149.46 (CH, C-aromatic), 150.15 (C, C-aromatic), 152.66 (CH, C-aromatic), 154.81 (C, C-aromatic), 156.63 (C, C-aromatic), 158.96 (C, C-aromatic) ppm.

Example 43

Synthesis of 2-(2-fluorophenyl)-6,7-dimethoxy-4H-benzo[d][1,3]oxazin-4-one (202)

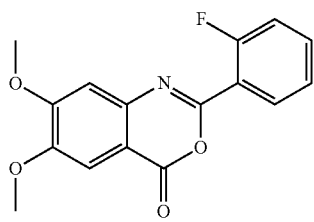

202

Compound 202 was obtained as a white powder in 78% yield. $^1$H-NMR (CDCl$_3$): δ 3.95 (s, 3H), 3.97 (s, 3H), 7.08 (s, 1H), 7.11-7.25 (m, 2H), 7.39-7.49 (m, 1H), 7.49-7.56 (m, 1H), 8.04 (td, J=1.8, 7.7 Hz, 1H) ppm. $^{13}$C-NMR (126 MHz, CDCl$_3$): δ 56.50 (CH$_3$, C-aliphatic), 56.59 (CH$_3$, C-aliphatic), 107.54 (CH, C-aromatic), 108.38 (CH, C-aromatic), 109.66 (C, C-aromatic), 117.16 (CH, C-aromatic), 124.32 (CH, C-aromatic), 130.91 (CH, C-aromatic), 133.65 (CH, C-aromatic), 143.04 (C, C-aromatic), 150.08 (C, C-aromatic), 154.10 (C, C-aromatic), 156.49 (C, C-aromatic), 159.18 (C, C-aromatic), 160.23 (C, C-aromatic), 162.29 (C, C-aromatic) ppm. $^{19}$F-NMR: δ −109.78 ppm.

Example 44

Synthesis of 8-methoxy-2-(pyridin-3-yl)-4H-benzo[d][1,3]oxazin-4-one (202)

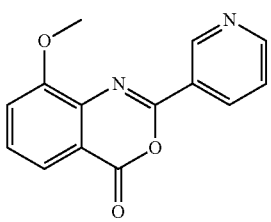

202

Compound 202 was obtained as a white powder in 72% yield. $^1$H-NMR (CDCl$_3$): δ 3.99 (s, 3H), 7.19 (s, 1H), 7.35-7.43 (m, 1H), 7.44 (t, J=8.0 Hz, 1H), 7.78 (dd, J=1.2, 7.9 Hz, 1H), 8.43-8.64 (m, 1H), 8.72 (dd, J=1.7, 4.8 Hz, 1H), 9.46 (dd, J=0.7, 2.2 Hz, 1H) ppm. $^{13}$C-NMR (126 MHz, CDCl$_3$): δ 56.66 (CH$_3$, C-aliphatic), 117.65 (CH, C-aromatic), 118.19 (C, C-aromatic), 119.97 (CH, C-aromatic), 123.43 (CH, C-aromatic), 126.53 (C, C-aromatic), 129.31 (CH, C-aromatic), 135.60 (CH, C-aromatic), 136.46 (C, C-aromatic), 149.69 (CH, C-aromatic), 152.92 (CH, C-aromatic), 154.50 (C, C-aromatic), 158.89 (CH, C-aromatic) ppm.

Example 45

Synthesis of 5,6,7-trimethoxy-2-(4-methoxyphenyl)-4H-benzo[d][1,3]oxazin-4-one (203)

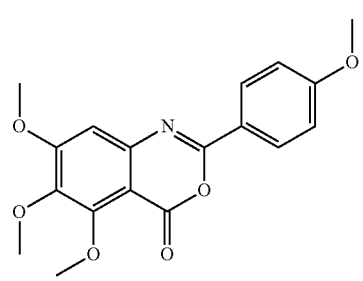

203

Compound 203 was obtained as a white solid in 93% yield. $^1$H-NMR (CDCl$_3$): δ 3.92 (s, 3H), 3.99 (s, 3H), 4.1 (s, 3H), 4.19 (s, 3H), 7.1 (d, J=9.05 Hz, 2H), 7.45 (s, 1H), 8.28 (d, J=8.9 Hz, 2H) ppm. $^{13}$C-NMR (126 MHz, CDCl$_3$): δ 55.52 (CH$_3$, C-aliphatic), 56.40 (CH$_3$, C-aliphatic), 61.53 (CH$_3$, C-aliphatic), 62, 73 (CH$_3$, C-aliphatic), 103.99 (CH, C-aromatic), 112.04 (C, C-aromatic), 114.10 (CH, C-aromatic), 122.79 (C, C-aromatic), 129.98 (CH, C-aromatic), 136.92 (C, C-aromatic), 147.61 (C, C-aromatic), 149.42 (C, C-aromatic), 152.97 (C, C-aromatic), 155.24 (C, C-aromatic), 159.77 (C, C-aromatic), 163.04 (C, C-aromatic) ppm.

Example 46

Synthesis of 2-(2-fluorophenyl)-5,6,7-trimethoxy-4H-benzo[d][1,3]oxazin-4-one (204)

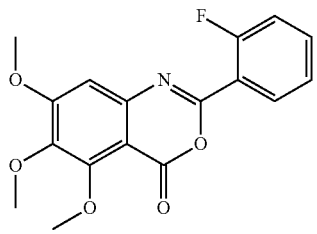

Compound 204 was obtained as a white solid in 68.66% yield. $^1$H-NMR (CDCl$_3$): δ 4.00 (s, 3H), 4.09 (s, 3H), 4.20 (s, 3H), 7.21-7.25 (m, 1H), 7.3 (td, J=1.2, 7.5 Hz, 1H), 7.47 (s, 1H), 7.52-7.57 (m, 2H), 8.16 (td, J=1.65, 7.7 Hz, 1H) ppm. $^{13}$C-NMR (126 MHz, CDCl$_3$): δ 56.46 (CH$_3$, C-aliphatic), 61.56 (CH$_3$, C-aliphatic), 62.78 (CH$_3$, C-aliphatic), 103.86 (CH, C-aromatic), 112.36 (C, C-aromatic), 117.26 (CH, C-aromatic), 119.13 (C, C-aromatic), 124.25 (CH, C-aromatic), 130.86 (CH, C-aromatic), 133.66 (CH, C-aromatic), 136.06 (C, C-aromatic), 148.03 (C, C-aromatic), 149.31 (C, C-aromatic), 153.74 (C, C-aromatic), 159.25 (C, C-aromatic), 160.41 (C, C-aromatic), 162.49 (C, C-aromatic) ppm.

Example 47

Synthesis of 5,6,7-trimethoxy-2-(pyridin-3-yl)-4H-benzo[d][1,3]oxazin-4-one (205)

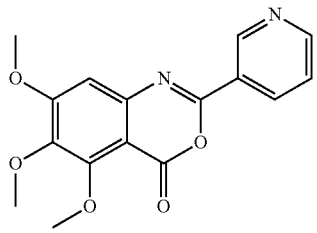

Compound 205 was obtained as a white solid in 50% yield. $^1$H-NMR (CDCl$_3$): δ 4.01 (s, 3H), 4.09 (s, 3H), 4.19 (s, 3H), 7.47 (s, 1H), 7.49 (dd, J=0.8, 7.55 Hz, 1H), 8.58 (dt, J=1.9, 8.1 Hz, 1H), 8.80 (dd, J=1.7, 4.75 Hz, 1H), 9.54 (d, J=1.95 Hz, 1H) ppm. $^{13}$C-NMR (126 MHz, CDCl$_3$): δ 56.49 (CH$_3$, C-aliphatic), 61.57 (CH$_3$, C-aliphatic), 62.89 (CH$_3$, C-aliphatic), 104.22 (CH, C-aromatic), 112.52 (C, C-aromatic), 123.58 (CH, C-aromatic), 126.72 (C, C-aromatic), 135.39 (CH, C-aromatic), 135.90 (C, C-aromatic), 148.02 (C, C-aromatic), 149.17 (CH, C-aromatic), 149.61 (C, C-aromatic), 152.35 (CH, C-aromatic), 153.23 (C, C-aromatic), 153.89 (C, C-aromatic), 158.89 (C, C-aromatic) ppm.

Example 48

Synthesis of 2-(2-(methylthio)pyridin-3-yl)-4H-benzo[d][1,3]oxazin-4-one (206)

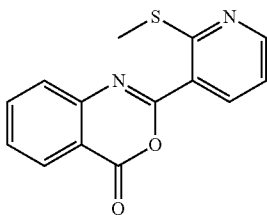

Compound 206 was obtained as a white solid in 85% yield. $^1$H-NMR (CDCl$_3$): δ 2.62 (s, 3H), 7.18 (dd, J=4.7, 7.9 Hz, 1H), 7.49-7.66 (m, 1H), 7.83 (dd, J=0.7, 8.1 Hz, 1H), 7.86-7.93 (m, 1H), 8.28 (dd, J=1.1, 7.9 Hz, 1H), 8.42 (dd, J=1.8, 7.9 Hz, 1H), 8.64 (dd, J=1.8, 4.7 Hz, 1H) ppm. $^{13}$C-NMR (126 MHz, CDCl$_3$): δ 14.73 (CH$_3$, C-aliphatic), 116.89 (C, C-aromatic), 118.22 (CH, C-aromatic), 123.64 (C, C-aromatic), 127.32 (CH, C-aromatic), 128.66 (CH, C-aromatic), 128.87 (CH, C-aromatic), 136.72 (CH, C-aromatic), 137.23 (C, C-aromatic), 146.20 (CH, C-aromatic), 151.14, 154.78 (C, C-aromatic), 159.32 (C, C-aromatic), 161.86 (C, C-aromatic) ppm.

General Procedure 2

The compounds of the application with the general formula below can be prepared according to the synthetic scheme shown in Scheme 2.

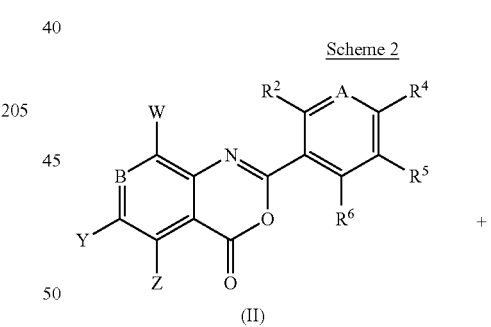

Scheme 2

+

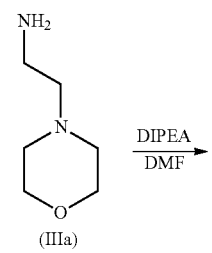

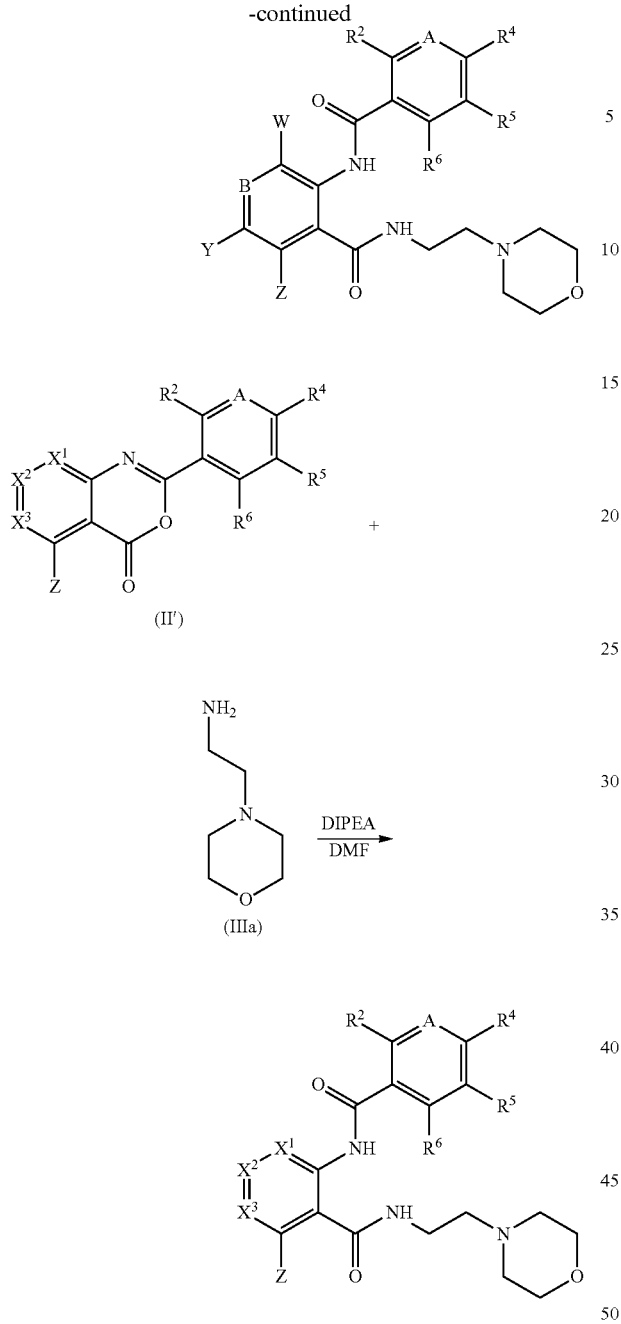

(II')

(IIIa)

To a solution of compound (II) or (II') (1 equivalent) in N,N-dimethyl-formamide (DMF) is added 2 equivalents of N,N-diisopropylethylamine (DIPEA) and 2.2 equivalent of 2-morpholinoethanamine (IIIa). The reaction mixture is stirred at about 15° C. to about 28° C. for about 12 hours to about 24 hours. The reaction mixture is diluted with water, washed with ethyl acetate, washed with brine, dried over $Mg_2SO_4$, filtered and evaporated to give a crude compound which is then purified by silica gel column using a mixture of Chloroform:Methanol (9:1) as eluent. The product is collected under reduced pressure to provide the compound with the general formula shown in Scheme 2.

Compounds 4, 5, 7-15, 17-33, 99, 103, 113, 145-148 were prepared according to General Procedure 2 substituting (II) or (II') with the appropriate substituted compound.

Example 49

Synthesis of 2-(3-aminobenzamido)-N-(2-morpholinoethyl)benzamide (4)

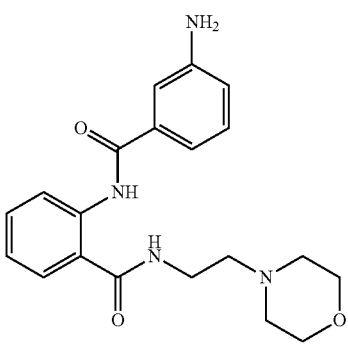 [SMILES: O=C(Nc1ccccc1C(=O)NCCN1CCOCC1)c1cccc([N+](=O)[O-])c1]

4

Compound 4 was obtained as a white powder in 47% yield. $^1$H-NMR (CDCl$_3$): δ 2.55 (s, 4H), 2.66 (t, J=5.9 Hz, 2H), 3.58 (dd, J=5.4, 11.1 Hz, 2H), 3.74-3.78 (m, 4H), 3.87 (s, 2H), 6.87 (dd, J=1.6, 7.9 Hz, 1H), 7.01 (s, 1H), 7.13-7.19 (m, 1H), 7.30-7.33 (m, 1H), 7.37-7.39 (m, 1H), 7.42 (d, J=7.7 Hz, 1H), 7.55 (dd, J=7.9, 16.7 Hz, 2H), 8.91-8.78 (m, 1H), 12.08 (s, 1H) ppm. $^{13}$C-NMR (126 MHz, CDCl$_3$): δ 35.93 (CH$_2$, C-aromatic), 53.27 (CH$_2$, C-aromatic), 56.54 (CH$_2$, C-aromatic), 66.94 (CH$_2$, C-aromatic), 114.10 (CH, C-aromatic), 117.07 (CH, C-aromatic), 118.35 (CH, C-aromatic), 121.73 (CH, C-aromatic), 122.82 (CH, C-aromatic), 126.53 (CH, C-aromatic), 129.70 (CH, C-aromatic), 132.72 (CH, C-aromatic), 135.75 (C, C-aromatic), 136.51 (C, C-aromatic), 140.09 (C, C-aromatic), 146.80 (C, C-aromatic), 165.67 (C, C-aromatic), 169.18 (C, C-aromatic) ppm. MS(ESI)$^+$: 369 [M+H]$^+$. m.p.: (from ethanol/water) 126-128° C.

Example 50

Synthesis of 2-(4-aminobenzamido)-N-(2-morpholinoethyl)benzamide (5)

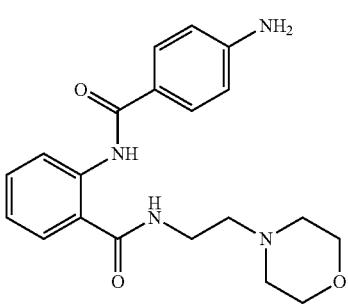 [SMILES: O=C(Nc1ccccc1C(=O)NCCN1CCOCC1)c1ccc([N+](=O)[O-])cc1]

5

Compound 5 was obtained as a light brown powder in 42% yield. $^1$H-NMR (CDCl$_3$): δ 2.54 (s, 4H), 2.65 (t, J=5.9 Hz, 2H), 3.51 (s, 4H), 3.55-3.61 (m, 1H), 3.73-3.78 (m, 1H), 4.05 (s, 2H), 6.75 (d, J=8.6 Hz, 2H), 7.03 (s, 1H), 7.12 (t, J=7.6 Hz, 1H), 7.53 (dd, J=7.8, 13.5 Hz, 2H), 7.90 (d, J=8.5 Hz, 2H), 8.81 (d, J=8.3 Hz, 1H), 11.99 (s, 1H) ppm. $^{13}$C-NMR (CDCl$_3$): δ 35.98 (CH$_2$, C-aliphatic), 53.27 (CH$_2$, C-aliphatic), 56.53 (CH$_2$, C-aliphatic), 66.97 (CH$_2$, C-aliphatic), 114.32 (CH, C-aromatic), 120.28 (C, C-aromatic), 121.61 (CH, C-aromatic), 122.35 (CH, C-aromatic), 124.42 (C, C-aromatic), 126.49 (CH, C-aromatic), 129.33 (CH, C-aromatic), 132.66 (CH, C-aromatic), 140.46 (C, C-aromatic), 149.92 (C, C-aromatic), 165.42 (C, C-aromatic), 169.31 (C, C-aromatic) ppm. MS(ESI)$^+$: 369.2 [M+H]$^+$. m.p.: (from ethanol/water) 101-105° C.

Example 51

Synthesis of 2-(3-chlorobenzamido)-N-(2-morpholinoethyl)benzamide (7)

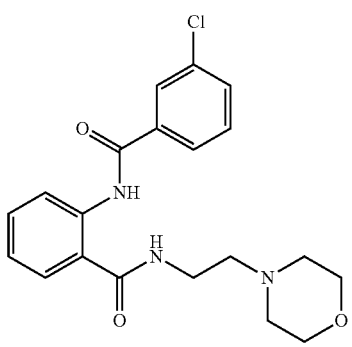

Compound 7 was obtained as a white powder in 10% yield. $^1$H-NMR (CDCl$_3$): δ 2.55 (s, 4H), 2.66 (t, J=5.9 Hz, 2H), 3.59 (dd, J=5.5, 11.1 Hz, 2H), 3.73-3.81 (m, 4H), 7.03 (s, 1H), 7.14-7.19 (m, 1H), 7.47 (t, J=7.8 Hz, 1H), 7.52-7.56 (m, 2H), 7.57-7.60 (m, 1H), 7.90-7.95 (m, 1H), 8.07 (t, J=1.8 Hz, 1H), 8.82 (dd, J=0.7, 8.4 Hz, 1H), 12.35 (s, 1H) ppm. $^{13}$C-NMR (CDCl$_3$): δ 36.03 (CH$_2$, C-aliphatic), 53.29 (CH$_2$, C-aliphatic), 56.55 (CH$_2$, C-aliphatic), 67.6 (CH$_2$, C-aliphatic), 120.25 (C, C-aromatic), 121.57 (CH, C-aromatic), 123.15 (CH, C-aromatic), 125.09 (CH, C-aromatic), 1226.64 (CH, C-aromatic), 128.09 (CH, C-aromatic), 128.41 (CH, C-aromatic), 130.05 (CH, C-aromatic), 131.84 (CH, C-aromatic), 132.77 (C, C-aromatic), 135.00 (C, C-aromatic), 136.74 (C, C-aromatic), 139.85 (C, C-aromatic), 164.16 (C, C-aromatic), 169.06 (C, C-aromatic) ppm. MS(ESI)$^+$: 388.2, 389.2 [M+H]+. m.p.: (from ethanol) 107-109° C.

Example 52

Synthesis of 2-(4-chlorobenzamido)-N-(2-morpholinoethyl)benzamide (8)

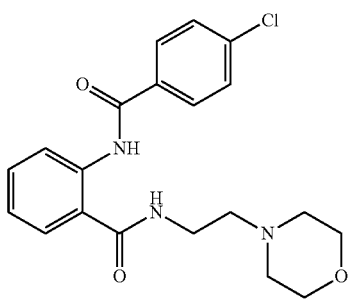

Compound 8 was obtained as a white powder in 40% yield. $^1$H-NMR (CDCl$_3$): δ 2.54 (s, 4H), 2.66 (t, J=5.9 Hz, 2H), 3.58 (dd, J=5.5, 11.1 Hz, 2H), 3.73-3.81 (m, 4H), 7.03 (s, 1H), 7.16-7.21 (m, 1H), 7.49-7.52 (m, 2H), 7.53-7.61 (m, 2H), 7.94-8.10 (m, 2H), 8.83 (d, J=8.4 Hz, 1H), 12.35 (s, 1H) ppm. $^{13}$C-NMR (CDCl$_3$): δ 35.97 (CH$_2$, C-aliphatic), 53.26 (CH$_2$, C-aliphatic), 56.43 (CH$_2$, C-aliphatic), 67.00 (CH$_2$, C-aliphatic), 120.14 (C, C-aromatic), 121.60 (CH, C-aromatic), 123.05 (CH, C-aromatic), 126.51 (CH, C-aromatic), 128.87 (CH, C-aromatic), 129.03 (CH, C-aromatic), 132.89 (CH, C-aromatic), 133.31 (C, C-aromatic), 138.11 (C, C-aromatic), 140.07 (C, C-aromatic), 164.47 (C, C-aromatic), 169.12 (C, C-aromatic) ppm. MS(ESI)$^+$: 388.1, 389.2 [M+H]$^+$. m.p.: (from ethanol/water) 93-95° C.

Example 53

Synthesis of N-(2-morpholinoethyl)-2-(2-(trifluoromethyl)benzamido) benzamide (9)

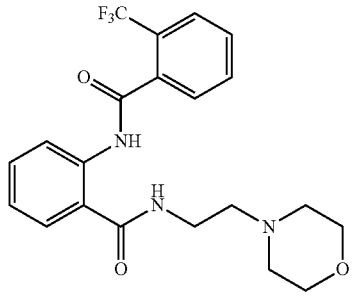

Compound 9 was obtained as a white powder in 59% yield. $^1$H-NMR (CDCl$_3$): δ 2.50-2.55 (m, 4H), 2.60 (dd, J=10.2, 16.1 Hz, 2H), 3.50 (dd, J=5.6, 11.1 Hz, 2H), 3.69-3.80 (m, 4H), 6.94 (s, 1H), 7.11-7.24 (m, 1H), 7.52 (dd, J=1.4, 7.9 Hz, 1H), 7.56-7.62 (m, 2H), 7.66 (t, J=7.4 Hz, 1H), 7.70 (t, J=7.4 Hz, 1H), 7.77 (d, J=7.8 Hz, 1H), 8.80 (d, J=8.3 Hz, 1H), δ 11.59 (s, 1H) ppm. $^{13}$C NMR (126 MHz, CDCl$_3$): 35.90 (CH$_2$, C-aliphatic), 53.27 (CH$_2$, C-aliphatic), 56.48 (CH$_2$, C-aliphatic), 66.98 (CH$_2$, C-aliphatic), 120.69 (C, C-aromatic), 121.82 (CH, C-aromatic), 123.46 (CH, C-aromatic), 124.64 (C, C-aromatic), 126.74 (CH, C-aromatic), 126.78 (C, C-aromatic), 127.80 (CH, C-aromatic), 128.15 (CH, C-aromatic), 130.01 (CH, C-aromatic), 132.17 (CH, C-aromatic), 132.79 (CH, C-aromatic), 139.46 (C, C-aromatic), 166.14 (C, C-aromatic), 168.71 (C, C-aromatic) ppm. $^{19}$F-NMR: δ −58.944 ppm. MS(ESI)$^+$: 422.3 [M+H]$^+$. m.p.: 90-92° C.

Example 54

Synthesis of N-(2-morpholinoethyl)-2-(3-(trifluoromethyl)benzamido) benzamide (10)

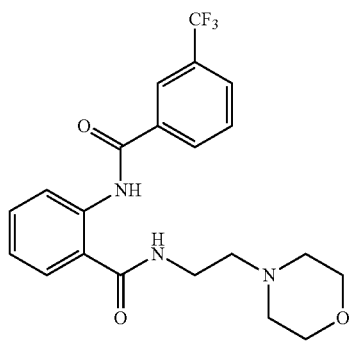

Compound 10 was obtained as a white powder in 63% yield. ¹H-NMR (CDCl₃): δ 2.53-2.57 (m, 4H), 2.64-2.68 (m, 2H), 3.50-3.63 (m, 2H), 3.74-3.82 (m, 4H), 7.02 (s, 1H), 7.16-7.26 (m, 1H), 7.54-7.62 (m, 2H), 7.67 (d, J=7.8 Hz, 1H), 7.82 (d, J=7.8 Hz, 1H), 8.22 (d, J=7.9 Hz, 1H), 8.38 (s, 1H), 8.85 (dd, J=0.9, 8.4 Hz, 1H), 12.51 (s, 1H) ppm. ¹³C NMR (126 MHz, CDCl₃): 36.00 ($CH_2$, C-aliphatic), 53.29 ($CH_2$, C-aliphatic), 56.46 ($CH_2$, C-aliphatic), 67.00 ($CH_2$, C-aliphatic), 120.18 (C, C-aromatic), 121.67 (CH, C-aromatic), 123.24 (C, C-aromatic), 125.04 (CH, C-aromatic), 125.07 (CH, C-aromatic), 126.47 (CH, C-aromatic), 128.30, 128.33 (CH, C-aromatic), 129.34 (CH, C-aromatic), 130.09 (CH, C-aromatic), 132.25 (C, C-aromatic), 132.92 (CH, C-aromatic), 135.85 (C, C-aromatic), 139.98 (C, C-aromatic), 164.04 (C, C-aromatic), 169.05 (C, C-aromatic) ppm. ¹⁹F-NMR: δ -62.90. ppm. MS(ESI)⁺: 422.1 [M+H]⁺.

Example 55

Synthesis of N-(2-morpholinoethyl)-2-(4-(trifluoromethyl)benzamido) benzamide (11)

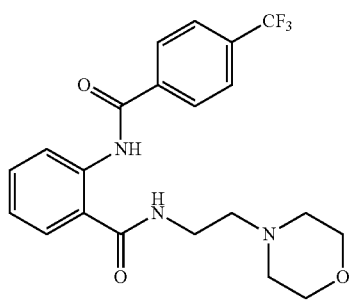

Compound 11 was obtained as a white powder in 22% yield. ¹H-NMR (CDCl₃): δ 2.56 (s, 4H), 2.67 (t, J=5.9 Hz, 2H), 3.50-3.60 (m, 2H), 3.71-3.79 (m, 4H), 7.09 (s, 1H), 7.14-7.21 (m, 1H), 7.55-7.62 (m, 2H), 7.80 (d, J=8.2 Hz, 2H), 8.18 (d, J=8.1 Hz, 2H), 8.86 (dd, J=0.8, 8.4 Hz, 1H), 12.53 (s, 1H) ppm. ¹³C NMR (126 MHz, CDCl₃): δ35.98 ($CH_2$, C-aliphatic), 53.28 ($CH_2$, C-aliphatic), 56.46 ($CH_2$, C-aliphatic), 66.96 ($CH_2$, C-aliphatic), 120.18 (C, C-aromatic), 121.62 (CH, C-aromatic), 123.28 (CH, C-aromatic), 125.82 (CH, C-aromatic), 126.51 (CH, C-aromatic), 127.87 (CH, C-aromatic), 132.95 (CH, C-aromatic), 137.85 (C, C-aromatic), 138.22 (C, C-aromatic), 139.99 (C, C-aromatic), 163.66 (C, C-aromatic), 168.94 (C, C-aromatic) ppm. ¹⁹F-NMR: δ -63.08 ppm. MS(ESI)⁺: 422.1 [M+H]⁺. m.p.: 99-101° C.

Example 56

Synthesis of 2-fluoro-4-methoxy-N-(2-((2-morpholinoethyl)carbamoyl)phenyl) benzamide (12)

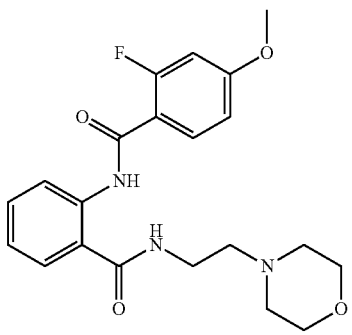

Compound 12 was obtained as a light brown powder in 57% yield. ¹H-NMR (CDCl₃): δ 2.54 (s, 4H), 2.64 (t, J=5.9 Hz, 2H), 3.58 (dd, J=5.4, 11.1 Hz, 2H), 3.73-3.78 (m, 4H), 3.88 (s, 3H), 6.71 (dd, J=2.4, 13.3 Hz, 1H), 6.79-6.84 (m, 1H), 6.90 (s, 1H), 7.12-7.21 (m, 1H), 7.49-7.58 (m, 2H), 8.06 (t, J=8.9 Hz, 1H), 8.74 (d, J=8.4 Hz, 1H), 11.69 (d, J=8.5 Hz, 1H) ppm. ¹³C-NMR (CDCl₃): δ 35.90 ($CH_2$, C-aliphatic), 53.28 ($CH_2$, C-aliphatic), 55.83 ($CH_3$, C-aliphatic), 56.65 ($CH_2$, C-aliphatic), 66.89 ($CH_2$, C-aliphatic), 101.87 (C, C-aromatic), 110.68 (CH, C-aromatic), 114.79 (C, C-aromatic), 122.07 (C, C-aromatic), 122.64 (CH, C-aromatic), 123.19 (CH, C-aromatic), 126.62 (CH, C-aromatic), 132.29 (CH, C-aromatic), 132.90 (CH, C-aromatic), 139.19 (C, C-aromatic), 160.60 (C, C-aromatic), 162.08 (C, C-aromatic), 162.59 (C, C-aromatic), 163.67 (C, C-aromatic), 163.76 (C, C-aromatic), 168.72 (C, C-aromatic) ppm. ¹⁹F-NMR (CDCl₃): δ -109.25 ppm. MS(ESI)⁺: 402.2 [M+H]⁺. m.p.: (from ethanol) 115-117° C.

Example 57

Synthesis of 2-fluoro-6-(2-fluorobenzamido)-N-(2-morpholinoethyl) benzamide (13)

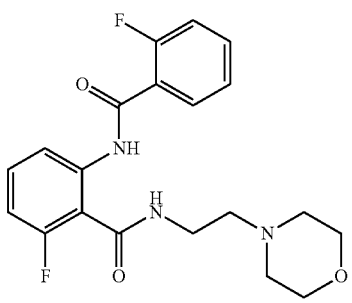

Compound 13 was obtained as a white powder in 23% yield. $^1$H-NMR (CDCl$_3$): δ 2.53 (s, 4H), 2.62 (t, J=6.0 Hz, 2H), 3.59 (dd, J=5.0, 10.6 Hz, 2H), 3.72-3.81 (m, 4H), 6.93 (dd, J=8.3, 11.8 Hz, 1H), 7.22 (dd, J=8.4, 11.2 Hz, 1H), 7.30-7.33 (m, 1H), 7.40-7.56 (m, 3H), 8.05 (td, J=7.7, 1.8 Hz, 1H), 8.61 (d, J=8.5 Hz, 1H), 12.08 (d, J=6.4 Hz, 1H) ppm. $^{13}$C-NMR (CDCl$_3$): δ 36.19 (CH$_2$, C-aliphatic), 53.14 (CH$_2$, C-aliphatic), 56.05 (CH$_2$, C-aliphatic), 67.00 (CH$_2$, C-aliphatic), 110.30 (C, C-aromatic), 110.85 (CH, C-aromatic), 116.59 (CH, C-aromatic), 118.35 (CH, C-aromatic), 124.65 (C, C-aromatic), 131.53 (CH, C-aromatic), 132.59 (CH, C-aromatic), 132.68 (CH, C-aromatic), 133.46 (CH, C-aromatic), 133.53 (CH, C-aromatic), 140.89 (C, C-aromatic), 159.55 (C, C-aromatic), 161.42 (C, C-aromatic), 162.45 (C, C-aromatic), 164.64 (C, C-aromatic) ppm. MS(ESI)$^+$: 390.2 [M+H]$^+$. $^{19}$F-NMR (CDCl$_3$): δ −112.34, −113.94 ppm. m.p.: 88-90° C.

Example 58

Synthesis of 4-fluoro-2-(2-fluorobenzamido)-N-(2-morpholinoethyl) benzamide (14)

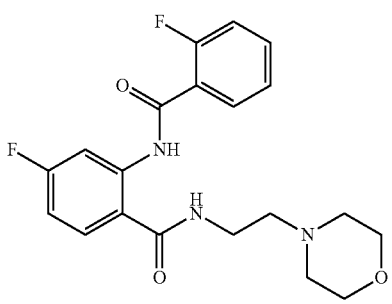

14

Compound 14 was obtained as a white powder in 47% yield. $^1$H-NMR (CDCl$_3$): δ 2.53 (s, 4H), 2.57-2.71 (m, 2H), 3.56 (dd, J=5.5, 11.1 Hz, 2H), 3.69-3.85 (m, 4H), 6.79-6.86 (m, 2H), 7.16-7.22 (m, 1H), 7.25-7.31 (m, 1H), 7.45-7.58 (m, 2H), 7.98-8.06 (m, 1H), 8.65 (dd, J=2.6, 11.9 Hz, 1H), 12.11 (d, J=6.7 Hz, 1H) ppm. $^{13}$C-NMR (126 MHz, CDCl$_3$): δ 35.97 (CH$_2$, C-aromatic), 53.28 (CH$_2$, C-aromatic), 56.53 (CH$_2$, C-aromatic), 66.97 (CH$_2$, C-aromatic), 110.19 (CH, C-aromatic), 110.37 (CH, C-aromatic), 116.50 (CH, C-aromatic), 117.53 (C, C-aromatic), 122.04 (C, C-aromatic), 124.73 (CH, C-aromatic), 128.42 (CH, C-aromatic), 131.57 (CH, C-aromatic), 133.69 (CH, C-aromatic), 159.33 (C, C-aromatic), 161.35 (C, C-aromatic), 163.72 (C, C-aromatic), 165.71 (C, C-aromatic), 168.01 (C, C-aromatic) ppm. $^{19}$F-NMR: δ −104.11, −112.36 ppm. MS(ESI)$^+$: 390.2 [M+H]$^+$. m.p.: 104-106° C.

Example 59

Synthesis of 2-(2-fluorobenzamido)-4-methoxy-N-(2-morpholinoethyl) benzamide (15)

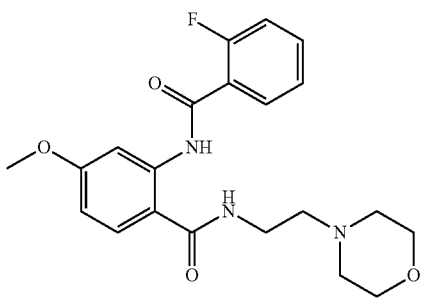

15

Compound 15 was obtained as a white powder in 36% yield. $^1$H-NMR (CDCl$_3$): δ 2.53 (s, 4H), 2.63 (t, J=5.9 Hz, 2H), 3.54 (dd, J=5.4, 11.1 Hz, 2H), 3.73-3.78 (m, 4H), 3.94 (s, 3H), 6.71 (dd, J=2.6, 8.7 Hz, 1H), 6.80 (s, 1H), 7.22 (dd, J=8.4, 10.5 Hz, 1H), 7.29-7.32 (m, 1H), 7.45 (d, J=8.8 Hz, 1H), 7.48-7.53 (m, 1H), 7.95-8.04 (m, 1H), 8.55 (d, J=2.6 Hz, 1H), δ 12.33 (d, J=5.3 Hz, 1H) ppm. $^{13}$C-NMR (CDCl$_3$): δ 35.83 (CH$_2$, C-aliphatic), 53.27 (CH$_2$, C-aliphatic), 55.58 (CH$_3$, C-aliphatic), 56.61 (CH$_2$, C-aliphatic), 67.00 (CH$_2$, C-aliphatic), 106.06 (CH, C-aromatic), 110.35 (CH, C-aromatic), 116.62 (C, C-aromatic), 124.60 (CH, C-aromatic), 127.87 (CH, C-aromatic), 131.29 (CH, C-aromatic), 133.31 (CH, C-aromatic), 141.66 (CH, C-aromatic) ppm. $^{19}$F-NMR: δ −112.57 ppm. MS(ESI)$^+$: 402.2 [M+H]$^+$. m.p.: (from ethanol/water) 114-116° C.

Example 60

Synthesis of 2-(3-fluorobenzamido)-3-methoxy-N-(2-morpholinoethyl) benzamide (17)

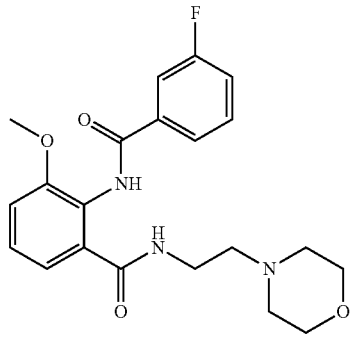

17

Compound 17 was obtained as a white powder in 88% yield. $^1$H-NMR (CDCl$_3$): δ 2.42-2.50 (m, 4H), 2.52-2.56 (m, 2H), 3.45-3.49 (m, 2H), 3.67-3.69 (m, 4H), 3.91 (s, 3H), 6.77-6.81 (m, 1H), 7.11-7.15 (m, 2H), 7.25-7.27 (m, 1H), 7.30-7.32 (m, 1H), 7.46-7.50 (m, 1H), 7.68-7.70 (m, 1H), 7.755 (d, J=7.55 Hz, 1H), 9.157 (d, J=7.42, 1H) ppm. $^{13}$C-NMR (126 MHz, CDCl$_3$): δ 36.00 (CH$_2$, C-aliphatic), 53.26 (CH$_2$, C-aliphatic), 56.24 (CH$_3$, C-aliphatic), 56.67 (CH$_2$, C-aliphatic), 66.92 (CH$_2$, C-aliphatic), 113.6 (CH, C-aromatic), 114.02 (CH, C-aromatic), 115.06 (CH, C-aromatic), 118.99 (CH, C-aromatic), 120.10 (CH, C-aromatic), 123.14 (CH, C-aromatic), 124.83 (C, C-aromatic), 126.96 (CH, C-aromatic), 130.34 (C, C-aromatic), 137.11 (C, C-aromatic), 154.17 (C, C-aromatic), 163.0 (C, C-aromatic), 168.38 (C, C-aromatic), 170.30 (C, C-aromatic) ppm. $^{19}$F-NMR: −111.75 ppm. MS(ESI)$^+$: 402.2 [M+H]$^+$. m.p.: 128-131° C.

Example 61

Synthesis of 2-(4-fluorobenzamido)-3-methoxy-N-(2-morpholinoethyl) benzamide (18)

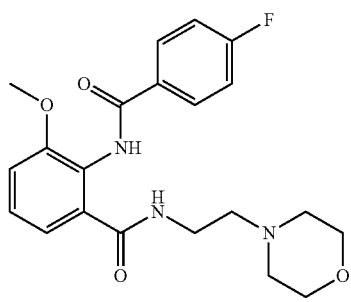

Compound 18 was obtained as a white powder in 30% yield. $^1$H-NMR (CDCl$_3$): δ 2.45 (t, J=4.36 Hz, 4H), 2.537 (dd, 4.18, 7.84 Hz, 2H), 3.45-3.49 (m, 2H), 3.687 (t, J=4.63 Hz, 4H), 3.913 (s, 3H), 6.79-6.80 (m, 1H), 7.10-7.19 (m, 3H), 7.291 (q, J=4.88 Hz, 2H), 7.98-8.02 (m, 2H), 9.101 (s, 1H) ppm. $^{13}$C-NMR (CDCl$_3$): 36.04 (CH$_2$, C-aliphatic), 53.27 (CH$_2$, C-aliphatic), 56.23 (CH$_3$, C-aliphatic), 56.71 (CH$_2$, C-aliphatic), 66.91 (CH$_2$, C-aliphatic), 114.02 (CH, C-aromatic), 115.59 (CH, C-aromatic), 115.77 (CH, C-aromatic), 119.13 (CH, C-aromatic), 126.83 (CH, C-aromatic), 130.03 (CH, C-aromatic), 130.10 (CH, C-aromatic), 130.49 (C, C-aromatic), 131.78 (C, C-aromatic), 154.23 (C, C-aromatic), 164.05 (C, C-aromatic), 164.92 (C, C-aromatic), 166.06 (C, C-aromatic), 168.42 (C, C-aromatic) ppm. $^{19}$F-NMR (CDCl$_3$CDCl$_3$): −107.695 ppm. MS(ESI)$^+$: 402.2 [M+H]$^+$. m.p.: 148-151° C.

Example 62

Synthesis of 2-(2-fluorobenzamido)-4,5-dimethoxy-N-(2-morpholinoethyl) benzamide (19)

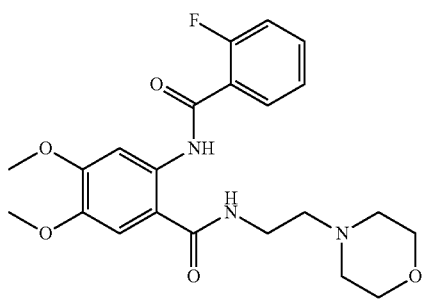

Compound 19 was obtained as a white solid in 16% yield. $^1$H-NMR (500 MHz, CDCl$_3$): δ 12.08 (d, J=5, 1H, ArNHCO), 8.58 (s, 1H, CONHCH$_2$), 8.04 (dt, J=7.65, 1.75, 1H, H), 7.53-7.48 (m, 1H), 7.29 (td, J=7.4, 1.15, 1H), 7.21 (dd, J=11.35, 0.9, 1H), 7.00 (s, 1H), 6.93 (s, 1H), 4.02 (s, 3H, OCH$_3$), 3.95 (s, 3H, OCH$_3$), 3.75 (t, J=4.25, 4H), 3.56 (q, J=5.8, 2H, NHCH$_2$CH$_2$), 2.66 (t, J=5.8, 2H, NHCH$_2$CH$_2$), 2.56 (s, 4H). $^{13}$C-NMR (126 MHz, CDCl$_3$) δ 168.39 (ArC=O), 162.32 (ArC=O), 161.36 (ArC), 159.37 (ArC), 152.11 (ArC), 144.50 (ArC), 134.91 (ArC), 133.31 (d, $J_{C-F}$=8.82, ArCH), 131.30 (d, $J_{C-F}$=1.26, ArCH), 124.63 (d, $J_{C-F}$=15, ArCH), 116.53 (d, $J_{C-F}$=23.94, ArCH), 112.87 (ArC), 109.52 (ArCH), 105.68 (ArCH), 66.94 (CH$_2$), 56.63 (CH$_2$), 56.45 (CH$_3$), 56.16 (CH$_3$), 53.23 (CH$_2$), 35.72 (CH$_2$). MS (ESI): 432.2 [M+1]. m.p. (from ethanol/water): 136° C.

Example 63

Synthesis of 6-(2-fluorobenzamido)-2,3,4-trimethoxy-N-(2-morpholinoethyl) benzamide (20)

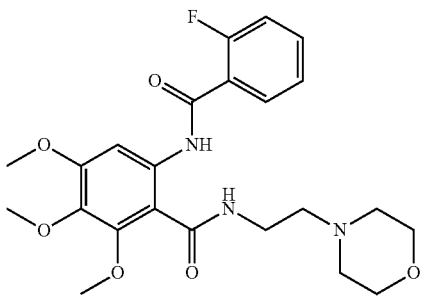

Compound 20 was obtained as a white solid in 41% yield. $^1$H-NMR (500 MHz, CDCl$_3$): δ 8.68 (d, J=13.2, ArNHCO), 8.16 (t, J=7.9, 1H, CONHCH$_2$), 7.56 (q, J=7.05, 1H), 7.32 (t, J=7.45, 1H), 7.23 (dd, J=11.9, 8.15, 1H), 7.00 (d, J=0.85, 1H), 6.94 (s, 1H), 3.94 (s, 3H, OCH$_3$), 3.93 (s, 3H, OCH$_3$), 3.92 (s, 3H, OCH$_3$), 3.59 (t, J=4, 4H), 3.5 (q, J=5.55, 2H, NHCH$_2$CH$_2$), 2.49 (t, J=5.9, NHCH$_2$CH$_2$), 2.37 (s, 4H). $^{13}$C-NMR (126 MHz, CDCl$_3$) δ 167.47 (ArC=O), 159.88 (ArC=O), 152.25 (ArC), 148.66 (ArC), 144.18 (ArC), 134.03 (d, $J_{C-F}$=10.08, ArCH), 132.27 (ArCH), 128.56 (ArC), 124.95 (d, $J_{C-F}$=2.52, ArCH), 121.17 (ArC), 116.38 (d, $J_{C-F}$=23.94, ArCH), 106.83 (ArCH), 66.69 (CH$_2$), 61.16 (CH$_3$), 61.02 (CH$_3$), 56.96 (CH$_2$), 56.29 (CH$_3$), 53.25 (CH$_2$), 36.03 (CH$_2$). MS (ESI): 462.20 [M+1]. m.p. (from ethanol/water): 141° C.

Example 64

Synthesis of 2-fluoro-6-(4-methoxybenzamido)-N-(2-morpholinoethyl) benzamide (21)

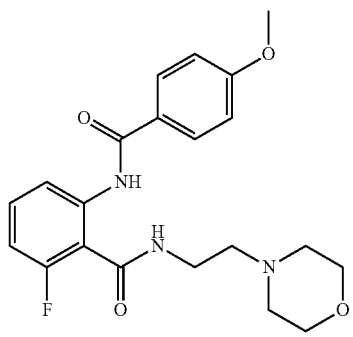

Compound 21 was obtained as a white powder in 51% yield. $^1$H-NMR (CDCl$_3$): δ 2.54 (s, 4H), 2.64 (t, J=6.0 Hz, 2H), 3.61 (dd, J=4.8, 10.5 Hz, 2H), 3.79-3.72 (m, 4H), 3.90 (s, 3H), 6.80-6.88 (m, 1H), 7.07-6.96 (m, 2H), 7.40-7.48 (m, 1H), 7.62 (d, J=11.8 Hz, 1H), 8.10-7.94 (m, 2H), 8.69 (d, J=8.5 Hz, 1H), 12.54 (s, 1H) ppm. $^{13}$C-NMR (CDCl$_3$CDCl$_3$): δ 36.24 (CH$_2$, C-aliphatic), 53.14 (CH$_2$, C-aliphatic), 55.46 (CH$_3$, C-aliphatic), 55.98 (CH$_2$, C-aliphatic), 67.02 (CH$_2$, C-aliphatic), 109.89 (CH, C-aromatic), 110.09 (CH, C-aromatic), 113.99 (CH, C-aromatic), 117.38 (CH, C-aromatic), 117.40 (C, C-aromatic), 127.07 (CH, C-aromatic), 129.40 (CH, C-aromatic), 132.95 (C, C-aromatic), 133.04 (C, C-aromatic), 142.26 (C, C-aromatic), 160.02 (C, C-aromatic), 161.97 (C, C-aromatic), 162.59 (C, C-aromatic), 165.24 (C, C-aromatic) ppm. $^{19}$F-NMR: δ –111.56 ppm. MS(ESI)$^+$: 402 [M+H]$^+$. m.p.: (from ethanol/water) 82-84° C.

Example 65

Synthesis of 4-fluoro-2-(4-methoxybenzamido)-N-(2-morpholinoethyl) benzamide (22)

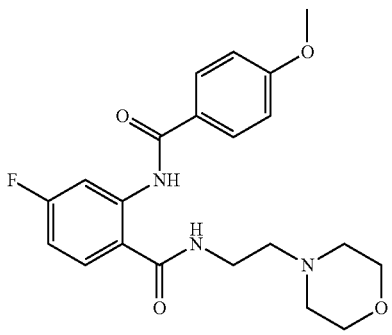

Compound 22 was obtained as a white powder in 23% yield. $^1$H-NMR (CDCl$_3$): δ 2.55 (s, 4H), 2.66 (t, J=6.0 Hz, 2H), 3.57 (dd, J=5.6, 11.0 Hz, 2H), 3.74-3.78 (m, 4H), 3.90 (s, 3H), 6.79-6.81 (m, 1H), 6.96 (s, 1H), 7.00-7.06 (m, 2H), 7.51 (dd, J=6.0, 8.7 Hz, 1H), 8.01-8.05 (m, 2H), 8.66-8.71 (m, 1H), 12.42 (s, 1H) ppm. $^{13}$C-NMR (126 MHz, CDCl$_3$): δ 35.49 (CH$_2$, C-aromatic), 41.09 (CH$_2$, C-aromatic), 55.46 (CH$_3$, C-aromatic), 108.69 (CH, C-aromatic), 109.58 (CH, C-aromatic), 114.06 (CH, C-aromatic), 126.81 (C, C-aromatic), 128.77 (CH, C-aromatic), 129.39 (CH, C-aromatic), 138.47 (C, C-aromatic), 142.54 (C, C-aromatic), 162.73 (C, C-aromatic), 165.29 (C, C-aromatic), 165.99 (C, C-aromatic), 168.60, 168.60 (C, C-aromatic) ppm. $^{19}$F-NMR: δ –104.27 ppm. MS(ESI)$^+$: 402 [M+H]$^+$. m.p.: (from ethanol/water) 114-116° C.

Example 66

Synthesis of 4-methoxy-2-(4-methoxybenzamido)-N-(2-morpholinoethyl) benzamide (23)

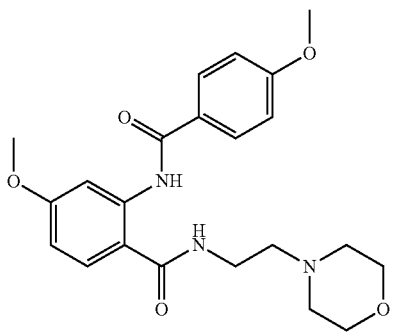

Compound 23 was obtained as a white powder in 27% yield. $^1$H-NMR (CDCl$_3$): δ 2.60 (s, 4H), 2.70 (s, 2H), 3.59 (d, J=5.2 Hz, 2H), 3.80 (s, 4H), 3.90 (s, 3H), 3.93 (s, 3H), 6.68 (dd, J=2.6, 8.8 Hz, 1H), 6.93-7.07 (m, 3H), 7.50 (d, J=8.9 Hz, 1H), 7.94-8.10 (m, 2H), 8.60 (d, J=2.6 Hz, 1H), 12.66 (s, 1H) ppm. $^{13}$C-NMR (CDCl$_3$): δ 35.85 (CH$_2$, C-aliphatic), 53.27 (CH$_2$, C-aliphatic), 55.45 (CH$_3$, C-aliphatic), 55.57 (CH$_3$, C-aliphatic), 56.58 (CH$_2$, C-aliphatic), 66.99 (CH$_2$, C-aliphatic), 104.84 (CH, C-aromatic), 109.97 (CH, C-aromatic), 111.90 (C, C-aromatic), 114.00 (CH, C-aromatic), 127.25 (C, C-aromatic), 127.83 (CH, C-aromatic), 129.32 (CH, C-aromatic), 142.85 (C, C-aromatic), 162.51 (C, C-aromatic), 163.01 (C, C-aromatic), 165.45 (C, C-aromatic), 169.10 (C, C-aromatic) ppm. MS(ESI)$^+$:414.2 [M+H]$^+$. m.p.: (from ethanol/water) 86-88° C.

Example 67

Synthesis of 3-methoxy-2-(4-methoxybenzamido)-N-(2-morpholinoethyl) benzamide (24)

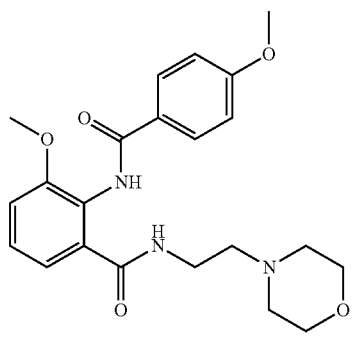

Compound 24 was obtained as a white powder in 41% yield. $^1$H-NMR (CDCl$_3$): δ 2.43 (s, 4H), 2.51 (t, J=6.0 Hz, 2H), 3.47 (dd, J=5.7, 11.4 Hz, 2H), 3.69-3.65 (m, 4H), 3.89 (s, 3H), 3.90 (s, 3H), 6.87 (s, 1H), 6.97-7.00 (m, 2H), 7.08 (d, J=7.9 Hz, 1H), 7.16 (dd, J=1.1, 7.8 Hz, 1H), 7.24-7.31 (m, 1H), 7.92-7.97 (m, 2H), 8.89 (s, 1H) ppm. $^{13}$C-NMR (126 MHz, CDCl$_3$): δ 35.99 (CH$_2$, C-aromatic), 53.24 (CH$_2$, C-aromatic), 55.49 (CH$_3$, C-aromatic), 56.21 (CH$_3$, C-aromatic), 56.78 (CH$_2$, C-aromatic), 66.88 (CH$_2$, C-aromatic), 113.70 (CH, C-aromatic), 113.85 (CH, C-aromatic), 119.42 (CH, C-aromatic), 124.97 (C, C-aromatic), 126.49 (C, C-aromatic), 126.71 (CH, C-aromatic), 129.57 (CH, C-aromatic), 132.25 (C, C-aromatic), 154.07 (C, C-aromatic), 162.61 (C, C-aromatic), 165.76 (C, C-aromatic), 168.45 (C, C-aromatic) ppm. MS(ESI)$^+$: 414 [M+H]$^+$. m.p.: (from ethanol/water) 133-135° C.

Example 68

Synthesis of 3-methoxy-2-(2-methoxybenzamido)-N-(2-morpholinoethyl) benzamide (25)

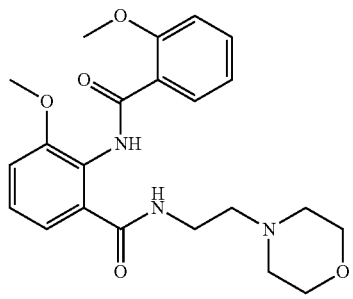

Compound 25 was obtained as a white powder in 41% yield. $^1$H-NMR (CDCl$_3$): 2.34 (d, J=14.65 Hz, 4H), 2.46 (t, J=6.06 Hz, 2H), 3.48 (q, J=5.71 Hz, 2H), 3.58 (t, J=4.41 Hz, 4H), 3.90 (s, 3H), 4.07 (s, 3H), 6.87-6.89 (m, 1H), 7.04-7.13 (m, 3H), 7.23 (dd, J=0.78 Hz, 7.58 Hz, 1H), 7.30-7.31 (m, 1H), 7.50-7.54 (m, 1H), 8.263 (dd, J=1.48, 7.73 Hz, 1H), 9.89 (d, J=0.39 Hz, 1H) ppm. $^{13}$C-NMR (CDCl$_3$): 36.12 (CH$_2$, C-aliphatic), 53.25 (CH$_2$, C-aliphatic), 56.20 (CH$_3$, C-aliphatic), 56.97 (CH$_2$, C-aliphatic), 66.83 (CH$_2$, C-aliphatic), 111.67 (CH, C-aromatic), 112.82 (CH, C-aromatic), 120.23 (CH, C-aromatic), 121.35 (CH, C-aromatic), 121.35 (C, C-aromatic), 123.56 (C, C-aromatic), 127.06 (CH, C-aromatic), 132.69 (CH, C-aromatic), 133.40 (CH, C-aromatic), 134.77 (C, C-aromatic), 153.73 (C, C-aromatic), 157.91 (C, C-aromatic), 164.56 (C, C-aromatic), 168.28 (C, C-aromatic) ppm. MS(ESI)$^+$: 414.2 [M+H]$^+$. m.p.: 105-107° C.

Example 69

Synthesis of 3-methoxy-2-(3-methoxybenzamido)-N-(2-morpholinoethyl) benzamide (26)

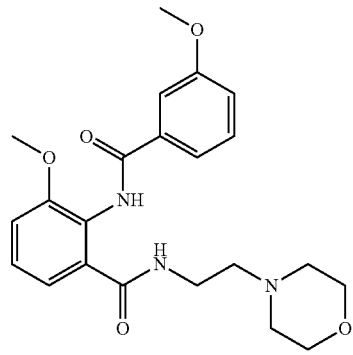

Compound 26 was obtained as a white powder in 37% yield. $^1$H-NMR (CDCl$_3$): δ 2.42 (t, J=4.21 Hz, 4H), 2.51 (t, J=6.02 Hz, 2H), 3.47 (q, J=5.69 Hz, 2H), 3.66 (t, J=4.62 Hz, 4H), 3.88 (s, 3H), 3.90 (s, 3H), 6.80 (s, 1H), 7.08-7.12 (m, 2H), 7.159 (dd, J=1.26, 7.77 Hz, 1H), 7.28-7.31 (m, 1H), 7.39-7.42 (m, 1H), 7.53-7.55 (m, 2H), 8.92 (s, 1H) ppm. $^{13}$C-NMR (CDCl$_3$): 36.04 (CH2, C-aliphatic), 53.27 (CH$_2$, C-aliphatic), 55.47 (CH$_3$, C-aliphatic), 56.21 (CH$_3$, C-aliphatic), 56.78 (CH$_2$, C-aliphatic), 66.89 (CH$_2$, C-aliphatic), 112.81 (CH, C-aromatic), 113.75 (CH, C-aromatic), 118.26 (CH, C-aromatic), 119.38 (CH. C-aromatic), 119.58 (CH, C-aromatic), 124.75 (C, C-aromatic), 126.87 (CH, C-aromatic), 126.69 (CH, C-v), 132.35 (C, C-aromatic), 135.69 (C, C-aromatic), 154.12 (C, C-aromatic), 159.89 (C, C-aromatic), 165.96 (C, C-aromatic), 168.32 (C, C-aromatic) ppm. MS(ESI)$^+$: 414.2 [M+H]$^+$. m.p.: 110-113° C.

Example 70

Synthesis of 2,3,4-trimethoxy-6-(4-methoxybenzamido)-N-(2-morpholino ethyl)benzamide (27)

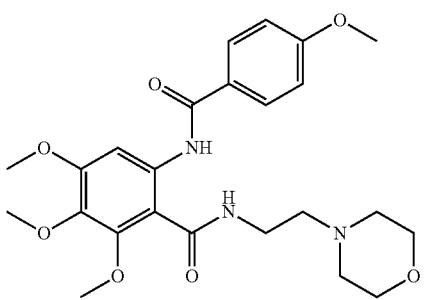

Compound 27 was obtained as a white solid in 18% yield. ¹H-NMR (500 MHz, CDCl₃): δ 8.49 (s, 1H, ArNHCO), 7.95 (d, J=8.2, 2H), 7.04 (s, 1H, CONHCH₂), 6.99 (d, J=7.3, 2H), 6.93 (s, 1H), 3.94 (s, 3H, OCH₃), 3.92 (s, 3H, OCH₃), 3.90 (s, 3H, OCH₃), 3.89 (s, 3H, OCH₃), 3.63 (t, J=4.2), 3.45 (q, J=5.45, 2H, NHCH₂CH₂), 2.47 (t, J=6.4, 2H, NHCH₂CH₂), 2.38 (s, 4H). ¹³C-NMR (126 MHz, CDCl₃) δ 167.86 (ArC=O), 166.76 (ArC=O), 162.75 (ArC), 151.94 (ArC), 149.10 (ArC), 144.44 (ArC), 129.47 (ArCH), 127.94 (ArC), 126.13 (ArC), 122.44 (ArC), 113.93 (ArCH), 106.55 (ArCH), 66.73 (CH₂), 61.11 (CH₃), 61.00 (CH₃), 56.92 (CH₂), 56.30 (CH₃), 55.51 (CH₃) 53.23 (CH₂), 36.04 (CH₂). MS (ESI): 474.2 [M+1]. m.p. (from ethanol/water): 143° C.

Example 71

Synthesis of 2-fluoro-N-(3-fluoro-2-(2-morpholino-ethyl)carbamoyl)phenyl)-4-methoxybenzamide (28)

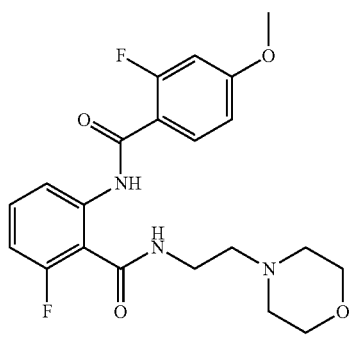

Compound 28 was obtained as a white powder in 40% yield. ¹H-NMR (CDCl₃): δ 2.53 (s, 4H), 2.62 (t, J=6.0 Hz, 2H), 3.60 (dd, J=0.6, 5.21 Hz, 2H), 3.73-3.77 (m, 4H), 3.88 (d, J=6.1 Hz, 3H), 6.71 (dd, J=2.3, 13.3 Hz, 1H), 6.83 (dd, J=2.3, 8.8 Hz, 1H), 6.91 (dd, J=8.6, 11.3 Hz, 1H), 7.38 (s, 1H), 7.46 (dd, J=8.3, 15.0 Hz, 1H), 8.04 (t, J=8.9 Hz, 1H), 8.56 (d, J=8.5 Hz, 1H), 11.89 (d, J=7.8 Hz, 1H) ppm. ¹³C-NMR (CDCl₃): δ 36.19 (CH₂, C-aliphatic), 53.14 (CH₂, C-aliphatic), 55.84 (CH₃, C-aliphatic), 56.08 (CH₂, C-aliphatic), 67.00 (CH₂, C-aliphatic), 101.79 (CH, C-aromatic), 102.00 (CH, C-aromatic), 110.47 (CH, C-aromatic), 110.67 (CH, C-aromatic), 110.73 (CH, C-aromatic), 110.76 (CH, C-aromatic), 118.43 (CH, C-aromatic), 132.44 (CH, C-aromatic), 132.53 (CH, C-aromatic), 132.87 (CH, C-aromatic), 132.90 (CH, C-aromatic), 140.98 (C, C-aromatic), 158.96 (C, C-aromatic), 160.52 (C, C-aromatic), 161.51 (C, C-aromatic), 162.09 (C, C-aromatic), 162.39 (C, C-aromatic), 163.65 (C, C-aromatic), 164.83 (C, C-aromatic) ppm. ¹⁹F-NMR: δ −109.44, −112.34 ppm. MS(ESI)⁺: 420 [M+H]⁺. m.p.: 105-107° C.

Example 72

Synthesis of 2-(2,4-dimethoxybenzamido)-3-methoxy-N-(2-morpholinoethyl) benzamide (29)

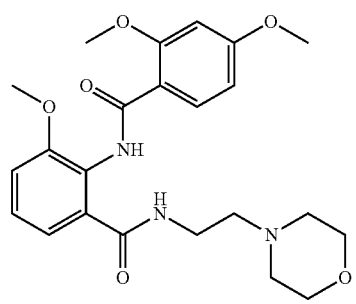

Compound 29 was obtained as a white powder in 41% yield. ¹H-NMR (CDCl₃): δ 2.345 (t, J=4.39 Hz, 4H), 2.454 (t, J=6.14 Hz, 2H), 3.476 (q, J=5.72 Hz, 2H), 3.596 (t, J=4.63 Hz, 4H), 3.892 (d, J=3.17 Hz, 6H), 4.043 (s, 3H), 6.561 (d, J=2.30 Hz, 1H), 6.635 (dd, J=2.32, 8.78 Hz, 1H), 6.933 (s, 1H), 7.035 (dd, J=1.44, 8.11 Hz, 1H), 7.23-7.30 (m, 2H), 8.22 (d, J=8.76 Hz, 1H), 9.72 (s, 1H) ppm. ¹³C-NMR (125 MHz, CDCl₃): δ 36.13 (CH₂, C-aliphatic), 53.26 (CH₂, C-aliphatic), 55.60 (CH₃, C-aliphatic), 56.15 (CH₃, C-aliphatic), 56.19 (CH₃, C-aliphatic), 56.99 (CH₂, C-aliphatic), 66.85 (CH₂, C-aliphatic), 98.74 (CH, C-aromatic), 105.51 (CH, C-aromatic), 112.73 (CH, C-aromatic), 114.33 (C, C-aromatic), 120.30 (CH, C-aromatic), 123.69 (C, C-aromatic), 126.95 (CH, C-aromatic), 134.37 (CH, C-aromatic), 134.93 (C, C-aromatic), 153.74 (C, C-aromatic), 159.29 (C, C-aromatic), 163.96 (C, C-aromatic), 164.51 (C, C-aromatic), 168.31 (C, C-aromatic) ppm. MS(ESI)⁺: 444.2 [M+H]⁺. m.p.: 103-106° C.

Example 73

Synthesis of N-(2-((2-morpholinoethyl)carbamoyl) phenyl)-1-naphthamide (30)

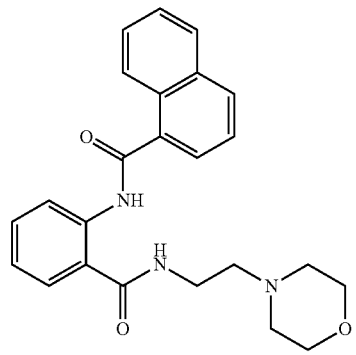

Compound 30 was obtained as a white powder in 41% yield. ¹H-NMR (CDCl₃): δ 2.44 (s, 4H), 2.52 (t, J=5.8 Hz, 2H), 3.41 (dd, J=5.5, 1.1 Hz, 2H), 3.59-3.72 (m, 4H), 7.11 (td, J=1.1, 7.8 Hz, 1H), 7.44-7.58 (m, 6H), 7.80 (dd, J=4.8, 11.9 Hz, 2H), 7.89 (d, J=8.3 Hz, 1H), 8.47 (d, J=8.3 Hz, 1H), 8.84 (d, J=8.0 Hz, 1H), 11.72 (s, 1H) ppm. $^{13}$C-NMR (CDCl$_3$): δ 35.90 (CH$_2$, C-aliphatic), 53.27 (CH$_2$, C-aliphatic), 56.54 (CH$_2$, C-aliphatic), 66.95 (CH$_2$, C-aliphatic), 120.75 (CH, C-aromatic), 121.76 (C, C-aromatic), 123.12 (CH, C-aromatic), 124.97 (CH, C-aromatic), 125.53 (CH, C-aromatic), 125.67 (CH, C-aromatic), 126.38 (CH, C-aromatic), 126.55 (CH, C-aromatic), 127.12 (CH, C-aromatic), 128.34 (C, C-aromatic), 130.49 (CH, C-aromatic), 131.21 (CH, C-aromatic), 132.70 (C, C-aromatic), 133.95 (CH, C-aromatic), 134.45 (C, C-aromatic), 140.00 (C, C-aromatic), 167.68 (C, C-aromatic), 168.95 (C, C-aromatic) ppm. MS(ESI)$^+$: 404.2 [M+H]$^+$. m.p.: (from DCM/n-hexane) 93-95° C.

Example 74

Synthesis of N-(2-(2-morpholinoethyl)carbamoyl)phenyl)-2-naphthamide (31)

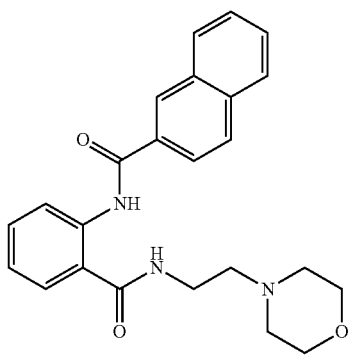

Compound 31 was obtained as a white powder in 28% yield. $^1$H-NMR (CDCl$_3$): δ 2.57 (s, 4H), 2.68 (t, J=5.8 Hz, 2H), 3.41-3.63 (m, 2H), 3.71-3.85 (m, 4H), 7.04 (s, 1H), 7.19 (t, J=7.1 Hz, 1H), 7.60 (m, 5H), 7.92 (d, J=7.7 Hz, 1H), 7.99 (d, J=8.6 Hz, 1H), 8.05 (d, J=7.6 Hz, 1H), 8.12 (dd, J=1.7, 8.6 Hz, 1H), 8.61 (s, 1H), 8.90 (d, J=8.2 Hz, 1H), 12.41 (s, 1H) ppm. $^{13}$C-NMR (CDCl$_3$): δ 35.98 (CH$_2$, C-aliphatic), 53.30 (CH$_2$, C-aliphatic), 56.61 (CH$_2$, C-aliphatic), 66.92 (CH$_2$, C-aliphatic), 120.47 (C, C-aromatic), 121.79 (CH, C-aromatic), 122.91 (CH, C-aromatic), 123.69 (CH, C-aromatic), 126.53 (CH, C-aromatic), 126.64 (CH, C-aromatic), 127.72 (CH, C-aromatic), 127.79 (CH, C-aromatic), 128.42 (CH, C-aromatic), 128.61 (CH, C-aromatic), 129.39 (CH, C-aromatic), 132.17 (C, C-aromatic), 132.64 (CH, C-aromatic), 132.79 (C, C-aromatic), 134.98 (C, C-aromatic), 140.23 (C, C-aromatic), 165.52 (C, C-aromatic), 169.19 (C, C-aromatic) ppm. MS(ESI)$^+$: 404.2 [M+H]$^+$. m.p.: (from DCM/n-hexane) 105-107° C.

Example 75

Synthesis of N-(2-((2-morpholinoethyl)carbamoyl)phenyl)nicotinamide (32)

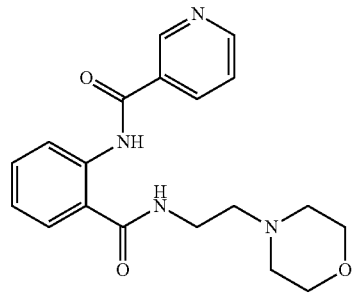

Compound 32 was obtained as a white solid in 48% yield. $^1$H-NMR (500 MHz, CDCl$_3$): δ 12.53 (s, 1H, ArNHCO), 9.32 (d, J=1.5, 1H, CONHCH$_2$), 8.84 (dd, J=9.1, 1H), 8.80 (dd, J=5.5, 1, 1H), 8.33 (dt, J=8.2, 1H), 7.61-7.56 (m, 2H), 7.47 (td, J=4.5, 0.5, 1H), 7.2 (td, J=8, 1.5, 1H), 7.14 (s, 1H), 3.78 (t, J=4.5, 4H), 3.60 (q, J=4.5, 2H, NHCH$_2$CH$_2$), 2.68 (t, J=6, 2H, NHCH$_2$CH$_2$), 2.57 (s, 4H). $^{13}$C-NMR (126 MHz, CDCl$_3$) δ 169.07 (ArC=O), 163.73 (ArC=O), 152.46 (ArCH), 149.13 (ArCH), 139.94 (ArC), 134.91 (ArCH), 132.94 (ArCH), 130.52 (ArC), 126.56 (ArCH), 123.46 (ArCH), 13.30 (ArCH), 121.64 (ArCH), 120.03 (ArC), 66.84 (CH$_2$), 56.60 (CH$_2$), 53.29 (CH$_2$), 35.92 (CH$_2$). MS (ESI): 355.2. m.p. (from ethanol/water): 85° C.

Example 76

Synthesis of N-(3,4,5-trimethoxy-2-((2-morpholinoethyl)carbamoyl)phenyl) nicotinamide (33)

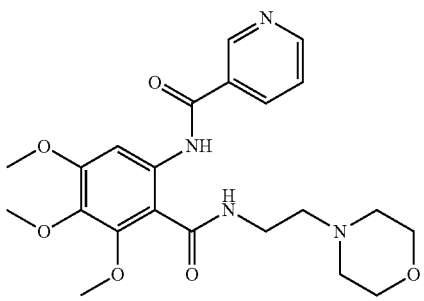

Compound 33 was obtained as a white solid. $^1$H-NMR (500 MHz, CDCl$_3$) δ 9.22 (s, 1H, ArNHCO), 9.09, (s, 1H, CONHCH$_2$), 8.79 (d, J=4.1), 8.28 (dt, J=7.95, 1.8, 1H), 7.45 (dd, J=7.65, 5.1, 1H), 6.98 (s, 1H), 6.9 (s, 1H), 3.94 (d, J=1.9, 6H, OCH$_3$), 3.93 (s, 3H, OCH$_3$), 3.70-3.66 (m, 4H), 3.51-3.45 (m, 2H, NHCH$_2$CH$_2$), 2.56 (t, J=5.6, 2H, NHCH$_2$CH$_2$), 2.48 (s, 4H). $^{13}$C-NMR (126 MHz, CDCl$_3$) δ 167.95 (ArC=O), 164.96 (ArC=O), 152.68 (ArCH), 152.04 (ArC), 149.26 (ArC), 148.90 (ArCH), 144.72 (ArC), 135.38 (ArCH), 129.81 (ArC), 123.52 (ArCH), 122.48 (ArC), 106.10 (ArCH), 66.58 (CH$_2$), 61.06 (CH$_3$), 61.00

(CH₃), 56.87 (CH2), 56.38 (CH₃), 53.22 (CH₂), 35.86 (CH₂). MS (ESI): 445.2 [M+1]. m.p. (from ethanol/water): 155° C.

Example 77

Synthesis of 3-(4-methoxybenzamido)-N-(2-morpholinoethyl)isonicotinamide (99)

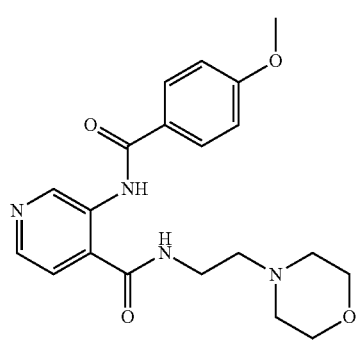

99

Compound 99 was obtained as a white powder in 43% yield. ¹H-NMR (CDCl₃): δ 2.55 (s, 4H), 2.67 (t, J=5.9 Hz, 2H), 3.59 (s, 2H), 3.75-3.79 (m, 4H), 3.91 (s, 3H), 7.02-7.05 (m, 2H), 7.21 (s, 1H), 7.34 (d, J=5.0 Hz, 1H), 8.01-8.04 (m, 2H), 8.46 (d, J=5.1 Hz, 1H), 10.12 (s, 1H), 11.80 (s, 1H) ppm. ¹³C-NMR (126 MHz, CDCl₃): δ 36.01 (CH₂, C-aromatic), 53.26 (CH₂, C-aromatic), 55.50 (CH₃, C-aromatic), 56.27 (CH₂, C-aromatic), 66.95 (CH₂, C-aromatic), 114.08 (CH, C-aromatic), 119.25 (CH, C-aromatic), 125.67 (C, C-aromatic), 126.31 (C, C-aromatic), 129.48 (CH, C-aromatic), 135.65 (C, C-aromatic), 143.85 (CH, C-aromatic), 144.61 (CH, C-aromatic), 162.81 (C, C-aromatic), 164.94 (C, C-aromatic), 167.32 (C, C-aromatic) ppm. MS(ESI)⁺: 395.1 [M+H]⁺. m.p.: 90-92° C.

Example 78

Synthesis of 2-chloro-N-(2-((2-morpholinoethyl)carbamoyl)phenyl)benzamide (103)

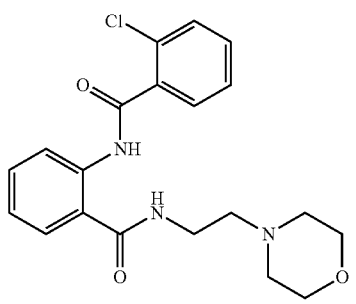

103

Compound 103 was obtained as a yellow powder in 80% yield. ¹H-NMR (CDCl₃): δ 2.54 (s, 4H), 2.63 (t, J=5.7 Hz, 2H), 3.52 (dd, J=5.4, 11.0 Hz, 2H), 3.76 (d, J=4.1 Hz, 4H), 6.99 (d, J=18.7 Hz, 1H), 7.20 (t, J=7.6 Hz, 1H), 7.30-7.39 (m, 2H), 7.48 (dd, J=1.2, 7.8 Hz, 1H), 7.54 (d, J=7.7 Hz, 1H), 7.58 (t, J=7.8 Hz, 1H), 7.68 (dd, J=2.0, 7.2 Hz, 1H), 8.83 (d, J=8.3 Hz, 1H), 11.65 (s, 1H) ppm. ¹³C-NMR (126 MHz, CDCl₃): δ 30.74 (CH₂, C-aliphatic), 35.74 (CH₂, C-aliphatic), 53.18 (CH₂, C-aliphatic), 66.13 (CH₂, C-aliphatic), 120.49 (CH, C-aromatic), 123.37 (CH, C-aromatic), 127.63 (CH, C-aromatic), 128.09 (CH, C-aromatic), 128.89 (CH, C-aromatic), 129.77 (C, C-aromatic), 130.17 (CH, C-aromatic), 131.73 (CH, C-aromatic), 132.02 (CH, C-aromatic), 136.24 (C, C-aromatic), 138.45 (C, C-aromatic), 162.27 (C, C-aromatic), 164.30 (C, C-aromatic), 168.06 (C, C-aromatic) ppm. MS(ESI)⁺: 388.1, 389.1 [M+H]⁺. m.p.: (from ethanol/water) 133-137° C.

Example 79

Synthesis of 2-fluoro-N-methyl-N-(2-((2-morpholinoethyl)carbamoyl)phenyl) benzamide (106)

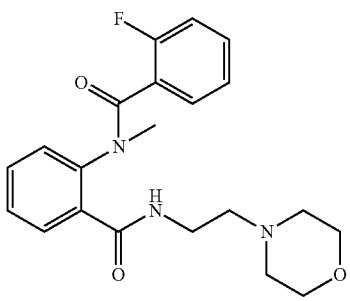

106

Compound 106 was obtained as an oil in 18% yield. ¹H-NMR (500 MHz, CDCl₃): δ 2.24 (d, J=12.3 Hz, 3H), 2.32-2.77 (m, 10H), 3.48 (dd, J=5.4, 11.2 Hz, 2H), 6.95-7.17 (m, 1H), 7.40-7.62 (m, 2H), 7.70 (d, J=8.2 Hz, 2H), 8.09 (d, J=8.1 Hz, 2H), 8.76 (d, J=8.4 Hz, 1H), 12.46 (s, 1H) ppm. ¹³C-NMR (126 MHz, CDCl₃): δ 35.84 (CH₃, C-aliphatic), 102.05 (CH, C-aromatic), 102.28 (CH, C-aromatic), 110.55 (CH, C-aromatic), 110.76 (CH, C-aromatic), 118.61 (CH, C-aromatic), 132.21 (CH, C-aromatic), 132.78 (CH, C-aromatic), 132.98 (CH, C-aromatic), 158.95 (C, C-aromatic), 160.53 (C, C-aromatic), 161.49 (C, C-aromatic), 162.06 (C, C-aromatic), 163.68 (C, C-aromatic), 164.82 (C, C-aromatic) ppm.

Example 80

Synthesis of 4-(4-methoxybenzamido)-N-(2-morpholinoethyl)nicotinamide (113)

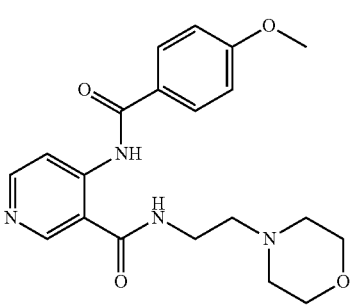

113

Compound 113 was obtained as a white powder in 55% yield. $^1$H-NMR (500 MHz, CDCl$_3$): δ 2.46 (d, J=4.2 Hz, 4H), 2.58 (t, J=5.9 Hz, 2H), 3.51 (dd, J=5.3, 11.1 Hz, 2H), 3.62-3.70 (m, 4H), 3.81 (s, 3H), 6.88-6.99 (m, 2H), 7.04 (s, 1H), 7.19 (s, 1H), 7.94 (dd, J=2.4, 9.4 Hz, 2H), 8.54 (d, J=5.8 Hz, 1H), 8.63-8.73 (m, 1H), 12.36 (s, 1H) ppm. $^{13}$C-NMR (126 MHz, CDCl$_3$): δ 35.93 (CH$_2$, C-aliphatic), 53.28 (CH$_2$, C-aliphatic), 55.49 (CH$_3$, C-aliphatic), 56.30 (CH$_2$, C-aliphatic), 66.95 (CH$_2$, C-aliphatic), 114.16 (CH, C-aromatic), 114.46 (CH, C-aromatic), 126.25 (C, C-aromatic), 129.59 (CH, C-aromatic), 147.22 (C, C-aromatic), 147.94 (CH, C-aromatic), 153.46 (CH, C-aromatic), 163.06 (C, C-aromatic), 165.50 (C, C-aromatic), 165.62 (C, C-aromatic), 167.69 (C, C-aromatic) ppm. MS (ESI)$^+$: 385.2 [M+H]$^+$. m.p. (from ethanol/water): 105-107° C.

Example 81

Synthesis of 2-(2-fluorobenzamido)-3-methoxy-N-(2-morpholinoethyl)benzamide (145)

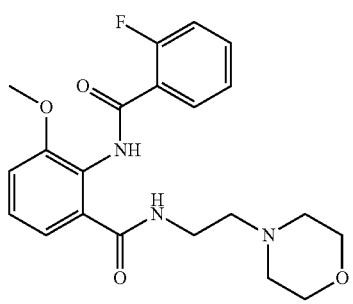

145

Compound 145 was obtained as a white powder in 31% yield. $^1$H-NMR (CDCl$_3$): δ 2.37-2.40 (m, 4H), 2.50-2.52 (m, 2H), 3.48-3.51 (m, 2H), 3.62-3.65 (m, 4H), 3.91 (s, 3H), 6.77-6.79 (m, 1H), 7.08-7.09 (m, 1H), 7.19-7.23 (m, 2H), 7.30-7.33 (m, 2H), 7.52-7.57 (m, 1H), 8.14-8.17 (m, 1H), 8.97-8.99 (m, 1H) ppm. $^{13}$C-NMR (126 MHz, CDCl$_3$): δ 36.07 (CH$_2$, C-aliphatic), 53.28 (CH$_2$, C-aliphatic), 56.20 (CH$_3$, C-aliphatic), 56.90 (CH$_2$, C-aliphatic), 66.87 (CH$_2$, C-aliphatic), 113.26 (CH, C-aromatic), 116.33 (CH, C-aromatic), 119.79 (CH—C-aromatic), 123.60 (C, C-aromatic), 124.76 (CH, C-aromatic), 127.26 (CH, C-aromatic), 132.26 (CH, C-aromatic), 133.77 (CH, C-aromatic), 134.19 (CH, C-aromatic), 138.90 (C, C-aromatic), 153.82 (C, C-aromatic), 159.93 (C, C-aromatic), 161.91 (C, C-aromatic), 168.07 (C, C-aromatic) ppm. $^{19}$F-NMR: δ −112.47 ppm. MS(ESI)$^+$: 402.2 [M+H]$^+$. m.p.: 105-107° C.

Example 82

Synthesis of N-(2-morpholinoethyl)-2-(3-nitrobenzamido)benzamide (146)

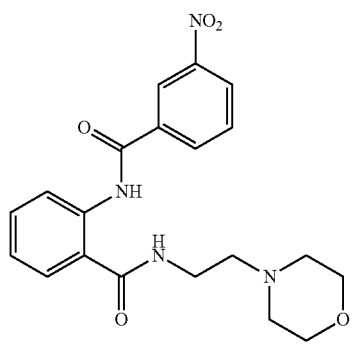

146

Compound 146 was obtained as a white powder in 51% yield. $^1$H-NMR (CDCl$_3$): δ 2.60 (s, 4H), 2.71 (s, 2H), 3.61 (d, J=5.2 Hz, 2H), 3.80 (s, 4H), 7.24 (t, J=7.2 Hz, 2H), 7.61 (t, J=7.4 Hz, 2H), 8.24 (d, J=8.8 Hz, 2H), 8.39 (d, J=8.7 Hz, 2H), 8.86 (d, J=8.1 Hz, 1H), 12.71 (s, 1H) ppm. $^{13}$C-NMR (126 MHz, CDCl$_3$): δ 36.58 (CH$_2$, C-aliphatic), 53.20 (CH$_2$, C-aliphatic), 56.93 (CH$_2$, C-aliphatic), 66.17 (CH$_2$, C-aliphatic), 120.64 (C, C-aromatic), 120.92 (CH, C-aromatic), 123.39 (CH, C-aromatic), 126.88 (CH, C-aromatic), 127.58 (CH, C-aromatic), 128.15 (CH, C-aromatic), 128.43 (CH, C-aromatic), 132.21 (CH, C-aromatic), 138.76 (CH, C-aromatic), 140.10 (C, C-aromatic), 149.41 (C, C-aromatic), 162.69 (C, C-aromatic), 168.38 (C, C-aromatic), 173.58 (C, C-aromatic) ppm. MS(ESI)$^+$: 399.2 [M+H]$^+$. m.p.: 147-149° C.

Example 83

Synthesis of N-(2-morpholinoethyl)-2-(2-nitrobenzamido)benzamide (147)

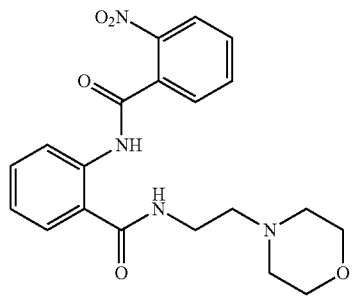

147

Compound 147 was obtained as a white powder in 43% yield. $^1$H-NMR (CDCl$_3$): δ 2.39 (t, J=4.7 Hz, 4H), 2.46 (t, J=6.8 Hz, 2H), 2.46 (t, J=6.8 Hz, H), 3.37 (q, J=6.5 Hz, 2H), 3.53 (t, J=4.6 Hz, 4H), 7.20-7.27 (m, 1H), 7.59 (t, J=8.2 Hz, 1H), 7.82 (m, 3H), 7.91 (t, J=15.2 Hz, 1H), 8.13 (d, J=8.3, 1H) ppm. $^{13}$C-NMR (126 MHz, CDCl$_3$): δ 36.48 (CH$_2$, C-aliphatic), 53.19 (CH$_2$, C-aliphatic), 56.95 (CH$_2$, C-aliphatic), 66.14 (CH$_2$, C-aliphatic), 120.89 (CH, C-aromatic), 121.76 (C, C-aromatic), 123.67 (CH, C-aromatic), 124.57

(CH, C-aromatic), 128.11 (CH, C-aromatic), 128.38 (CH, C-aromatic), 131.68 (CH, C-aromatic), 131.58 (CH, C-aromatic), 132.02 (C, C-aromatic), 134.11 (CH, C-aromatic), 138.23 (C, C-aromatic), 147.02 (C, C-aromatic), 163.35 (C, C-aromatic), 168.01 (C, C-aromatic) ppm. MS(ESI)⁺: 399.19 [M+H]⁺. m.p.: 138-140° C.

Example 84

Synthesis of N-(2-morpholinoethyl)-2-(4-nitrobenzamido)benzamide (148)

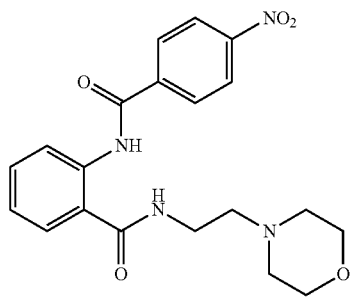

148

Compound 148 was obtained as a white powder in 51% yield. ¹H-NMR (CDCl₃): δ 2.44 (m, 6H), 3.44 (q, J=6.5 Hz, 2H), 3.54 (t, J=4.6 Hz, 4H), 7.20-7.27 (m, 1H), 7.57-7.60 (m, 1H), 7.85 (dd, J=1.5, 8.0 Hz, 1H), 8.16 (d, J=8.9 Hz, 2H), 8.44 (d, J=8.9 Hz, 2H), 8.59 (d, J=8.4 Hz, 1H), 8.83 (s, 1H), 12.70 (s, 1H) ppm. ¹³C-NMR (126 MHz, CDCl₃): δ 36.58 (CH₂, C-aliphatic), 53.20 (CH₂, C-aliphatic), 56.93 (CH₂, C-aliphatic), 66.17 (CH₂, C-aliphatic), 120.64 (CH, C-aromatic), 120.92 (C, C-aromatic), 123.47 (CH, C-aromatic), 124.13 (CH, C-aromatic), 128.15 (CH, C-aromatic), 128.43 (CH, C-aromatic), 132.21 (CH, C-aromatic), 138.76 (C, C-aromatic), 140.10 (C, C-aromatic), 149.41 (C, C-aromatic), 162.69 (C, C-aromatic), 168.38 (CH, C-aromatic) ppm. MS(ESI)⁺: 399.2 [M+H]⁺. m.p.: 147-149° C.

General Procedure 3

The compounds of the application with the general formula shown below can be prepared according to the synthetic scheme in Scheme 3.

Scheme 3

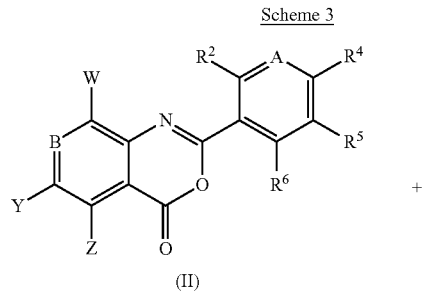

(II)

+

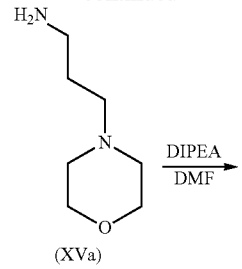

(XVa)

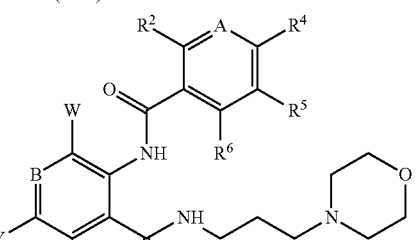

+

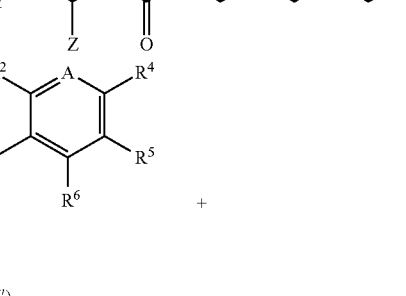

(II')

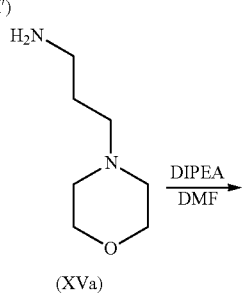

(XVa)

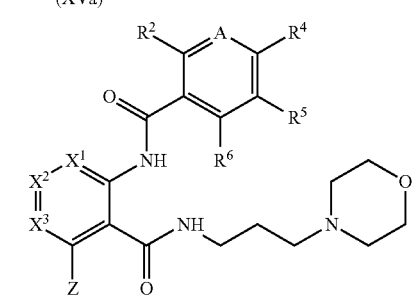

To a solution of compound (II) or (II') (1 equivalent) in N,N-dimethyl-formamide (DMF) is added 2 equivalents of N,N-diisopropylethylamine (DIPEA) and 2.2 equivalent of 3-morpholinopropylamine (XVa). The reaction mixture is stirred at about 15° C. to about 28° C. for about 6 hours to about 24 hours. The reaction mixture is diluted with water, washed with ethyl acetate, washed with brine, dried over Mg₂SO₄, filtered and evaporated to give a crude compound which is then purified by silica gel column using a mixture of Chloroform:Methanol (9:1) as eluent. The product is collected under reduced pressure to provide the compound with the general formula shown in Scheme 3.

Compounds 34-37, 126-128, 130-134, 138, 139, and 141-143 were prepared according to General Procedure 3 substituting (II) or (II') with the appropriate substituted compound.

Example 85

Synthesis of 2-fluoro-N-(2-((3-morpholinopropyl)carbamoyl)phenyl) benzamide (34)

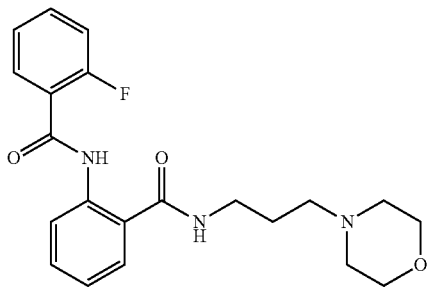

34

Compound 34 was obtained as a white precipitate in 25% yield. $^1$H-NMR (500 MHz, CDCl$_3$): δ 1.82 (2H, m), 2.57 (6H, m), 3.59 (2H, td, J=4.89, 5.91 Hz), 3.72 (4H, d, J=0.49 Hz), 7.20 (2H, m), 7.29 (1H, m), 7.55 (3H, m), 8.06 (1H, td, J=1.85, 7.71 Hz), 8.45 (1H, m), 8.80 (1H, dd), 12.01 (1H, m) ppm. $^{19}$F-NMR (CDCl$_3$): δ −112.48 ppm. MS (ESI)$^+$: 386.2 [M+H]$^+$. Melting point: 76-79° C.

Example 86

Synthesis of 2-(4-methoxybenzamido)-N-(3-morpholinopropyl)benzamide (35)

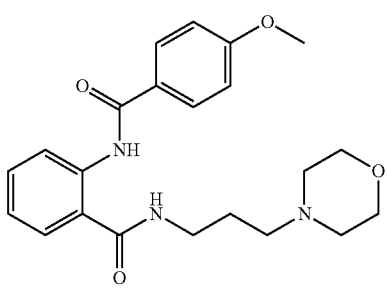

35

Compound 35 was obtained as a white powder in 64% yield. $^1$H-NMR (500 MHz, CDCl$_3$): δ 1.85 (2H, m), 2.54 (4H, m), 2.63 (2H, dd, J=3.88, 7.36 Hz), 3.61 (2H, m), 3.74 (4H, t, J=4.29 Hz), 3.90 (3H, s), 7.02 (2H, m), 7.13 (1H, td, J=0.98, 7.59 Hz), 7.55 (1H, m), 7.62 (1H, dd, J=1.03, 7.80 Hz), 8.05 (2H, m), 8.60 (1H, m), 8.84 (1H, dd, J=1.00, 8.44 Hz), 12.32 (1H, s) ppm. $^{13}$C-NMR (126 MHz, CDCl$_3$): δ 23.41 (CH$_2$, C-aliphatic), 40.97 (CH$_2$, C-aliphatic), 53.82 (CH$_2$, C-aliphatic), 55.42 (CH$_3$, C-aliphatic), 58.95 (CH$_2$, C-aliphatic), 66.79 (CH$_2$, C-aliphatic), 113.95 (CH, C-aromatic), 120.23 (C, C-aromatic), 121.52 (CH, C-aromatic), 122.30 (CH, C-aromatic), 126.77 (CH, C-aromatic), 127.34 (C, C-aromatic), 129.33 (CH, C-aromatic), 132.62 (CH, C-aromatic), 140.41 (C, C-aromatic), 162.46 (C, C-aromatic), 165.19 (C, C-aromatic), 169.28 (C, C-aromatic) ppm. MS (ESI)$^+$: 398.2 [M+H]$^+$. Melting point (from DCM/n-hexane): 112-114° C.

Example 87

Synthesis of N-(2-((3-morpholinopropyl)carbamoyl)phenyl)-1-naphthamide (36)

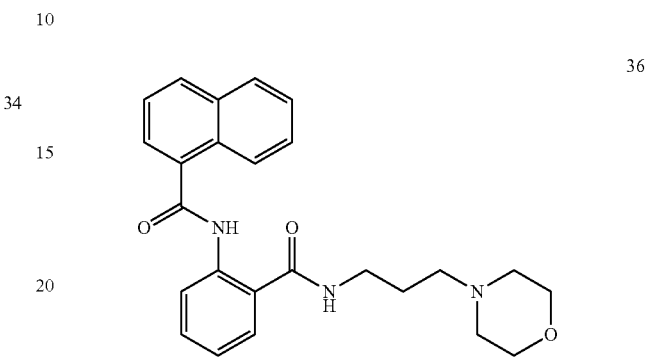

36

Compound 36 was obtained as a white powder in 74% yield. $^1$H-NMR (500 MHz, CDCl$_3$): δ 1.77 (2H, m), 2.56 (3H, s), 2.58 (3H, s), 3.52 (2H, dd, J=5.7, 10.9 Hz), 3.74 (4H, s), 7.20 (1H, td, J=1.05, 7.62 Hz), 7.55-7.75 (5H, m), 7.91 (2H, m), 7.98 (1H, d, J=8.33 Hz), 8.57 (2H, m), 8.95 (1H, m), 12.03 (1H, s) ppm. $^{13}$C-NMR (126 MHz, CDCl$_3$): δ 23.38 (CH$_2$, C-aliphatic), 40.62 (CH$_2$, C-aliphatic), 53.72 (CH$_2$, C-aliphatic), 58.68 (CH$_2$, C-aliphatic), 66.65 (CH$_2$, C-aliphatic), 120.72 (C, C-aromatic), 121.64 (CH, C-aromatic), 122.86 (CH, C-aromatic), 125.00 (CH, C-aromatic), 125.56 (CH, C-aromatic), 125.70 (CH, C-aromatic), 126.35 (CH, C-aromatic), 126.88 (CH, C-aromatic), 127.08 (CH, C-aromatic), 128.32 (CH, C-aromatic), 130.52 (C, C-aromatic), 131.15 (CH, C-aromatic), 132.63 (CH, C-aromatic), 133.95 (C, C-aromatic), 134.51 (C, C-aromatic), 140.08 (C, C-aromatic), 167.90 (C, C=O), 168.91 (C, C=O) ppm. MS (ESI)$^+$: 418.2 [M+H]$^+$. Melting point (from DCM/n-hexane): 110-112° C.

Example 88

Synthesis of N-(2-((3-morpholinopropyl)carbamoyl)phenyl)-2-naphthamide (37)

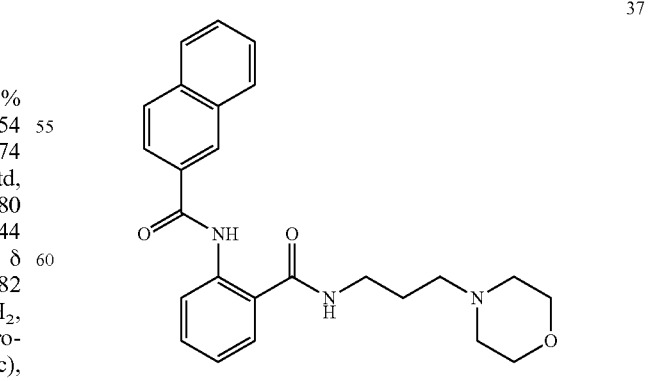

37

Compound 37 was obtained as a white powder in 53% yield. $^1$H-NMR (500 MHz, CDCl$_3$): δ 1.85 (2H, m), 2.56

(4H, m), 2.64 (2H, m), 3.63 (2H, m), 3.74 (4H, m), 7.18 (1H, dd), 7.59 (3H, m), 7.65 (1H, m), 7.92 (1H, d, J=7.79 Hz), 7.99 (1H, s), 8.05 (1H, m), 8.14 (1H, m), 8.63 (2H, m), 8.90 (1H, d, J=8.43 Hz), 12.58 (1H, s) ppm. $^{13}$C-NMR (126 MHz, CDCl$_3$): δ 23.44 (CH$_2$, C-aliphatic), 40.91 (CH$_2$, C-aliphatic), 53.80 (CH$_2$, C-aliphatic), 58.88 (CH$_2$, C-aliphatic), 66.76 (CH$_2$, C-aliphatic), 120.57 (C, C-aromatic), 121.70 (CH, C-aromatic), 122.64 (CH, C-aromatic), 123.72 (CH, C-aromatic), 126.60 (CH, C-aromatic), 126.83 (CH, C-aromatic), 127.70 (CH, C-aromatic), 128.43 (CH, C-aromatic), 128.59 (CH, C-aromatic), 129.40 (CH, C-aromatic), 132.23 (C, C-aromatic), 132.66 (CH, C-aromatic), 132.82 (C, C-aromatic), 134.96 (C, C-aromatic), 140.24 (C, C-aromatic), 165.69 (C, C=O), 169.22 (C, C=O) ppm. MS (ESI)$^+$: 418.2 [M+H]$^+$. Melting point (from DCM/n-hexane): 103-105° C.

Example 89

Synthesis of N-(2-methoxy-6-(3-morpholinopropyl-carbamoyl)phenyl)-2-naphthamide (121)

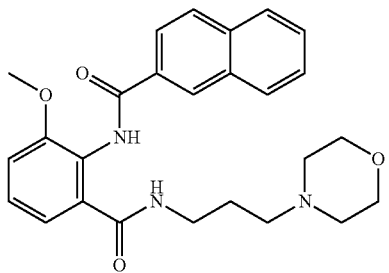

Compound 121 was obtained as a white powder in 38% yield. $^1$H-NMR (500 MHz, CDCl$_3$): δ 1.51-1.78 (m, 3H), 2.32 (s, 3H), 2.39 (t, J=6.0 Hz, 2H), 3.38 (dd, J=5.6, 11.3 Hz, 2H), 3.50-3.53 (m, 4H), 3.84 (s, 3H), 7.05 (dd, J=8.0, 15.8 Hz, 2H), 7.21 (s, 1H), 7.46-7.53 (m, 2H), 7.81-7.93 (5H, m), 8.45 (1H, s), 9.46 (1H, s) ppm. $^{13}$C-NMR (126 MHz, CDCl$_3$): δ 24.30 (—CH2, C-aliphatic), 40.19 (CH2, C-aliphatic), 53.67 (CH2, C-aliphatic), 56.27 (CH3, C-aliphatic), 58.18 (CH2, C-aliphatic), 66.89 (—CH2, C-aliphatic), 114.09 (CH, C-aromatic), 119.02 (CH, C-aromatic), 124.20 (CH, C-aromatic), 125.59 (C, C-aromatic), 126.56 (CH, C-aromatic), 126.72 (CH, C-aromatic), 127.75 (CH, C-aromatic), 127.82 (CH, C-aromatic), 128.49 (CH, C-aromatic), 128.51 (CH, C-aromatic), 129.21 (CH, C-aromatic) 131.57 (C, C-aromatic), 131.68 (C, C-aromatic), 132.70 (C, C-aromatic), 135.01 (C, C-aromatic), 154.44 (C, C-aromatic), 166.10 (C, C-aromatic), 168.45 (C, C-aromatic) ppm. MS (ESI)$^+$: 448.2 [M+H]$^+$. Melting point (from methanol/water) 140-142° C.

Example 90

Synthesis of 4,5-dimethoxy-2-(4-methoxybenzamido)-N-(3-morpholinopropyl)benzamide (126)

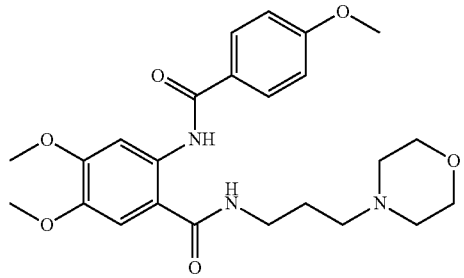

Compound 126 was obtained as a white powder in 39% yield. $^1$H-NMR (500 MHz, CDCl$_3$): δ 1.73 (dt, J=6.0, 12.0 Hz, 3H), 2.27 (s, 3H), 2.35 (bs, 6H), 2.51-2.56 (m, 3H), 3.47 (dd, J=5.8, 11.2 Hz, 2H), 3.95 (s, 3H), 7.15 (d, J=8.3 Hz, 1H), 7.20 (dd, J=1.2, 7.8 Hz, 1H), 7.24-7.34 (m, 1H), 7.54-7.63 (m, 2H), 7.91 (d, J=7.9 Hz, 1H), 7.95 (d, J=8.6 Hz, 1H), 8.00 (d, J=7.9 Hz, 1H), 8.06 (dd, J=1.8, 8.6 Hz, 1H), 8.26 (s, 1H), 8.55 (s, 1H), 9.77 (s, 1H) ppm. $^{13}$C-NMR (126 MHz, CDCl$_3$): δ 24.22 (CH$_2$, C-aliphatic), 40.38 (CH$_2$, C-aliphatic), 53.84 (CH$_2$, C-aliphatic), 55.44 (CH$_3$, C-aliphatic), 56.07 (CH$_3$, C-aliphatic), 57.60 (CH$_3$, C-aliphatic), 58.42 (CH$_2$, C-aliphatic), 66.77 (CH$_2$, C-aromatic), 104.91 (CH, C-aromatic), 111.78 (CH, C-aromatic), 113.99 (CH, C-aromatic), 127.30 (C, C-aromatic), 129.23 (CH, C-aromatic), 136.58 (C, C-aromatic), 143.99 (C, C-aromatic), 153.04 (C, C-aromatic), 162.45 (C, C-aromatic), 165.19 (C, C-aromatic), 165.55 (C, C-aromatic), 169.09 (C, C-aromatic) ppm. MS (ESI)$^+$: 448.2 [M+H]$^+$. Melting point (from acetone/n-hexane) 102-104° C.

Example 91

Synthesis of N-(5-methoxy-2-(3-morpholinepropyl-carbamoyl)phenyl)-2-naphthamide (127)

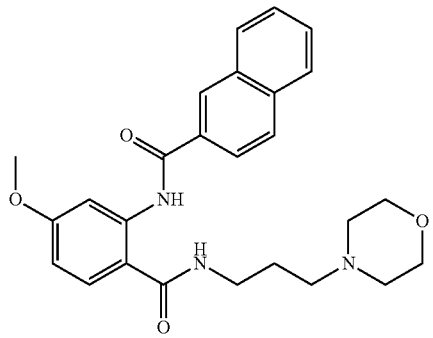

Compound 127 was obtained as a white powder in 44% yield. $^1$H-NMR (500 MHz, CDCl$_3$): δ 1.74 (dt, J=5.9, 11.6, 2H), 2.46 (s, 4H), 2.55-2.50 (m, 2H), 3.55 (dd, J=5.9, 10.9 Hz, 2H), 3.61-3.73 (m, 4H), 3.87 (3H, s), 6.60 (dd, J=2.6, 8.8 Hz, 1H), 7.41-7.53 (m, 1H), 7.82 (d, J=7.9 Hz, 2H), 7.89 (d, J=8.6 Hz, 1H), 7.96 (d, J=7.8 Hz, 2H), 8.05 (dd, J=1.8, 8.6 Hz, 2H), 8.39 (s, 1H), 8.49-8.62 (m, 1H), 12.87-12.94 (m, 1H) ppm. $^{13}$C-NMR (126 MHz, CDCl$_3$): δ 23.52 (CH$_2$, C-aliphatic), 41.02 (CH$_2$, C-aliphatic), 53.91 (CH$_2$, C-aliphatic), 55.59 (CH$_3$, C-aliphatic), 59.16 (CH$_2$, C-aliphatic), 66.94 (CH$_2$, C-aliphatic), 105.16 (CH, C-aromatic), 109.86 (CH, C-aromatic), 112.44 (C, C-aromatic), 123.66 (CH, C-aromatic), 126.60 (CH, C-aromatic), 127.71 (CH, C-aromatic), 127.78 (CH, C-aromatic), 128.15 (CH, C-aromatic), 128.54 (CH, C-aromatic), 128.63 (CH, C-aromatic), 129.46 (CH, C-aromatic), 132.21 (C, C-aromatic), 132.83 (C, C-aromatic), 134.98 (C, C-aromatic), 142.61 (C, C-aromatic), 162.93 (C, C-aromatic), 165.94 (C, C-aromatic), 169.10 (C, C-aromatic) ppm. Melting point (from ethanol/water) 131-133° C.

Example 92

Synthesis of N-(2-methoxy-6-(3-morpholinopropyl-carbamoyl)phenyl)-1-naphthamide (128)

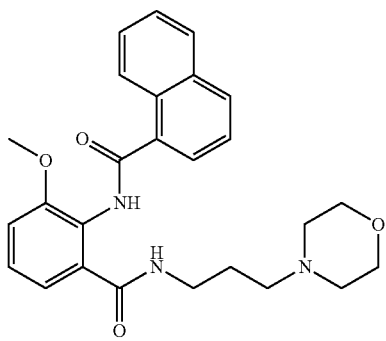

128

Compound 128 was obtained as a white powder in 24% yield. $^1$H-NMR (500 MHz, CDCl$_3$): δ 1.68-1.93 (m, 2H), 2.45 (s, 4H), 2.52 (t, J=6.0 Hz, 2H), 3.53 (dd, J=5.8, 11.6 Hz, 2H), 3.63 (s, 4H), 3.95 (s, 3H), 7.01-7.24 (m, 2H), 7.48-7.61 (m, 3H), 7.85 (s, 1H), 7.89-7.94 (m, 2H), 7.98 (d, J=8.2 Hz, 1H), 8.59 (d, J=7.3 Hz, 2H), 11.58 (s, 1H) ppm. $^{13}$C-NMR (126 MHz, CDCl$_3$): δ 24.59 (CH$_2$, C-aliphatic), 39.98 (CH$_2$, C-aliphatic), 53.61 (CH$_2$, C-aliphatic), 56.18 (CH$_3$, C-aliphatic), 57.96 (CH$_2$, C-aliphatic), 66.85 (CH$_2$, C-aliphatic), 113.55 (CH, C-aromatic), 119.17 (CH, C-aromatic), 124.86 (CH, C-aromatic), 125.78 (CH, C-aromatic), 125.96 (CH, C-aromatic), 126.38 (CH, C-aromatic), 126.93 (CH, C-aromatic), 127.16 (CH, C-aromatic), 127.20 (C, C-aromatic), 128.28 (CH, C-aromatic), 130.55 (C, C-aromatic), 131.09 (CH, C-aromatic), 133.09 (C, C-aromatic), 133.17 (C, C-aromatic), 133.80 (C, C-aromatic), 133.95 (C, C-aromatic), 154.22 (C, C-aromatic), 168.37 (C, C-aromatic) ppm. Melting point (from ethanol/water) 130-132° C.

Example 93

Synthesis of N-(3-fluoro-2-((3-morpholinopropyl)carbamoyl)phenyl) nicotinamide (130)

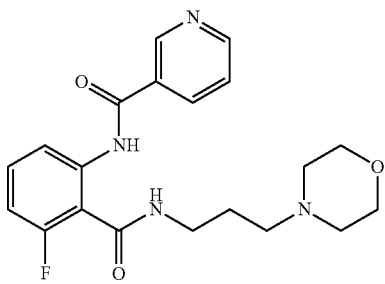

130

Compound 130 was obtained as a white powder in 79% yield. $^1$H-NMR (500 MHz, CDCl$_3$): δ 1.75 (dt, J=5.8, 11.6 Hz, 2H), 2.46 (s, 4H), 2.52-2.56 (m, 2H), 3.52 (dd, J=5.9, 10.6 Hz, 2H), 3.64 (t, J=4.5 Hz, 4H), 7.10 (td, J=1.1, 7.8 Hz, 1H), 7.37 (ddd, J=0.7, 4.8, 7.9 Hz, 1H), 7.47-7.51 (m, 1H), 7.54-7.58 (m, 1H), 8.25 (ddd, J=1.7, 2.2, 8.0 Hz, 1H), 8.67 (s, 1H), 8.70 (dd, J=1.6, 4.8 Hz, 1H), 8.76 (dd, J=1.0, 8.4 Hz, 1H), 9.24 (d, J=1.8 Hz, 1H), 12.62 (s, 1H) ppm. $^{13}$C-NMR (126 MHz, CDCl$_3$): δ 30.41 (CH$_2$, C-aliphatic), 33.58 (CH$_2$, C-aliphatic), 39.82 (CH$_2$, C-aliphatic), 57.62 (CH$_2$, C-aliphatic), 60.10 (CH$_2$, C-aliphatic), 124.46 (CH, C-aromatic), 128.52 (CH, C-aromatic), 128.73 (CH, C-aromatic), 130.07 (C,C-aromatic), 130.47 (CH, C-aromatic), 132.85 (CH, C-aromatic), 134.86 (CH, C-aromatic), 139.73 (C, C-aromatic), 141.21 (C, C-aromatic), 149.20 (CH, C-aromatic), 152.48 (CH, C-aromatic), 163.75 (C, C-aromatic), 169.01 (C, C-aromatic) ppm. $^{19}$F-NMR (CDCl$_3$): δ -110.50 ppm. Melting point (from acetone/n-hexane) 120-122° C.

Example 94

Synthesis of 3,4,5-trimethoxy-2-(4-methoxybenzamido)-N-(3-morpholinopropyl)benzamide (131)

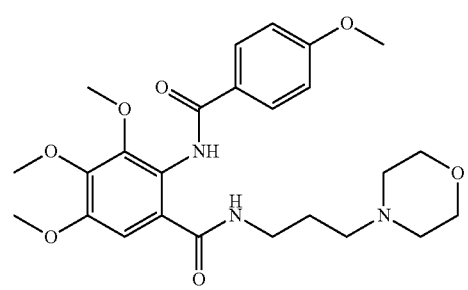

131

Compound 131 was obtained as a white powder in 63% yield. $^1$H-NMR (500 MHz, CDCl$_3$): δ 1.58 (dt, J=6.6, 13.2 Hz, 2H), 2.29 (dd, J=9.5, 16.2 Hz, 4H), 3.33 (dd, J=6.4, 12.1 Hz, 2H), 3.41-3.64 (m, 4H), 3.81 (s, 3H), 3.82 (s, 3H), 3.83 (s, 3H), 3.85 (s, 3H), 6.75-6.88 (m, 2H), 6.89-6.98 (m, 4H), 7.67-7.89 (m, 4H), 8.47 (s, 2H) ppm. $^{13}$C-NMR (126 MHz, CDCl$_3$): δ 25.36 (CH$_2$, C-aliphatic), 39.23 (CH$_2$, C-aliphatic), 53.59 (CH$_2$, C-aliphatic), 55.50 (CH$_3$, C-aliphatic), 56.58 (CH₃, C-aliphatic), 57.18 (CH₃, C-aliphatic), 61.01 (CH₃, C-aliphatic), 61.07 (CH₂, C-aliphatic), 66.94 (CH₂, C-aliphatic), 106.66 (CH, C-aromatic), 113.96 (CH, C-aromatic), 122.67 (C, C-aromatic), 126.22 (C, C-aromatic), 128.41 (C, C-aromatic), 129.49 (CH, C-aromatic), 144.66 (C, C-aromatic), 149.46 (C, C-aromatic), 152.01 (C, C-aromatic), 162.75 (C, C-aromatic), 166.96 (C, C-aromatic), 167.99 (C, C-aromatic) ppm. MS(ESI)⁺: 458.2 [M+H]⁺ Melting point (from acetone/n-hexane) 121-123° C.

Example 95

Synthesis of N-(2,3,4-trimethoxy-6-((3-morpholinopropyl)carbamoyl)phenyl) nicotinamide (132)

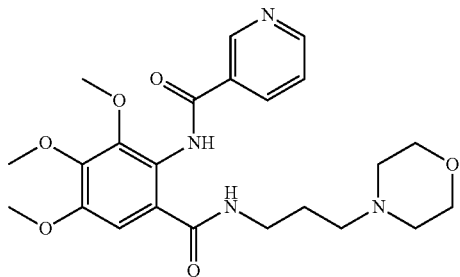

Compound 132 was obtained as a white powder in 23% yield. ¹H-NMR (500 MHz, CDCl₃): δ 1.70-1.76 (m, 2H), 2.43 (s, 2H), 2.48 (t, J=5.5 Hz, 2H), 3.42-3.52 (m, 8H), 3.66 (t, J=4.4 Hz, 3H), 3.94 (s, 3H), 3.96 (s, 3H), 6.85 (s, 1H), 7.45 (dd, J=4.8, 7.9 Hz, 1H), 7.52 (d, J=26.4 Hz, 1H), 8.22-8.29 (m, 1H), 8.80 (dd, J=4.8, 1.5 Hz, 1H), 9.25-9.13 (m, 2H) ppm. ¹³C-NMR (126 MHz, CDCl₃): δ 24.82 (CH₂, C-aliphatic), 39.85 (CH₂, C-aliphatic), 53.69 (CH₂, C-aliphatic), 56. (CH₃, C-aliphatic), 57.73 (CH₂, C-aliphatic), 60.99 (CH₃, C-aliphatic), 61.02 (CH₃, C-aliphatic), 66.93 (CH₃, C-aliphatic), 106.38 (CH, C-aromatic), 123.03 (C, C-aromatic), 123.50 (CH, C-aromatic), 126.44 (C, C-aromatic), 130.09 (C, C-aromatic), 135.28 (CH, C-aromatic), 144.86 (C, C-aromatic), 148.95 (CH, C-aromatic), 149.11 (C, C-aromatic), 151.64 (C, C-aromatic), 152.63 (CH, C-aromatic), 164.99 (C, C-aromatic), 168.06 (C, C-aromatic) ppm. MS(ESI)⁺: 458.2 [M+H]⁺. Melting point (from acetone/n-hexane) 120-122° C.

Example 96

Synthesis of N-(5-fluoro-2-(3-morpholinopropylcarbamoyl)phenyl)nicotinamide (133)

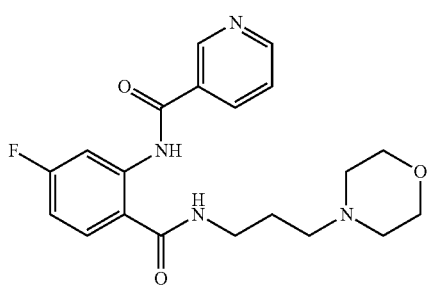

Compound 133 was obtained as a white powder in 57% yield. ¹H-NMR (500 MHz, CDCl₃): δ 1.72-1.88 (m, 2H), 2.36-2.47 (m, 2H), 2.53 (bs, 4H), 3.52 (dd, J=5.8, 10.6 Hz, 2H), 3.65 (s, 4H), 6.79 (ddd, J=2.6, 7.4, 8.8 Hz, 1H), 7.37 (s, 1H), 7.55 (dd, J=6.2, 8.5 Hz, 1H), 8.19-8.30 (m, 1H), 8.61 (dd, J=2.6, 11.6 Hz, 1H), 8.64 (d, J=14.1 Hz, 1H), 8.71 (dd, J=1.5, 4.8 Hz, 1H), 9.23 (d, J=1.8 Hz, 1H), 12.89 (s, 1H) ppm. ¹³C-NMR (126 MHz, CDCl₃): δ 23.15 (CH₂, C-aliphatic), 41.20 (CH₂, C-aliphatic), 53.84 (CH₂, C-aliphatic), 59.11 (CH₂, C-aliphatic), 66.86 (CH₂, C-aliphatic), 108.76 (CH, C-aromatic), 109.97 (CH, C-aromatic), 116.08 (C, C-aromatic), 123.51 (CH, C-aromatic), 128.62 (CH, C-aromatic), 130.18 (C, C-aromatic), 134.91 (CH, C-aromatic), 142.23 (C, C-aromatic), 149.23 (CH, C-aromatic), 152.65 (CH, C-aromatic), 163.95 (C, C-aromatic), 165.97 (C, C-aromatic), 168.42 (C, C-aromatic) ppm. ¹⁹F-NMR (CDCl₃): δ −103.82 ppm. Melting point (from dichloromethane/n-hexane) 127-129° C.

Example 97

Synthesis of N-(2-(3-morpholinopropylcarbamoyl)phenyl)nicotinamide (134)

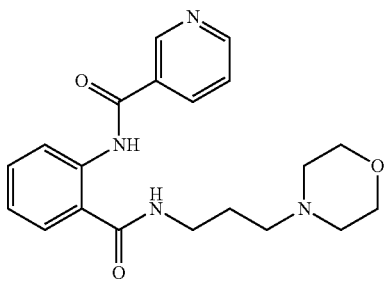

Compound 134 was obtained as a white powder in 79% yield. ¹H-NMR (500 MHz, CDCl₃): δ 1.72-1.77 (m, 2H), 2.43-2.46 (m, 4H), 2.54 (t, J=5.9 Hz, 2H), 3.52 (td, J=4.5, 6 Hz, 2H), 3.64 (t, J=4.5 Hz, 4H), 7.10 (td, J=1.5, 7.75 Hz, 1H), 7.38 (ddd, J=1, 5, 8 Hz, 1H), 7.47-7.51 (m, 1H), 7.55 (dd, J=1.5, 8 Hz, 1H), 8.24-8.26 (m, 1H), 8.67 (s, 1H), 8.70 (dd, J=1.5, 4.5 Hz, 1H), 8.76 (dd, J=1.2, 8.5 Hz, 1H), 9.24 (dd, J=1.1, 2.25 MHz, 1H), 12.62 (bs, H) ppm. ¹³C-NMR (126 MHz, CDCl₃): δ 23.30 (CH₂, C-aliphatic), 41.02 (CH₂, C-aliphatic), 53.88 (CH₂, C-aliphatic), 59.09 (CH₂, C-aliphatic), 66.89 (CH₂, C-aliphatic), 120.23 (C, C-aromatic), 121.55 (CH, C-aromatic), 123.03 (CH, C-aromatic), 123.49 (CH, C-aromatic), 126.86 (CH, C-aromatic), 130.50 (C, C-aromatic), 132.82 (CH, C-aromatic), 134.90 (CH, C-aromatic), 139.75 (C, C-aromatic), 149.19 (CH, C-aromatic), 152.41 (CH, C-aromatic), 163.69 (C, C-aromatic), 168.96 (C, C-aromatic) ppm. Melting point (from ethanol) 99-101° C.

Example 98

Synthesis of 2-(4-methoxybenzamido)-N-(3-morpholinopropyl)benzamide (138)

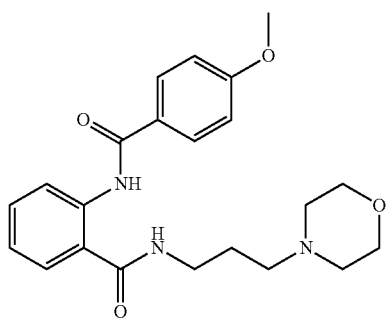

138

Compound 138 was obtained as a white powder in 67% yield. $^1$H-NMR (500 MHz, CDCl$_3$): δ 1.74 (dt, J=5.9, 11.6 Hz, 2H), 2.45 (s, 4H), 2.53 (d, J=5.5 Hz, 2H), 3.52 (dd, J=5.8, 10.7 Hz, 2H), 3.63 (t, J=4.4 Hz, 4H), 3.80 (s, 3H), 6.83-6.96 (m, 2H), 7.04 (td, J=1.2, 7.8 Hz, 1H), 7.42-7.48 (m, 1H), 7.51 (dd, J=1.3, 7.9 Hz, 1H), 7.99-7.79 (m, 2H), 8.55 (s, 1H), 8.75 (dd, J=1.0, 8.4 Hz, 1H), 12.23 (s, 1H) ppm. $^{13}$C-NMR (126 MHz, CDCl$_3$): δ 23.37 (CH$_2$, C-aliphatic), 41.15 (CH$_2$, C-aliphatic), 53.87 (CH$_2$, C-aliphatic), 55.44 (CH$_3$, C-aliphatic), 59.12 (CH$_2$, C-aliphatic), 66.89 (CH$_2$, C-aliphatic), 113.95 (CH, C-aromatic), 120.35 (C, C-aromatic), 121.53 (CH, C-aromatic), 122.30 (CH, C-aromatic), 126.77 (CH, C-aromatic), 127.33 (C, C-aromatic), 129.34 (CH, C-aromatic), 132.64 (CH, C-aromatic), 140.40 (C, C-aromatic), 162.46 (C, C-aromatic), 165.20 (C, C-aromatic), 169.26 (C, C-aromatic) ppm. Melting point (from dichloromethane) 108-110° C.

Example 99

Synthesis of N-(4,5-dimethoxy-2-(3-morpholinopropylcarbamoyl)phenyl) nicotinamide (139)

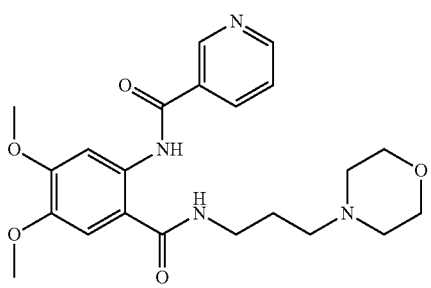

139

Compound 139 was obtained as a white powder in 74% yield. $^1$H-NMR (500 MHz, CDCl$_3$): δ 1.81 (d, J=16.7 Hz, 2H), 1.83-1.91 (m, 2H), 2.53 (s, 3H), 2.58 (dd, J=11.0, 17.1 Hz, 2H), 3.60 (dd, J=5.6, 11.4 Hz, 2H), 3.73 (d, J=4.0 Hz, 3H), 3.95 (s, 3H), 4.04 (d, J=7.5 Hz, 2H), 7.10 (s, 1H), 7.47-7.64 (m, 1H), 7.98 (s, 1H), 8.24-8.43 (m, 1H), 8.63 (d, J=22.8 Hz, 1H), 8.79 (dd, J=1.4, 4.8 Hz, 1H), 9.32 (d, J=1.8 Hz, 1H), 12.85 (s, 1H) ppm. $^{13}$C-NMR (126 MHz, CDCl$_3$): δ 24.17 (CH$_2$, C-aliphatic), 40.30 (CH$_2$, C-aliphatic), 53.82 (CH$_2$, C-aliphatic), 56.12 (CH$_3$, C-aliphatic), 57.56 (CH$_3$, C-aliphatic), 58.34 (CH$_2$, C-aliphatic), 66.74 (CH$_2$, C-aliphatic), 104.93 (CH, C-aromatic), 111.67 (CH, C-aromatic), 111.77 (C, C-aromatic), 123.49 (CH, C-aromatic), 130.57 (C, C-aromatic), 134.78 (CH, C-aromatic), 136.03 (C, C-aromatic), 144.47 (C, C-aromatic), 149.14 (CH, C-aromatic), 152.37 (CH, C-aromatic), 153.09 (C, C-aromatic), 163.66 (C, C-aromatic), 168.95 (C, C-aromatic) ppm. Melting point (from ethyl acetate/n-hexane) 69-71° C.

Example 100

Synthesis of 2-(2-fluorobenzamido)-4,5-dimethoxy-N-(3-morpholinopropyl) benzamide (141)

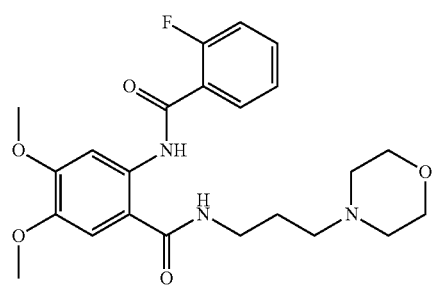

141

Compound 141 was obtained as a white powder. $^1$H-NMR (500 MHz, CDCl$_3$): δ 1.71 (dd, J=26.1, 31.9 Hz, 2H). 2.43 (s, 3H), 2.46 (bs, 4H), 3.47 (dt, J=15.4, 30.9 Hz, 2H), 3.51-3.71 (m, 3H), 3.85 (s, 3H), 3.93 (s, 3H), 6.98 (s, 1H), 7.12 (ddd, J=0.9, 8.3, 11.2 Hz, 2H), 7.42 (dddd, J=1.8, 5.1, 7.1, 8.3 Hz, 1H), 7.67 (s, 1H), 7.95 (td, J=1.8, 7.7 Hz, 1H), 8.47 (s, 1H), 12.01 (s, 1H) ppm. $^{13}$C-NMR (126 MHz, CDCl$_3$): δ 24.30 (CH$_2$, C-aliphatic), 40.11 (CH$_2$, C-aliphatic), 53.76 (CH$_2$, C-aliphatic), 56.09 (CH$_3$, C-aliphatic), 57.34 (CH$_3$, C-aliphatic), 58.24 (CH$_2$, C-aliphatic), 66.72 (CH$_2$, C-aliphatic), 105.82 (CH, C-aromatic), 111.34 (CH, C-aromatic), 116.50 (CH, C-aromatic), 116.69 (CH, C-aromatic), 124.59 (CH, C-aromatic), 124.62 (CH, C-aromatic), 131.26 (CH, C-aromatic), 133.28 (C, C-aromatic), 135.04 (C, C-aromatic), 144.51 (C, C-aromatic), 152.48 (C, C-aromatic), 159.03 (C, C-aromatic), 161.27 (C, C-aromatic), 162.99 (C, C-aromatic), 168.55 (C, C-aromatic) ppm. $^{19}$F-NMR (CDCl$_3$): δ −112.59 ppm. Melting point 75-77° C.

Example 101

Synthesis of N-(2-methoxy-6-((3-morpholinopropyl)carbamoyl)phenyl) nicotinamide (142)

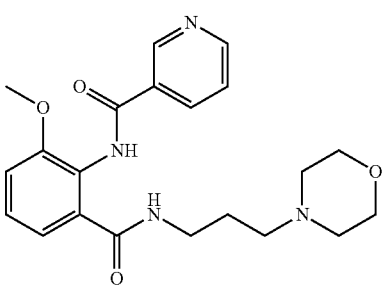

142

Compound 142 was obtained as a white powder in 51% yield. $^1$H-NMR (500 MHz, CDCl$_3$): δ 1.70 (dd, J=5.9, 11.9 Hz, 2H), 2.44 (s, 3H), 2.47 (d, J=18.6 Hz, 4H), 3.24-3.42 (m, 2H), 3.65 (bs, 4H), 3.84 (s, 3H), 7.04 (bs, 2H), 7.32-7.47 (m, 1H), 8.03 (s, 1H), 8.12-8.24 (m, 1H), 8.69 (dd, J=1.6, 4.8 Hz, 1H), 9.14 (d, J=1.7 Hz, 1H), 9.55 (s, 1H) ppm. $^{13}$C-NMR (126 MHz, CDCl$_3$): δ 23.91 (CH$_2$, C-aliphatic), 40.17 (CH$_2$, C-aliphatic), 53.61 (CH$_2$, C-aliphatic), 56.26 (CH$_3$, C-aliphatic), 58.20 (CH$_2$, C-aliphatic), 66.67 (CH$_2$, C-aliphatic), 114.31 (CH, C-aromatic), 118.90 (CH, C-aromatic), 123.42 (CH, C-aromatic), 125.38 (C, C-aromatic), 126.68 (CH, C-aromatic), 130.14 (C, C-aromatic), 130.89 (C, C-aromatic), 135.36 (CH, C-aromatic), 149.19 (CH, C-aromatic), 152.47 (CH, C-aromatic), 154.33 (C, C-aromatic), 163.94 (C, C-aromatic), 168.40 (C, C-aromatic) ppm. Melting point (from ethanol) 125-127° C.

Example 102

Synthesis of 2-(methylthio)-N-(2-((3-morpholino-propyl)carbamoyl)phenyl) nicotinamide (143)

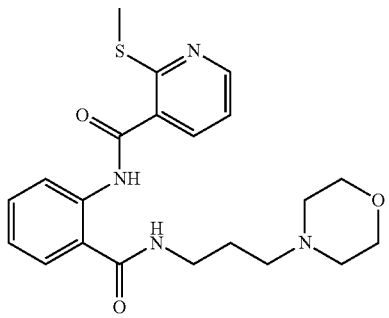

143

Compound 143 was obtained as a white powder in 68% yield. $^1$H-NMR (500 MHz, CDCl$_3$): δ 1.73 (dt, J=5.9, 11.4 Hz, 2H), 2.46 (s, 3H), 2.48 (s, 4H), 2.51-2.55 (m, 2H), 3.47 (dd, J=5.8, 10.7 Hz, 2H), 3.64 (d, J=4.1 Hz, 4H), 7.02 (dd, J=12.0, 16.9 Hz, 1H), 7.04-7.14 (m, 1H), 7.43-7.52 (m, 1H), 7.52 (d, J=7.8 Hz, 1H), 7.89 (dd, J=1.7, 7.7 Hz, 1H), 8.49 (dd, J=1.7, 4.8 Hz, 1H), 8.61 (s, 1H), 8.71 (dd, J=0.9, 8.4 Hz, 1H), 12.11 (s, 1H) ppm. $^{13}$C-NMR (126 MHz, CDCl$_3$): δ 13.91 (CH$_3$, C-aliphatic), 23.25 (CH$_2$, C-aliphatic), 40.96 (CH$_2$, C-aliphatic), 53.79 (CH$_2$, C-aliphatic), 58.96 (CH$_2$, C-aliphatic), 66.76 (CH$_2$, C-aliphatic), 118.49 (CH, C-aromatic), 120.47 (C, C-aromatic), 121.76 (CH, C-aromatic), 123.02 (CH, C-aromatic), 126.79 (CH, C-aromatic), 129.04 (C, C-aromatic), 132.71 (CH, C-aromatic), 134.84 (CH, C-aromatic), 139.75 (C, C-aromatic), 150.69 (CH, C-aromatic), 160.57 (C, C-aromatic), 165.19 (C, C-aromatic), 169.02 (C, C-aromatic) ppm. Melting point 128-130° C.

General Procedure 4

The compounds of the application with the general formula below can be prepared according to the synthetic scheme shown in Scheme 4.

Scheme 4

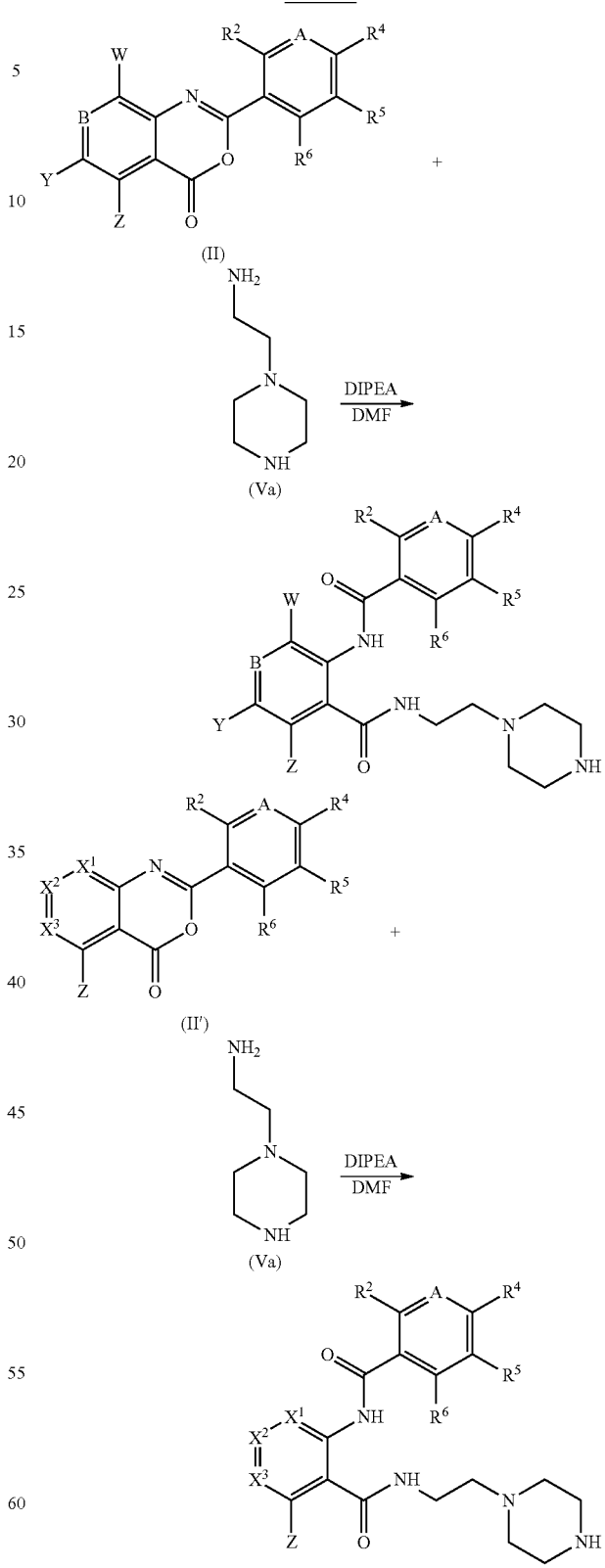

To a solution of compound (II) or (II') (1 equivalent) in N,N-dimethyl-formamide (DMF) is added 2 equivalents of N,N-diisopropylethylamine (DIPEA) and 2.2 equivalent of 2-(4-methylpiperazin-1-yl)ethanamine (Va). The reaction mixture is stirred at about 15° C. to about 28° C. for about 6 hours to about 24 hours. The reaction mixture is diluted with water, washed with ethyl acetate, washed with brine, dried over $Mg_2SO_4$, filtered and evaporated to give a crude compound which is then purified by silica gel column using a mixture of Chloroform:Methanol (9:1) as eluent. The product is collected under reduced pressure to provide the compound shown in Scheme 4.

Compounds 38-46, 102, 111, 112, and 118 were prepared according to General Procedure 4 substituting (II) or (II') with the appropriate substituted compound.

Example 103

Synthesis of 2-(4-nitrobenzamido)-N-(2-(piperazin-1-yl)ethyl)benzamide (38)

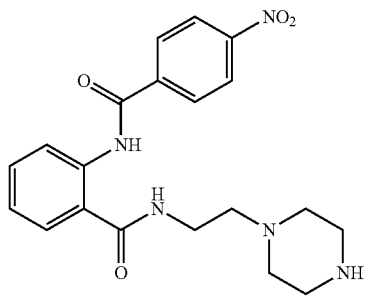

38

Compound 38 was obtained as a yellow solid in 13% yield. $^1$H-NMR (500 MHz, $CDCl_3$): δ 12.73 (s, 1H, ArNHCO), 8.85 (d, J=8.25, 1H, CONHCH$_2$), 8.39 (d, J=9, 2H), 8.24 (d, J=9, 2H), 7.6 (q, J=7.5, 2H), 7.22 (t, J=6.75, 1H), 7.2 (s, 1H), 3.58 (q, J=5.25, 2H, NHCH$_2$CH$_2$), 3.00 (t, J=4.7, 4H), 2.67 (t, J=6.05, 2H, NHCH$_2$CH$_2$), 2.6 (s, 5H). $^{13}$C-NMR (126 MHz, $CDCl_3$): δ 169.02 (ArC=O), 163.29 (ArC=O), 149.76 (ArC), 140.50 (ArC), 139.85 (ArC), 133.06 (ArCH), 128.61 (ArCH), 126.61 (ArCH), 123.99 (ArCH), 123.57 (ArCH), 121.54 (ArCH), 119.80 (ArC), 56.33 ($CH_2$), 53.35 ($CH_2$), 45.71 ($CH_2$), 36.07 ($CH_2$). MS (ESI): 398.2 [M+1]. m.p. (from ethanol/water): 98° C.

Example 104

Synthesis of 2-(4-chlorobenzamido)-N-(2-(piperazin-1-yl)ethyl)benzamide (39)

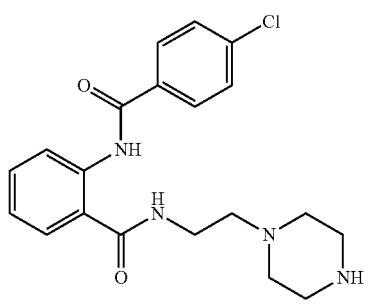

39

Compound 39 was obtained as a yellow solid in 63% yield. $^1$H-NMR (500 MHz, $CDCl_3$): δ 12.38 (s, 1H, ArNHCO), 8.78 (d, J=8.4, 1H, CONHCH$_2$), 7.98 (d, J=8.4, 2H), 7.56-7.50 (m, 2H), 7.47 (d, J=8.4, 2H'), 7.26-7.24 (m, 1H), 7.13 (t, J=7.35, 1H), 3.54 (q, J=5.8, 2H, NHCH$_2$CH$_2$), 2.91 (t, J=4.2, 4H), 2.61 (t, J=5.75, 2H, NHCH$_2$CH$_2$), 2.56-2.41 (m, 5H). $^{13}$C-NMR (126 MHz, $CDCl_3$): δ 169.10 (ArC=O), 164.47 (ArC=O), 139.96 (ArC), 138.06 (ArC), 133.29 (ArC), 132.73 (ArCH), 129.00 (ArCH), 128.85 (ArCH), 126.71 (ArCH), 123.04 (ArCH), 121.44 (ArCH), q20.18 (ArC), 56.58 ($CH_2$), 53.91 ($CH_2$), 45.96 ($CH_2$), 36.13 ($CH_2$). MS (ESI): 387.2 [M+1]. m.p. (from ethanol/water): 60° C.

Example 105

Synthesis of N-(2-(piperazin-1-yl)ethyl)-2-(3-(trifluoromethyl)benzamido) benzamide (40)

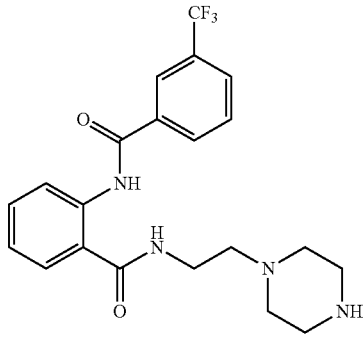

40

Compound 40 was obtained as a white powder in 36% yield. $^1$H-NMR ($CDCl_3$): δ 1.70 (s, 1H), 2.52 (s, 4H), 2.64 (s, 2H), 2.94 (s, 4H), 3.57 (d, J=4.7 Hz, 2H), 7.14-7.22 (m, 2H), 7.58 (dd, J=7.4, 13.1 Hz, 2H), 7.67 (t, J=7.5 Hz, 1H), 7.82 (d, J=7.5 Hz, 1H), 8.22 (d, J=7.7 Hz, 1H), 8.38 (s, 1H), 8.84 (d, J=8.1 Hz, 1H), 12.56 (s, 1H) ppm. $^{13}$C-NMR ($CDCl_3$): δ 36.08 ($CH_2$, C-aliphatic), 46.12 ($CH_2$, C-aliphatic), 54.01 ($CH_2$, C-aliphatic), 56.44 ($CH_2$, C-aliphatic), 120.22 (C, C-aromatic), 121.61 (CH, C-aromatic), 123.22 (CH, C-aromatic), 125.07 (CH, C-aromatic), 125.10 (CH, C-aromatic), 126.52 (CH, C-aromatic), 128.27 (CH, C-aromatic), 128.30 (CH, C-aromatic), 129.33 (CH, C-aromatic), 130.08 (CH, C-aromatic), 131.51 (C, C-aromatic), 132.85 (CH, C-aromatic), 135.88 (C, C-aromatic), 139.99 (C, C-aromatic), 164.04 (C, C-aromatic), 169.00 (C, C-aromatic) ppm. $^{19}$F-NMR ($CDCl_3$): δ −62.90 ppm. MS(ESI)$^+$: 421.2 [M+H]$^+$. m.p.: (from ethanol/$H_2O$) 67-70° C.

Example 106

Synthesis of N-(2-(piperazin-1-yl)ethyl)-2-(2-(trifluoromethyl)benzamido) benzamide (41)

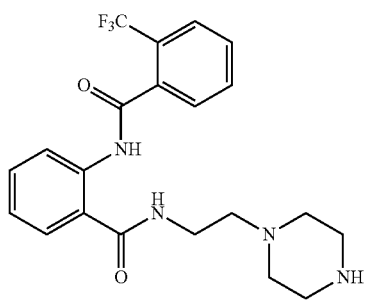

41

Compound 41 was obtained as a white powder in 21% yield. ¹H-NMR (CDCl₃): δ 1.76 (s, 1H), 2.50 (s, 4H), 2.59 (dd, J=10.4, 16.3 Hz, 2H), 2.94 (t, J=4.8 Hz, 4H), 3.48 (dd, J=5.7, 10.9 Hz, 2H), 7.03 (s, 1H), 7.20 (td, J=1.1, 7.8 Hz, 1H), 7.52 (dt, J=5.7, 11.3 Hz, 1H), 7.58 (td, J=2.9, 8.1 Hz, 2H), 7.66 (t, J=7.2 Hz, 1H), 7.71 (d, J=7.5 Hz, 1H), 7.77 (d, J=7.8 Hz, 1H), 8.80 (d, J=8.3 Hz, 1H), 11.65 (s, 1H) ppm. ¹³C-NMR (CDCl₃): δ 35.99 (CH₂, C-aliphatic), 46.05 (CH₂, C-aliphatic), 53.91 (CH₂, C-aliphatic), 56.47 (CH₂, C-aliphatic), 120.46 (C, C-aromatic), 121.76 (CH, C-aromatic), 123.45 (CH, C-aromatic), 126.49 (CH, C-aromatic), 126.73 (CH, C-aromatic), 126.77 (CH, C-aromatic), 128.15 (CH, C-aromatic), 129.99 (CH, C-aromatic), 132.17 (CH, C-aromatic), 132.73 (C, C-aromatic), 136.35 (C, C-aromatic), 139.48 (C, C-aromatic), 166.12 (C, C-aromatic), 168.67 (C, C-aromatic) ppm. ¹⁹F-NMR (CDCl₃): δ −58.94 ppm. MS(ESI)⁺: 421.2 [M+H]⁺.

Example 107

Synthesis of 2-(4-methoxybenzamido)-N-(2-(piperazin-1-yl)ethyl)benzamide (42)

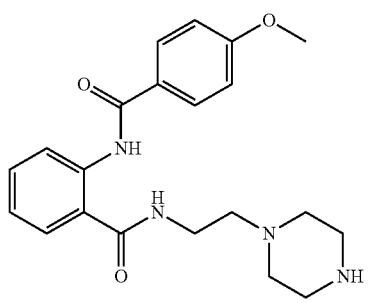

42

Compound 42 was obtained as a yellow solid in 23% yield. ¹H-NMR (500 MHz, CDCl₃): δ 12.19 (s, 1H, ArN-HCO), 8.83 (d, J=8.05, 1H, CONHCH2), 8.03 (d, J=8.05, 2H), 7.58-7.49 (m, 2H), 7.16-7.07 (m, 2H), 7.01 (d, J=6.9, 2H), 3.89 (s, 3H, OCH₃), 3.56 (q, J=4.55, 2H, NHCH₂CH₂), 2.99-2.91 (m, 4H), 2.63 (t, J=5.7, 2H, NHCH₂CH₂), 2.60-2.48 (m, 5H). ¹³C-NMR (126 MHz, CDCl₃): δ 169.20 (ArC=O), 165.18 (ArC=O), 162.47 (ArC), 140.33 (ArC), 132.68 (ArCH), 129.31 (ArCH), 127.23 (ArC), 126.57 (ArCH), 122.60 (ArCH), 121.53 (ArCH), 120.25 (ArC), 113.96 (ArCH), 56.46 (CH₂), 55.45 (CH₃), 53.67 (CH₂), 45.93 (CH₂), 36.10 (CH₂). MS (ESI): 383.2 [M+1]. m.p. (from ethanol/water): 91° C.

Example 108

Synthesis of 3,5-difluoro-N-(2-((2-(piperazin-1-yl)ethyl)carbamoyl)phenyl) benzamide (43)

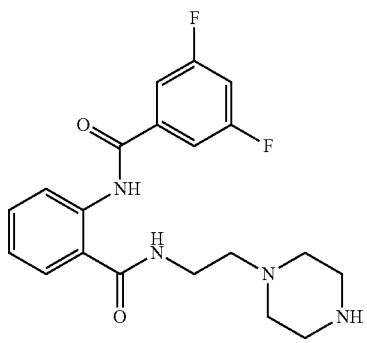

43

Compound 43 was obtained as a yellow solid in 17% yield. ¹H-NMR (500 MHz, CDCl₃): δ 12.5 (s, 1H, ArN HCO), 8.78 (d, J=7.9, 1H, CONHCH₂), 7.61-7.52 (m, 4H), 7.18 (q, J=7.3, 2H), 7.00 (t, J=9.8, 1H), 3.57 (q, J=4.15, 2H, NHCH₂CH₂), 2.95 (t, J=4.55, 4H), 2.64 (t, J=5.3, 2H, NHCH₂CH₂), 2.59-2.44 (m, 5H). ¹³C-NMR (126 MHz, CDCl₃): δ 168.96 (ArC=O), 163.03 (ArC=O), 139.79 (ArC), 138.47 (ArC), 132.90 (ArCH), 126.59 (ArCH), 123.39 (ArCH), 121.57 (ArCH), 120.09 (ArC), 110.75 (d, $J_{C-F}$=6.3, ArCH), 110.59 (d, $J_{C-F}$=6.3, ArCH), 107.16 (t, $J_{C-F}$=26.46, 25.2, ArCH), 56.47 (CH₂), 53.57 (CH₂), 45.82 (CH₂), 36.06 (CH₂). MS (ESI): 389.2 [M+1]. m.p. (from ethanol/water): 68° C.

Example 109

Synthesis of 2,6-difluoro-N-(2-((2-(piperazin-1-yl)ethyl)carbamoyl)phenyl) benzamide (44)

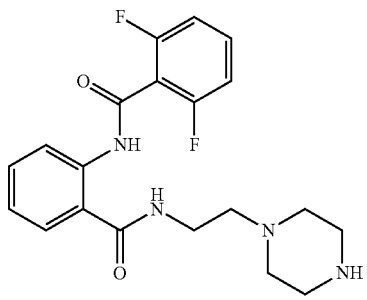

44

Compound 44 was obtained as a white solid in 33.5% yield. ¹H-NMR (500 MHz, CDCl₃): δ 11.81 (s, 1H, ArN HCO), 8.81 (d, J=7.25, 1H, CONHCH₂), 7.57-7.50 (m, 2H), 7.39 (q, J=7.25, 1H), 7.18-7.12 (m, 2H), 7.0 (t, J=7.25, 2H), 3.49 (q, J=5.2, 2H, NHCH₂CH₂), 2.94-2.88 (m, 4H), 2.59 (t, J=5.2, 2H, NHCH₂CH₂), 2.47 (s, 4H), 1.96 (s, 1H). ¹³C-NMR (126 MHz, CDCl₃): δ 168.63 (ArC=O), 160.97 (d, J$_{C-F}$=7.56, ArC), 158.93 (t, J=7.56, ArC), 139.15 (ArC), 132.64 (ArCH), 131.78 (t, J$_{C-F}$=10.08, 10.08, ArCH), 126.58 (ArCH), 123.57 (ArCH), 121.75 (ArCH), 120.69 (ArC), 112.24 (d, J$_{C-F}$=5.04, ArCH), 112.07 (d, J$_{C-F}$=3.78, ArCH), 56.52 (CH₂), 54.12 (CH₂), 46.16 (CH₂), 36.04 (CH₂). MS (ESI): 389.2 [M+1]. m.p. (from ethanol/water): 79° C.

Example 110

Synthesis of 2,4-difluoro-N-(2-((2-(piperazin-1-yl)ethyl)carbamoyl)phenyl) benzamide (45)

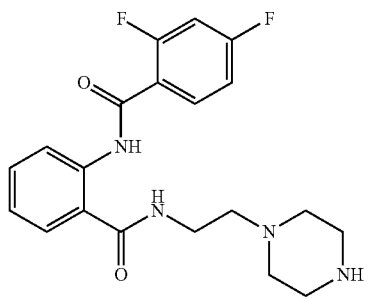

Compound 45 was obtained as a white solid in 12% yield. ¹H-NMR (500 MHz, CDCl₃): δ 11.86 (d, J=6.5, 1H, ArNHCO), 8.7 (d, J=8.5, 1H, CONHCH₂), 8.07 (q, J=6.9, 1H), 7.54-7.47 (m, 2H), 7.16-7.09 (m, 2H), 6.99 (t, J=7.95, 1H'), 6.92 (t, J=9.8, 1H), 3.51 (q, J=5.35, 2H, NHCH₂CH₂), 2.9 (t, J=4.75, 4H), 2.58 (t, 5.85, 2H, NHCH₂CH₂), 2.49 (s, 4H), 1.25 (s, 1H). ¹³C-NMR (126 MHz, CDCl₃): δ 168.68 (ArC=O), 161.29 (ArC=O), 138.99 (ArC), 133.35 (d, J$_{C-F}$=10.08, ArCH), 132.45 (ArCH), 126.68 (ArCH), 123.54 (ArCH), 121.77 (ArC), 112.26 (d, J$_{C-F}$=21.42, ArCH), 104.70 (t, J$_{C-F}$=26.46, ArCH), 56.42 (CH₂), 52.01 (CH₂), 44.86 (CH2), 36.11 (CH₂). MS (ESI): 389.2 [M+1]. m.p. (from ethanol/water): 84° C.

Example 111

Synthesis of 2-fluoro-4-methoxy-N-(2-((2-(piperazin-1-yl)ethyl)carbamoyl) phenyl)benzamide (46)

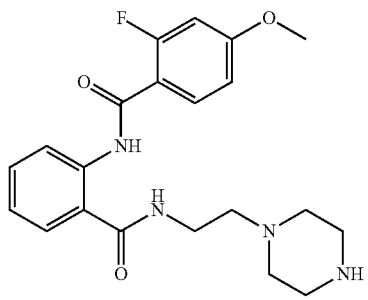

Compound 46 was obtained as a yellow powder in 23% yield. ¹H-NMR (500 MHz, CDCl₃): δ 2.48 (4H, s), 2.54 (2H, m), 2.90 (4H, t, J=4.82 Hz), 3.47 (2H, m), 3.79 (3H, s), 6.62 (1H, dd, J=2.42, 13.31 Hz), 6.76 (1H, dd, J=2.44, 13.30 Hz), 7.07 (1H, td, J=1.08, 7.59 Hz), 7.43 (3H, m), 7.96 (1H, t, J=8.90 Hz), 8.64 (1H, dd, J=0.70, 8.46 Hz), 11.59 (1H, m) ppm. m.p. (from DCM/n-hexane): 107-109° C.

Example 112

Synthesis of 2-(3-chlorobenzamido)-N-(2-(piperazin-1-yl)ethyl)benzamide (102)

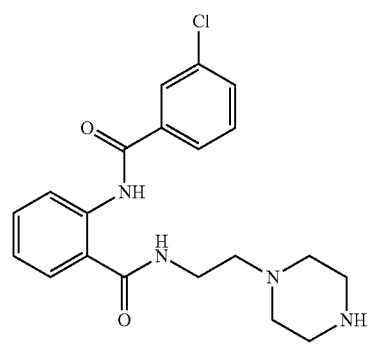

Compound 102 was obtained as a yellow solid in 63% yield. ¹H-NMR (500 MHz, CDCl₃): δ 2.41-2.56 (m, 5H), 2.61 (t, J=5.75 Hz, 2H), 2.91 (t, J=4.2 Hz, 4H), 3.54 (q, J=5.8 Hz, 2H), 7.13 (t, J=7.35 Hz, 1H), 7.24-7.28 (m, 1H), 7.47 (d, J=8.4 Hz, 2H), 7.50-7.56 (m, 2H), 7.98 (d, J=8.4 Hz, 2H), 8.78 (d, J=8.4 Hz, 1H), 12.38 (s, 1H) ppm. ¹³C-NMR (126 MHz, CDCl₃): δ 36.13 (CH₂, C-aliphatic), 45.96 (CH₂, C-aliphatic), 53.91 (CH₂, C-aliphatic), 56.58 (CH₂, C-aliphatic), 120.18 (C, C-aromatic), 121.44 (CH, C-aromatic), 123.04 (CH, C-aromatic), 126.71 (CH, C-aromatic), 128.85 (CH, C-aromatic), 129.00 (CH, C-aromatic), 132.73 (CH, C-aromatic), 133.29 (C, C-aromatic), 138.06 (C, C-aromatic), 139.96 (C, C-aromatic), 164.47 (C, C-aromatic), 169.10 (C, C-aromatic) ppm. MS (ESI)⁺: 387.2 [M+H]⁺. m.p. (from ethanol/water): 59-61° C.

Example 113

Synthesis of 2-fluoro-6-(4-methoxybenzamido)-N-(2-(piperazin-1-yl)ethyl)benzamide (111)

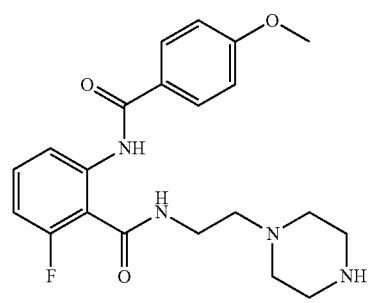

Compound 111 was obtained as a white powder in 34% yield. ¹H-NMR (500 MHz, CDCl₃): 2.25 (d, J=14.7 Hz, 4H), 2.58 (dd, J=21.6, 15.7 Hz, 8H), 3.49 (s, 3H), 7.05 (s, 1H), 7.09 (dd, J=16.9, 9.5 Hz, 1H), 7.52-7.44 (m, 2H), 7.58 (t, J=7.8 Hz, 1H), 7.73 (d, J=7.8 Hz, 1H), 8.13 (d, J=7.8 Hz, 1H), 8.29 (s, 1H), 8.75 (d, J=8.4 Hz, 1H), 12.46 (s, 1H) ppm. $^{13}$C-NMR (CDCl3): δ 36.37 (CH$_2$, C-aliphatic), 46.13 (CH$_2$, C-aliphatic), 53.98 (CH$_2$, C-aliphatic), 55.47 (CH$_3$, C-aliphatic), 56.03 (CH$_2$, C-aliphatic), 109.92 (CH, C-aromatic), 113.99 (CH, C-aromatic), 117.33 (CH, C-aromatic), 127.07 (C, C-aromatic), 129.40 (CH, C-aromatic), 132.89 (CH, C-aromatic), 132.98, 141.87 (C, C-aromatic), 159.62 (C, C-aromatic), 161.79 (C, C-aromatic), 162.57 (C, C-aromatic), 165.27 (C, C-aromatic) ppm. $^{19}$F-NMR (CDCl3): δ −111.78 ppm. MS(ESI)$^+$: 401.2 [M+H]$^+$. Melting point: (from Ethanol/water) 96-98° C.

Example 114

Synthesis of 2-fluoro-6-(3-methoxybenzamido)-N-(2-(piperazin-1-yl)ethyl) benzamide (112)

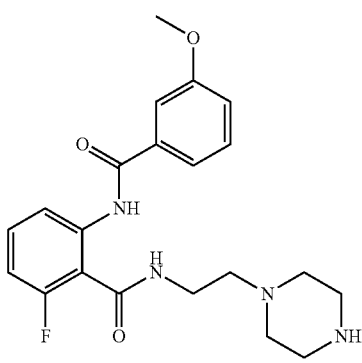

112

Compound 112 was obtained as a white powder in 45% yield. $^1$H-NMR (CDCl3): δ 1.30 (s, 1H), 2.04 (d, J=32.0 Hz, 1H), 2.52 (s, 3H), 2.61 (dd, J=10.8, 16.8 Hz, 2H), 2.95 (t, J=4.4 Hz, 4H), 3.59 (d, J=5.2 Hz, 2H), 3.91 (s, 3H), 6.90 (dd, J=8.5, 11.7 Hz, 1H), 7.09-7.14 (m, 1H), 7.41-7.52 (m, 2H), 7.60-7.70 (m, 3H), 8.70 (d, J=8.4 Hz, 1H), 12.67 (s, 1H) ppm. $^{13}$C-NMR (CDCl3): δ 36.35 (—CH$_2$, C-aliphatic), 45.85 (—CH$_2$, C-aliphatic), 53.48 (—CH$_2$, C-aliphatic), 55.46 (—CH$_3$, C-aliphatic), 55.97 (—CH$_2$, C-aliphatic), 108.99 (C, C-aromatic), 110.26 (CH, C-aromatic), 110.46 (CH, C-aromatic), 112.50 (CH, C-aromatic), 117.42 (CH, C-aromatic), 118.51 (CH, C-aromatic), 119.26 (CH, C-aromatic), 129.84 (CH, C-aromatic), 132.97 (C, C-aromatic), 136.24 (C, C-aromatic), 141.88 (C, C-aromatic), 159.94 (C, C-aromatic), 161.79 (C, C-aromatic), 165.55 (C, C-aromatic) ppm. $^{19}$F-NMR (CDCl3): δ −111.66 ppm. MS(ESI)$^+$: 401.2 [M+H]$^+$. Melting point: (from Ethanol/water) 83-85° C.

Example 115

Synthesis of N-(2-(piperazin-1-yl)ethyl)-2-(4-(trifluoromethyl)benzamido) benzamide (118)

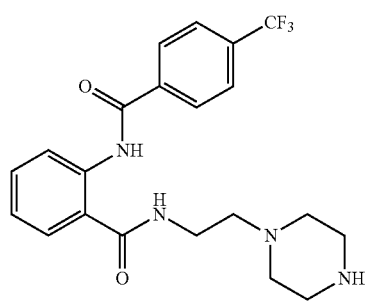

118

Compound 118 was obtained as a white powder in 18% yield. $^1$H-NMR (CDCl3): δ 1.67 (s, 2H), 2.42-2.57 (m, 4H), 2.59-2.72 (m, 2H), 2.95 (t, J=4.8 Hz, 3H), 3.55 (dt, J=12.7, 25.5 Hz, 2H), 7.00-7.19 (m, 1H), 7.13 (s, 1H), 7.49-7.64 (m, 2H), 7.80 (d, J=8.2 Hz, 2H), 8.10-8.18 (m, 2H), 8.86 (dt, J=3.3, 6.5 Hz, 1H), 12.50 (d, J=62.6 Hz, 1H) ppm. $^{13}$C-NMR (CDCl3): δ 36.07 (CH$_2$, C-aliphatic), 46.07 (CH$_2$, C-aliphatic), 53.92 (CH$_2$, C-aliphatic), 56.41 (CH$_2$, C-aliphatic), 120.46 (C, C-aromatic), 121.58 (CH, C-aromatic), 123.26 (CH, C-aromatic), 125.82 (CH, C-aromatic), 126.54 (CH, C-aromatic), 127.87 (CH, C-aromatic), 132.89 (CH, C-aromatic), 138.60 (C, C-aromatic), 140.01 (C, C-aromatic), 164.70 (C, C-aromatic), 166.14 (C, C-aromatic), 168.65 (C, C-aromatic) ppm. $^{19}$F-NMR (CDCl3): δ −62.98 ppm. MS(ESI)$^+$: 421.2 [M+H]$^+$.

General Procedure 5

The compounds of the application with the general formula shown below can be prepared according to the synthetic scheme shown in Scheme 5.

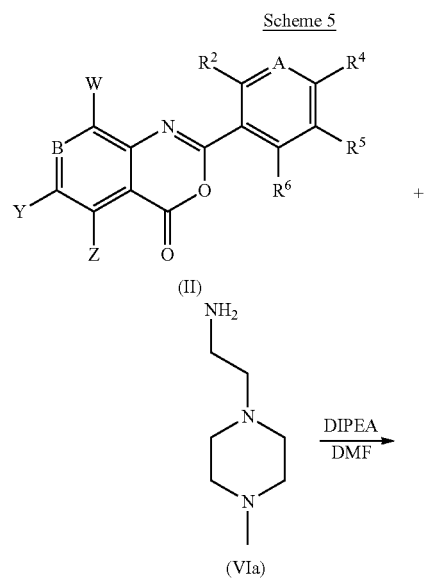

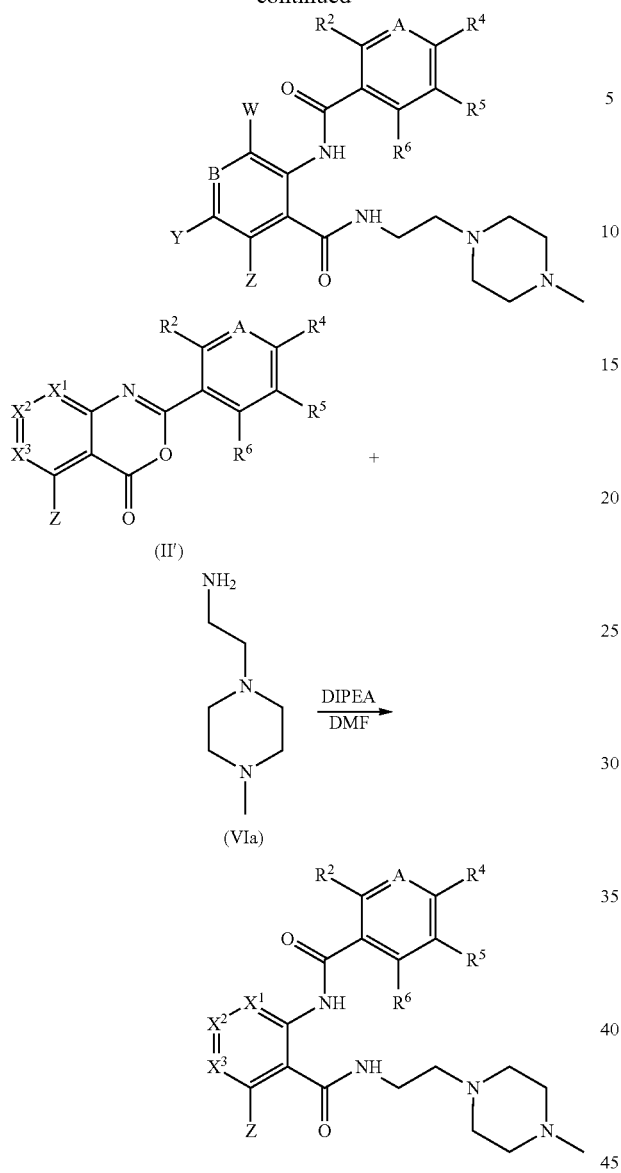

(II')

(VIa)

To a solution of compound (II) or (II') (1 equivalent) in N,N-dimethyl-formamide (DMF) is added 2 equivalents of N,N-diisopropylethylamine (DIPEA) and 2.2 equivalent of 2-(4-methylpiperazin-1-yl)ethanamine (VIa). The reaction mixture is stirred at about 15° C. to about 28° C. for about 6 hours to about 24 hours. The reaction mixture is diluted with water, washed with ethyl acetate, washed with brine, dried over $Mg_2SO_4$, filtered and evaporated to give a crude compound which is then purified by silica gel column using a mixture of Chloroform:Methanol (9:1) as eluent. The product is collected under reduced pressure to provide the compound with the general formula shown in Scheme 5.

Compounds 47-65, 101, 107-110, and 114-117 were prepared according to General Procedure 5 substituting (II) or (II') with the appropriate substituted compound.

Example 116

Synthesis of 2-benzamido-N-(2-(4-methylpiperazin-1-yl)ethyl)benzamide (47)

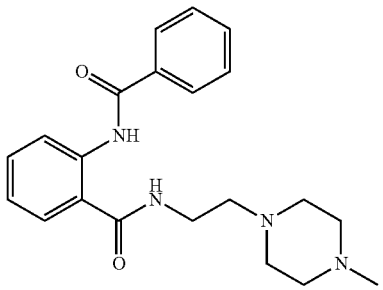

47

Compound 47 was obtained as a white powder in 88% yield. $^1$H-NMR (500 MHz, CDCl$_3$): δ 12.28 (s, 1H, ArNHCO), 8.86 (dd, J=8.5, 0.8 1H, CONHCH$_2$), 8.07 (dd, J=8.2, 1.3, 2H), 7.58-7.51 (m, 5H), 7.16 (td, J=7.6, 0.9, 1H), 7.07 (s, 1H), 3.57 (q, J=5.45, 2H, NHCH$_2$CH$_2$), 2.66 (t, J=5.45, 2H, NHCH$_2$CH$_2$), 2.64-2.38 (m, 8H), 2.34 (s, 3H, CH$_3$). $^{13}$C-NMR (126 MHz, CDCl$_3$): δ 169.11 (ArC=O), 165.57 (ArC=O), 140.17 (ArC), 134.92 (ArC), 132.69 (ArCH), 131.78 (ArCH), 128.75 (ArCH), 127.41 (ArCH), 126.56 (ArCH), 122.84 (ArCH), 121.62 (ArCH), 120.42 (ArC), 55.90 (CH$_2$), 55.10 (CH$_2$), 52.66 (CH$_2$), 45.92 (CH$_3$), 36.27 (CH$_2$). MS (ESI): 367.2 [M+1]. m.p. (from ethanol/water): 80° C.

Example 117

Synthesis of N-(2-(4-methylpiperazin-1-yl)ethyl)-2-(4-nitrobenzamido) benzamide (48)

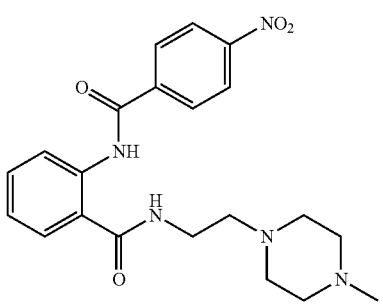

48

Compound 48 was obtained as a white solid in 85% yield. $^1$H-NMR (500 MHz, CDCl$_3$): δ 12.73 (s, 1H, ArNHCO), 8.85 (dd, J=8.45, 0.9, 1H, CONHCH$_2$), 8.37 (d, J=8.95, 2H), 8.23 (d, J=8.9, 2H), 7.61-7.55 (m, 2H), 7.21 (td, J=7.35, 1.15, 1H), 7.18 (s, 1H), 3.57 (q, J=5.35, 2H, NHCH$_2$CH$_2$), 2.67 (t, J=5.9, 2H, NHCH$_2$CH$_2$), 2.65-2.42 (m, 8H), 2.34 (s, 3H, CH$_3$). $^{13}$C-NMR (126 MHz, CDCl$_3$): δ 168.98 (C=O), 163.27 (ArC=O), 149.77 (ArC), 140.51 (ArC), 139.87 (ArC), 132.97 (ArCH), 128.59 (ArCH), 126.61 (ArCH), 123.96 (ArCH), 123.51 (ArCH), 121.51, 119.99 (ArC), 55.79 (CH$_2$), 55.11 (CH$_2$), 52.68 (CH$_2$), 45.94 (CH$_3$), 36.27 (CH$_2$). MS (ESI): 412.2 [M+1]. m.p. (from ethanol/water): 122° C.

Example 118

Synthesis of 2-fluoro-N-(2-((2-(4-methylpiperazin-1-yl)ethyl)carbamoyl) phenyl)benzamide (49)

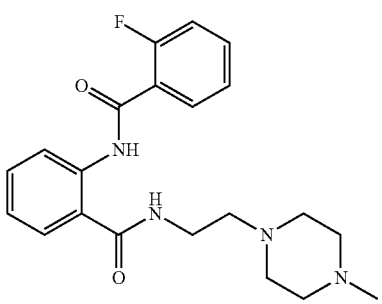

49

Compound 49 was obtained as a white solid in 25% yield. ¹H-NMR (500 MHz, CDCl₃): δ 11.83 (d, J=6.5, 1H, ArNHCO), 8.73 (d, J=8.1, 1H, CONHCH₂), 8.03 (td, J=7.7, 1.85, 1H), 7.52-7.45 (m, 3H), 7.26 (td, J=7.55, 1, 1H), 7.18 (dd, J=8.3, 0.9, 1H), 7.13 (td, J=7.65, 1.05, 1H), 7.0 (s, 1H), 3.51 (q, J=4.5, 2H, NHCH₂CH₂), 2.60 (t, J=6.1, 2H, NHCH2CH₂), 2.58-2.33 (m, 8H), 2.29 (s, 3H, CH₃). ¹³C-NMR (126 MHz, CDCl₃): δ 168.61 (ArC), 162.28 (d, J$_{C-F}$=2.52, ArC), 161.33 (ArC=O), 159.3 (ArC), 139.05 (ArC), 133.32 (d, J$_{C-F}$=8.82, ArC), 132.21 (ArCH), 131.46 (ArCH), 126.68 (ArCH), 124.59 (ArCH), 123.34 (ArCH), 122.80 (ArCH), 122.37 (ArCH), 121.96 (ArC), 116.52 (d, J$_{C-F}$=23.94, ArC), 55.99 (CH₂), 55.11 (CH₂), 52.70 (CH₂), 45.94 (CH₃), 36.31 (CH₂). MS (ESI): 385.2 [M+1]. m.p. (from ethanol/water): 116° C.

Example 119

Synthesis of 2-(3-fluorobenzamido)-N-(2-(4-methylpiperazin-1-yl)ethyl) benzamide (50)

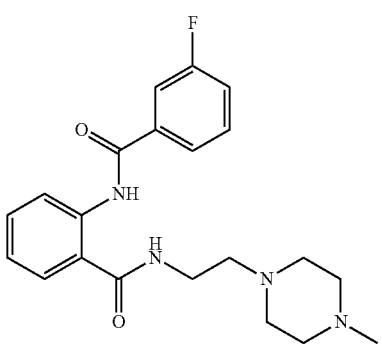

50

Compound 50 was obtained as a white solid in 67% yield. ¹H-NMR (500 MHz, CDCl₃): δ 12.40 s, 1H, ArNHCO), 8.83 (d, J=9.75, 1H, CONHCH₂), 7.83 (d, J=4.98, 1H), 7.78 (d, J=9.95, 1H), 7.60-7.54 (m, 2H), 7.53-7.48 (m, 1H), 7.26 (td, J=4.99, 1H), 7.18 (t, J=9.41, 1H), 7.12 (s, 1H), 3.57 (q, J=4.98, 2H, NHCH₂CH₂), 2.67 (t, J=5, 2H, NHCH₂CH₂), 2.65-2.37 (m, 8H), 2.35 (s, 3H, CH₃). ¹³C-NMR (126 MHz, CDCl₃): δ 169.04 (ArC=O), 164.24 (ArC=O), 163.94 (ArC), 161.97 (ArC), 139.97 (ArC), 137.33 (ArC), 132.81 (ArCH), 130.41 (d, J$_{C-F}$=7.56, ArCH), 126.60 (ArCH), 123.12 (ArCH), 122.73 (d, J$_{C-F}$=2.52, ArCH), 121.58 (ArCH), 120.23 (ArC), 118.82 (d, J$_{C-F}$=21.42, ArCH), 115.92 (d, J$_{C-F}$=22.68, ArCH), 55.86 (CH₂), 55.03 (CH₂), 52.59 (CH₂), 45.88 (CH₃), 36.23 (CH₂). MS (ESI): 385.2 [M+1]. m.p. (from ethanol/water): 81° C.

Example 120

Synthesis of 2-(3-chlorobenzamido)-N-(2-(4-methylpiperazin-1-yl)ethyl) benzamide (51)

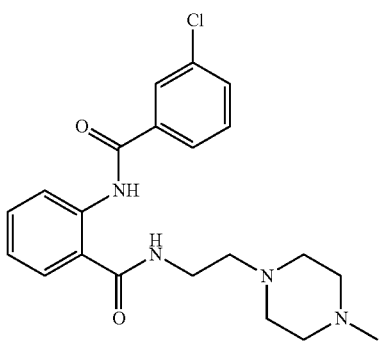

51

Compound 51 was obtained as a white solid in 7% yield. ¹H-NMR (500 MHz, CDCl₃): δ 12.39 (s, ArNHCO), 8.83 (d, J=8.1, 1H, CONHCH₂), 8.01 (d, J=8.1, 2H), 7.59-7.53 (m, 2H), 7.49 (d, J=8.1, 2H), 7.18 (t, J=7.55, 1H), 7.13 (s, 1H), 3.57 (q, J=5, NHCH₂CH₂), 2.68 (t, J=5.6, 2H, NHCH₂CH₂), 2.66-2.40 (m, 8H), 2.35 (s, 3H, CH₃). ¹³C-NMR (126 MHz, CDCl₃): δ 169.10 (ArC=O), 164.46 (ArC=O), 140.08 (ArC), 138.09 (ArC), 133.33 (ArC), 132.83 (ArCH), 129.02 (ArCH), 128.87 (ArCH), 126.61 (ArCH), 123.04 (ArCH), 121.53 (ArCH), 120.13 (ArC), 55.84 (CH₂), 55.00 (CH₂), 52.54 (CH₂), 45.85 (CH₃), 36.21 (CH₂). MS (ESI): 401.2 [M+1]. m.p. (from ethanol/water): 104° C.

Example 121

Synthesis of 2-(4-chlorobenzamido)-N-(2-(4-methylpiperazin-1-yl)ethyl) benzamide (52)

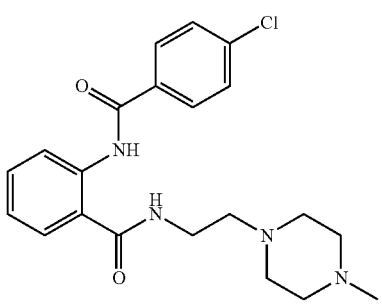

52

Compound 52 was obtained as a white solid in 6% yield. ¹H-NMR (500 MHz, CDCl₃): δ 12.56 (s, 1H, ArNHCO), 9.32 (d, J=5.02, 1H, CONHCH₂), 8.84 (d, J=10.03, 1H), 8.79 (dd, J=5, 0.0065, 1H), 8.33 (dt, J=10.00, 4.99, 1H), 7.62-7.55 (m, 2H), 7.47 (dd, J=9.9, 4.9, 1H), 7.20 (t, J=9.95, 1H), 7.17 (s, 1H), 3.57 (t, J=5.02, 2H, NHCH$_2$CH$_2$), 2.68 (t, J=5.27, 2H, NHCH$_2$CH$_2$), 2.66-2.42 (m, 8H), 2.35 (s, 3H, CH$_3$). $^{13}$C-NMR (126 MHz, CDCl$_3$): δ 169.08 (ArC=O), 164.46 (ArC=O), 140.06 (ArC), 138.08 (ArC), 133.32 (ArC), 132.80 (ArCH), 129.01 (ArCH), 128.87 (ArCH), 126.59 (ArCH), 123.03 (ArCH), 121.52 (ArCH), 120.15 (ArC), 55.82 (CH$_2$), 55.09 (CH$_2$), 52.65 (CH$_2$), 45.94 (CH$_3$), 36.25 (CH$_2$). MS (ESI): 401.2 [M+1]. m.p. (from ethanol/water): 99° C.

Example 122

Synthesis of 2-methoxy-N-(2-((2-(4-methylpiperazin-1-yl)ethyl)carbamoyl) phenyl)benzamide (53)

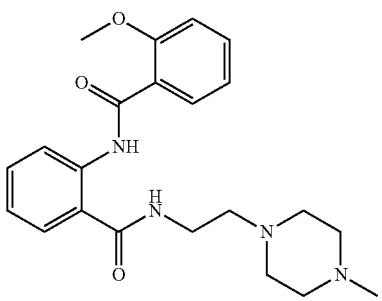

Compound 53 was obtained as a yellow solid in 78% yield. $^1$H-NMR (500 MHz, CDCl$_3$): δ 11.76 (s, 1H, ArNHCO), 8.71 (d, 1H, NHCH$_2$CH$_2$), 8.22 (dd, J=8, 1.5, 1H), 7.54-7.44 (m, 3H), 7.14 (t, J=8, 1H), 7.10 (t, J=8, 1, 1H), 7.03 (d, J=8, 1H), 6.73 (s, 1H), 3.55 (q, J=5.5, 2H, NHCH$_2$CH$_2$), 2.61 (t, J=6, 2H, NHCH$_2$CH$_2$), 2.59-2.36 (m, 8H), 2.31 (s, 3H, CH$_3$). $^{13}$C-NMR (126 MHz, CDCl$_3$): δ 168.71 (ArC=O), 164.21 (ArC=O), 157.75 (ArC), 138.41 (ArC), 133.07 (ArCH), 132.28 (ArCH), 131.63 (ArCH), 126.64 (ArCH), 124.45 (ArC), 123.18 (ArCH), 123.11 (ArCH), 122.51 (ArC) 120.92 (ArCH), 11.38 (ArCH), 56.23 (CH$_2$), 55.69 (CH$_3$), 55.04 (CH$_2$), 52.69 (CH$_2$), 45.88 (CH$_3$), 36.25 (CH$_2$). MS (ESI): 397.2 [M+1]. m.p. (from ethanol/water): 111° C.

Example 123

Synthesis of 2-(4-methoxybenzamido)-N-(2-(4-methylpiperazin-1-yl)ethyl) benzamide (54)

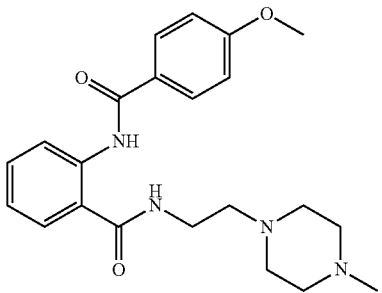

Compound 54 was obtained as a white solid in 76% yield. $^1$H-NMR (500 MHz, CDCl$_3$): δ 12.18 (s, 1H, ArNHCO), 8.80 (d, J=10, 1H, CONHCH$_2$), 8.1 (d, J=8.45, 2H), 7.54-7.48 (m, 2H), 7.15 (s, 1H), 7.09 (t, J=6, 1H), 7.0 (d, J=9, 2H), 3.90 (s, 3H, OCH$_3$), 3.54 (q, J=5.1, 2H, NHCH$_2$CH$_2$), 2.63 (t, J=6, 2H, NHCH$_2$CH$_2$), 2.61-2.34 (m, 8H), 2.30 (s, 3H, CH$_3$). $^{13}$C-NMR (126 MHz, CDCl$_3$): δ 169.21 (ArC=O), 165.18 (ArC=O), 162.49 (ArC), 140.30 (ArC), 132.58 (ArCH), 129.30 (ArCH), 127.25 (ArC), 126.63 (ArCH), 122.56 (ArCH), 121.46 (ArCH), 120.27 (ArC), 113.96 (ArCH), 56.00 (CH$_2$), 55.42 (CH$_3$), 55.08 (CH$_2$), 52.70 (CH$_2$), 45.92 (CH$_3$), 36.33 (CH$_2$). MS (ESI): 397.2 [M+1]. m.p. (from ethanol/water): 114° C.

Example 124

Synthesis of 2,6-difluoro-N-(2-((2-(4-methylpiperazin-1-yl)ethyl)carbamoyl) phenyl)benzamide (55)

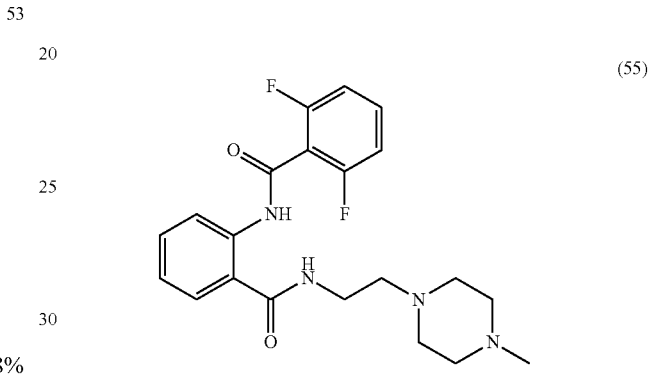

Compound 55 was obtained as a white solid in 54% yield. $^1$H-NMR (500 MHz, CDCl$_3$): δ 11.8 (s, ArNHCO), 8.81 (d, J=8.05, 1H, CONHCH$_2$), 7.57-7.52 (m, 2H), 7.40 (q, J=6.5, 1H), 7.18 (t, J=7.5, 1H), 7.08 (s, 1H), 6.99 (t, J=8, 2H), 3.50 (q, J=6, 2H, NHCH$_2$CH$_2$), 2.62 (t, J=6.5, 2H, NHCH$_2$CH$_2$), 2.60-2.38 (m, 8H), 2.32 (s, 3H, CH$_3$). $^{13}$C-NMR (126 MHz, CDCl$_3$): δ168.64 (ArC=O), 161.69 (d, J$_{C-F}$=7.56, ArC), 158.95 (t, J$_{C-F}$=12.6, 7.56, ArC), 156.44 (ArC), 149.33 (ArC), 143.33 (ArC), 129.91 (ArCH), 122.76 (ArC), 114.13 (ArC), 55.92 (CH$_2$), 55.08 (CH$_2$), 52.66 (CH$_2$), 50.59 (CH$_2$), 56.43 (CH$_3$), 36.23 (CH$_2$). MS (ESI): 314.1 [M+1]. m.p. (from ethanol/water): 81° C.

Example 125

Synthesis of 3,5-difluoro-N-(2-((2-(4-methylpiperazin-1-yl)ethyl)carbamoyl) phenyl)benzamide (56)

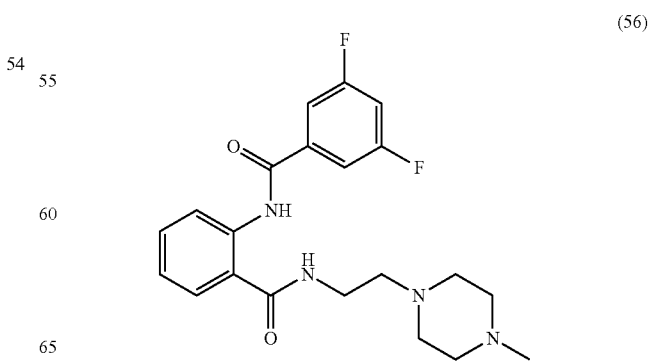

Compound 56 was obtained as a white solid in 65% yield. ¹H-NMR (500 MHz, CDCl₃): δ 12.51 (s, 1H, ArNHCO), 8.8 (d, J=8.1, 1H, CONHCH₂), 7.59 (d, J=7.85, 3H), 7.55 (d, J=7.80, 1H, H⁶), 7.19 (td, J=7.2, 0.9, 1H), 7.11 (s, 1H), 7.00 (tt, J=8.65, 2.1, 1H), 3.57 (q, J=5.4, 2H, NHCH₂CH₂), 2.66 (t, J=5.85, 2H, NHCH₂CH₂), 2.64-2.37 (m, 8H), 2.33 (s, 3H, CH₃). ¹³C-NMR (126 MHz, CDCl₃): δ 168.92 (ArC=O), 164.08 (d, $J_{C-F}$=12.6, ArC), 163.11 (ArC=O), 162.54 (d, $J_{C-F}$=11.34, ArC), 139.84 (ArC), 132.85 (ArCH), 126.54 (ArCH), 123.33 (ArCH), 121.57 (ArCH), 120.13 (ArC), 110.75 (d, $J_{C-F}$=7.56, ArCH), 110.59 (d, $J_{C-F}$=7.56, ArCH), 107.12 (t, $J_{C-F}$=25.2, ArCH), 55.85 (CH₂), 55.13 (CH₂), 55.70 (CH₂), 45.96 (CH₃), 36.25 (CH₂). MS (ESI): 403.2 [M+1]. m.p. (from ethanol/water): 111° C.

Example 126

Synthesis of 2,4-difluoro-N-(2-((2-(4-methylpiperazin-1-yl)ethyl)carbamoyl) phenyl)benzamide (57)

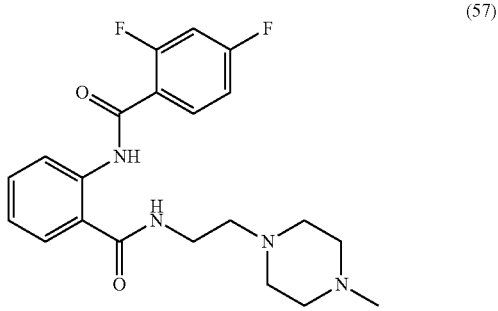 [SMILES: CN1CCN(CCNC(=O)c2ccccc2NC(=O)c2ccc(F)cc2F)CC1]
(57)

Compound 57 was obtained as a yellow solid in 85% yield. ¹H-NMR (500 MHz, CDCl₃): δ 11.89 (s, 1H, ArNHCO), 8.75 (d, J=8.3, 1H, CONHCH₂), 8.11 (q, J=8.85, 1H), 7.55 (t, J=8.05, 1H), 7.51 (dd, J=7.8, 1.25, 1H), 7.2 (td, J=7.6, 1, 1H), 7.02 (t, J=8.2, 1H), 6.97-6.92 (m, 2H), 3.54 (q, J=5.45, 2H, NHCH₂CH₂), 2.64 (t, J=6.1, 2H, NHCH₂CH₂), 2.61-2.36 (m, 8H), 2.32 (s, 3H, CH₃). ¹³C-NMR (126 MHz, CDCl₃): δ 168.59 (ArC=O), 165.88 (ArC=O), 163.85 (ArC), 161.93 (ArC), 161.32 (ArC), 139.10 (ArC), 133.31 (dd, J=3.78, ArCH), 132.35 (ArCH), 126.59 (ArCH), 123.44 (ArCH), 122.46 (ArCH), 121.83 (ArC), 112.17 (dd, $J_{C-F}$=2.52, 18.9, ArCH), 104.67 (t, $J_{C-F}$=27.72, 25.2, ArCH), 55.92 (CH₂), 55.16 (CH₂), 52.73 (CH₂), 45.98 (CH₃), 36.25 (CH₂). MS (ESI): 403.2 [M+1]. m.p. (from ethanol/water): 121-122° C. Acc. Mass (CI, M+1) C₂₁H₂₆FN₄O₂, calc.: 385.2034. found: 385.2036.

Example 127

Synthesis of 2-fluoro-4-methoxy-N-(2-((2-(4-methylpiperazin-1-yl)ethyl) carbamoyl)phenyl)benzamide (58)

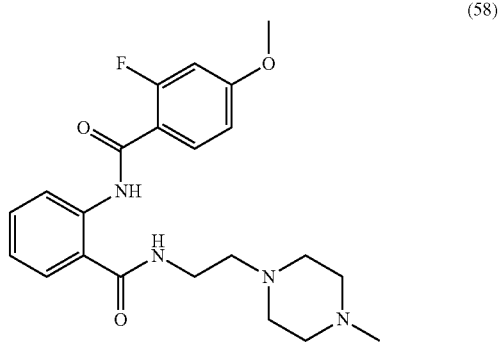 [SMILES: COc1ccc(C(=O)Nc2ccccc2C(=O)NCCN2CCN(C)CC2)c(F)c1]
(58)

Compound 58 was obtained as a yellow powder in 30% yield. ¹H-NMR (500 MHz, CDCl₃): δ 1.36 (1H, d, J=2.37 Hz), 2.29 (3H, s), 2.56 (8H, m), 3.48 (3H, s), 3.79 (3H, s), 6.62 (1H, dd, J=2.44, 13.30 Hz), 6.74 (1H, t, J=4.44 Hz), 6.8 (1H, s) 7.07 (1H, m), 7.44 (2H, m), 7.97 (1H, d, J=8.91 Hz), 8.64 (1H, dd, J=0.99, 8.76 Hz), 11.60 (1H, d, J=7.7 Hz) ppm. ¹³C-NMR (126 MHz, CDCl₃): δ 36.14 (CH₂, C-aliphatic), 45.36 (CH₃, C-aliphatic), 52.02 (CH₂, C-aliphatic), 54.56 (CH₂, C-aliphatic), 55.82 (CH₃, C-aliphatic), 56.16 (CH2, C-aliphatic), 101.87 (CH, C-aromatic), 110.70 (CH, C-aliphatic), 122.06 (C, C-aromatic), 122.62 (CH, C-aromatic), 123.71 (CH, C-aromatic), 126.71 (CH, C-aromatic), 132.26 (CH, C-aromatic), 132.89 (CH, C-aromatic), 139.18 (C, C-aromatic), 160.3 (C, C-aliphatic), 162.5 (C, C-aliphatic) 168.78 (C, C-aliphatic), 178.0 (C, C=O), 179.7 (C, C=O) ppm. ¹⁹F-NMR (CDCl₃): δ −109.26 ppm. MS (ESI)⁺: 415.2 [M+H]⁺. m.p.: 110-112° C.

Example 128

Synthesis of 2-(2-fluorobenzamido)-4,5-dimethoxy-N-(2-(4-methylpiperazin-1-yl)ethyl)benzamide (59)

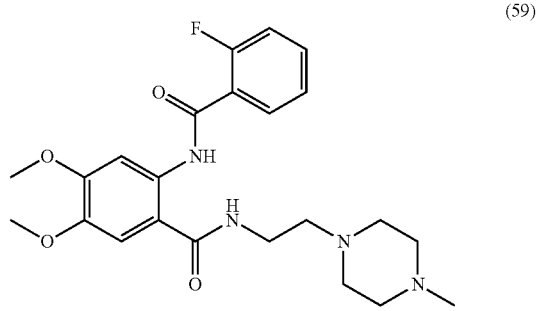
(59)

Compound 59 was obtained as a white solid in 89% yield. ¹H-NMR (500 MHz, CDCl₃): δ 12.12 (d, J=5.5, 1H, ArNHCO), 8.49 (s, 1H, CONHCH₂), 7.95 (t, J=6.65, 1H), 7.43 (q, J=6.35, 1H'), 7.20 (t, J=6.95, 1H), 7.18-7.09 (m, 2H), 6.99 (s, 1H), 3.93 (s, 3H, C₅OCH₃), 3.84 (s, 3H, C₄OCH₃), 3.44 (q, J=5.45, 2H, NHCH₂CH₂), 2.54 (t, J=5.51, 2H, NHCH$_2$CH$_2$), 2.52-2.24 (m, 8H), 2.21 (s, 3H). $^{13}$C-NMR (126 MHz, CDCl$_3$): δ 168.32 (ArC=O), 162.25 (ArC=O), 161.25 (ArC), 159.25 (ArC), 151.81 (ArC), 144.37 (ArC), 134.75 (ArC), 133.24 (d, J$_{C-F}$=8.82, ArCH), 131.12 (d, J$_{C-F}$=1.26, ArCH), 124.57 (d, J$_{C-F}$=2.52, ArCH), 116.52 (d, J$_{C-F}$=22.68, ArCH), 112.82 (ArC), 109.48 (ArCH), 105.43 (ArCH), 56.21 (CH$_3$), 56.04 (CH$_3$), 55.99 (CH$_2$), 55.14 (CH$_2$), 52.57 (CH$_2$), 45.95 (CH$_3$), 36.09 (CH$_2$). MS (ESI): 445.2 [M+1]. m.p. (from ethanol/water): 60° C.

Example 129

Synthesis of 6-(2-fluorobenzamido)-2,3,4-trimethoxy-N-(2-(4-methyl piperazin-1-yl)ethyl) benzamide (60)

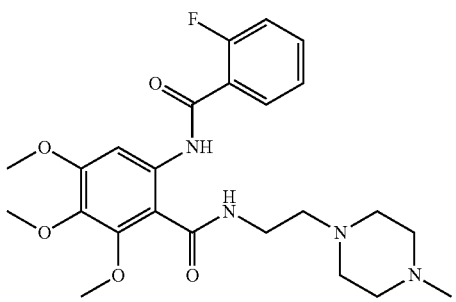

(60)

Compound 60 was obtained as a white solid in 51.4% yield. $^1$H-NMR (500 MHz, CDCl$_3$): δ 8.71 (d, J=13.65, 1H, ArNHCO), 8.16 (t, J=6.85, 1H), 7.57 (q, J=5.7, 1H), 7.32 (t, J=6.85, 1H), 7.23 (dd, J=11.2, 8.55, 1H), 6.99 (s, 1H), 6.92 (s, 1H, CONHCH$_2$), 3.94 (s, 3H, OCH$_3$), 3.93 (s, 3H, OCH$_3$), 3.92 (s, 3H, OCH$_3$), 3.49 (q, J=5.1, NHCH$_2$CH$_2$), 2.58-2.48 (m, 2H, NHCH$_2$CH$_2$), 2.48-2.33 (m, 8H), 2.29 (s, 3H, N—CH$_3$). $^{13}$C-NMR (126 MHz, CDCl$_3$): δ 167.41 (ArC=O), 163.09 (ArC=O), 161.87 (ArC), 159.89 (ArC), 152.16 (ArC), 148.75 (ArC), 144.19 (ArC), 133.33 (d, J$_{C-F}$=8.82, ArCH), 132.28 (ArCH), 128.47 (ArC), 124.90 (d, J$_{C-F}$=3.78, ArCH), 121.35 (ArC), 116.36 (d, J$_{C-F}$=25.2, ArCH), 106.74 (ArCH), 61.11 (CH$_3$), 61.01 (CH$_3$), 56.30 (CH$_2$), 56.27 (CH$_3$), 54.91 (CH$_2$), 52.64 (CH$_2$), 45.90 (CH$_3$), 36.40 (CH$_2$). MS (ESI): 475.3 [M+1]. m.p. (from ethanol/water): 130° C.

Example 130

Synthesis of 4,5-dimethoxy-2-(4-methoxybenzamido)-N-(2-(4-methyl piperazin-1-yl)ethyl)benzamide (61)

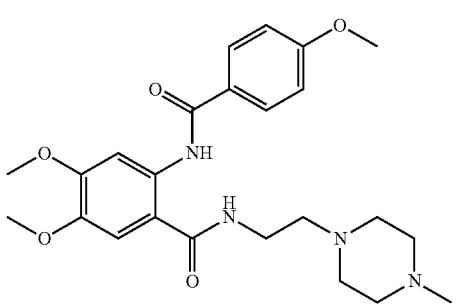

(61)

Compound 61 was obtained as a white solid in 6% yield. $^1$H-NMR (500 MHz, CDCl$_3$): δ 12.49 (s, 1H, ArNHCO), 8.65 (s, 1H, CONHCH$_2$), 8.03 (d, J=8.9, 2H), 7.12 (s, 1H), 7.02 (s, 1H), 7.00 (d, J=1.55, 2H), 4.02 (s, 3H, OCH$_3$), 3.94 (s, 3H, OCH$_3$), 3.88 (s, 3H, OCH$_3$), 3.55 (q, J=5.25, 2H, NHCH$_2$CH$_2$), 2.68 (t, J=6.15, NHCH$_2$CH$_2$), 2.66-2.35 (m, 8H), 2.32 (s, 3H, N-CH$_3$). $^{13}$C-NMR (126 MHz, CDCl$_3$): δ 168.87 (ArC=O), 165.18 (ArC=O), 162.43 (ArC), 152.43 (ArC), 143.95 (ArC), 136.39 (ArC), 129.20 (ArCH), 127.27 (ArC), 113.98 (ArCH), 11.14 (ArC), 109.37 (ArCH), 104.61 (ArCH), 56.42 (CH$_3$), 56.13 (CH$_3$), 55.78 (CH$_2$), 55.43 (CH$_2$), 55.22 (CH$_3$), 52.56 (CH$_2$), 46.01 (CH$_3$), 35.98 (CH$_2$). MS (ESI): 457.3 [M+1]. m.p. (from ethanol/water): 70° C.

Example 131

Synthesis of 2,3,4-trimethoxy-6-(4-methoxybenzamido)-N-(2-(4-methylpiperazin-1-yl)ethyl)benzamide (62)

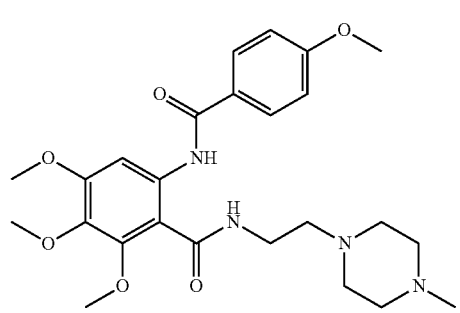

(62)

Compound 62 was obtained as a white solid in 38% yield. $^1$H-NMR (500 MHz, CDCl$_3$): δ 8.65 (s, 1H, ArNHCO), 7.95 (d, J=8.5, 2H), 7.03-7.00 (1H, CONHCH$_2$), 6.98 (d, J=8.5, 2H), 6.91 (s, 1H), 3.93 (s, 3H, C$_4$'OCH$_3$), 3.91 (s, 3H, OCH$_3$), 3.9 (s, 3H, OCH$_3$), 3.89 (s, 3H, OCH$_3$), 3.43 (q, J=5.3, 2H, NHCH$_2$CH$_2$), 2.47 (t, J=5.7, 2H, NHCH$_2$CH$_2$), 2.44-2.31 (m, 8H), 2.27 (s, 3H, N—CH$_3$). $^{13}$C-NMR (126 MHz, CDCl$_3$): δ 167.83 (ArC=O), 166.67 (ArC=O), 162.72 (ArC), 151.87 (ArC), 149.18 (ArC), 144.50 (ArC), 129.49 (ArCH), 127.65 (ArC), 126.22 (ArC), 122.68 (ArC), 113.95 (ArCH), 106.43 (ArCH), 61.07 (CH$_3$), 61.00 (CH$_3$), 56.32 (CH$_3$), 56.23 (CH$_2$), 55.51 (CH$_2$), 54.77 (CH$_3$), 52.38 (CH$_2$), 45.71 (CH$_3$), 36.32 (CH$_2$). MS (ESI): 487.3 [M+1]. m.p. (from ethanol/water): 115° C.

Example 132

Synthesis of N-(2-((2-(4-methylpiperazin-1-yl)ethyl) carbamoyl)phenyl) nicotinamide (63)

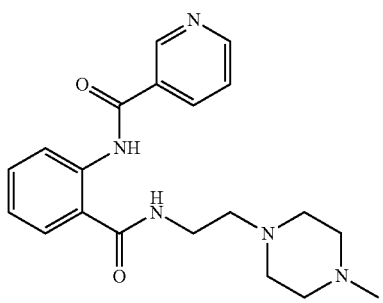

(63)

Compound 63 was obtained as a white solid in 27% yield. $^1$H-NMR (500 MHz, CDCl$_3$): δ 12.56 (s, 1H, ArNHCO), 9.31 (d, J=1.95, 1H, CONHCH$_2$), 8.83 (d, J=8.1, 1H), 8.78 (dd, J=4.9, 1.55, 1H), 8.32 (dt, J=8.05, 1.95, 1H), 7.59-7.52 (m, 2H), 7.45 (dd, J=7.8, 5, 1H), 7.17 (td, J=7.45, 0.95, 1H), 7.14 (s, 1H), 3.55 (q, J=5.5, 2H, NHCH$_2$CH$_2$), 2.65 (t, J=5.7, 2H, NHCH$_2$CH$_2$), 2.63-2.24 (m, 8H), 2.32 (s, 3H, CH$_3$). $^{13}$C-NMR (126 MHz, CDCl$_3$): δ 168.98 (ArC=O), 163.73 (ArC=O), 152.43 (ArCH), 149.20 (ArCH), 139.92 (ArC), 134.83 (ArCH), 132.81 (ArCH), 130.50 (ArC), 126.56 (ArCH), 123.44 (ArCH), 123.25 (ArCH), 121.58 (ArCH), 120.15 (ArC), 55.83 (CH$_2$), 55.17 (CH$_2$), 52.74 (CH$_2$), 45.99 (CH$_3$), 29.68 (CH$_2$). MS (ESI): 368.2 [M+1]. m.p. (from ethanol/water): 99° C. Acc. Mass (CI, M+1) C$_{20}$H$_{26}$N$_5$O$_2$, calc.: 368, 2081. found: 368.2083.

Example 133

Synthesis of N-(4,5-dimethoxy-2-((2-(4-methylpiperazin-1-yl)ethyl)carbamoyl) phenyl)nicotinamide (64)

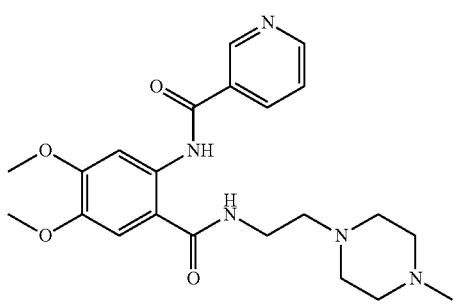

(64)

Compound 64 was obtained as a white solid in 46.84% yield. $^1$H-NMR (500 MHz, CDCl$_3$): δ 12.86 (s, 1H, ArNHCO), 9.28 (d, J=2.05, 1H, CONHCH$_2$), 8.75 (dd, J=4.9, 1.6, 1H), 8.59 (s, 1H), 8.30 (dt, J=8.15, 1.8, 1H), 7.44 (dd, J=7.9, 4.85, 1H), 7.27 (s, 1H), 7.03 (s, 1H), 3.99 (s, 3H, OCH$_3$), 3.91 (s, 3H, OCH$_3$), 3.53 (q, J=5.3, 2H, NHCH$_2$CH$_2$), 2.65 (t, J=6.1, 2H, NHCH$_2$CH$_2$), 2.62-2.30 (m, 8H), 2.28 (s, 3H, N—CH$_3$). $^{13}$C-NMR (126 MHz, CDCl$_3$): δ 168.73 (ArC=O), 163.59 (ArC=O), 152.39 (ArC), 152.32 (ArCH), 149.10 (ArCH), 144.38 (ArC), 135.75 (ArC), 134.73 (ArCH), 130.53 (ArC), 123.49 (ArCH), 111.18 (ArC), 109.27 (ArCH), 104.56 (ArCH), 56.31 (CH$_3$), 56.15 (CH$_3$), 55.87 (CH$_2$), 55.25 (CH2), 55.62 (CH$_2$), 46.04 (CH$_3$), 36.03 (CH$_2$). MS (ESI): 428.2 [M+1]. m.p. (from ethanol/water): 126° C.

Example 134

Synthesis of N-(3,4,5-trimethoxy-2-((2-(4-methylpiperazin-1-yl)ethyl) carbamoyl)phenyl)nicotinamide (65)

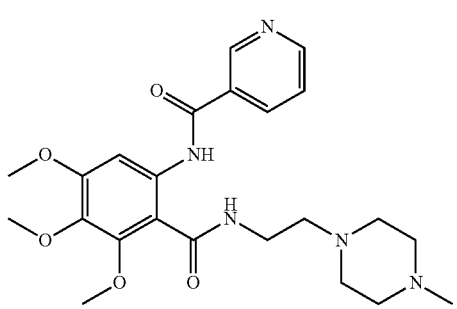

(65)

Compound 65 was obtained as a white solid in 7% yield. $^1$H-NMR (500 MHz, CDCl$_3$): δ 9.22 (d, J=2.1, 1H, ArNHCO), 9.2 (s, 1H, CONHCH$_2$), 8.8 (dd, J=5.1, 1.5, 1H), 8.28 (td, J=8.1, 1.8, 1H), 7.45 (dd, J=7.8, 4.8, 1H), 7.02 (s, 1H), 6.9 (s, 1H), 3.95 (s, 3H, OCH$_3$), 3.94 (s, 3H, OCH$_3$), 3.93 (s, 3H, OCH$_3$), 3.47 (q, J=5.7, 2H, NHCH$_2$CH$_2$), 2.58 (t, J=6, NHCH$_2$CH$_2$), 2.55-2.34 (m, 8H), 2.32 (s, 3H, N—CH$_2$). $^{13}$C-NMR (126 MHz, CDCl$_3$): δ 167.89 (ArC=O), 164.90 (ArC=O), 152.66 (ArCH), 151.98 (ArC), 149.30 (ArC), 148.94 (ArCH), 144.77 (ArC), 135.37 (ArCH), 129.84 (ArC), 126.40 (ArC), 123.53 (ArCH), 122.68 (ArC), 106.06 (ArCH), 61.04 (CH$_3$), 61.01 (CH$_3$), 56.39 (CH$_3$), 56.17 (CH$_2$), 54.65 (CH$_2$), 52.38 (CH$_2$), 45.70 (CH$_3$), 36.15 (CH$_2$). MS (ESI): 458.3 [M+1]. m.p. (from ethanol/water): 143° C.

Example 135

Synthesis of 2-(3-methoxybenzamido)-N-(2-(4-methylpiperazin-1-yl)ethyl)benzamide (101)

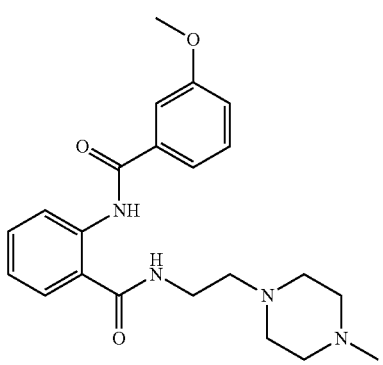

101

Compound 101 was obtained as a white solid in 76% yield. ¹H-NMR (500 MHz, CDCl₃): δ 2.30 (s, 3H), 2.61-2.34 (m, 8H), 2.63 (t, J=6 Hz, 2H), 3.54 (q, J=5.1 Hz, 2H), 3.90 (s, 3H), 7.0 (d, J=9 Hz, 2H), 7.09 (t, J=6, 1H), 7.15 (s, 1H), 7.48-7.54 (m, 2H), 8.1 (d, J=8.45 Hz, 2H), 8.80 (d, J=10 Hz, 1H), 12.18 (s, 1H) ppm. ¹³C-NMR (126 MHz, CDCl₃): δ 36.33 (CH₂, C-aliphatic), 45.92 (CH₃, C-aliphatic), 52.70 (CH₂, C-aliphatic), 55.08 (CH₂, C-aliphatic), 55.42 (CH₃, C-aliphatic), 56.00 (CH₂, C-aliphatic), 113.96 (CH, C-aromatic), 120.27 (C, C-aromatic), 121.46 (CH, C-aromatic), 122.56 (CH, C-aromatic), 126.63 (CH, C-aromatic), 127.25 (C, C-aromatic), 129.30 (CH, C-aromatic), 132.58 (CH, C-aromatic), 140.30 (C, C-aromatic), 162.49 (C, C-aromatic), 165.18 (C, C-aromatic), 169.21 (C, C-aromatic) ppm. MS (ESI)⁺: 397.2 [M+H]⁺. m.p. (from ethanol/water): 113-115° C.

Example 136

Synthesis of 2-(4-fluorobenzamido)-N-(2-(4-methylpiperazin-1-yl)ethyl)benzamide (107)

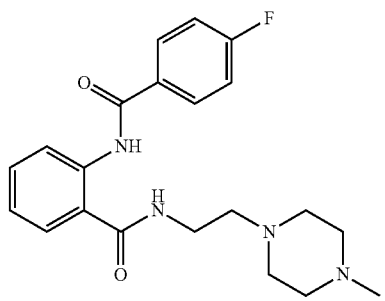

Compound 107 was obtained as a yellow powder in 44% yield. ¹H-NMR (500 MHz, CDCl₃): δ 2.24 (d, J=9.6 Hz, 3H), 2.50 (s, 7H), 2.54-2.61 (m, 3H), 3.47 (dd, J=5.6, 10.9 Hz, 2H), 7.00 (s, 1H), 7.08-7.16 (m, 3H), 7.39-7.51 (m, 2H), 8.03-7.93 (m, 2H), 8.79-8.68 (m, 1H), 12.26 (s, 1H) ppm. ¹³C-NMR (126 MHz, CDCl₃): δ 36.24 (CH₂, C-aliphatic), 45.96 (CH₃, C-aliphatic), 52.67 (CH₂, C-aliphatic), 55.13 (CH₂, C-aliphatic), 55.80 (CH₂, C-aliphatic), 115.80 (CH, C-aromatic), 120.16 (C, C-aromatic), 121.53 (CH, C-aromatic), 122.93 (CH, C-aromatic), 126.56 (CH, C-aromatic), 129.79 (CH, C-aromatic), 129.87 (CH, C-aromatic), 132.81 (C, C-aromatic), 140.17 (C, C-aromatic), 163.70 (C, C-aromatic), 164.46 (C, C-aromatic), 166.10 (C, C-aromatic), 169.12 (C, C-aromatic) ppm. ¹⁹F-NMR (CDCl₃): δ −107.64 ppm. MS (ESI)⁺: 385.2 [M+H]⁺. m.p. (from diethyl ether/n-hexane): 89-91° C.

Example 137

Synthesis of N-(2-(4-methylpiperazin-1-yl)ethyl)-2-(4-trifluoromethyl)benzamido) benzamide (108)

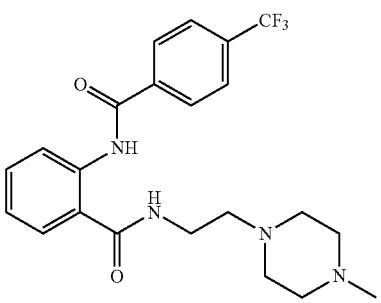

Compound 108 was obtained as a yellow powder in 23% yield. ¹H-NMR (500 MHz, CDCl₃): δ 2.26 (s, 3H), 2.49 (d, J=41.4 Hz, 7H), 2.57-2.62 (m, 2H), 3.45-3.50 (m, 2H), 7.04-7.13 (m, 2H), 7.46-7.53 (m, 2H), 7.70 (d, J=8.2 Hz, 2H), 8.09 (d, J=8.1 Hz, 2H), 8.76 (d, J=7.8 Hz, 1H), 12.46 (s, 1H) ppm. ¹³C-NMR (126 MHz, CDCl₃): δ 36.23 (CH₂, C-aliphatic), 45.82 (CH₃, C-aliphatic), 52.56 (CH₂, C-aliphatic), 54.97 (CH₂, C-aliphatic), 55.89 (CH₂, C-aliphatic), 120.12 (C, C-aromatic), 121.57 (CH, C-aromatic), 123.26 (CH, C-aromatic), 125.76 (CH, C-aromatic), 125.82 (CH, C-aromatic), 126.61 (CH, C-aromatic), 127.87 (CH, C-aromatic), 132.89 (C, C-aromatic), 133.26 (C, C-aromatic), 138.26 (C, C-aromatic), 139.99 (C, C-aromatic), 164.17 (C, C-aromatic), 169.06 (C, C-aromatic) ppm. ¹⁹F-NMR (CDCl₃): δ −63.1 ppm. MS (ESI)⁺: 435.2 [M+H]⁺. m.p. (from diethyl ether/n-hexane): 68-71° C.

Example 138

Synthesis of 2-fluoro-6-(4-methoxybenzamido)-N-(2-(4-methylpiperazin-1-yl)ethyl)benzamide (109)

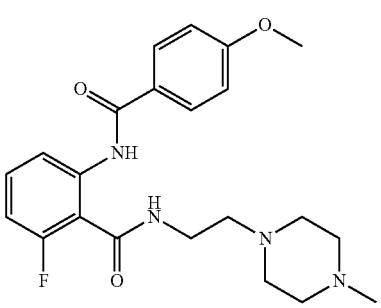

Compound 109 was obtained as a white powder in 45% yield. ¹H-NMR (500 MHz, CDCl₃): δ 2.36 (s, 3H), 2.48-

2.81 (m, 10H), 3.41-3.60 (m, 2H), 3.81 (s, 3H), 6.79 (dd, J=8.3, 11.6 Hz, 1H), 6.93 (d, J=8.8 Hz, 2H), 7.40 (dt, J=10.2, 15.0 Hz, 2H), 7.94 (d, J=8.9 Hz, 2H), 8.58 (d, J=8.5 Hz, 1H), 12.40 (s, 1H) ppm. $^{13}$C-NMR (126 MHz, CDCl$_3$): δ 36.48 (CH$_2$, C-aliphatic), 45.16 (CH$_3$, C-aliphatic), 51.46 (CH$_2$, C-aliphatic), 54.68 (CH$_2$, C-aliphatic), 55.38 (CH$_2$, C-aliphatic), 55.48 (CH$_3$, C-aliphatic), 108.49 (C, C-aromatic), 109.89 (CH, C-aromatic), 114.01 (CH, C-aromatic), 117.44 (CH, C-aromatic), 128.88 (CH, C-aromatic), 132.96 (C, C-aromatic), 142.18 (CH, C-aromatic), 142.22 (C, C-aromatic), 159.95 (C, C-aromatic), 161.91 (C, C-aromatic), 162.63 (C, C-aromatic), 165.50 (C, C-aromatic) ppm. $^{19}$F-NMR (CDCl$_3$): δ −111.87 ppm. MS (ESI)$^+$: 415.2 [M+H]$^+$. m.p. (from diethyl ether/n-hexane): 81-83° C.

Example 139

Synthesis of 2-fluoro-6-(3-methoxybenzamido)-N-(2-(4-methylpiperazin-1-yl)ethyl)benzamide (110)

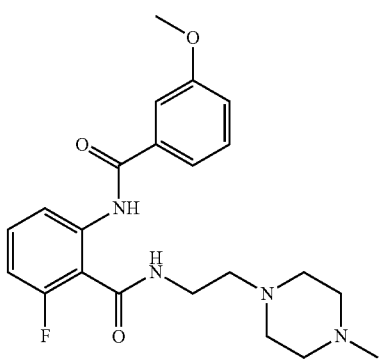

Compound 110 was obtained as a white powder in 18% yield. $^1$H-NMR (500 MHz, CDCl$_3$): δ 2.30 (s, 3H), 2.41-2.73 (m, 10H), 2.80 (s, 3H), 3.48-3.55 (m, 2H), 6.79 (dd, J=8.3, 11.6 Hz, 1H), 6.93 (d, J=8.8 Hz, 2H), 7.40 (dt, J=10.2, 15.0 Hz, 2H), 7.94 (d, J=8.9 Hz, 2H), 8.58 (d, J=8.5 Hz, 1H), 12.20 (s, 1H) ppm. $^{13}$C-NMR (126 MHz, CDCl$_3$): δ 36.43 (CH$_2$, C-aliphatic), 51.76 (CH$_2$, C-aliphatic), 55.39 (CH$_2$, C-aliphatic), 55.47 (CH$_3$, C-aliphatic), 55.62 (CH$_2$, C-aliphatic), 112.56 (CH, C-aromatic), 119.23 (CH, C-aromatic), 121.06 (CH, C-aromatic), 123.14 (CH, C-aromatic), 123.18 (CH, C-aromatic), 129.88 (CH, C-aromatic), 131.04 (C, C-aromatic), 137.28 (CH, C-aromatic), 137.36 (C, C-aromatic), 142.22 (C, C-aromatic) 148.74 (C, C-aromatic), 159.90 (C, C-aromatic), 160.86 (C, C-aromatic), 162.99 (C, C-aromatic) ppm. $^{19}$F-NMR (CDCl$_3$): δ −106.45 ppm. MS (ESI)$^+$: 415.2 [M+H]$^+$. m.p. (from diethyl ether/n-hexane): 108-110° C.

Example 140A

Synthesis of N-(2-(4-methylpiperazin-1-yl)ethyl)-2-(3-(trifluoromethyl)benzamido) benzamide (114)

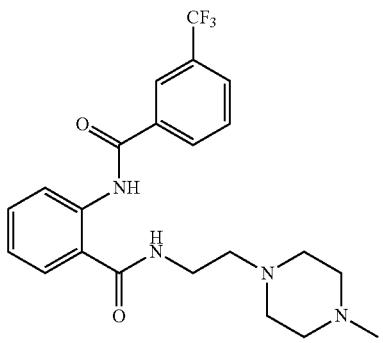

Compound 114 was obtained as a white powder in 40.28% yield. $^1$H-NMR (500 MHz, CDCl$_3$): δ 2.27 (s, 3H), 2.64-2.39 (m, 10H), 3.49 (dd, J=5.3, 11.2 Hz, 2H), 7.10 (dd, J=4.1, 11.0 Hz, 2H), 7.46-7.52 (m, 2H), 7.58 (t, J=7.8 Hz, 1H), 7.73 (d, J=7.8 Hz, 1H), 8.13 (d, J=7.8 Hz, 1H), 8.29 (s, 1H), 8.74 (d, J=8.3 Hz, 1H), 12.46 (s, 1H) ppm. $^{13}$C-NMR (126 MHz, CDCl$_3$): δ 36.19 (CH$_2$, C-aliphatic), 45.82 (CH$_3$, C-aliphatic), 52.53 (CH$_2$, C-aliphatic), 54.93 (CH$_2$, C-aliphatic), 5.89 (CH$_2$, C-aliphatic), 120.14 (CH, C-aromatic), 121.59 (CH, C-aromatic), 123.26 (CH, C-aromatic), 125.10 (CH, C-aromatic), 126.63 (CH, C-aromatic), 128.34 (CH, C-aromatic), 129.37 (CH, C-aromatic), 130.07 (C, C-aromatic), 132.90 (CH, C-aromatic), 135.82 (C, C-aromatic), 139.93 (C, C-aromatic), 164.06 (C, C-aromatic), 169.07 (C, C-aromatic), 171.98 (C, C-aromatic) ppm. $^{19}$F-NMR (CDCl$_3$): δ −62.69 ppm. MS (ESI)$^+$: 435.2 [M+H]$^+$. m.p.: 101-103° C.

Example 140B

Synthesis of 2-fluoro-N-(2-((2-(4-methylpiperazin-1-yl)ethyl)carbamoyl)phenyl)-4-(trifluoromethoxy) benzamide (115)

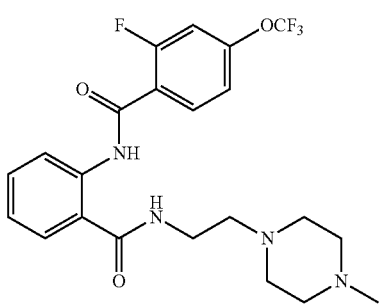

Compound 115 was obtained as a white powder in 34% yield. $^1$H-NMR (500 MHz, CDCl$_3$): δ 2.23 (s, 3H), 2.35-2.56 (m, 8H), 2.54 (t, J=5.9 Hz, 2H), 3.45 (dd, J=5.4, 10.7 Hz, 2H), 6.85 (s, 1H), 7.00 (d, J=11.1 Hz, 1H), 7.05-7.13 (m, 2H), 7.41-7.49 (m, 2H), 8.04 (t, J=8.5 Hz, 1H), 8.67 (d, J=8.4 Hz, 1H), 11.89 (d, J=5.5 Hz, 1H) ppm. $^{13}$C-NMR (126

MHz, CDCl₃): δ 36.23 (CH₂, C-aliphatic), 45.95 (CH₃, C-aliphatic), 52.69 (CH₂, C-aliphatic), 55.12 (CH₂, C-aliphatic), 55.90 (CH₂, C-aliphatic), 109.33 (CH, C-aromatic), 116.56 (CH, C-aromatic), 121.41 (C, C-aromatic), 122.43 (CH, C-aromatic), 123.59 (CH, C-aromatic), 126.61 (CH, C-aromatic), 132.44 (CH, C-aromatic), 133.01 (CH, C-aromatic), 139.07 (C, C-aromatic), 151.86 (C,C-aromatic), 159.33 (C, C-aromatic), 160.83 (C, C-aromatic), 161.81 (C, C-aromatic), 168.28 (C, C-aromatic) ppm. ¹⁹F-NMR (CDCl₃): δ −57.86, −108.13 ppm. MS (ESI)⁺: 469.2 [M+H]⁺. m.p. (from diethyl ether/n-hexane): 69-71° C.

Example 141

Synthesis of 4-(4-methoxybenzamido)-N-(2-(4-methylpiperazin-1-yl)ethyl)nicotinamide (116)

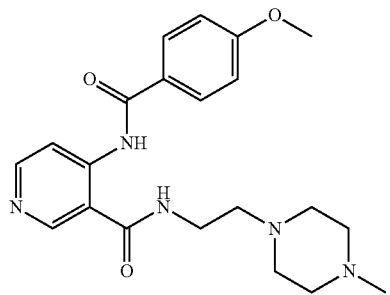

Compound 116 was obtained as a white powder in 15% yield. ¹H-NMR (500 MHz, CDCl₃): δ 2.25 (s, 3H), 2.35-2.56 (m, 7H), 2.56-2.61 (m, 3H), 3.49 (dd, J=5.6, 10.8 Hz, 2H), 3.81 (s, 3H), 6.91-6.96 (m, 2H), 7.12 (s, 1H), 7.89-8.00 (m, 2H), 8.53 (d, J=5.8 Hz, 1H), 8.68 (s, 1H), 8.70 (d, J=5.8 Hz, 1H), 12.41 (s, 1H) ppm. ¹³C-NMR (126 MHz, CDCl₃): δ 36.16 (CH₂, C-aliphatic), 45.91 (CH₃, C-aliphatic), 52.63 (CH₂, C-aliphatic), 55.09 (CH₂, C-aliphatic), 55.48 (CH₃, C-aliphatic), 55.56 (CH₂, C-aliphatic), 114.16 (CH, C-aromatic), 114.43 (CH, C-aromatic), 114.95 (C, C-aromatic), 126.23 (C, C-aromatic), 129.60 (CH, C-aromatic), 147.25 (C, C-aromatic), 147.99 (CH, C-aromatic), 153.37 (CH, C-aromatic), 163.04 (C, C-aromatic), 165.22 (C, C-aromatic), 167.68 (C, C-aromatic) ppm. MS (ESI)⁺: 398.2 [M+H]⁺. m.p. (from dichloromethane/n-hexane): 83-85° C.

Example 142

Synthesis of N-(2-(piperazin-1-yl)ethyl)-2-(4-(trifluoromethyl)benzamido) benzamide (117)

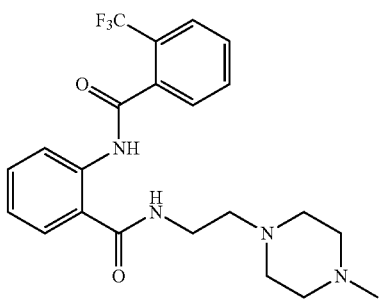

Compound 117 was obtained as a white powder in 38% yield. ¹H-NMR (500 MHz, CDCl₃): δ 2.24 (s, 3H), 2.35-2.47 (m, 7H), 2.51 (dd, J=8.3, 14.2 Hz, 3H), 3.39 (dd, J=5.6, 11.0 Hz, 2H), 6.91 (s, 1H), 7.11 (td, J=1.1, 7.8 Hz, 1H), 7.42 (dd, J=1.3, 7.9 Hz, 1H), 7.46-7.52 (m, 2H), 7.56 (t, J=7.3 Hz, 1H), 7.61 (d, J=7.4 Hz, 1H), 7.67 (d, J=7.8 Hz, 1H), 8.71 (d, J=8.3 Hz, 1H), 11.55 (s, 1H) ppm. ¹³C-NMR (126 MHz, CDCl₃): δ 36.17 (CH₂, C-aliphatic), 46.00 (CH₃, C-aliphatic), 52.73 (CH₂, C-aliphatic), 55.18 (CH₂, C-aliphatic), 55.80 (CH₂, C-aliphatic), 113.80 (C, C-aromatic), 120.68 (C, C-aromatic), 121.76 (CH, C-aromatic), 123.43 (CH, C-aromatic), 126.46 (CH, C-aromatic), 126.74 (CH, C-aromatic), 126.77 (C, C-aromatic), 128.14 (CH, C-aromatic), 129.99 (CH, C-aromatic), 132.17 (CH, C-aromatic), 132.72 (CH, C-aromatic), 139.50 (C, C-aromatic), 166.14 (C, C-aromatic), 168.65 (C, C-aromatic) ppm. ¹⁹F-NMR (CDCl₃): δ −58.93 ppm. MS (ESI)⁺: 435.2 [M+H]⁺. m.p. (from ethanol/water): 124-126° C.

General Procedure 6

The compounds of the application with the general formula shown below can be prepared according to the synthetic scheme shown in Scheme 6.

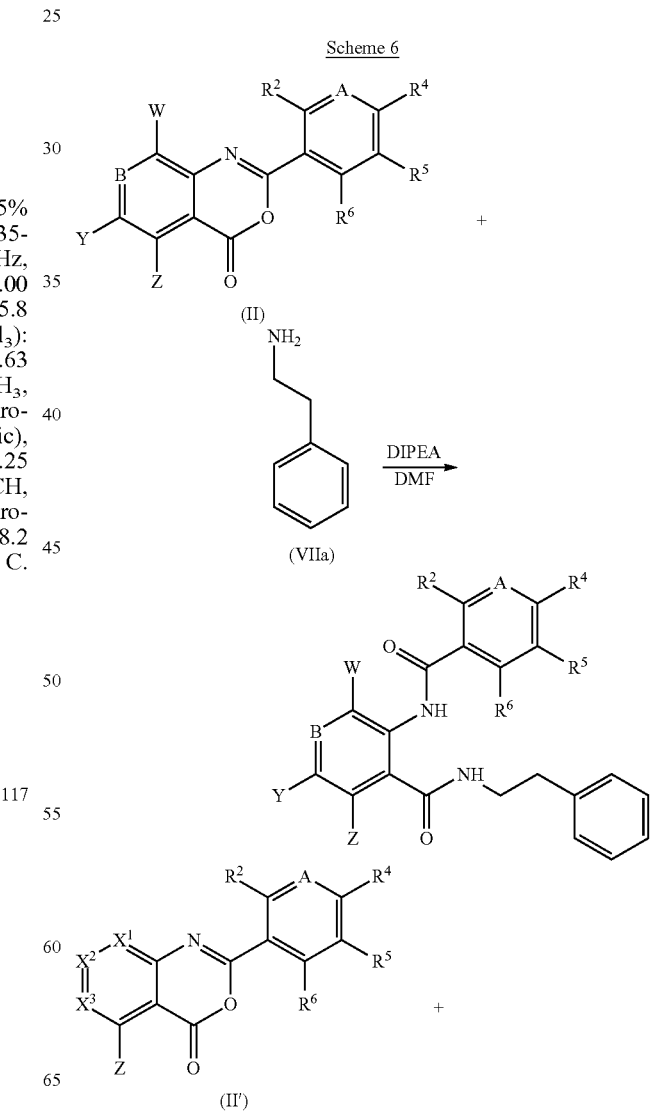

-continued

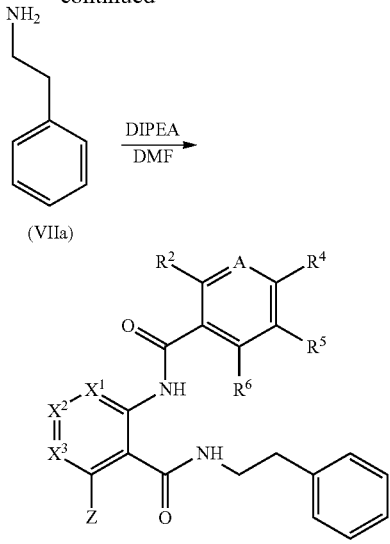

(VIIa)

To a solution of compound (II) or (II') (1 equivalent) in N,N-dimethyl-formamide (DMF) is added 2 equivalents of N,N-diisopropylethylamine (DIPEA) and 2.2 equivalent of 2-phenethylamine (VIIa). The reaction mixture is stirred at about 15° C. to about 28° C. for about 12 hours to about 24 hours. The reaction mixture is diluted with water, washed with ethyl acetate, washed with brine, dried over $Mg_2SO_4$, filtered and evaporated to give a crude compound which is then purified by silica gel column using a mixture of Chloroform:Methanol (9:1) as eluent. The product is collected under reduced pressure to provide the compound with the general formula shown in Scheme 6.

Compounds 70-94, 100, 119, 122 were prepared according to General Procedure 6 substituting (II) or (II') with the appropriate substituted compound.

Example 143

Synthesis of 2-nitro-N-(2-(phenethylcarbamoyl)phenyl)benzamide (70)

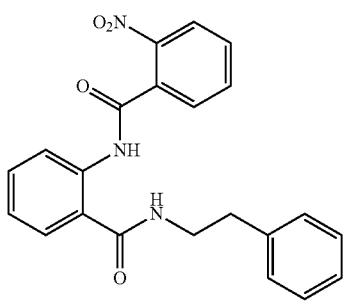

Compound 70 was obtained as a white powder in 45% yield. $^1$H-NMR (CDCl$_3$): δ 2.94 (t, J=6.8 Hz, 2H), 3.69 (dd, J=6.8, 12.8 Hz, 2H), 6.30 (s, 1H), 7.24-7.28 (m, 3H), 7.36 (t, J=7.4 Hz, 3H), 7.56 (t, J=7.3 Hz, 1H), 7.58-7.67 (m, 1H), 7.7-7.79 (m, 3H), 8.07-8.12 (m, 1H), 8.72 (d, J=8.3 Hz, 1H), 11.67 (s, 1H) ppm. $^{13}$C-NMR (CDCl$_3$): δ 35.43 (CH$_2$, C-aliphatic), 41.09 (CH$_2$, C-aliphatic), 120.63 (C, C-aromatic), 121.98 (CH, C-aromatic), 123.65 (CH, C-aromatic), 124.74 (CH, C-aromatic), 126.28 (CH, C-aromatic), 126.81 (CH, C-aromatic), 128.49 (CH, C-aromatic), 128.80 (CH, C-aromatic), 128.85 (CH, C-aromatic), 130.78 (CH, C-aromatic), 132.88 (CH, C-aromatic), 133.06 (CH, C-aromatic), 133.77 (C, C-aromatic), 138.45 (CH, C-aromatic), 139.23 (C, C-aromatic), 147.02 (C, C-aromatic), 164.36 (C, C-aromatic), 168.81 (C, C-aromatic) ppm. MS(ESI)$^+$: 390.2 [M+H]$^+$. m.p.: (from ethanol/water) 101-105° C.

Example 144

Synthesis of 2-(3-nitrobenzamido)-N-phenethylbenzamide (71)

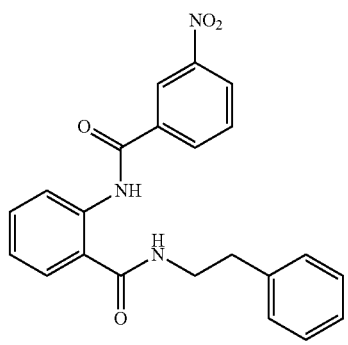

Compound 71 was obtained as a white powder in 14% yield. $^1$H-NMR (CDCl$_3$): δ 2.94 (t, J=6.8 Hz, 2H), 3.70 (dd, J=6.7, 12.8 Hz, 2H), 6.27 (s, 1H), 7.12 (dd, J=4.2, 11.0 Hz, 1H), 7.25 (t, J=8.4 Hz, 2H), 7.35 (t, J=7.3 Hz, 3H), 7.38-7.44 (m, 2H), 7.49 (dd, J=1.2, 7.9 Hz, 1H), 7.52-7.57 (m, 1H), 7.68 (dd, J=1.8, 7.4 Hz, 1H), 8.79 (d, J=8.4 Hz, 1H), 11.50 (s, 1H) ppm. $^{13}$C-NMR (CDCl$_3$): δ 35.50 (CH$_2$, C-aliphatic), 41.16 (CH$_2$, C-aliphatic), 120.14 (C, C-aromatic), 121.59 (CH, C-aromatic), 123.06 (CH, C-aromatic), 123.47 (CH, C-aromatic), 126.26 (CH, C-aromatic), 126.34 (CH, C-aromatic), 126.86 (CH, C-aromatic), 128.80 (CH, C-aromatic), 128.86 (CH, C-aromatic), 129.96 (CH, C-aromatic), 132.76 (CH, C-aromatic), 133.02 (CH, C-aromatic), 136.79 (C, C-aromatic), 138.42 (C, C-aromatic), 139.66 (C, C-aromatic), 148.64 (C, C-aromatic), 163.06 (C, C-aromatic), 169.08 (C, C-aromatic) ppm. MS(ESI)$^+$: 379.1 [M+H]$^+$. m.p.: (from ethanol) 102-104° C.

Example 145

Synthesis of 2-(4-nitrobenzamido)-N-phenethylbenzamide (72)

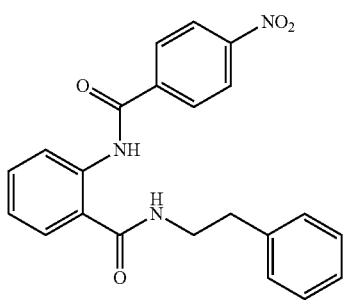

(72)

Compound 72 was obtained as a white powder in 34% yield. $^1$H-NMR (CDCl$_3$): δ2.99 (t, J=6.8 Hz, 4H), 3.78 (dd, J=6.7, 12.8 Hz, 4H), 6.36 (s, 2H), 7.15 (td, J=7.8, 1.1 Hz, 2H), 7.27 (d, J=4.8 Hz, 3H), 7.43-7.33 (m, 6H), 7.64-7.54 (m, 2H), 8.26-8.15 (m, 4H), 8.45-8.35 (m, 4H), 8.82 (dd, J=0.8, 8.4 Hz, 2H), 12.54 (s, 2H) ppm. $^{13}$C-NMR (CDCl$_3$): δ 35.51 (CH$_2$, C-aliphatic), 41.14 (CH$_2$, C-aliphatic), 120.17 (C, C-aromatic), 121.55 (CH, C-aromatic), 123.54 (CH, C-aromatic), 124.01 (CH, C-aromatic), 126.35 (CH, C-aromatic), 126.90 (CH, C-aromatic), 128.62 (CH, C-aromatic), 128.79 (CH, C-aromatic), 128.88 (CH, C-aromatic), 133.06 (CH, C-aromatic), 138.36 (C, C-aromatic), 139.65 (C, C-aromatic), 140.39 (C, C-aromatic), 150.01 (C, C-aromatic), 162.99 (C, C-aromatic), 168.95 (C, C-aromatic) ppm. MS(ESI)$^+$: 390.2 [M+H]$^+$. m.p.: (from ethanol/H$_2$O) 133-137° C.

Example 146

Synthesis of 2-fluoro-N-(2-(phenethylcarbamoyl)phenyl)benzamide (73)

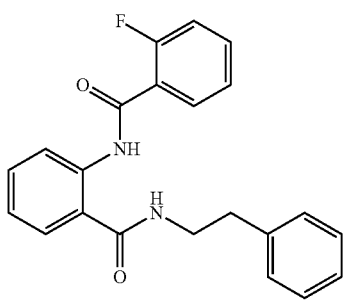

(73)

Compound 73 was obtained as a white powder in 40% yield. $^1$H-NMR (CDCl$_3$): δ 2.95 (t, J=6.8 Hz, 2H), 3.75 (dd, J=6.7, 12.8 Hz, 2H), 6.22 (s, 1H), 7.10 (t, J=7.7 Hz, 1H), 7.21-7.25 (m, 3H), 7.28-7.37 (m, 5H), 7.51-7.55 (m, 2H), 7.95-8.09 (m, 1H), 8.76 (d, J=8.4 Hz, 1H), 11.67 (d, J=7.1 Hz, 1H) ppm. $^{13}$C-NMR (CDCl$_3$): δ 35.52 (CH$_2$, C-aliphatic), 41.03 (CH$_2$, C-aliphatic), 116.56 (C, C-aromatic), 122.18 (C, C-aromatic), 122.48 (CH, C-aromatic), 123.39 (CH, C-aromatic), 124.63 (CH, C-aromatic), 124.65 (CH, C-aromatic), 126.39 (CH, C-aromatic), 126.74 (CH, C-aromatic), 128.80 (CH, C-aromatic), 131.58 (CH, C-aromatic), 132.34 (CH, C-aromatic), 133.37 (CH, C-aromatic), 133.44 (CH, C-aromatic), 138.58 (C, C-aromatic), 138.87 (C, C-aromatic), 168.69 (C, C-aromatic) ppm. $^{19}$F-NMR: δ −112.39 ppm. MS(ESI)+: 385.1 [M+Na]$^+$. m.p.: (from ethanol/water) 95-97° C.

Example 147

Synthesis of 2-chloro-N-(2-(phenethylcarbamoyl)phenyl)benzamide (74)

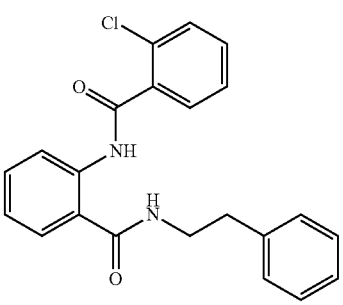

(74)

Compound 74 was obtained as a white powder in 37% yield. $^1$H-NMR (CDCl$_3$): δ 2.94 (t, J=6.8 Hz, 4H), 3.70 (dd, J=6.7, 12.9 Hz, 4H), 6.27 (s, 2H), 7.11 (t, J=7.6 Hz, 2H), 7.25 (t, J=8.3 Hz, 5H), 7.32-7.44 (m, 10H), 7.49 (dd, J=1.3, 7.8 Hz, 2H), 7.55 (t, J=7.9 Hz, 2H), 7.68 (dd, J=1.8, 7.4 Hz, 2H), 8.79 (d, J=8.4 Hz, 2H), 11.50 (s, 2H) ppm. $^{13}$C-NMR (CDCl$_3$): δ 35.48 (CH$_2$, C-aliphatic), 41.04 (CH$_2$, C-aliphatic), 121.80 (C, C-aromatic), 123.37 (CH, C-aromatic), 126.34 (CH, C-aromatic), 126.80 (CH, C-aromatic), 127.14 (CH, C-aromatic), 128.78 (CH, C-aromatic), 128.82 (CH, C-aromatic), 129.32 (CH, C-aromatic), 130.62 (C, C-aromatic), 131.34 (CH, C-aromatic), 132.67 (CH, C-aromatic), 136.16 (C, C-aromatic), 138.49 (C, C-aromatic), 139.18 (C, C-aromatic), 165.41 (C, C-aromatic), 168.76 (C, C-aromatic). MS(ESI)$^+$: 379.1, 380.1 [M+H]$^+$. m.p.: (from ethanol) 101-103° C.

Example 148

Synthesis of 2-(3-chlorobenzamido)-N-phenethylbenzamide (75)

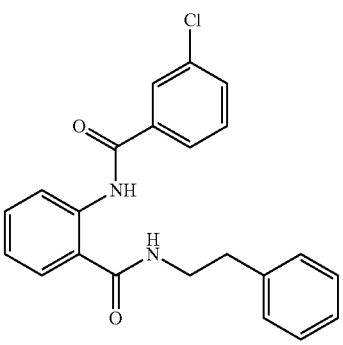

(75)

Compound 75 was obtained as a white powder in 63% yield. ¹H-NMR (CDCl₃): δ 2.98 (t, J=6.8 Hz, 2H), 3.78 (dd, J=6.7, 12.8 Hz, 2H), 6.31 (s, 1H), 7.07-7.13 (m, 1H), 7.23-7.30 (m, 3H), 7.33-7.38 (m, 3H), 7.48 (t, J=7.8 Hz, 1H), 7.52-7.58 (m, 2H), 7.91 (d, J=7.7 Hz, 1H), 8.07 (t, J=1.8 Hz, 1H), 8.79 (d, J=8.4 Hz, 1H), 12.19 (s, 1H) ppm. ¹³C-NMR (CDCl₃): δ 35.53 (CH₂, C-aliphatic), 41.09 (CH₂, C-aliphatic), 120.42 (C, C-aromatic), 121.66 (CH, C-aromatic), 123.13 (CH, C-aromatic), 125.10 (CH, C-aromatic), 126.30 (CH, C-aromatic), 126.84 (CH, C-aromatic), 128.15 (CH, C-aromatic), 128.80 (CH, C-aromatic), 128.85 (CH, C-aromatic), 130.05 (CH, C-aromatic), 131.87 (CH, C-aromatic), 132.84 (CH, C-aromatic), 135.04 (C, C-aromatic), 136.72 (C, C-aromatic), 138.45 (C, C-aromatic), 139.75 (C, C-aromatic), 164.19 (C, C-aromatic), 169.07 (C, C-aromatic). MS(ESI)⁺: 379.1, 380.1 [M+H]⁺. m.p.: (from ethanol) 103-105° C.

Example 149

Synthesis of 2-(4-chlorobenzamido)-N-phenethylbenzamide (76)

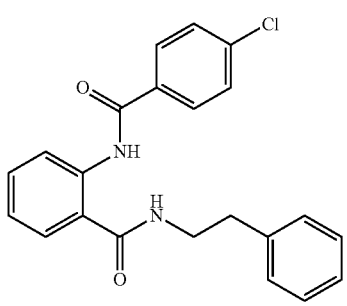

(76)

Compound 76 was obtained as a white powder in 61% yield. ¹H-NMR (CDCl₃): δ 2.98 (t, J=6.8 Hz, 2H), 3.76 (dd, J=6.7, 12.8 Hz, 2H), 6.37 (s, 1H), 7.04-7.12 (m, 1H), 7.24-7.29 (m, 3H), 7.34-7.40 (m, 3H), 7.53 (ddd, J=8.6, 7.6, 1.5 Hz, 3H), 7.97-8.02 (m, 2H), 8.79 (d, J=8.4 Hz, 1H), 12.20 (s, 1H) ppm. ¹³C-NMR (CDCl₃): δ 40.70 (CH₂, C-aliphatic), 42.03 (CH₂, C-aliphatic), 120.30 (CH, C-aromatic), 120.44, 122.99 (CH, C-aromatic), 126.10 (CH, C-aromatic), 128.08 (CH, C-aromatic), 128.25 (CH, C-aromatic), 128.36 (CH, C-aromatic), 128.62 (CH, C-aromatic), 128.82 (CH, C-aromatic), 129.07 (CH, C-aromatic), 132.18 (CH, C-aromatic), 133.27 (C, C-aromatic), 136.89 (C, C-aromatic), 139.05 (C, C-aromatic), 139.11 (C, C-aromatic), 139.26 (C, C-aromatic), 163.27 (C=O), 168.6 (C=O). MS(ESI)⁺: 379.1, 380.1 [M+H]⁺. m.p.: 104-106° C.

Example 150

Synthesis of N-phenethyl-2-(3-(trifluoromethyl)benzamido)benzamide (77)

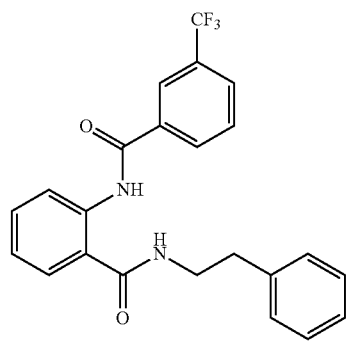

(77)

Compound 77 was obtained as a white powder in 51% yield. ¹H-NMR (CDCl₃): δ 2.98 (t, J=6.8 Hz, 2H), 3.78 (dd, J=6.7, 12.8 Hz, 2H), 6.32 (s, 1H), 7.12 (t, J=7.6 Hz, 1H), 7.26 (d, J=7.4 Hz, 3H), 7.34-7.39 (m, 3H), 7.59-7.53 (m, 1H), 7.69 (t, J=7.8 Hz, 1H), 7.83 (d, J=7.7 Hz, 1H), 8.21 (d, J=7.8 Hz, 1H), 8.38 (s, 1H), 8.81 (d, J=8.4 Hz, 1H), 12.35 (s, 1H) ppm. ¹³C NMR (126 MHz, CDCl₃): 34.85 (CH₂, C-aromatic), 41.04 (CH₂, C-aromatic), 120.17 (C, C-aromatic), 121.14 (CH, C-aromatic), 123.00 (CH, C-aromatic), 125.10 (CH, C-aromatic), 126.06 (CH, C-aromatic), 126.74 (CH, C-aromatic), 128.38 (CH, C-aromatic), 128.90 (CH, C-aromatic), 130.39 (CH, C-aromatic), 132.63 (CH, C-aromatic), 132.90 (C, C-aromatic), 135.70 (C, C-aromatic), 137.85 (C, C-aromatic), 139.71 (C, C-aromatic), 163.66 (C, C-aromatic), 168.95 (C, C-aromatic) ppm. ¹⁹F-NMR: δ −62.72 ppm. MS(ESI)⁺: 422.2 [M+H]⁺. m.p.: (from ethanol/water) 103-105° C.

Example 151

Synthesis of N-phenethyl-2-(4-(trifluoromethyl)benzamido)benzamide (78)

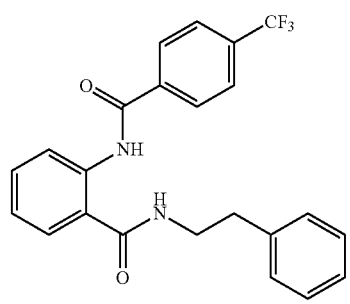

(78)

Compound 78 was obtained as a white powder in 53% yield. ¹H-NMR (CDCl₃): δ 3.06-2.90 (m, 2H), 3.78 (dd, J=6.8, 12.7 Hz, 2H), 6.31 (s, 1H), 6.95-7.12 (m, 1H), 7.19-7.26 (m, 3H), 7.40-7.31 (m, 4H), 7.59-7.54 (m, 1H), 7.81 (d, J=8.2 Hz, 2H), 8.18 (d, J=8.1 Hz, 2H), 8.83 (dd, J=0.9, 8.4 Hz, 1H), 12.36 (s, 1H) ppm. ¹³C NMR (126 MHz, CDCl₃): δ 34.84 (CH₂, C-aliphatic), 40.75 (CH₂, C-aliphatic), 119.87 (C, C-aromatic), 121.14 (CH, C-aromatic), 123.01 (CH, C-aromatic), 125.47 (CH, C-aromatic), 126.06 (CH, C-aromatic), 126.74 (CH, C-aromatic), 127.92 (CH, C-aromatic), 128.66 (CH, C-aromatic), 128.90 (CH, C-aromatic), 132.93 (CH, C-aromatic), 138.52 (C, C-aromatic), 140.02 (C, C-aromatic), 148.16 (C, C-aromatic), 157.09 (C, C-aromatic), 163.97 (C, C-aromatic), 188.19 (C, C-aromatic) ppm. $^{19}$F-NMR: δ −63.09 ppm. MS(ESI)$^+$: 435.1 [M+H]$^+$. m.p.: (from ethanol/water) 96-98° C.

Example 152

Synthesis of 2-(4-methoxybenzamido)-N-phenethylbenzamide (79)

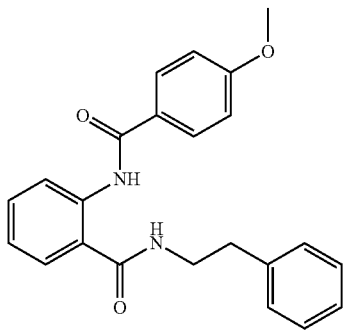

(79)

Compound 79 was obtained as a white powder in 62% yield. $^1$H-NMR (CDCl$_3$): δ 2.98-3.11 (m, 2H), 3.79-3.71 (m, 2H), 3.91 (S, 3H), 6.32 (s, 1H), 7.00-7.08 (m, 3H), 7.20-7.29 (m, 5H), 7.34 (dq, J=7.3, 14.4 Hz, 4H), 7.42-7.53 (m, 1H), 7.91-8.10 (m, 2H), 8.79 (d, J=8.4 Hz, 1H), 12.01 (s, 1H) ppm. $^{13}$C-NMR (CDCl$_3$): δ 35.53 (CH$_2$, C-aliphatic), 41.08 (CH$_2$, C-aliphatic), 55.46 (CH$_3$, C-aliphatic), 113.98 (CH, C-aromatic), 120.38 (C, C-aromatic), 121.55 (CH, C-aromatic), 122.58 (CH, C-aromatic), 126.31 (CH, C-aromatic), 126.81 (CH, C-aromatic), 127.20 (CH, C-aromatic), 128.82 (CH, C-aromatic), 129.33 (CH, C-aromatic), 132.71 (CH, C-aromatic), 138.52 (C, C-aromatic), 140.15 (C, C-aromatic), 162.51 (C, C-aromatic), 165.71 (C, C-aromatic), 169.26 (C, C-aromatic) ppm. MS(ESI)$^+$: 375.2 [M+H]$^+$. m.p.: (from ethanol) 124-126° C.

Example 153

Synthesis of 2-fluoro-4-methoxy-N-(2-(phenethyl-carbamoyl) phenyl)benzamide (80)

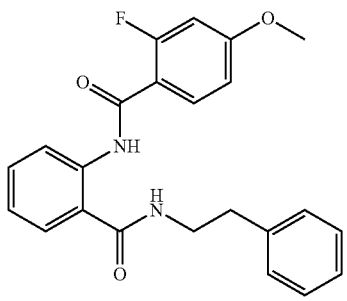

(80)

Compound 80 was obtained as an orange powder in 21% yield. $^1$H-NMR (CDCl$_3$): δ 2.97 (t, J=6.8 Hz, 2H), 3.75 (dd, J=6.7, 12.9 Hz, 2H), 3.89 (d, J=4.9 Hz, 3H), 6.17 (s, 1H), 6.73 (dd, J=2.4, 13.3 Hz, 1H), 6.84 (dd, J=2.4, 8.8 Hz, 1H), 7.09 (dd, J=4.2, 10.9 Hz, 1H), 7.26 (d, J=6.1 Hz, 3H), 7.31-7.37 (m, 3H), 7.51 (dd, J=4.3, 11.5 Hz, 1H), 8.06 (t, J=8.9 Hz, 1H), 8.71 (d, J=8.4 Hz, 1H), 11.55 (d, J=8.8 Hz, 1H) ppm. $^{13}$C-NMR (CDCl$_3$): δ 35.53 (CH$_2$, C-aliphatic), 41.02 (CH$_2$, C-aliphatic), 55.84 (CH$_3$, C-aliphatic), 101.76 (CH, C-aromatic), 101.98 (CH, C-aromatic), 110.72 (CH, C-aromatic), 117.4 (C, C-aromatic), 122.32 (C, C-aromatic), 122.59 (CH, C-aromatic), 123.16 (CH, C-aromatic), 125.10 (C, C-aromatic), 126.37 (CH, C-aromatic), 126.73 (CH, C-aromatic), 128.79 (CH, C-aromatic), 132.25 (CH, C-aromatic), 132.91 (CH, C-aromatic), 138.62 (C, C-aromatic), 138.97 (C, C-aromatic), 158.9 (C, C-aromatic), 163.2 (C, C-aromatic), 168.74 (C, C-aromatic) ppm. $^{19}$F-NMR (CDCl$_3$): δ −109.11 ppm. MS(ESI)$^+$: 415.2 [M+Na]$^+$. m.p.: (from ethanol/water) 139-141° C.

Example 154

Synthesis of 2-fluoro-6-(2-fluorobenzamido)-N-phenethylbenzamide (81)

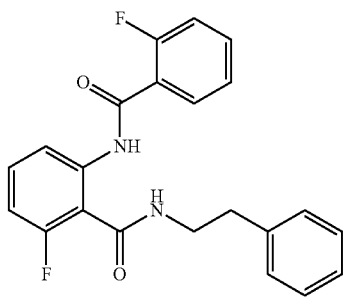

(81)

Compound 81 was obtained as a white powder in 48% yield. $^1$H-NMR (CDCl$_3$): δ 2.96 (t, J=6.9 Hz, 2H), 3.74-3.81 (m, 2H), 6.68 (s, 1H), 6.88 (m, 1H), 7.20-7.27 (m, 4H), 7.29-7.35 (m, 3H), 7.38-7.49 (m, 1H), 7.51-7.58 (m, 1H), 7.92-8.05 (m, 1H), 8.59 (d, J=8.5 Hz, 1H), 11.96 (d, J=6.3 Hz, 1H) ppm. $^{13}$C-NMR (CDCl$_3$): δ 35.42 (CH$_2$, C-aliphatic), 41.22 (CH$_2$, C-aliphatic), 110.70 (C, C-aromatic), 116.61 (CH, C-aromatic), 118.33 (CH, C-aromatic), 122.68 (CH, C-aromatic), 124.67 (CH, C-aromatic), 126.69 (CH, C-aromatic), 128.75 (CH, C-aromatic), 131.54 (CH, C-aromatic), 132.65 (CH, C-aromatic), 133.53 (CH, C-aromatic), 138.47 (C, C-aromatic), 140.80 (C, C-aromatic), 159.37 (C, C-aromatic), 161.35 (C, C-aromatic), 162.44 (C, C-aromatic), 164.70 (C, C-aromatic) ppm. F-NMR (CDCl$_3$): δ −111.60, −112.88 ppm. MS(ESI)$^+$: 381.1 [M+H]$^+$. m.p.: 96-98° C.

Example 155

Synthesis of 4-fluoro-2-(2-fluorobenzamido)-N-phenethylbenzamide (82)

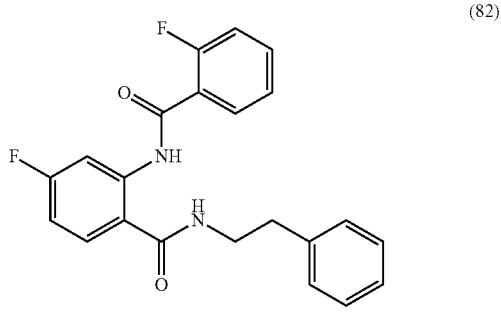 [SMILES: O=C(Nc1cc(F)ccc1C(=O)NCCc1ccccc1)c1ccccc1F]

(82)

Compound 82 was obtained as a white powder in 44% yield. ¹H-NMR (CDCl₃): δ 2.96 (t, J=6.8 Hz, 2H), 3.75 (dd, J=6.7, 12.8 Hz, 2H), 6.13 (s, 1H), 6.76-6.79 (m, 1H), 7.23-7.27 (m, 4H), 7.30-7.38 (m, 4H), 7.47-7.61 (m, 1H), 7.91-8.07 (m, 1H), 8.63 (dd, J=2.6, 11.8 Hz, 1H), 11.95 (d, J=6.8 Hz, 1H) ppm. ¹³C-NMR (126 MHz, CDCl₃): δ 35.47 (CH₂, C-aromatic), 41.06 (CH₂, C-aromatic), 109.49 (CH, C-aromatic), 110.15 (CH, C-aromatic), 116.52 (CH, C-aromatic), 122.02 (CH, C-aromatic), 124.74 (C, C-aromatic), 126.80 (CH, C-aromatic), 128.11 (CH, C-aromatic), 128.19 (CH, C-aromatic), 128.80 (CH, C-aromatic), 128.83 (CH, C-aromatic), 131.62 (C, C-aromatic), 133.65 (CH, C-aromatic), 133.72 (C, C-aromatic), 161.12 (C, C-aromatic), 162.98 (C, C-aromatic), 165.22 (C, C-aromatic), 167.69 (C, C-aromatic), 170.3 (C, C-aromatic) ppm. ¹⁹F-NMR: δ −103.79, −113.02 ppm. MS(ESI)⁺: 403.1 [M+Na]⁺. m.p.: (from ethanol/water) 104-106° C.

Example 156

Synthesis of 2-(2-fluorobenzamido)-4-methoxy-N-phenethylbenzamide (83)

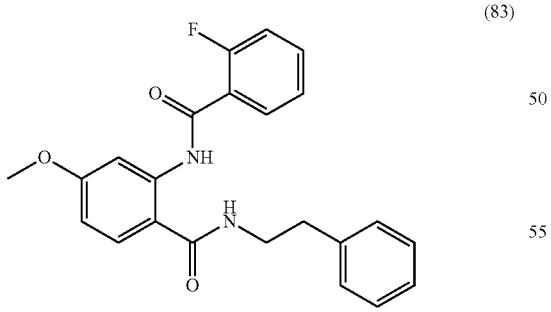

(83)

Compound 83 was obtained as a white powder in 51% yield. ¹H-NMR (CDCl₃): δ 0.2.95 (t, J 6.71 Hz, 2H), 3.61 (q, J 6.71 Hz, 2H), 3.90 (s, 3H), 6.13 (s, 1H), 6.64 (dd, J=2.43, 5.80, 1 Hz), 7.23 (t, J=8.42, 5H), 7.32 (q, J=8.42, 3H), 7.56-7.52 (m, 1H), 8.00-8.10 (m, 1H), 8.51 (d, J=2.50 Hz, 1H), 12.17 (d, J=5.9 Hz, 1H) ppm. ¹³C-NMR (CDCl₃): δ 35.58 (CH₂, C-aliphatic), 40.93 (CH₂, C-aliphatic), 55.55 (CH₃, C-aliphatic), 106.16 (CH, C-aromatic), 110.23 (CH, C-aromatic), 113.62 (C, C-aromatic), 116.63 (d, J$_{C-F}$=23.9 Hz, C, C-aromatic), 124.61 (CH, C-aromatic), 124.64 (CH, C-aromatic), 126.70 (CH, C-aromatic), 127.70 (CH, C-aromatic), 128.78 (CH, C-aromatic), 128.82 (CH, C-aromatic), 131.31 (CH, C-aromatic), 133.36 (CH, C-aromatic), 138.72 (C, C-aromatic), 141.41 (C, C-aromatic), 162.68 (C, C-aromatic) ppm. ¹⁹F-NMR: δ −112.49 ppm. MS(ESI)⁺: 415.1 [M+Na]+. m.p.: (from ethanol/water) 108-110° C.

Example 157

Synthesis of 2-(2-fluorobenzamido)-3-methoxy-N-phenethylbenzamide (84)

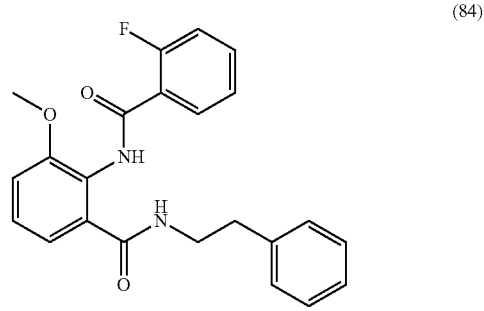 [SMILES: COc1cccc(C(=O)NCCc2ccccc2)c1NC(=O)c1ccccc1F]

(84)

Compound 84 was obtained as a white powder in 66% yield. ¹H-NMR (CDCl₃): δ 2.87 (t, J=7.12 Hz, 2H), 3.65 (dd, J=5.96, 7.10 Hz, 2H), 3.89 (s, 3H), 6.38-6.40 (m, 1H), 7.07 (m, 2H), 7.18-7.23 (m, 4H), 7.26-7.32 (m, 4H), 7.52-7.56 (m, 1H), 8.12-8.15 (m, 1H), 8.83-8.86 (m, 1H) ppm. ¹³C-NMR (CDCl₃): 35.53 (CH₂, C-aliphatic), 41.02 (CH₂, C-aliphatic), 56.16 (CH₃, C-aliphatic), 113.21 (CH, C-aromatic), 116.32 (CH, C-aromatic), 119.59 (CH, C-aromatic), 123.36 (C, C-aromatic), 124.75 (CH, C-aromatic), 126.42 (CH, C-aromatic), 127.41 (CH, C-aromatic), 128.56 (CH, C-aromatic), 128.73 (CH, C-aromatic), 132.25 (CH, C-aromatic), 133.74 (CH, C-aromatic), 134.06 (C, C-aromatic), 138.91 (C, C-aromatic), 153.95 (C, C-aromatic), 159.92 (C, C-aromatic), 161.90 (C, C-aromatic), 168.10 (C, C-aromatic) ppm. ¹⁹F-NMR (CDCl₃): −112.645 ppm. MS(ESI)⁺: 393.2 [M+H]⁺. m.p.: 130-132° C.

Example 158

Synthesis of 2-(3-fluorobenzamido)-3-methoxy-N-phenethylbenzamide (85)

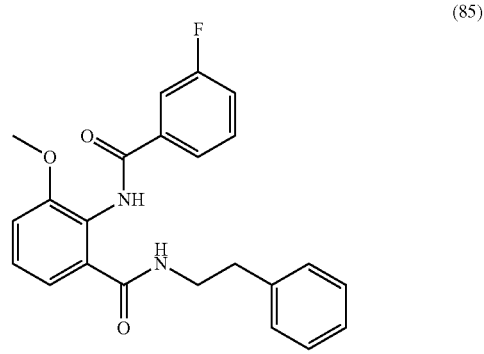 [SMILES: COc1cccc(C(=O)NCCc2ccccc2)c1NC(=O)c1cccc(F)c1]

(85)

Compound 85 was obtained as a white powder in 42% yield. ¹H-NMR (CDCl₃): δ 2.875 (t, J=7.10 Hz, 2H), 3.62-3.66 (m, 2H), 3.89-3.89 (m, 6H), 6.38-6.39 (m, 1H), 7.02-7.07 (m, 2H), 7.10-7.12 (m, 1H), 7.20-7.26 (m, 4H), 7.28-7.31 (m, 2H), 7.40 (t, J=8.15 Hz, 1H), 7.52-7.53 (m, 2H), 8.81 (s, 1H) ppm. ¹³C-NMR (CDCl₃): δ 35.50 (CH, C-aliphatic), 41.04 (CH, C-aliphatic), 55.47 (CH3 C-aliphatic), 56.16 (CH3, C-aliphatic), 112.75 (CH, C-aromatic), 113.69 (CH, C-aromatic), 118.33 (CH, C-aromatic), 119.24 (CH, C-aromatic), 119.61 (CH, C-aromatic), 124.54 (C, C-aromatic), 126.50 (CH, C-aromatic), 126.99 (CH, C-aromatic), 128.61 (CH, C-aromatic), 128.74 (CH, C-aromatic), 129.70 (CH, C-aromatic), 132.77 (C, C-aromatic), 135.68 (C, C-aromatic), 138.78 (C, C-aromatic), 154.20 (C, C-aromatic), 159.89 (C, C-aromatic), 166.32 (C, C-aromatic), 168.31 (C, C-aromatic) ppm. ¹⁹F-NMR (CDCl₃): −111.82 ppm. MS(ESI)⁺: 393.2 [M+H]⁺. m.p.: 99-101° C.

Example 159

Synthesis of 2-(4-fluorobenzamido)-3-methoxy-N-phenethylbenzamide (86)

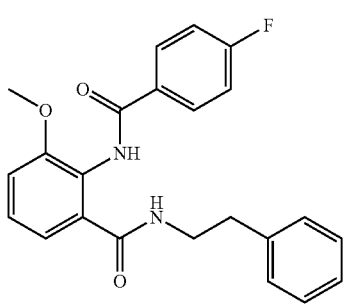

(86)

Compound 86 was obtained as a white powder in 36% yield. ¹H-NMR (CDCl₃): δ 2.47-2.38 (m, 4H), 2.60-2.49 (m, 2H), 3.47 (dd, J=5.6, 11.4 Hz, 2H), 3.71-3.63 (m, 4H), 3.91 (s, 3H), 6.79 (s, 1H), 7.19-7.09 (m, 4H), 7.32-7.26 (m, 2H), 8.07-7.94 (m, 2H), 9.11 (s, 1H) ppm. ¹³C-NMR (CDCl₃): δ 35.89 (CH₂, C-aromatic), 40.58 (CH₂, C-aromatic), 56.33 (CH₃, C-aromatic), 113.99 (CH, C-aromatic), 119.30 (CH, C-aromatic), 124.88 (C, C-aromatic), 125.48 (CH, C-aromatic), 126.07 (CH, C-aromatic), 127.04 (CH, C-aromatic), 127.92 (CH, C-aromatic), 129.80 (CH, C-aromatic), 130.39 (C, C-aromatic), 131.66 (CH, C-aromatic), 138.89 (C, C-aromatic), 154.26 (C, C-aromatic), 163.95 (C, C-aromatic), 165.21 (C, C-aromatic), 166.41 (C, C-aromatic), 167.98 (C, C-aromatic) ppm. ¹⁹F-NMR (CDCl₃): −111.86 ppm. MS(ESI)⁺: 415.1[M+Na]⁺. m.p.: 140-142° C.

Example 160

Synthesis of 2-fluoro-6-(4-methoxybenzamido)-N-phenethylbenzamide (87)

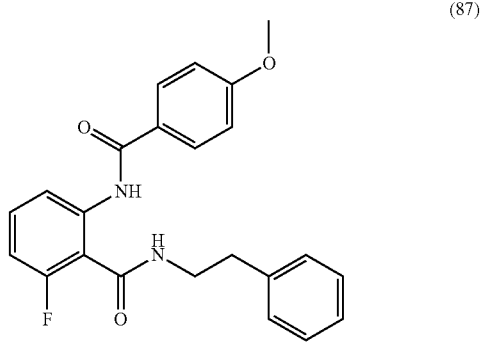 [SMILES: COc1ccc(C(=O)Nc2cccc(F)c2C(=O)NCCc2ccccc2)cc1]

(87)

Compound 87 was obtained as a white powder in 45% yield. ¹H-NMR (CDCl₃): δ 2.98 (t, J=6.9 Hz, 2H), 3.74-3.84 (m, 2H), 3.91 (s, 3H), 6.79-6.92 (m, 2H), 7.01-7.06 (m, 2H), 7.23-7.28 (m, 3H), 7.35 (t, J=7.5 Hz, 2H), 7.32-7.45 (m, 1H), 8.01-8.05 (m, 2H), 8.68 (d, J=8.5 Hz, 1H), 12.47 (s, 1H) ppm. ¹³C-NMR (CDCl₃): δ 35.41 (CH₂, C-aliphatic), 41.26 (CH₂, C-aliphatic), 55.47 (CH₃, C-aliphatic), 109.81 (CH, C-aromatic), 110.01 (CH, C-aromatic), 114.01 (CH, C-aromatic), 117.41 (CH, C-aromatic), 126.76 (CH, C-aromatic), 127.06 (CH, C-aromatic), 128.76 (C, C-aromatic), 129.42 (CH, C-aromatic), 132.99 (CH, C-aromatic), 133.08 (CH, C-aromatic), 138.43 (C, C-aromatic), 159.86 (C, C-aromatic), 161.81 (C, C-aromatic), 162.61 (C, C-aromatic), 165.26 (C, C-aromatic) ppm. ¹⁹F-NMR: δ −111.18 ppm. MS(ESI)⁺: 393 [M+H]⁺. m.p.: (from ethanol/water) 103-105° C.

Example 161

Synthesis of 4-fluoro-2-(4-methoxybenzamido)-N-phenethylbenzamide (88)

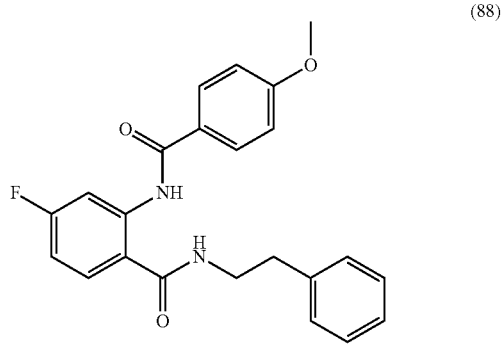 [SMILES: COc1ccc(C(=O)Nc2cc(F)ccc2C(=O)NCCc2ccccc2)cc1]

(88)

Compound 88 was obtained as a white powder in 72% yield. $^1$H-NMR (CDCl$_3$): δ2.97 (d, J=6.8 Hz, 1H), 3.76 (dd, J=6.8, 12.7 Hz, 2H), 3.91 (s, 3H), 6.28 (s, 1H), 6.63-6.73 (m, 1H), 7.02-7.06 (m, 2H), 7.24-7.40 (m, 7H), 7.94-8.05 (m, 2H), 8.65 (dd, J=2.6, 11.9 Hz, 1H), 12.26 (s, 1H) ppm. $^{13}$C-NMR (126 MHz, CDCl$_3$): δ 35.49 (CH$_2$, C-aromatic), 41.09 (CH$_2$, C-aromatic), 55.46 (CH$_3$, C-aromatic), 108.47 (CH, C-aromatic), 108.69 (CH, C-aromatic), 109.40 (CH, C-aromatic), 109.58 (C, C-aromatic), 114.06 (CH, C-aromatic), 126.84 (CH, C-aromatic), 128.16 (CH, C-aromatic), 128.77 (CH, C-aromatic), 129.39 (CH, C-aromatic), 138.47 (C, C-aromatic), 142.47 (C, C-aromatic), 162.73 (C, C-aromatic), 164.47 (C, C-aromatic), 165.29 (C, C-aromatic), 165.99 (C, C-aromatic), 168.60 (C, C-aromatic) ppm. $^{19}$F-NMR (CDCl$_3$): −104.11 ppm. MS(ESI)$^+$: 415.1 [M+Na]$^+$. m.p.: (from ethanol/water) 12-129° C.

Example 162

Synthesis of 4-methoxy-2-(4-methoxybenzamido)-N-phenethylbenzamide (89)

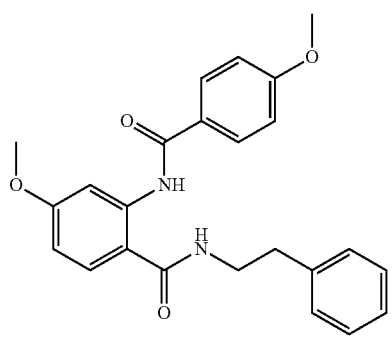

(89)

Compound 89 was obtained as a white powder in 14% yield. $^1$H-NMR (CDCl$_3$): δ 2.97 (t, J=6.8 Hz, 2H), 3.75 (dd, J=6.7, 12.8 Hz, 2H), 3.89 (s, 6H), 6.13 (d, J=61.2 Hz, 1H), 6.58 (dd, J=2.5, 8.7 Hz, 1H), 7.04 (d, J=8.8 Hz, 2H), 7.27 (d, J=8.3 Hz, 3H), 7.36 (t, J=7.6 Hz, 3H), 8.05 (d, J=8.8 Hz, 2H), 8.57 (d, J=2.5 Hz, 1H), 12.51 (s, 1H) ppm. $^{13}$C-NMR (CDCl$_3$): δ 35.61 (CH$_2$, C-aliphatic), 40.98 (CH$_2$, C-aliphatic), 55.46 (CH$_3$, C-aliphatic), 55.55 (CH$_3$, C-aliphatic), 104.90 (CH, C-aromatic), 109.86 (CH, C-aromatic), 112.07 (C, C-aromatic), 114.01 (CH, C-aromatic), 126.77 (CH, C-aromatic), 127.22 (C, C-aromatic), 127.62 (CH, C-aromatic), 128.81 (CH, C-aromatic), 129.34 (CH, C-aromatic), 138.66 (C, C-aromatic), 142.68 (C, C-aromatic), 162.53 (C, C-aromatic), 162.97 (C, C-aromatic), 165.45 (C, C-aromatic), 169.10 (C, C-aromatic) ppm. MS(ESI)$^+$: 405 [M+H]$^+$. m.p.: (from ethanol/water) 138-140° C.

Example 163

Synthesis of 3-methoxy-2-(2-methoxybenzamido)-N-phenethylbenzamide (90)

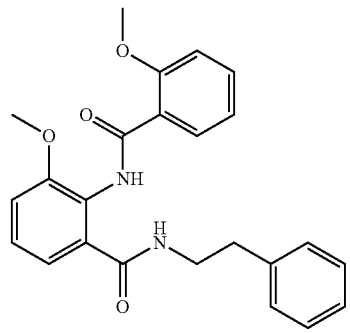

(90)

Compound 90 was obtained as a white powder in 43% yield. $^1$H-NMR (CDCl$_3$): δ 2.83 (t, J=7.3 Hz, 2H), 3.65-3.59 (m, 2H), 3.88 (s, 3H), 4.06 (s, 3H), 6.65 (s, 1H), 7.04 (dd, J=8.3, 14.5 Hz, 2H), 7.13 (d, J=7.7 Hz, 3H), 7.19 (d, J=7.4 Hz, 3H), 7.27-7.22 (m, 2H), 7.55-7.50 (m, 1H), 8.25 (t, J=9.1 Hz, 1H), 9.78-9.70 (m, 1H). $^{13}$C-NMR (CDCl$_3$): δ 39.14 (CH$_2$, C-aliphatic), 40.73 (CH$_2$, C-aliphatic), 56.24 (CH$_3$, C-aliphatic), 56.26 (CH$_3$, C-aliphatic), 111.15 (CH, C-aromatic), 113.01 (CH, C-aromatic), 120.16 (CH, C-aromatic), 121.14 (CH, C-aromatic), 122.99 (C, C-aromatic), 123.30 (C, C-aromatic), 126.36 (CH, C-aromatic), 127.03 (CH, C-aromatic), 128.90 (CH, C-aromatic), 132.26 (CH, C-aromatic), 133.52 (CH, C-aromatic), 135.40 (CH, C-aromatic), 138.82 (C, C-aromatic), 153.73 (C, C-aromatic), 157.76 (C, C-aromatic), 164.55 (C, C-aromatic), 167.98 (C, C-aromatic) ppm. MS(ESI)$^+$: 405.2 [M+H]$^+$. m.p.: (from methanol/water) 133-136° C.

Example 164

Synthesis of 3-methoxy-2-(3-methoxybenzamido)-N-phenethylbenzamide (91)

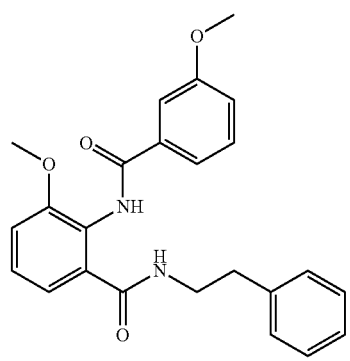

(91)

Compound 91 was obtained as a white powder in 42% yield. ¹H-NMR (CDCl₃): δ 2.87 (t, J=7.10 Hz, 2H), 3.62-3.66 (m, 2H), 3.89-3.89 (m, 6H), 6.38-6.39 (m, 1H), 7.02-7.07 (m, 2H), 7.10-7.12 (m, 1H), 7.20-7.26 (m, 4H), 7.28-7.31 (m, 2H), 7.40 (t, J=8.15 Hz, 1H), 7.51-7.53 (m, 2H), 8.81 (s, 1H) ppm. ¹³C-NMR (CDCl₃): δ 35.50 (CH, C-aliphatic), 41.04 (CH, C-aliphatic), 55.47 (CH3 C-aliphatic), 56.16 (CH3, C-aliphatic), 112.75 (CH, C-aromatic), 113.69 (CH, C-aromatic), 118.33 (CH, C-aromatic), 119.24 (CH, C-aromatic), 119.61 (CH, C-aromatic), 124.54 (C, C-aromatic), 126.50 (CH, C-aromatic), 126.99 (CH, C-aromatic), 128.61 (CH, C-aromatic), 128.74 (CH, C-aromatic), 129.70 (CH, C-aromatic), 132.77 (C, C-aromatic), 135.68 (C, C-aromatic), 138.78 (C, C-aromatic), 154.20 (C, C-aromatic), 159.89 (C, C-aromatic), 166.32 (C, C-aromatic), 168.31 (C, C-aromatic) ppm. MS(ESI)⁺: 405.2 [M+H]⁺. m.p.: 100-102° C.

Example 165

Synthesis of 3-methoxy-2-(4-methoxybenzamido)-N-phenethylbenzamide (92)

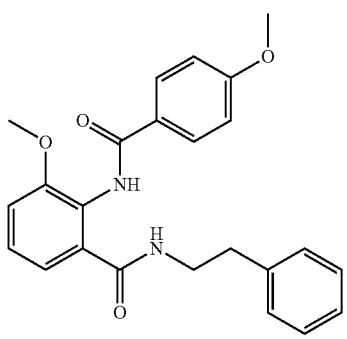

(92)

Compound 92 was obtained as a white powder in 74% yield. ¹H-NMR (CDCl₃): δ 2.80 (t, J=7.0 Hz, 2H), 3.61 (dd, J=7.1, 13.2 Hz, 2H), 3.88 (s, 3H), 3.89 (s, 3H), 6.56 (t, J=5.6 Hz, 1H), 6.97-7.01 (m, 3H), 7.04 (dd, J=2.9, 8.0 Hz, 2H), 7.19-7.34 (m, 5H), 7.91-7.99 (m, 2H), 8.82 (s, 1H) ppm. ¹³C-NMR (126 MHz, CDCl₃): δ 35.49 (CH₂, C-aromatic), 41.05 (CH₂, C-aromatic), 55.48 (CH₃, C-aromatic), 56.17 (CH₃, C-aromatic), 113.62 (CH, C-aromatic), 113.88 (CH, C-aromatic), 119.28 (CH, C-aromatic), 124.74 (CH, C-aromatic), 126.37 (C, C-aromatic), 126.50 (C, C-aromatic), 126.87 (CH, C-aromatic), 128.62 (CH, C-aromatic), 128.76 (CH, C-aromatic), 129.59 (CH, C-aromatic), 132.75 (C, C-aromatic), 138.81 (C, C-aromatic), 154.18 (C, C-aromatic), 162.61 (C, C-aromatic), 166.12 (C, C-aromatic), 168.42 (C, C-aromatic) ppm. MS(ESI)⁺: 405 [M+H]⁺. m.p.: (from ethanol/water) 136-138° C.

Example 166

Synthesis of 2-(2,4-dimethoxybenzamido)-3-methoxy-N-phenethylbenzamide (93)

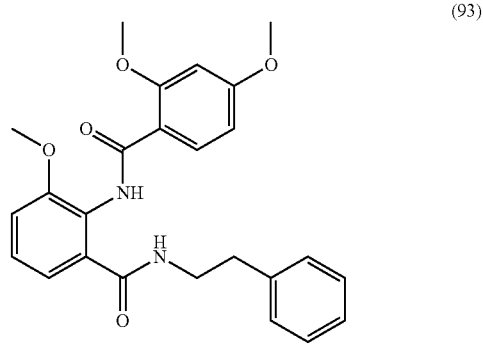 [SMILES: COc1ccc(C(=O)Nc2c(OC)cccc2C(=O)NCCc2ccccc2)c(OC)c1]

(93)

Compound 93 was obtained as a white powder in 68% yield. ¹H-NMR (CDCl₃): δ 2.81 (t, J=7.33 Hz, 2H), 3.59-3.63 (m, 2H), 3.87 (s, 3H), 3.900 (s, 3H), 4.02 (s, 3H), 6.56 (d, J=2.32 Hz, 1H), 6.64 (dd, J=2.33, 8.80 Hz, 1H), 6.75 (s, 1H), 7.01 (dd, J=1.28, 8.28 Hz, 1H), 7.14-7.20 (m, 4H), 7.24-7.27 (m, 3H), 8.228 (d, J=8.76 Hz, 1H), 9.608 (s, 1H) ppm. ¹³C-NMR (CDCl₃): δ 35.56 (CH₂, C-aliphatic), 41.03 (CH₂, C-aliphatic), 55.58 (CH₃, C-aliphatic), 56.13 (CH₃, C-aliphatic), 56.15 (CH₃, C-aliphatic), 98.75 (CH, C-aromatic), 105.55 (CH, C-aromatic), 112.71 (CH, C-aromatic), 114.27 (C, C-aromatic), 120.13 (CH, C-aromatic), 123.51 (C, C-aromatic), 126.25 (CH, C-aromatic), 127.25 (CH, C-aromatic), 128.45 (CH, C-aromatic), 128.70 (CH, C-aromatic), 128.82 (CH, C-aromatic), 134.38 (CH, C-aromatic), 135.64 (C, C-aromatic), 139.11 (C, C-aromatic), 154.04 (C, C-aromatic), 159.32 (C, C-aromatic), 163.96 (C, C-aromatic), 165.10 (C, C-aromatic), 168.33 (C, C-aromatic) ppm. MS(ESI)⁺: 435.2 [M+H]⁺. m.p.: 132-134° C.

Example 167

Synthesis of N-(2-(phenethylcarbamoyl)phenyl)nicotinamide (94)

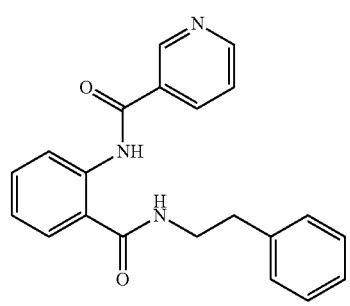

(94)

Compound 94 was obtained as a white solid in 99% yield. ¹H-NMR (500 MHz, CDCl₃): δ 12.40 (s, 1H, ArNHCO), 9.30 (s, 1H, CONHCH₂), 8.79-8.76 (m, 2H), 8.31 (dt, J=10.2, 1H), 7.52 (t, J=4.95, 1H), 7.48 (dd, J=9.92, 4.98, 1H), 7.40 (dd, J=9.96, 0.05, 1H), 7.34 (t, 9.90, 2H), 7.26 (q, J=10.02, 3H), 7.08 (t, J=9.97, 1H), 6.62 (s, 1H), 3.76 (q, J=10.0, 2H, NHCH₂CH₂), 2.97 (t, J=10, 2H, NHCH₂CH₂). ¹³C-NMR (126 MHz, CDCl₃): δ 169.12 (ArC=O), 163.64 (ArC=O), 152.30 (ArCH), 149.01 (ArCH), 139.60 (ArC), 138.50 (ArC), 135.03 (ArCH), 132.80 (ArCH), 130.51 (ArC), 128.81 (ArCH), 126.79 (ArCH), 126.51 (ArCH), 123.59 (ArCH), 123.29 (ArCH), 121.54 (ArCH), 120.32 (ArC), 41.17 (CH₂), 35.52 (CH₂). MS (ESI): 346.2 [M+1]. m.p. (from ethanol/water): 94° C.

Example 168

Synthesis of 3-(4-methoxybenzamido)-N-phenethylisonicotinamide (100)

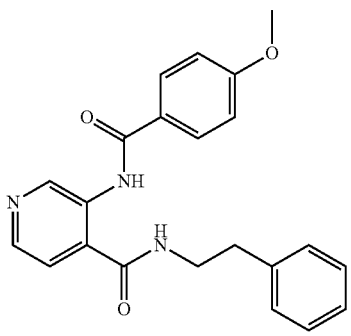

Compound 100 was obtained as a white powder in 34% yield. ¹H-NMR (CDCl3): δ 2.99 (t, J=6.8 Hz, 2H), 3.78 (dd, J=6.8, 12.8 Hz, 2H), 3.91 (s, 3H), 6.73 (s, 1H), 7.03-7.06 (m, 2H), 7.14 (d, J=5.0 Hz, 1H), 7.21-7.27 (m, 2H), 7.25-7.34 (m, 3H), 7.99-8.02 (m, 2H), 8.32 (d, J=5.1 Hz, 1H), 10.04 (s, 1H), 11.63 (s, 1H) ppm. ¹³C-NMR (126 MHz, CDCl3): δ35.34 (CH₂, C-aromatic), 41.21 (CH₂, C-aromatic), 55.51 (CH₃, C-aromatic), 114.11 (CH, C-aromatic), 119.23 (CH, C-aromatic), 126.04 (C, C-aromatic), 126.23 (C, C-aromatic), 126.94 (CH, C-aromatic), 128.49 (CH, C-aromatic), 128.78 (CH, C-aromatic), 128.89 (CH, C-aromatic), 129.50 (CH, C-aromatic), 135.37 (C, C-aromatic), 138.23 (C, C-aromatic), 143.80 (CH, C-aromatic), 144.46 (CH, C-aromatic), 162.85 (C, C-aromatic), 164.99 (C, C-aromatic), 167.35 (C, C-aromatic) ppm. MS(ESI)⁺: 376 [M+H]⁺. m.p.: (from ethanol/water) 120-122° C.

Example 169

Synthesis of N-(2-methoxy-6-(phenethylcarbamoyl)phenyl)-2-naphthamide (119)

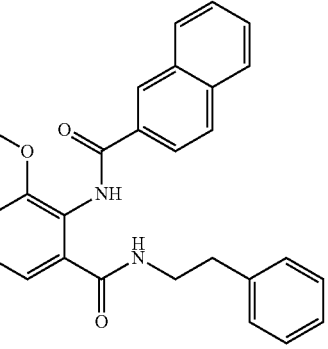

Compound 119 was obtained as a white powder in 50% yield. ¹H-NMR (CDCl₃): δ 2.86-2.89 (2H, m), 3.62-3.66 (2H, m), 3.899 (3H, s), 6.40-6.43 (1H, m, N), 7.04-7.06 (1H, m), 7.08-7.10 (1H, m), 7.195 (3H, t), 7.25-7.28 (3H, m), 7.57-7.63 (2H, m), 7.92-8.04 (4H, m), 8.511 (1H, d), 9.03 (1H, s, N) ppm. ¹³C-NMR (CDCl₃): δ 35.46 (CH₂, C-aliphatic), 41.005 (CH₂, C-aliphatic), 56.20 (—CH₃, C-aliphatic), 113.72 (CH, C-aromatic), 119.23 (CH, C-aromatic), 124.07 (CH, C-aromatic), 124.49 (C, C-aromatic), 126.51 (CH, C-aromatic), 126.78 (CH, C-aromatic), 127.07 (CH, C-aromatic), 127.79 (CH, C-aromatic), 127.89 (CH, C-aromatic), 128.42 (CH, C-aromatic), 128.59 (CH, C-aromatic) 128.62 (CH, C-aromatic), 128.76 (CH, C-aromatic), 129.21 (CH, C-aromatic), 131.34 (C, C-aromatic), 132.67 (C, C-aromatic), 135.07 (C, C-aromatic), 138.74 (C, C-aromatic), 154.18 (C, C-aromatic), 165.66 (C, C-aromatic), 166.57 (C, C-aromatic) ppm. MS(ESI)⁺: 425.2 [M+H]⁺. m.p.: 188-190° C.

Example 170

Synthesis of N-(5-methoxy-2-(phenethylcarbamoyl)phenyl)-2-naphthamide (122)

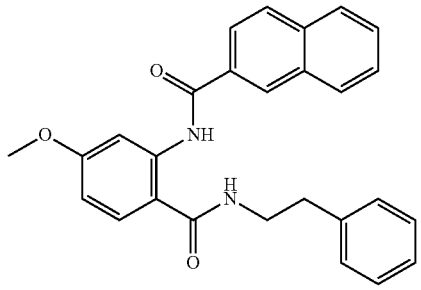

Compound 122 was obtained as a white powder in 29% yield. ¹H-NMR (CDCl₃): δ 2.99 (t, J=6.8 Hz, 2H), 3.78 (dd, J=1.7, 6.8 Hz, 2H), 6.18 (s, 1H), 3.95 (s, 3H), 6.63 (dd, J=2.6, 8.8 Hz, 1H), 7.25-7.32 (m, 7H), 7.34-7.41 (m, 2H), 7.56-7.66 (m, 2H), 7.93 (d, J=7.7 Hz, 1H), 8.01 (d, J=8.6 Hz, 1H), 8.07 (d, J=7.7 Hz, 1H), 8.14 (dd, J=1.8, 8.6 Hz, 1H), 8.58-8.70 (m, 2H), 12.77 (s, 1H) ppm. $^{13}$C-NMR (CDCl$_3$): δ 35.65 (CH$_2$, C-aliphatic), 40.99 (CH$_2$, C-aliphatic), 55.58 (CH$_3$, C-aliphatic), 105.22 (CH, C-aromatic), 110.10 (CH, C-aromatic), 112.34 (C, C-aromatic), 123.66 (CH, C-aromatic), 126.64 (CH, C-aromatic), 126.77 (CH, C-aromatic), 127.62 (CH, C-aromatic), 127.72 (CH, C-aromatic), 127.83 (CH, C-aromatic), 127.85 (CH, C-aromatic), 128.52 (CH, C-aromatic), 128.66 (CH, C-aromatic), 128.82 (CH, C-aromatic) 129.47 (CH, C-aromatic), 132.13 (C, C-aromatic), 132.82 (C, C-aromatic), 135.01 (C, C-aromatic), 138.66 (C, C-aromatic), 142.54 (C, C-aromatic), 163.02 (C, C-aromatic), 135.92 (C, C-aromatic), 169.05 (C, C-aromatic) ppm. MS(ESI)$^+$: 448.2 [M+H]$^+$. m.p. (from ethanol/water): 119-121° C.

General Procedure 7

The compounds of the application with the general formula shown below can be prepared according to the synthetic scheme shown in Scheme 7.

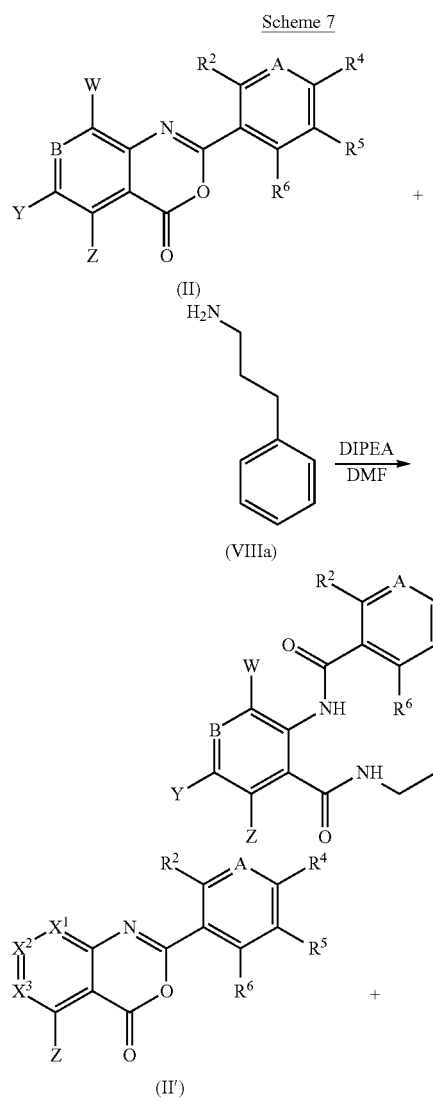

Scheme 7

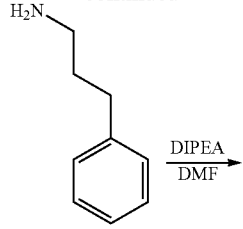

(VIIIa)

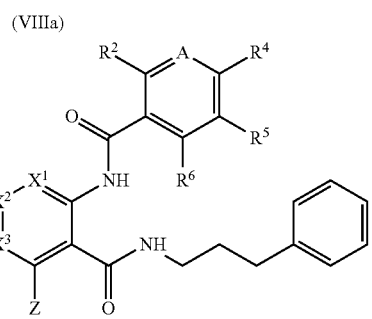

To a solution of compound (II) or (II') (1 equivalent) in N,N-dimethyl-formamide (DMF) is added 2 equivalents of N,N-diisopropylethylamine (DIPEA) and 2.2 equivalent of 3-phenyl-1-propylamine (VIIIa). The reaction mixture is stirred at about 15° C. to about 28° C. for about 6 hours to about 24 hours. The reaction mixture is diluted with water, washed with ethyl acetate, washed with brine, dried over Mg$_2$SO$_4$, filtered and evaporated to give a crude compound which is then purified by silica gel column using a mixture of Chloroform:Methanol (9:1) as eluent. The product is collected under reduced pressure to provide the compound with the general formula shown in Scheme 7.

Compounds 95-98, 120, 124, 125, 129, 136, and 140 were prepared according to General Procedure 7 substituting (II) or (II') with the appropriate substituted compound.

Example 171

Synthesis of 2-fluoro-N-(2-((3-phenylpropyl)carbamoyl)phenyl)benzamide (95)

(95)

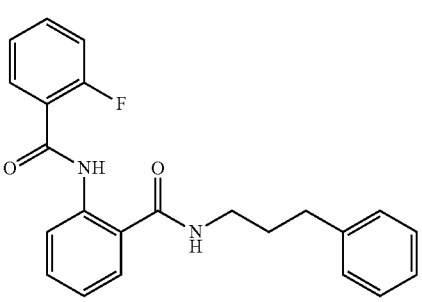

Compound 95 was obtained as a white powder in 63% yield. $^1$H-NMR (500 MHz, CDCl$_3$): 2.01 (2H, q, J=7.0 Hz), 2.77 (2H, q, J=7.20 Hz), 3.53 (2H, q, J=6.40 Hz), 6.14 (1H, s), 7.09-7.12 (1H, m), 7.30-7.33 (8H, m), 7.49-7.54 (2H, m), 8.06-8.08 (1H, m), 8.74 (1H, dd, J=1, 4.40 Hz), 11.7 (1H, d, J=6.11 Hz) ppm. $^{13}$C-NMR (126 MHz, CDCl$_3$): δ 33.19 (CH$_2$, C-aliphatic), 39.82 (CH$_2$, C-aliphatic), 41.54 (CH$_2$, C-aliphatic), 116.44 (CH, C-aromatic), 116.63 (CH, C-aromatic), 122.17 (C, C-aromatic), 122.49 (CH, C-aromatic), 123.30 (CH, C-aromatic), 124.61 (CH, C-aromatic), 125.83 (CH, C-aromatic), 126.17 (CH, C-aromatic), 126.39 (CH, C-aromatic), 128.37 (CH, C-aromatic), 128.64 (CH, C-aromatic), 131.54 (CH, C-aromatic), 132.27 (CH, C-aromatic), 133.30 (CH, C-aromatic), 138.87 (C, C-aromatic), 141.30 (C, C-aromatic), 141.90 (C, C-aromatic), 168.64 (C, C=O) ppm. $^{19}$F-NMR (CDCl$_3$): δ −112.40 ppm. MS (ESI)$^+$: 399.1 [M+Na]$^+$. m.p. (from DCM/n-hexane): 61-63° C.

Example 172

Synthesis of 2-(4-methoxybenzamido)-N-(3-phenylpropyl)benzamide (96)

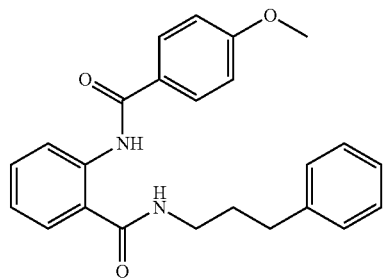

(96)

Compound 96 was obtained as a white powder in 62% yield. MS (ESI)$^+$: 411.2 [M+Na]$^+$. m.p. (from DCM/n-hexane): 93-94° C.

Example 173

Synthesis of N-(2-((3-phenylpropyl)carbamoyl)phenyl)-1-naphthamide (97)

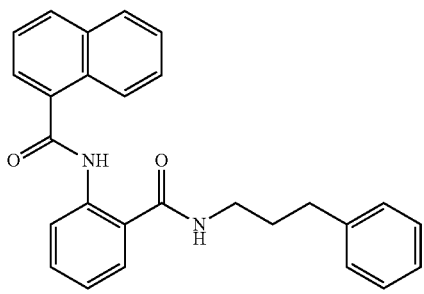

(97)

Compound 97 was obtained as a white powder in 59% yield. $^1$H-NMR (500 MHz, CDCl$_3$): δ 1.97 (2H, q, J=7.22 Hz), 2.74 (2H, t, J=7.40 Hz), 3.46 (2H, m), 6.16 (1H, s), 7.13 (1H, dd, J=1.16, 7.43 Hz), 7.19-7.25 (4H, m), 7.30 (2H, dd, J=4.4, 12.3 Hz), 7.57 (4H, m), 7.90 (2H, m), 7.99 (1H, d, J=8.29 Hz), 8.56 (1H, m), 8.91 (1H, dd, J=0.90, 8.45 Hz), 11.71 (1H, s) ppm. $^{13}$C-NMR (126 MHz, CDCl$_3$): δ 30.80 (CH$_2$, C-aliphatic), 33.54 (CH$_2$, C-aliphatic), 39.80 (CH$_2$, C-aliphatic), 120.96 (C, C-aliphatic), 121.71 (CH, C-aromatic), 123.04 (CH, C-aromatic), 124.99 (CH, C-aromatic), 125.56 (CH, C-aromatic), 125.63 (CH, C-aromatic), 126.18 (CH, C-aromatic), 126.38 (CH, C-aromatic), 126.43 (CH, C-aromatic), 127.13 (CH, C-aromatic), 128.36 (CH, C-aromatic), 128.65 (CH, C-aromatic), 130.46 (C, C-aromatic), 131.22 (CH, C-aromatic), 132.57 (CH, C-aromatic), 133.94 (C, C-aromatic), 134.40 (C, C-aromatic), 139.72 (C, C-aromatic), 141.22 (C, C-aromatic), 167.93 (C, C=O), 168.82 (C, C=O) ppm. MS (ESI)$^+$: 431.2 [M+Na]$^+$. m.p. (from Ethanol/Water): 98-100° C.

Example 174

Synthesis of N-(2-((3-phenylpropyl)carbamoyl)phenyl)-2-naphthamide (98)

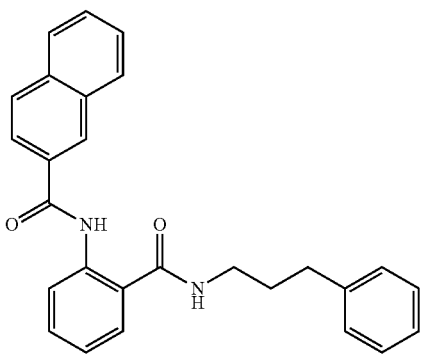

(98)

Compound 98 was obtained as a white powder in 57% yield. $^1$H-NMR (500 MHz, CDCl$_3$): δ 2.01-2.08 (2H, m), 2.67-2.71 (2H, m), 3.56 (2H, dd, J=6.9, 12.8 Hz), 6.32 (1H, s), 7.09 (1H, m), 7.22 (3H, t, J=6.5 Hz), 7.30-7.34 (3H, m), 7.53-7.64 (3H, m), 7.93 (1H, d, J=7.93 Hz), 7.99 (1H, d, J=8.6 Hz), 8.05 (1H, d, J=7.8 Hz), 8.11 (1H, dd, J=1.8, 8.6 Hz), 8.60 (1H, s), 8.78-8.89 (1H, m), 12.29 (1H, s) ppm. $^{13}$C-NMR (126 MHz, CDCl$_3$): δ 30.84 (CH$_2$, C-aliphatic), 33.60 (CH$_2$, C-aliphatic), 39.90 (CH$_2$, C-aliphatic), 120.67 (C, C-aromatic), 121.72 (CH, C-aromatic), 122.79 (CH, C-aromatic), 123.69 (CH, C-aromatic), 125.83 (CH, C-aromatic), 126.21 (CH, C-aromatic), 126.38 (CH, C-aromatic), 126.63 (CH, C-aromatic), 127.71 (CH, C-aromatic), 127.79 (CH, C-aromatic), 128.39 (CH, C-aromatic), 128.41 (CH, C-aromatic), 126.66 (CH, C-aromatic), 129.41 (CH, C-aromatic), 132.14 (C, C-aromatic), 132.63 (CH, C-aromatic), 132.81 (C, C-aromatic), 134.98 (C, C-aromatic), 139.96 (C, C-aromatic), 141.25 (C, C-aromatic), 165.68 (C, C=O), 169.16 (C, C=O) ppm. MS (ESI)$^+$: 431.2 [M+Na]$^+$. m.p.: 99-101° C.

Example 175

Synthesis of N-(2-methoxy-6-((3-phenylpropyl)carbamoyl)phenyl)-2-naphthamide (120)

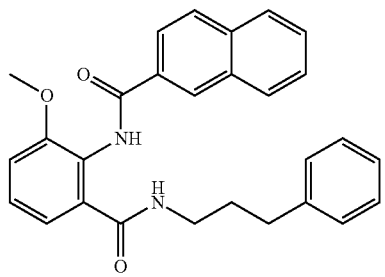

120

Compound 120 was obtained as a white powder in 45% yield. ¹H-NMR (500 MHz, CDCl$_3$): δ 1.81-1.93 (m, 2H), 2.60-2.66 (m, 2H), 3.40 (dd, J=6.8, 13.1 Hz, 2H), 3.90 (s, 3H), 6.55 (s, 1H), 7.07 (t, J=7.0 Hz, 4H), 7.16 (dq, J=7.0, 14.2 Hz, 2H), 7.26-7.32 (m, 2H), 7.60 (ddd, J=6.8, 13.7, 14.9 Hz, 2H), 7.89-7.99 (m, 3H), 8.00 (dd, J=11.9, 13.5 Hz, 1H), 8.52 (s, 1H), 8.91 (s, 1H) ppm. ¹³C-NMR (126 MHz, CDCl$_3$): δ 30.97 (CH$_2$, C-aliphatic), 32.26 (CH$_2$, C-aliphatic), 39.56 (CH$_2$, C-aliphatic), 56.18 (CH$_3$, C-aliphatic), 113.49 (CH, C-aromatic), 119.44 (CH, C-aromatic), 124.01 (CH, C-aromatic), 125.89 (CH, C-aromatic), 126.80 (CH, C-aromatic), 127.40 (CH, C-aromatic), 127.78 (CH, C-aromatic), 127.92 (CH, C-aromatic), 128.31 (CH, C-aromatic), 128.37 (CH, C-aromatic), 128.48 (CH, C-aromatic) 128.62 (CH, C-aromatic), 129.22 (CH, C-aromatic), 131.20 (C, C-aromatic), 132.67 (C, C-aromatic), 133.64 (C, C-aromatic), 135.07 (C, C-aromatic), 141.34 (C, C-aromatic), 154.32 (C, C-aromatic), 167.08 (C, C-aromatic), 168.34 (C, C-aromatic) ppm. MS (ESI)⁺: 439.2 [M+H]⁺. m.p. (from methanol/water): 152-154° C.

Example 176

Synthesis of 2-(2-fluorobenzamido)-3,4,5-trimethoxy-N-(3-phenylpropyl)benzamide (124)

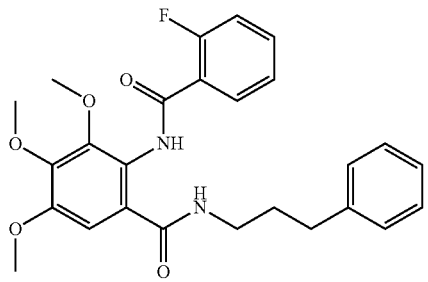

124

Compound 124 was obtained as a white powder in 78% yield. ¹H-NMR (500 MHz, CDCl$_3$): δ 1.73 (dt, J=7.5, 14.8 Hz, 2H), 2.60-2.44 (m, 2H), 3.31 (dd, J=7.0, 13.0 Hz, 2H), 3.82 (s, 3H), 3.83 (s, 3H), 3.84 (s, 3H), 6.56 (s, 1H), 6.84 (s, 1H), 7.03-6.97 (m, 2H), 7.05-7.13 (m, 2H), 7.11-7.18 (m, 3H), 7.39-7.48 (m, 1H), 8.02 (td, J=1.8, 7.8 Hz, 1H), 8.37 (d, J=13.7 Hz, 1H) ppm. ¹³C-NMR (126 MHz, CDCl$_3$): δ 31.06 (CH$_2$, C-aliphatic), 33.14 (CH$_2$, C-aliphatic), 39.54 (CH$_2$, C-aliphatic), 56.29 (CH$_3$, C-aliphatic), 61.03 (CH$_3$, C-aliphatic), 61.23 (CH$_3$, C-aliphatic), 106.76 (CH, C-aromatic), 116.27 (CH, C-aromatic), 116.47 (CH, C-aromatic), 120.59 (C, C-aromatic), 124.95 (CH, C-aromatic), 125.87 (CH, C-aromatic), 128.30 (CH, C-aromatic), 128.35 (CH, C-aromatic), 130.25 (C, C-aromatic), 132.24 (CH, C-aromatic), 134.03 (CH, C-aromatic) 134.10 (CH, C-aromatic), 141.37 (C, C-aromatic), 144.07 (C, C-aromatic), 149.13 (C, C-aromatic), 152.73 (C, C-aromatic), 159.87 (C, C-aromatic), 161.85 (C, C-aromatic), 166.92 (C, C-aromatic), 167.53 (C, C-aromatic) ppm. ¹⁹F-NMR (CDCl$_3$) δ –112.27 ppm. MS (ESI)⁺: 489.2 [M+H]⁺. m.p.: 145-147° C.

Example 177

Synthesis of N-(2-methoxy-6-((3-phenylpropyl)carbamoyl)phenyl)-1-naphthamide (125)

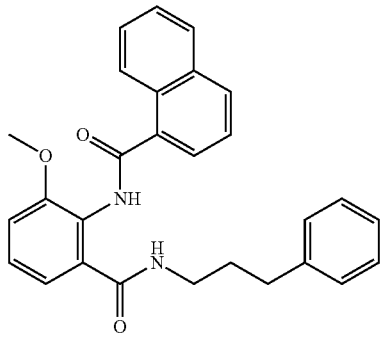

125

Compound 125 was obtained as a white powder in 69% yield. ¹H-NMR (500 MHz, CDCl$_3$): δ 1.82-2.00 (m, 2H), 2.59-2.81 (m, 2H), 3.47 (dd, J=7.0, 13.1 Hz, 2H), 3.93 (s, 3H), 6.48 (s, 1H), 7.04-7.12 (m, 2H), 7.17 (dd, J=7.1, 18.8 Hz, 3H), 7.24 (t, J=7.2 Hz, 2H), 7.31 (t, J=8.1 Hz, 1H), 7.47-7.53 (m, 1H), 7.55-7.59 (m, 2H), 7.87 (d, J=6.9 Hz, 1H), 7.90-7.96 (m, 1H), 7.99 (d, J=8.2 Hz, 1H), 8.21 (s, 1H), 8.55 (dd, J=3.6, 6.1 Hz, 1H) ppm. ¹³C-NMR (126 MHz, CDCl$_3$): δ 31.13 (CH$_2$, C-aliphatic), 33.35 (CH$_2$, C-aliphatic), 39.73 (CH$_2$, C-aliphatic), 56.13 (CH$_3$, C-aliphatic), 113.28 (CH, C-aromatic), 119.51 (CH, C-aromatic), 123.54 (C, C-aromatic), 124.83 (CH, C-aromatic), 125.64 (CH, C-aromatic), 125.91 (CH, C-aromatic), 125.97 (CH, C-aromatic), 126.44 (CH, C-aromatic), 127.25 (CH, C-aromatic), 127.52 (CH, C-aromatic), 128.31 (CH, C-aromatic) 128.40 (CH, C-aromatic), 128.42 (CH, C-aromatic), 130.45 (C, C-aromatic), 131.21 (CH, C-aromatic), 133.73 (C, C-aromatic), 133.79 (C, C-aromatic), 134.30 (C, C-aromatic), 141.42 (C, C-aromatic), 154.23 (C, C-aromatic), 168.34 (C, C-aromatic), 168.96 (C, C-aromatic) ppm. MS (ESI)⁺: 461.2 [M+Na]⁺. m.p. (from ethyl acetate/n-hexane): 150-152° C.

Example 178

Synthesis of N-(2-((3-phenylpropyl)carbamoyl)phenyl)nicotinamide (129)

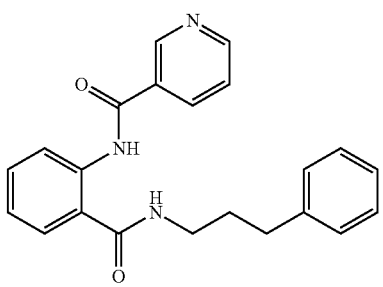
129

Compound 129 was obtained as a white powder in 65% yield. $^1$H-NMR (500 MHz, CDCl$_3$): δ 1.80-2.00 (m, 2H), 2.59-2.77 (m, 2H), 3.45 (dd, J=6.9, 12.7 Hz, 2H), 6.18 (s, 1H), 7.00 (tt, J=4.2, 8.4 Hz, 1H), 7.13-7.17 (m, 4H), 7.22-7.25 (m, 3H), 7.34-7.40 (m, 1H), 7.43-7.48 (m, 1H), 8.14-8.31 (m, 1H), 8.43-8.83 (m, 2H), 9.22 (s, 1H), 12.33 (s, 1H) ppm. $^{13}$C-NMR (126 MHz, CDCl$_3$): δ 30.77 (CH$_2$, C-aliphatic), 33.64 (CH$_2$, C-aliphatic), 39.95 (CH$_2$, C-aliphatic), 120.19 (CH, C-aromatic), 121.61 (CH, C-aromatic), 123.16 (C, C-aromatic), 123.48 (CH, C-aromatic), 126.34 (CH, C-aromatic), 128.40 (CH, C-aromatic), 128.73 (CH, C-aromatic), 130.11 (C,C-aromatic), 130.47 (CH, C-aromatic), 132.85 (CH, C-aromatic), 134.86 (CH, C-aromatic), 139.73 (C, C-aromatic), 141.21 (C, C-aromatic), 149.20 (CH, C-aromatic), 152.48 (CH, C-aromatic), 163.75 (C, C-aromatic), 169.01 (C, C-aromatic) ppm. m.p. (from ethanol/water): 74-76° C.

Example 179

Synthesis of N-(3-fluoro-2-((3-phenylpropyl)carbamoyl)phenyl)nicotinamide (136)

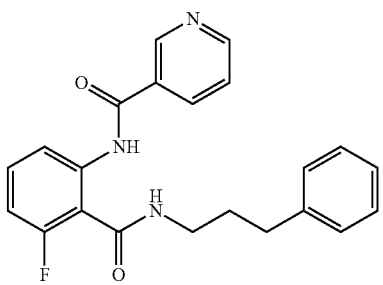
136

Compound 136 was obtained as a white powder in 67% yield. $^1$H-NMR (500 MHz, CDCl$_3$): δ 1.91-2.09 (m, 2H), 2.71-2.80 (m, 2H), 3.55 (td, J=1.4, 7.2 Hz, 2H), 6.93 (ddd, J=1.0, 8.3, 12.6 Hz, 2H), 7.20-7.27 (m, 1H), 7.27-7.35 (m, 4H), 7.43-7.53 (m, 2H), 8.27-8.39 (m, 1H), 8.71 (d, J=8.5 Hz, 1H), 8.82 (s, 1H), 9.33 (s, 1H), 12.93 (s, 1H) ppm. $^{13}$C-NMR (126 MHz, CDCl$_3$): δ 30.72 (CH$_2$, C-aliphatic), 33.21 (CH$_2$, C-aliphatic), 39.63 (CH$_2$, C-aliphatic), 110.60 (CH, C-aromatic), 110.80 (CH, C-aromatic), 117.58 (CH, C-aromatic), 123.51 (CH, C-aromatic), 126.17 (CH, C-aromatic), 128.36 (CH, C-aromatic), 128.56 (CH, C-aromatic), 133.21 (CH, C-aromatic), 133.31 (CH, C-aromatic), 134.93 (CH, C-aromatic), 140.97 (C, C-aromatic), 141.83 (C, C-aromatic), 149.24 (CH, C-aromatic), 152.61 (CH, C-aromatic), 159.96 (C, C-aromatic), 161.91 (C, C-aromatic), 163.90 (C, C-aromatic), 165.62 (C, C-aromatic), 210.12 (C, C-aromatic) ppm. $^{19}$F-NMR (CDCl$_3$): δ −110.84 ppm. m.p. (from ethanol/water): 79-81° C.

Example 180

Synthesis of 2-(4-methoxybenzamido)-N-(3-phenylpropyl)benzamide (140)

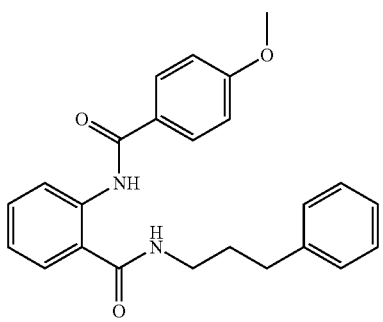
140

Compound 140 was obtained as a white powder in 52% yield. $^1$H-NMR (500 MHz, CDCl$_3$): 1.99-2.09 (m, 2H), 2.79 (t, J=7.4 Hz, 2H), 3.54 (dd, J=6.9, 12.8 Hz, 2H), 3.90 (s, 3H), 6.24 (s, 1H), 6.98-7.10 (m, 3H), 7.20-7.30 (m, 4H), 7.33-7.42 (m, 2H), 7.39-7.57 (m, 1H), 7.88-8.06 (m, 2H), 8.80 (d, J=7.7 Hz, 1H), 12.03 (s, 1H) ppm. $^{13}$C-NMR (126 MHz, CDCl$_3$): δ 30.83 (CH$_2$, C-aliphatic), 33.60 (CH$_2$, C-aliphatic), 39.88 (CH$_2$, C-aliphatic), 55.45 (CH$_3$, C-aliphatic), 113.98 (CH, C-aromatic), 120.37 (C, C-aromatic), 121.55 (CH, C-aromatic), 122.49 (CH, C-aromatic), 126.23 (CH, C-aromatic), 126.32 (C, C-aromatic), 127.23 (CH, C-aromatic), 128.40 (CH, C-aromatic), 128.70 (CH, C-aromatic), 129.32 (CH, C-aromatic), 132.64 (CH, C-aromatic), 140.14 (C, C-aromatic), 141.25 (C, C-aromatic), 162.50 (C, C-aromatic), 165.23 (C, C-aromatic), 169.21 (C, C-aromatic) ppm. m.p. (from ethyl acetate/n-hexane): 103-105° C.

General Procedure 8

The compounds of the application with the general formula shown below can be prepared according to the synthetic scheme shown in Scheme 8.

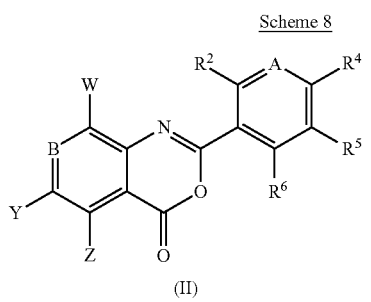

Scheme 8

(II)

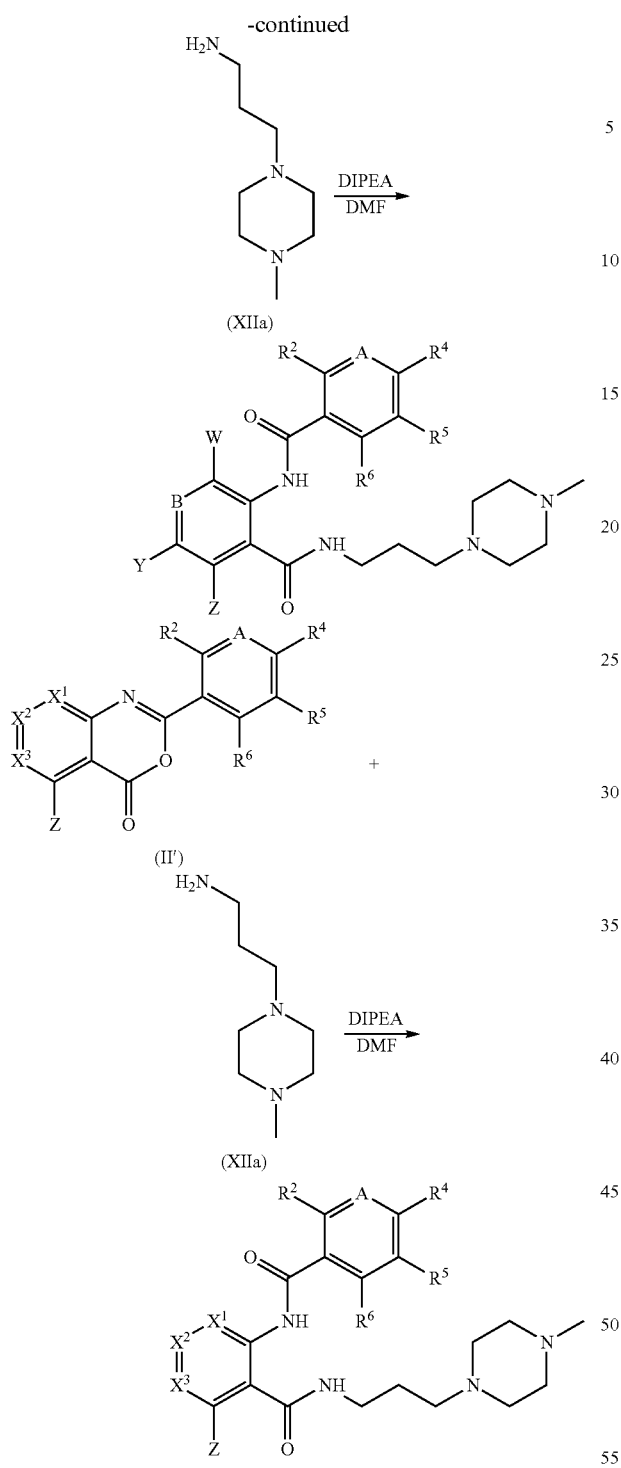

(XIIa)

(II')

(XIIa)

To a solution of compound (II) or (II') (1 equivalent) in N,N-dimethyl-formamide (DMF) is added 2 equivalents of N,N-diisopropylethylamine (DIPEA) and 2.2 equivalent of 2-(4-methylpiperazin-1-yl)ethanamine (XIIa). The reaction mixture is stirred at about 15° C. to about 28° C. for about 6 hours to about 24 hours. The reaction mixture is diluted with water, washed with ethyl acetate, washed with brine, dried over $Mg_2SO_4$, filtered and evaporated to give a crude compound which is then purified by silica gel column using a mixture of Chloroform:Methanol (9:1) as eluent. The product is collected under reduced pressure to provide the compound with the general formula shown in Scheme 8.

Compounds 66-69, 123, 135, and 137 were prepared according to General Procedure 8 substituting (II) or (II') with the appropriate substituted compound.

Example 181

Synthesis of 2-fluoro-N-(2-((3-(4-methylpiperazin-1-yl)propyl)carbamoyl) phenyl)benzamide (66)

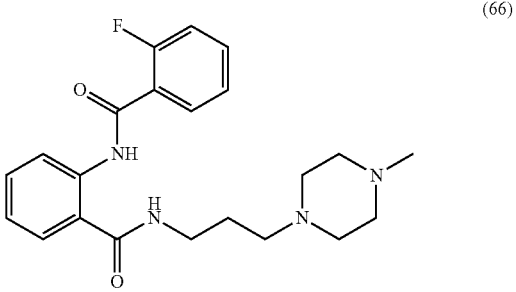 [SMILES: CN1CCN(CCCNC(=O)c2ccccc2NC(=O)c2ccccc2F)CC1]

(66)

Compound 66 was obtained as a white powder in 69% yield. $^1$H-NMR (500 MHz, CDCl$_3$): δ 1.68 (2H, m), 2.23 (3H, s), 2.31-2.49 (8H, m), 2.51 (2H, d, J=5.59 Hz), 3.43 (2H, m), 7.07 (1H, m), 7.51 (5H, m), 7.81 (2H, ddd, J=7.61, 3.12, 1.17 Hz), 7.88 (1H, d, J=0.31 Hz), 8.50 (1H, m), 8.84 (2H, m), 12.02 (1H, t, J=0.37 Hz) ppm. $^{13}$C-NMR (126 MHz, CDCl$_3$): δ 23.43 (CH$_2$, C-aliphatic), 41.37 (CH$_2$, C-aliphatic), 46.10 (CH$_3$, C-aliphatic), 53.38 (CH$_2$, C-aliphatic), 55.10 (CH$_2$, C-aliphatic), 58.75 (CH$_2$, C-aliphatic), 120.75 (C, C-aromatic), 121.51 (CH, C-aromatic), 122.71 (CH, C-aromatic), 125.02 (CH, C-aromatic), 125.58 (CH, C-aromatic), 125.72 (CH, C-aromatic), 126.32 (CH, C-aromatic), 127.05 (CH, C-aromatic), 127.39 (CH, C-aromatic), 128.31 (CH, C-aromatic), 130.53 (C, C-aromatic), 131.12 (CH, C-aromatic), 132.49 (CH, C-aromatic), 133.96 (C, C-aromatic), 134.54 (C, C-aromatic), 140.13 (C, C-aromatic), 167.94 (C, C=O), 168.82 (C, C=O) ppm. MS (ESI)$^+$: 431.2 [M+H]$^+$. m.p.: 98-100° C.

Example 182

Synthesis of 2-(4-methoxybenzamido)-N-(3-(4-methylpiperazin-1-yl)propyl)benzamide (67)

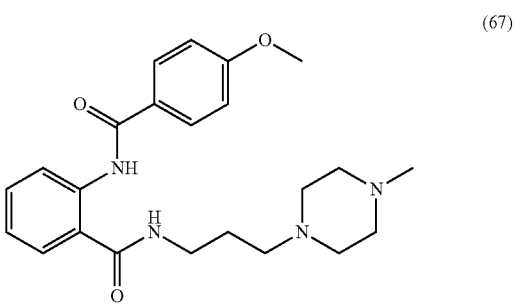 [SMILES: COc1ccc(C(=O)Nc2ccccc2C(=O)NCCCN2CCN(C)CC2)cc1]

(67)

Compound 67 was obtained as a white powder in 69% yield. m.p.: (from Acetone/n-hexane): 79-80° C.

Example 183

Synthesis of N-(2-((3-(4-methylpiperazin-1-yl)propyl)carbamoyl)phenyl)-1-naphthamide (68)

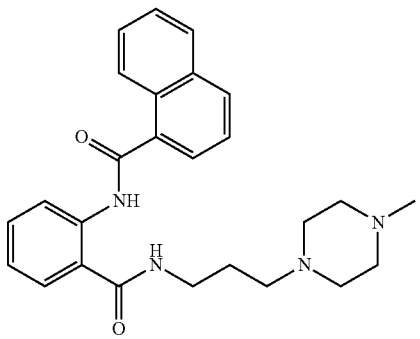

(68)

Compound 68 was obtained as a white powder in 69% yield. $^1$H-NMR (500 MHz, CDCl$_3$): δ 1.68 (2H, m), 2.23 (3H, s), 2.31-2.49 (8H, m), 2.51 (2H, d, J=5.59 Hz), 3.43 (2H, m), 7.07 (1H, m), 7.51 (5H, m), 7.81 (2H, ddd, J=7.61, 3.12, 1.17 Hz), 7.88 (1H, d, J=0.31 Hz), 8.50 (1H, m), 8.84 (2H, m), 12.02 (1H, t, J=0.37 Hz) ppm. $^{13}$C-NMR (126 MHz, CDCl$_3$): δ 23.43 (CH$_2$, C-aliphatic), 41.37 (CH$_2$, C-aliphatic), 46.10 (CH$_3$, C-aliphatic), 53.38 (CH$_2$, C-aliphatic), 55.10 (CH$_2$, C-aliphatic), 58.75 (CH$_2$, C-aliphatic), 120.75 (C, C-aromatic), 121.51 (CH, C-aromatic), 122.71 (CH, C-aromatic), 125.02 (CH, C-aromatic), 125.58 (CH, C-aromatic), 125.72 (CH, C-aromatic), 126.32 (CH, C-aromatic), 127.05 (CH, C-aromatic), 127.39 (CH, C-aromatic), 128.31 (CH, C-aromatic), 130.53 (C, C-aromatic), 131.12 (CH, C-aromatic), 132.49 (CH, C-aromatic), 133.96 (C, C-aromatic), 134.54 (C, C-aromatic), 140.13 (C, C-aromatic), 167.94 (C, C=O), 168.82 (C, C=O) ppm. MS (ESI)$^+$: 431.2 [M+H]$^+$. m.p.: 98-100° C.

Example 184

Synthesis of N-(2-((3-(4-methylpiperazin-1-yl)propyl)carbamoyl)phenyl)-2-naphthamide (69)

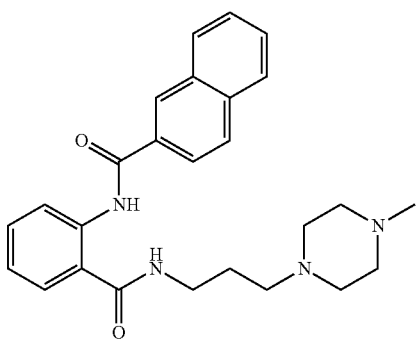

(69)

Compound 69 was obtained as a white powder in 99% yield. $^1$H-NMR (500 MHz, CDCl$_3$): δ 1.30 (3H, m), 1.84 (2H, m), 2.33 (3H, s), 2.38-2.57 (5H, m), 2.65 (2H, d, J=5.47 Hz), 3.36 (2H, m), 7.16 (1H, td, J=0.95, 7.59 Hz), 7.29 (1H, s), 7.60 (3H, dd, J=6.42 Hz), 7.69 (1H, dd, J=1.30, 7.87 Hz), 7.93 (1H, d, J=0.39 Hz), 7.99 (1H, s), 8.06 (1H, m), 8.14 (1H, d, J=6.74 Hz), 8.63 (1H, t, J=0.62 Hz), 8.95 (2H, m), 12.67 (1H, d, J=0.19 Hz) ppm. $^{13}$C-NMR (126 MHz, CDCl$_3$): δ 23.50 (CH$_2$, C-aliphatic), 41.32 (CH$_2$, C-aliphatic), 46.02 (CH$_3$, C-aliphatic), 53.29 (CH$_2$, C-aliphatic), 54.98 (CH$_2$, C-aliphatic), 58.62 (CH$_2$, C-aliphatic), 120.56 (C, C-aromatic), 121.58 (CH, C-aromatic), 122.55 (CH, C-aromatic), 123.75 (CH, C-aromatic), 126.58 (CH, C-aromatic), 127.37 (CH, C-aromatic), 127.70 (CH, C-aromatic), 127.73 (CH, C-aromatic), 128.44 (CH C-aromatic), 128.59 (CH, C-aromatic), 129.42 (CH, C-aromatic), 132.26 (C, C-aromatic), 132.55 (CH, C-aromatic), 132.82 (C, C-aromatic), 134.96 (C, C-aromatic), 140.26 (C, C-aromatic), 165.00 (C, C=O), 169.18 (C, C=O) ppm. MS (ESI)$^+$: 431.2 [M+H]$^+$. m.p.: 71-72° C.

Example 185

Synthesis of N-(2-methoxy-6-((3-(4-methylpiperazin-1-yl)propyl)carbamoyl)phenyl)-2-naphthamide (123)

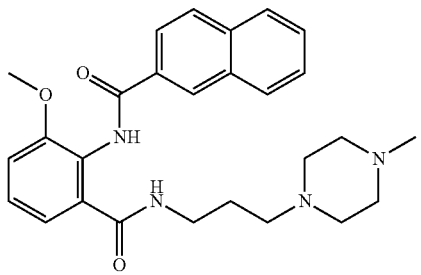

123

Compound 123 was obtained as a white powder in 29% yield. $^1$H-NMR (500 MHz, CDCl$_3$): δ 1.73 (dt, J=6.0, 12.0 Hz, 3H), 2.27 (s, 3H), 2.35 (bs, 6H), 2.51-2.56 (m, 3H), 3.47 (dd, J=5.8, 11.2 Hz, 2H), 3.95 (s, 3H), 7.15 (d, J=8.3 Hz, 1H), 7.20 (dd, J=1.2, 7.8 Hz, 1H), 7.24-7.34 (m, 1H), 7.54-7.63 (m, 2H), 7.91 (d, J=7.9 Hz, 1H), 7.95 (d, J=8.6 Hz, 1H), 8.00 (d, J=7.9 Hz, 1H), 8.06 (dd, J=1.8, 8.6 Hz, 1H), 8.26 (s, 1H), 8.55 (s, 1H), 9.77 (s, 1H) ppm. $^{13}$C-NMR (126 MHz, CDCl$_3$): δ 24.31 (CH$_2$, C-aliphatic), 40.44 (CH$_2$, C-aliphatic), 45.93 (CH$_3$, C-aliphatic), 53.07 (CH$_2$, C-aliphatic), 54.94 (CH$_2$, C-aliphatic), 56.28 (CH$_3$, C-aliphatic), 57.79 (CH$_2$, C-aliphatic), 114.25 (CH, C-aromatic), 119.38 (CH, C-aromatic), 124.25 (CH, C-aromatic), 125.99 (C, C-aromatic), 126.29 (CH, C-aromatic), 126.65 (CH, C-aromatic), 127.74 (CH, C-aromatic), 128.47 (CH, C-aromatic), 128.47 (CH, C-aromatic), 128.50 (CH, C-aromatic), 129.23 (CH, C-aromatic), 131.21 (C, C-aromatic), 131.68 (C, C-aromatic), 132.73 (C, C-aromatic), 135.01 (C, C-aromatic), 154.46 (C, C-aromatic), 165.94 (C, C-aromatic), 168.42 (C, C-aromatic) ppm. MS (ESI)$^+$: 448.2 [M+H]$^+$. m.p. (from methanol/water): 119-121° C.

Example 186

Synthesis of N-(3-fluoro-2-((3-(4-methylpiperazin-1-yl)propyl)carbamoyl)phenyl)nicotinamide (135)

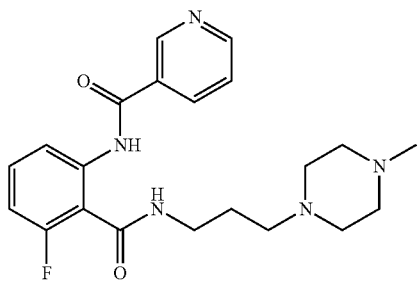

135

Compound 135 was obtained as a white powder in 24% yield. $^1$H-NMR (500 MHz, CDCl$_3$): δ 1.60-1.68 (m, 2H), 1.72-1.83 (m, 2H), 2.19 (s, 5H), 2.32 (s, 3H), 2.43-2.55 (m, 3H), 3.53 (dd, J=5.0, 11.0 Hz, 2H), 6.83 (ddd, J=1.0, 8.3, 11.6 Hz, 1H), 7.32-7.42 (m, 2H), 8.23 (ddd, J=1.7, 2.3, 8.0 Hz, 1H), 8.43 (s, 1H), 8.52 (t, J=23.0 Hz, 1H), 8.71 (dd, J=1.6, 4.8 Hz, 1H), 9.22 (d, J=1.7 Hz, 1H), 12.54 (s, 1H) ppm. $^{13}$C-NMR (126 MHz, CDCl$_3$): δ 24.28 (CH$_2$, C-aliphatic), 40.47 (CH$_2$, C-aliphatic), 46.01 (CH$_3$, C-aliphatic), 53.27 (CH$_2$, C-aliphatic), 54.87 (CH$_2$, C-aliphatic), 57.68 (CH$_2$, C-aliphatic), 110.75 (CH, C-aromatic), 117.42 (CH, C-aromatic), 123.48 (CH, C-aromatic), 130.29 (C, C-aromatic), 132.86 (CH, C-aromatic), 134.89 (CH, C-aromatic), 141.22 (C, C-aromatic), 149.26 (CH, C-aromatic), 152.60 (CH, C-aromatic), 159.40 (C, C-aromatic), 161.36 (C, C-aromatic), 163.80 (C, C-aromatic), 164.91 (C, C-aromatic) ppm. $^{19}$F-NMR (CDCl$_3$): δ −110.05 ppm. m.p.: 72-74° C.

Example 187

Synthesis of 3,4,5-trimethoxy-2-(4-methoxybenzamido)-N-(3-(4-methylpiperazin-1-yl)propyl)benzamide (137)

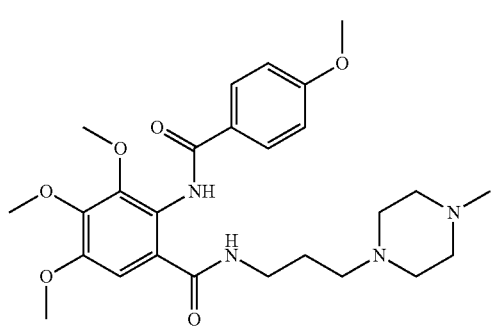

137

Compound 137 was obtained as a white powder in 30% yield. $^1$H-NMR (500 MHz, CDCl$_3$): δ 1.48-1.73 (m, 2H), 2.18 (s, 4H), 2.35 (t, J=6.5 Hz, 9H), 3.34 (dd, J=6.2, 11.9 Hz, 2H), 3.80 (s, 3H), 3.82 (s, 3H), 3.85 (s, 3H), 3.85 (s, 3H), 6.79 (s, 1H), 6.85-6.96 (m, 2H), 7.54 (s, 1H), 7.83-7.92 (m, 2H), 8.63 (s, 1H) ppm. $^{13}$C-NMR (126 MHz, CDCl$_3$): δ 25.22 (CH$_2$, C-aliphatic), 39.24 (CH$_2$, C-aliphatic), 45.70 (CH$_3$, C-aliphatic), 52.71 (CH$_2$, C-aliphatic), 54.65 (CH$_2$, C-aliphatic), 55.49 (CH$_3$, C-aliphatic), 56.62 (CH$_2$, C-aliphatic), 56.70 (CH$_3$, C-aliphatic), 61.01 (CH$_3$, C-aliphatic), 61.03 (CH$_3$, C-aliphatic), 106.79 (CH, C-aromatic), 113.95 (CH, C-aromatic), 123.01 (C, C-aromatic), 126.35 (C, C-aromatic), 127.81 (C, C-aromatic), 129.51 (CH, C-aromatic), 144.73 (C, C-aromatic), 149.41 (C, C-aromatic), 151.82 (C, C-aromatic), 162.68 (C, C-aromatic), 166.67 (C, C-aromatic), 168.05 (C, C-aromatic) ppm. m.p.: 94-96° C.

Example 188

Synthesis of 2-fluoro-4-methoxybenzoylchloride (207)

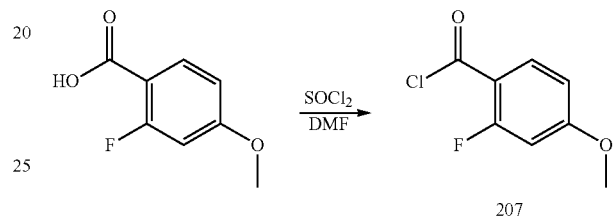

207

To a stirred solution of 2-fluoro-4-methoxybenzoic acid (0.0059 moles, 1.00 g) in SOCl$_2$ (0.3835 moles, 30 mL, 1.635 g/mL) was added 4 drops of N, N-Dimethylformamide (DMF). The reaction mixture was heated under reflux for 8 hours. The excess reagent was then removed under reduced pressure to give the crude compound 207 in 98.2% yield.

Example 189

Synthesis of 2-(4-methyl-piperazin-1-yl)ethanamide. (208)

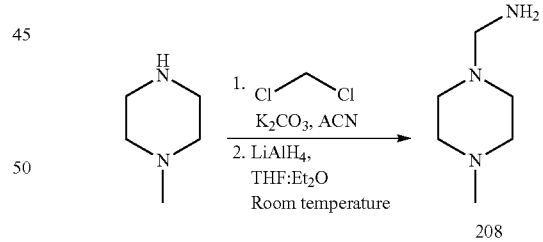

208

Step 1:
A solution of N-methyl-piperazine (0.018 moles, 1.99 mL), 1.4 mL of chloroacetonitrile (0.022 moles, 1.193 g/mL) and potassium carbonate (K$_2$CO$_3$) (0.086 moles, 12 g) in acetonitrile (CAN) (18 mL) is stirred for 96 hours at room temperature. The reaction was filtered under a vacuum and the filtrate was evaporated. Desired product was obtained in 5.18% yield.

Step 2:
4 g of the product obtained in step 1 (0.028 moles) was dissolved in a 1:1 mixture of Tetrahydrofuran:Diethylether and was added drop wise to a suspension of lithium aluminium hydride (3.2 g) in diethylether (20 mL) at 0° C.

The reaction was stirred at room temperature for 24 hours, cooled to 0° C. and 10 mL of NaOH 6N was added and mixture stirred for 20 minutes. The solid was removed by filtration and filtrate was evaporated to give the title compound (208) in 4.74% yield.

General Procedure 9

The compounds of general formula (XIV) can be prepared according to the synthetic scheme shown in Scheme 9.

Scheme 9

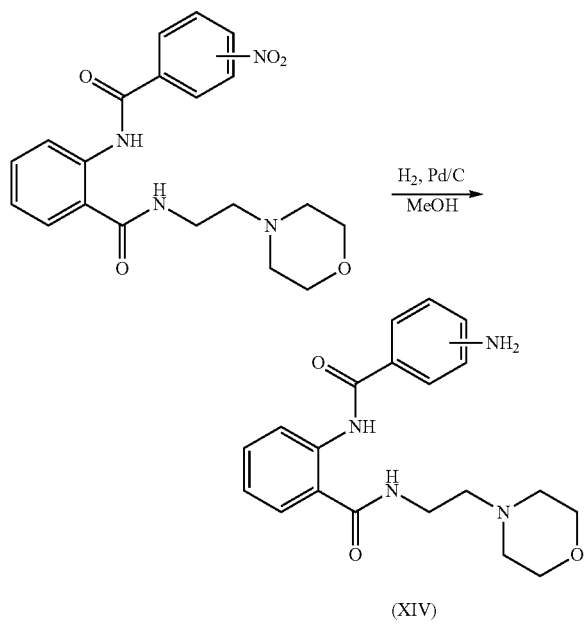

(XIV)

A solution of methanol (2 mL), the starting nitro-compound 0.100 g; 0.00026 mol) and Pd—C (0.010 g) was stirred under $H_2$ flow for 24 hours at room temperature. The solution was filtered on a celite bed and the filtrate was evaporated to give a solid which as purified by silica gel column chromatography using Chloroform:Ethanol (9:1) as eluent. The final compound was re-crystallized in ethanol and water to furnish the final compound (XIV).

General Procedure 10: The Preparation of Salts of Compound 12

Example 190

Synthesis of 4-(2-(2-(2-fluoro-4-methoxybenzamido)benzamido)ethyl)morpholin-4-ium chloride Procedure:
A solution of 12 (1 equivalent) is diluted in dichloromethane and HCl 12 M (1 equivalent) is added. The solvent is removed and the crude product is collected under reduced pressure The product was obtained as colorless oil in 90% yield. $^1$H-NMR (500 MHz, CDCl$_3$): δ 2.85 (t, J=18.7 Hz, 2H), 3.23 (s, 2H), 3.60 (t, J=17.2 Hz, 2H), 3.79 (s, 3H), 3.99-3.83 (m, 4H), 4.17 (t, J=12.1 Hz, 2H), 6.60 (dd, J=2.4, 13.3 Hz, 1H), 6.73 (dd, J=2.4, 8.8 Hz, 1H), 7.04 (dd, J=14.9, 22.0 Hz, 1H), 7.38 (dd, J=8.9, 16.3 Hz, 1H), 7.96 (t, J=8.9 Hz, 1H), 8.34 (t, J=7.7 Hz, 1H), 8.60 (s, 1H), 8.98 (s, 1H), 11.75 (d, J=8.1 Hz, 1H), 12.20 (s, 1H) ppm. $^{13}$C-NMR (126 MHz, CDCl$_3$): δ 33.99 (CH$_2$, C-aliphatic), 53.18 (CH$_2$, C-aliphatic), 55.83 (CH$_3$, C-aliphatic), 58.90 (CH$_2$, C-aliphatic), 63.54 (CH$_2$, C-aliphatic), 110.56 (CH, C-aromatic), 114.79 (CH, C-aromatic), 120.10 (CH, C-aromatic), 122.14 (C, C-aromatic), 123.53 (CH, C-aromatic), 126.87 (CH, C-aromatic), 132.82 (CH, C-aromatic), 133.09 (CH, C-aromatic), 139.63 (C, C-aromatic), 161.93 (C, C-aromatic), 162.41 (C, C-aromatic), 163.55 (C, C-aromatic), 163.72 (C, C-aromatic), 169.46 (C, C-aromatic) ppm. $^{19}$F-NMR (CDCl3): δ −109.20 ppm. MS (ESI)$^+$: 402.2 [M+H]$^+$.

Example 191

Synthesis of 4-(2-(2-(2-fluoro-4-methoxybenzamido)benzamido)ethyl)morpholin-4-ium methanesulfonate Procedure:
A solution of 12 (1 equivalent) is diluted in acetone and methane sulfonic acid (1 equivalent) is added. The solvent is removed and the crude product is collected under reduced pressure. The product was obtained as colorless oil in 90% yield. $^1$H-NMR (500 MHz, CDCl$_3$): δ 2.37 (s, 3H), 2.51 (dd, J=3.6, 1.8 Hz, 6H), 3.88 (s, 3H), 3.95 (s, 6H), 6.77-7.07 (m, 2H), 7.14-7.25 (m, 1H), 7.61-7.68 (m, 1H), 7.91 (t, J=8.9 Hz, 2H), 8.00-8.06 (m, 1H), 8.72 (d, J=7.8 Hz, 1H), 11.89 (d, J=6.6 Hz, 1H), 13.06-13.32 (bs, 1H) ppm. $^{13}$C-NMR (126 MHz, CDCl$_3$): δ 39.50 (CH$_2$, C-aliphatic), 40.00 (CH$_2$, C-aliphatic), 52.22 (CH$_2$, C-aliphatic), 56.81 (CH$_3$, C-aliphatic), 58.65 (CH$_3$, C-aromatic), 110.52 (CH, C-aromatic), 111.90 (CH, C-aromatic), 117.24 (CH, C-aromatic), 120.98 (C, C-aromatic), 123.54 (CH, C-aromatic), 131.69 (CH, C-aromatic), 132.76 (CH, C-aromatic), 134.60 (CH, C-aromatic), 141.19 (C, C-aromatic), 160.75 (C, C-aromatic), 161.86 (C, C-aromatic), 162.16 (C, C-aromatic), 163.82 (C, C-aromatic), 169.25 (C, C-aromatic) ppm. $^{19}$F-NMR (CDCl3): δ −109.78 ppm.

Example 192

Synthesis of 4-(2-(2-(2-fluoro-4-methoxybenzamido)benzamido)ethyl)morpholin-4-ium 2-carboxyacetate Procedure:
A solution of 12 (1 equivalent) is diluted in dichloromethane and malonic acid (1 equivalent) is added. The solvent is removed and the crude product is collected under reduced pressure. The product was obtained as yellow oil in 90% yield. $^1$H-NMR (500 MHz, DMSO-d6): δ 2.37 (s, 3H), 2.59-2.72 (m, 4H), 3.01-3.16 (m, 3H), 3.56-3.65 (m, 4H), 3.80-3.93 (m, 3H), 6.96 (dd, J=2.4, 8.8 Hz, 1H), 7.02 (dd, J=13.5, 2.4 Hz, 1H), 7.18-7.26 (m, 1H), 7.52-7.59 (m, 1H), 7.75 (dt, J=5.8, 11.7 Hz, 1H), 7.87 (t, J=8.9 Hz, 1H), 8.56 (d, J=7.7 Hz, 1H), 8.78 (t, J=5.1 Hz, 1H), 11.86 (d, J=6.4 Hz, 1H) ppm. $^{13}$C-NMR (126 MHz, DMSO-d6): δ 39.83 (CH$_2$, C-aliphatic), 41.72 (CH$_2$, C-aliphatic), 53.21 (CH$_2$, C-aliphatic), 56.58 (CH$_3$, C-aliphatic), 57.09 (CH$_2$, C-aliphatic), 65.93 (CH$_2$, C-aliphatic), 102.35 (CH, C-aromatic), 111.79 (CH, C-aromatic), 114.97 (C, C-aromatic), 115.07 (CH, C-aromatic), 121.63 (C, C-aromatic), 122.13 (CH, C-aromatic), 123.54 (C, C-aromatic), 128.54 (CH, C-aromatic), 132.35 (CH, C-aromatic), 132.60 (CH, C-aromatic), 139.04 (C, C-aromatic), 160.22 (C, C-aromatic), 161.59 (C, C-aromatic), 162.20 (C, C-aromatic), 168.77 (C, C-aromatic), 169.59 (C, C-aromatic) ppm. $^{19}$F-NMR (CDCl3): δ −109.78 ppm.

Additional Compounds

Example 193

Synthesis of 2-(2-fluoro-N-methylbenzamido)benzoic acid (104)

Procedure:
To a solution of N-methyl anthranilic acid (0.755 g; 0.0050 mol) in 30 mL of pyridine, 2-fluorobenzoyl chloride (0.011 mol; 1.30 mL; 1.342 g/mL) is added dropwise over a period of 30 minutes under an argon atmosphere at 0° C. The reaction mixture are stirred for 10 hours at room temperature and then poured into ice water (200 mL) and acidified with HCl 37% (25 mL). The precipitate was filtered off and the filtrate was extracted with diethyl ether. The combined organic phases are dried with $Na_2SO_4$ and evaporated to dryness to afford viscous product.

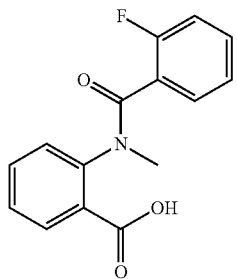

104

Compound 104 was obtained as a white powder in 17% yield. $^1$H-NMR (500 MHz, $CDCl_3$): δ 3.51 (s, 3H), 6.20 (s, 1H), 6.81 (t, J=9.0 Hz, 1H), 6.96 (t, J=7.2 Hz, 1H), 7.17 (td, J=1.7, 7.3 Hz, 1H), 7.29-7.33 (m, 2H), 7.37 (d, J=8.0 Hz, 1H), 7.50 (td, J=1.5, 7.8 Hz, 1H), 7.92 (dd, J=1.4, 7.8 Hz, 1H) ppm. $^{13}$C-NMR (126 MHz, $CDCl_3$): δ 36.91 ($CH_3$, C-aliphatic), 115.24 (CH, C-aromatic), 123.86 (CH, C-aromatic), 128.05 (CH, C-aromatic), 128.67 (CH, C-aromatic), 128.88 (C, C-aromatic), 129.94 (CH, C-aromatic), 131.00 (CH, C-aromatic), 131.14 (CH, C-aromatic), 132.88 (CH, C-aromatic), 142.58 (C, C-aromatic), 156.00 (C, C-aromatic), 158.16 (C, C-aromatic), 164.79 (C, C-aromatic), 166.27 (C, C-aromatic) ppm. $^{19}$F-NMR (CDCl3): δ −112.50 ppm. m.p.: (from diethyl ether/n-hexane) 128-130° C.

Example 194

2-(2-fluorobenzamido)nicotinic acid (105)

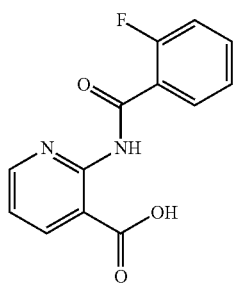

105

Compound 105 was obtained as a white powder in 17% yield. $^1$H-NMR (500 MHz, $CDCl_3$): δ 7.05 (dd, J=5.0, 7.3 Hz, 1H), 7.28-7.36 (m, 2H), 7.57 (ddd, J=1.7, 5.2, 15.1 Hz, 1H), 7.73 (td, J=1.8, 7.6 Hz, 1H), 8.18-8.31 (m, 2H), 14.85 (s, 1H) ppm. $^{13}$C-NMR (126 MHz, $CDCl_3$): δ 118.31 (CH, C-aromatic), 124.54 (CH, C-aromatic), 129.78 (CH, C-aromatic), 132.53 (CH, C-aromatic), 139.30 (CH, C-aromatic), 140.03 (CH, C-aromatic), 145.46 (C, C-aromatic), 148.13 (CH, C-aromatic), 152.26 (C, C-aromatic), 165.02 (C, C-aromatic) ppm. $^{19}$F-NMR (CDCl3): δ −109.57 ppm. MS (ESI)$^+$: 261.1 [M+H]$^+$. m.p.: >90° C.

Biological Assays

Example 195: Cell Toxicity Titer Blue Assay

A cell toxicity titer blue assay is run to determine the cell toxicity of the compounds of Formula (I) or Formula (Ia).

Compounds are dissolved in DMSO in order to store them in a 10 mM concentration. In order to use them in the cell toxicity blue assay, two different concentrations of each compound are prepared: 10 nM and 100 nM. Hence, to prepare the 10 nM concentrations 1 μl of the stored solution of each compound is diluted in 999 μl of culture media. To prepare the 100 nM concentration, 10 μl of the previous concentration is diluted in 990 μl of media.

Cells are kept in a 96 well plate, at low confluency, in 100 μl of complete growth media containing the compounds. The cells are in triplicates: each compound at each concentration is put in three wells, hence data are obtained in triplicate for each compound and for each concentration. They had been incubated for 24 hours at 37° C. and 5% $CO_2$.

In each well containing 100 μl of media with the specific compound, 20 μl Cell Titre Blue reagent is added. The 96 well plate is incubated for one hour at 37° C. and 5% $CO_2$.

Fluorescence is measured using Fluorostar Optima plate reader and using an excitation/emission of 560/590 nm. The results are analyzed using Microsoft Excel.

Results are shown in FIGS. 1*a*-1*h*. Ref A refers to Reference Compound A.

Example 196: Scratch Assay

A Scratch assay is run to determine the migration of cells in the presence of a compound of Formula (I) or Formula (Ia).

It is necessary to prepare the solution of the compounds at 1 micromolar. In six well plates, the complete growth media of the seeded cells (density 11*10E$^{-6}$ in 20 mL) is removed and replaced by 3 mL of a fresh media containing compounds of Formula (I) or Formula (Ia) (20 mL and 2 μl of compounds). Media is used as a negative compound.

After a 24 h incubation period at 5% $CO_2$ and 37° C., the media is removed and a scratch is performed in each well. 1 mL of fresh complete growth media is used to wash the wells. After its removal, 3 mL of a solution containing a compound of Formula (I) or Formula (Ia) is added in each well in triplicate. Pictures of these wells are then taken. After 24 h, pictures of the wells are again taken. The comparison between the two images provides a measure of the migration of the cells.

Figure 2:
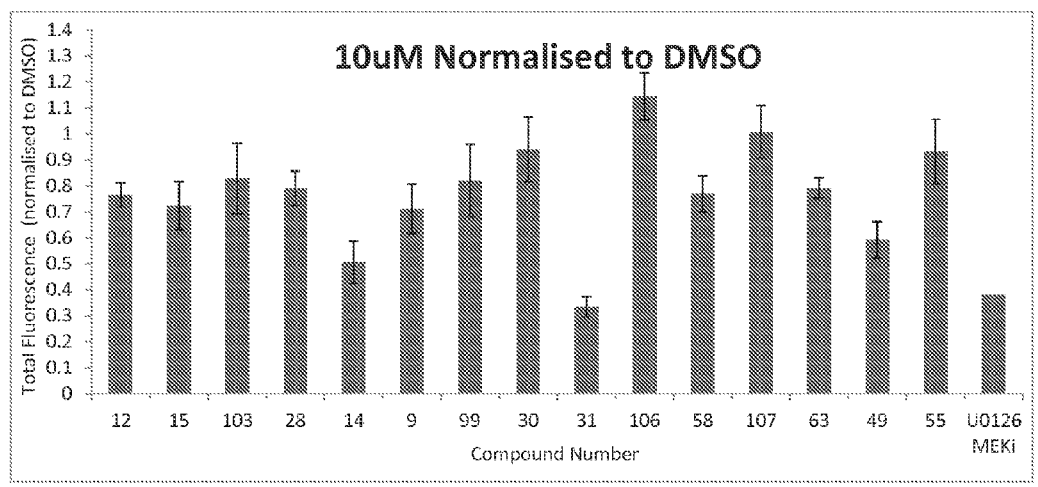
FIG. 2 is a graph showing the effect of a number of compounds of the application on cell migration of human breast cancer cell line MDA-MB-436 during a scratch assay.

Example 196a: Anti-Migration Activity of Compounds Tested During the Scratch Assay (FIG. 2)

The cell migration assay used was the transwell (Boyden chamber) assay of cell migration in human breast cancer cell line MDA-MB-436. After a scratch was performed in each well the cells were incubated with a 10 micromolar solution of compound for 24 hours prior to passage into transwell chambers where they were maintained in the presence of compound for a further 24 hours before assessment of migration (measured by total fluorescence on opposing surface of transwell membrane following staining). Reduced fluorescence directly correlates with number of cells migrated. The data show that 7 of the compounds that were tested significantly reduce cell migration compared to DMSO and that 2 of the compounds tested reduce migration significantly better than compound 12. Additionally, compound 31 was more effective at reducing cell migration than the known potent cell migration inhibitor MEKi, used here as a positive control. These 'hits' were confirmed in a second breast cancer cell line (MDA-MB-231).

Example 197: Determination of NF-kB Activity in Cells

For NF-κB luciferase assays, cells were seeded into clear bottom black 96-well plates (Corning Inc., Lowell, US) in antibiotic free culture media in appropriate density. After 24 hrs, cells were transfected with 10 ng of 3×κB luciferase plasmid and 10 ng of pcDNA3.1-Lacl plasmid per well. Empty pcDNA3.1 plasmid was also included to normalize the total weight of DNA transfected to 100 ng. For positive and negative controls respectively, 10 ng of pGL3control or pGL3basic were transfected in place of 3×KB luciferase plasmid. Transfection was carried out using Lipofectamine LTX reagents (Invitrogen, Paisley, UK).

After 48 hrs post-transfection with luciferase reporter plasmid, the media was aspirated and cells were lyzed using 50 μl/well of Glo-lysis buffer (Promega, Southampton, UK). The plate was left on a rocker for 20 min to facilitate complete cell lysis. Then, 20 μl of lysate from each well was removed and transferred into a new clear bottom black well plate for measuring LacZ activity as a transfection efficiency control and followed by addition of 20 ul/well of Beta-Glo substrate (Promega, Southampton, UK) and cultivation at room temperature for at least 20 min. Subsequently, 30 μl/well of Bright-Glo luciferase substrate (Promega, Southampton, UK) was added to the original plate and assess immediately for luminescence activity. The luminescence produced from either reaction was read using a Flurostar Optima plate reader (BMG tabtech, Bucks, UK). The resulting luciferase activity was then normalized against lacZ activity obtained from Beta-glo measurement and is displayed as relative light units (R.t.U).

Example 197a: NF-kB Activity of Compound 12

The effect of Compound 12 and reference compound A (depicted below) on NF-κB activity was determined by NF-KB luciferase assay in MDA-MB-231 cells. This assay was performed in MDA-MB-231 human breast cancer cells stably expressing an NF-kB promoter Luciferase reporter.

MDA-MB-231 cells were stored in a small flask with complete growth media (5 mL) in incubator at 37° C. and 5% $CO_2$. Every 72-96 hours, the cells are split. Trypsin (1 mL) is added and the flask is stirred and stored in the incubator for 5 minutes. Once the cells are floating, complete growth media is added and all the solution is moved in a 25 mL falcon. 500 μl of this solution is kept in the flask and 6 mL of complete growth media is added in order to keep the cell growing. The flask is incubated at and 5% $CO_2$ and 37° C.

Figure 3:
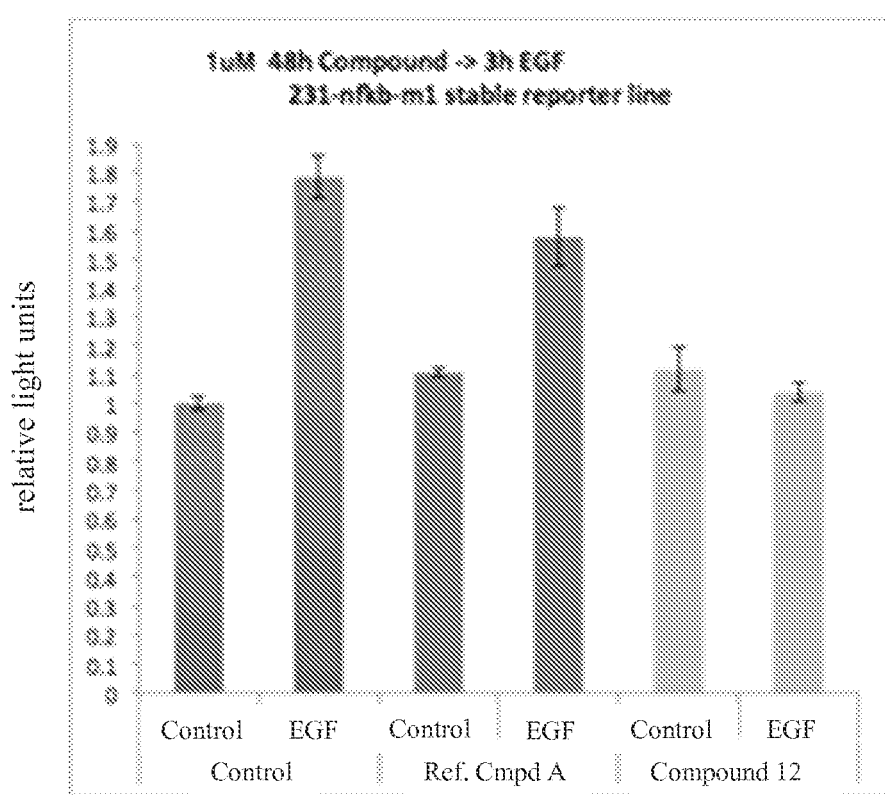
FIG. 3 is a graph showing the effect of compound 12, Reference compound A (Ref. Cmpd A), or control on EGF-induced NF-kB activity.

MDA-MB-231 breast cancer cells stably expressing an NF-kB promoter luciferase reporter were incubated for 20 hours with 1 micromolar compound 12, Reference compound A, or vehicle control prior to treatment with 100 ng/ml epithelial growth factor (EGF) for 3 hours and analysed for NF-κB activity. Luciferase expression was then measured by Clariostar plate reader. Data represents mean of 6 replicates, error bars=standard error of mean. Results for compound 12 are shown in FIG. 3.

At 1 micromolar, compound 12 showed complete suppression (100%) of EGF induced NF-kB activity in human breast cancer cells in vitro. Compound 12 demonstrated 25% greater of suppression NF-kB activity as compared to reference compound A.

Example 198: In Vivo Metastasis Mouse Model

Figure 4:
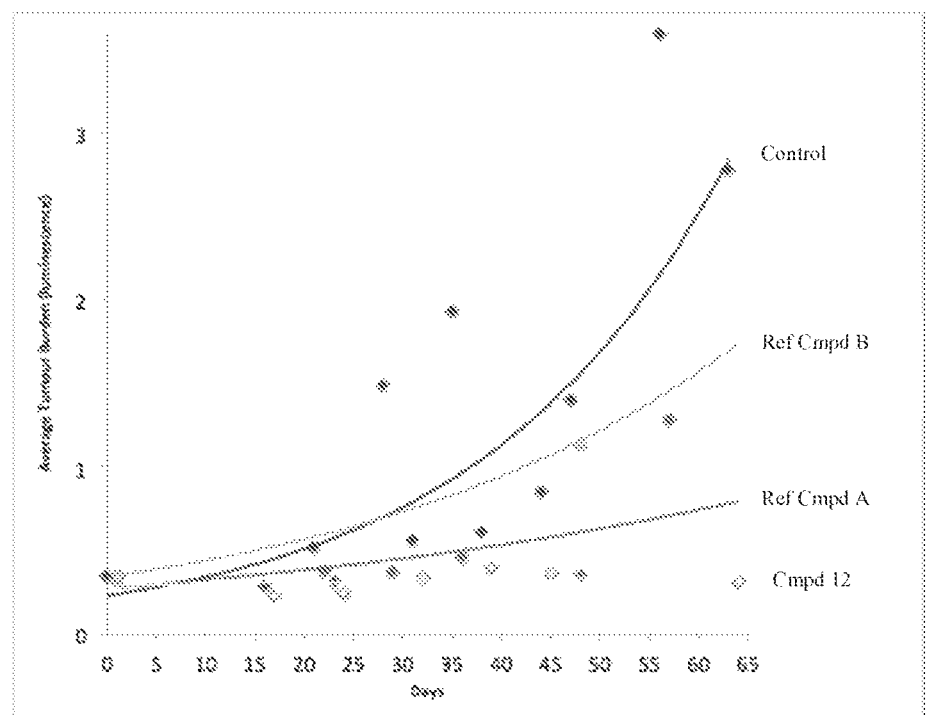
FIG. 4 is a graph showing the effect of compound 12 (Cmpd 12), Reference compound A (Ref. Cmpd A), Reference compound B (Ref. Cmpd B), or control on the disease free survival in a mouse metastasis model.

Nude mice were injected i.v. with 200,000 highly metastatic human breast cancer cells expressing luciferase (MDA-MB-231-Luc) then given 3.5 mg/Kg of compound 12, reference compound A, or Reference compound B once daily for 10 days and monitored for tumours by total body scan using Xenogen-IVIS. Mice with a luciferase signal above background in repeated scans in any part of their torso were scored as having metastatic disease. Total light emission in abdominal region was quantified at time points up to 49 days post surgery and plotted as mean total light yield. Control n=12, Reference compound A n=10, Reference compound B n=4; compound 12 n=4. Results are shown in FIG. 4.

The results in the in vivo mouse models of metastatic breast cancer show the following disease free survival: 33% survival in untreated controls; 70% survival in animal treated with Reference compound A; 50% Reference compound B treated animals (n=4); 100% survival in animals treated with compound 12 (n=4).

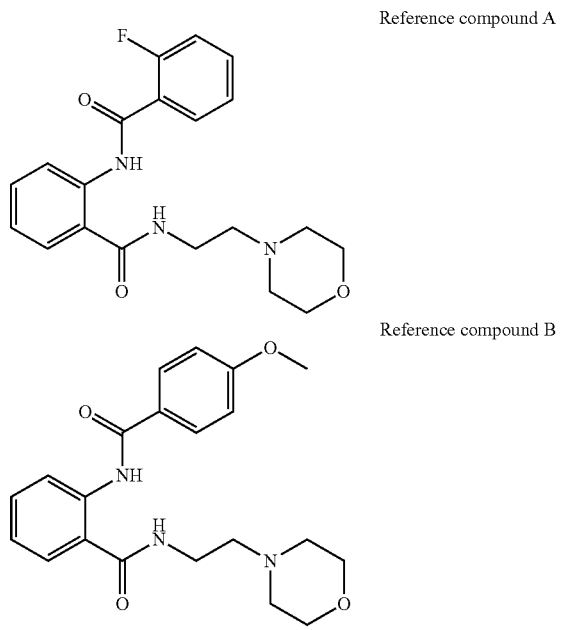

Example 199: In Vivo Metastasis Mouse Model 1

Model 1 tested the effect of Bcl3i compounds to inhibit the seeding and early colonization of circulating tumour cells at distal sites, most commonly in the lungs and liver. Human tumour cell lines were injected into the bloodstream of recipient mice, followed by single daily intraperitoneal injections of Bcl3 inhibitor (3.5 mg/kg in 1% DMSO) for 10 consecutive days. Tumour burden was monitored longitudinally for up to 8 weeks in vivo by live luminescence imaging, and subsequently histology performed on affected organs at the end of the experiment.

Figure 5:
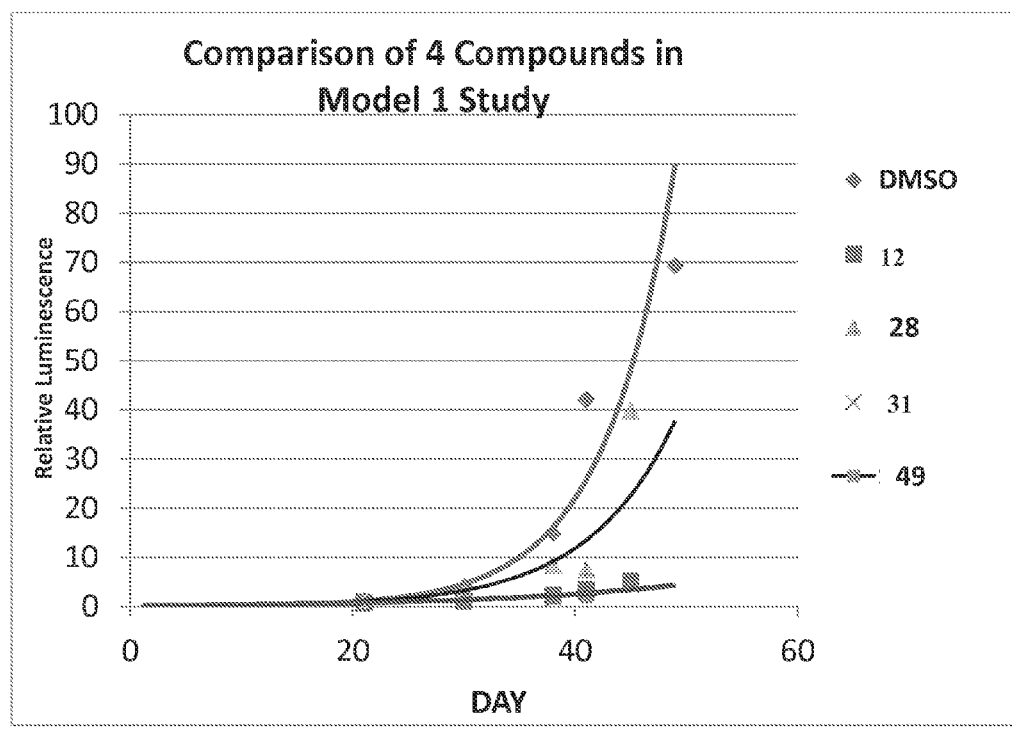
FIG. 5 is a graph which demonstrates the comparative effect of various compounds in human breast cancer MDA-MB-231 xenograft in vivo studies.

FIG. 5 shows the comparative effect of compounds of the application (each at 3.5 mg/Kg) on Model 1 (seeding and subsequent growth of human breast cancer MDA-MB-231 xenograft). The X axis represents the number of days after xenograft and the Y axis is the relative luminescence of the thoracic region by Xenon IVIS scanning of mice following injection of d-luciferin for 10 minutes. Consistent with in vitro data, compounds 31 and 49 exhibited more potent effects than compound 28. Compounds 31 and 49 exhibited equivalent inhibition of metastasis in vivo to compound 12. Compound 28 exhibited a significant reduction in tumour burden compared to controls but reduced effect compared to compound 12. n=5 for each treatment arm, except compound 12 and DMSO where n=20.

Example 200: Comparative Tumour Growth Kinetics in Mouse Model 4

Model 4 tested the effect of compounds of the application to inhibit the growth of tumour cells at the transplantation site. Human tumour cell lines were injected subcutaneously into recipient mice, followed 2 days later by single daily intraperitoneal injections of Bcl3 inhibitor (3.5 mg/kg in 1% DMSO) for the entire course of the experiment. Tumour burden was monitored longitudinally for up to 12 weeks in vivo by palpation and caliper measurements of tumour volume, and subsequently histology performed on tumours at the end of the experiment.

Figure 6:
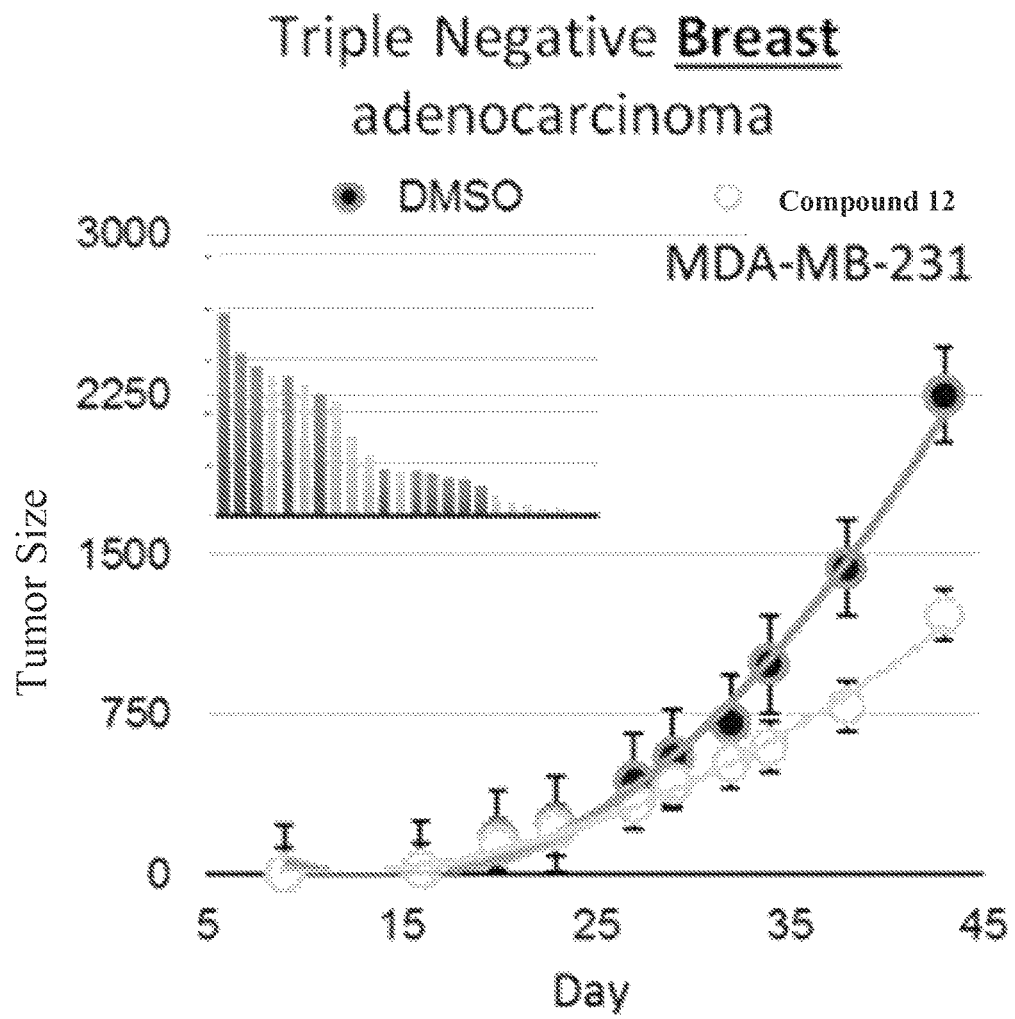
FIG. 6 is a graph which demonstrates the effect of compound 12 (to inhibit the growth of human breast cancer (MDA-MB-231) at the tumor transplant site.
Figure 7:
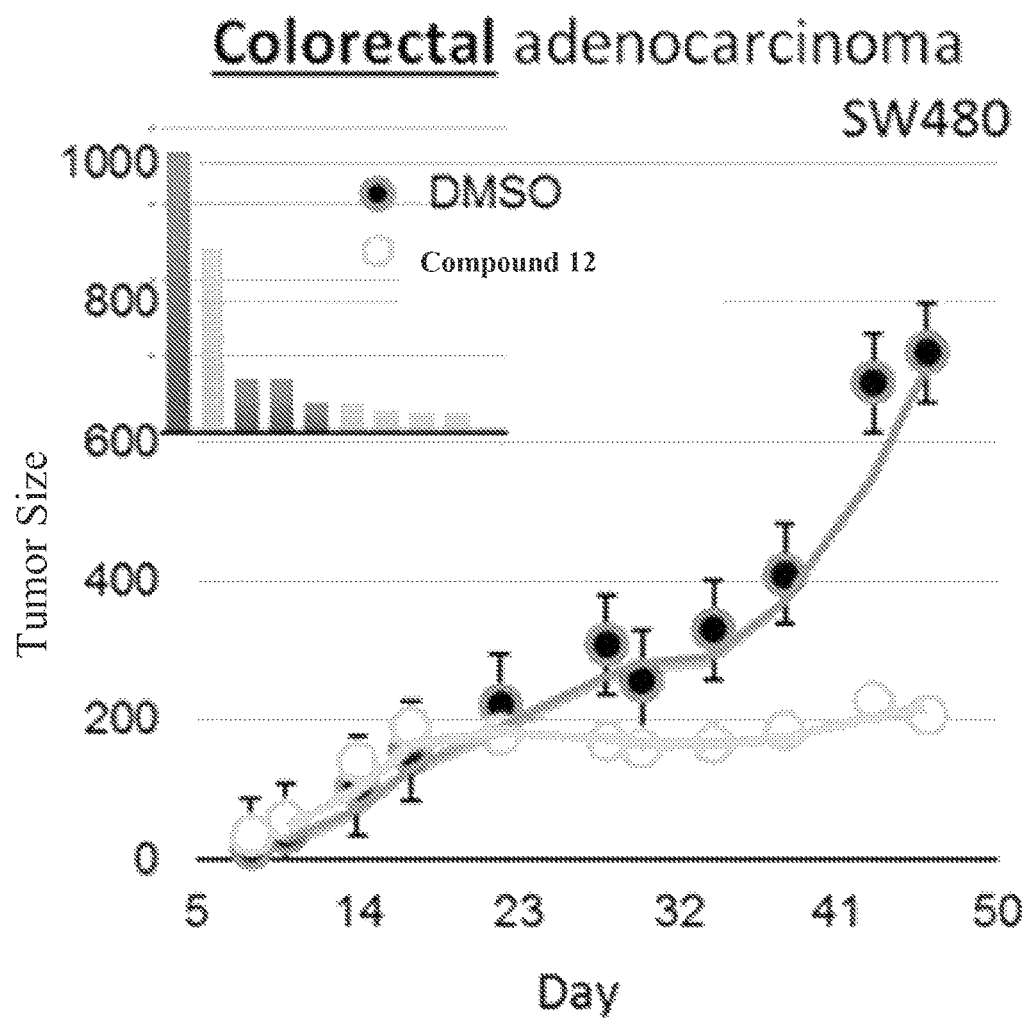
FIG. 7 is a graph which demonstrates the effect of compound 12 to inhibit the growth of human colorectal cell lines (SW480) at the tumor transplant site.

FIGS. 6 and 7 show the comparative effect of compound 12 (3.5 mg/kg intraperitoneal injection) on Model 4 in human breast cancer (MDA-MB-231) and human colorectal cell lines (SW480), respectively. The data show significant reductions in average tumour growth for both cell lines. The inserted waterfall plots demonstrate the extent of the biological variability between individual xenograft tumours, and they highlight the distribution of tumour sizes between treated (light grey) and untreated (dark grey) tumours.

Example 201: Effect of Compound 12 in Metastatic Breast Cancer

Figure 8:
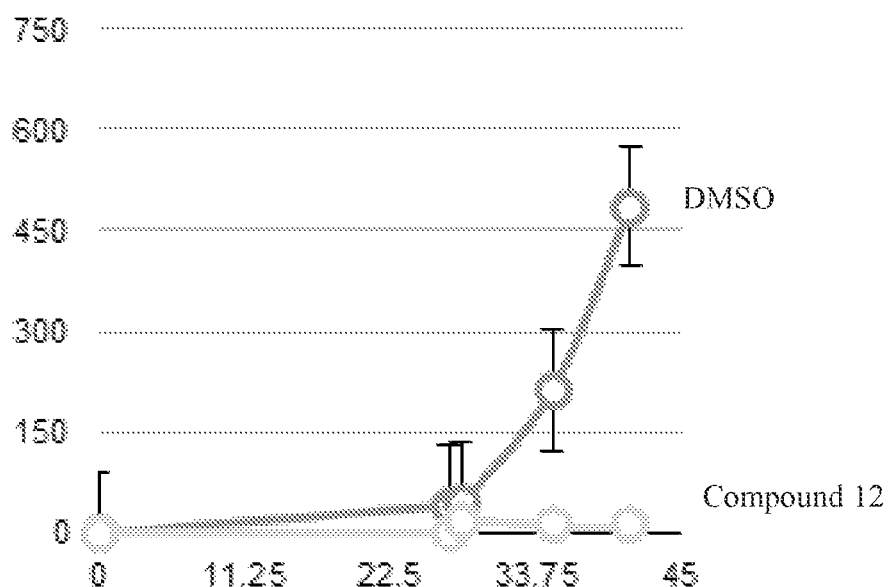
FIG. 8 is a graph which demonstrates the effect of compound 12 to inhibit the seeding and early colonization of circulating tumour cells at distal sites.
Figure 9:
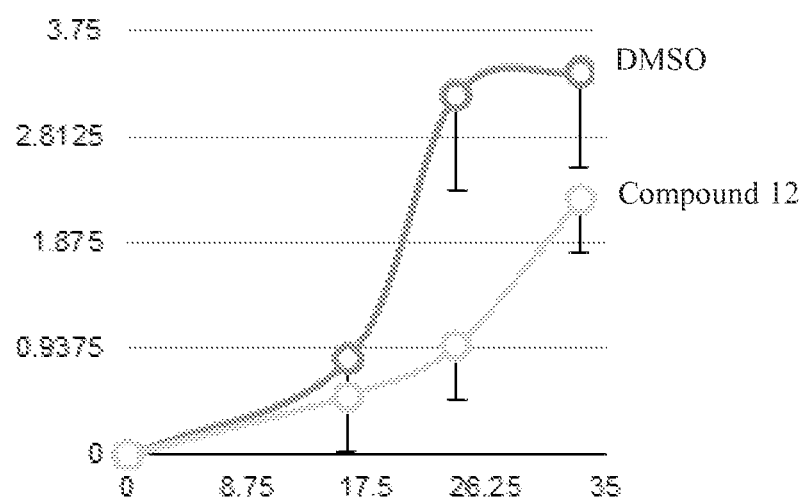
FIG. 9 is a graph which demonstrates the effect of compound 12 to inhibit the colonization and subsequent growth and spread of secondary lesions at distal sites.
Figure 10:
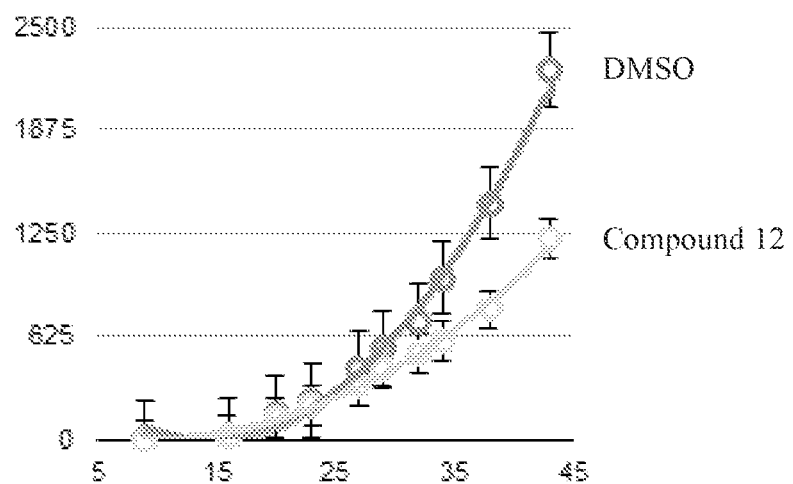
FIG. 10 is a graph which demonstrates the effect of compound 12 to inhibit the growth of tumour cells at the transplantation site.

Method:

MDA-MB-231 human breast cancer cells were used in each of the three xenograft models of metastatic breast cancer. Each of FIGS. 8, 9, 10 shows the effect of Compound 12 (3.5 mg/kg) administered intraperitoneally daily on tumour growth, dissemination or seeding. The most profound effect is seen in FIG. 8, tumour cell seeding at distal sites, but significant effects are also observed in subsequent growth and spread of the secondary tumours (FIG. 9) and on the growth of tumour at the xenograft site (FIG. 10).

Figure 11:
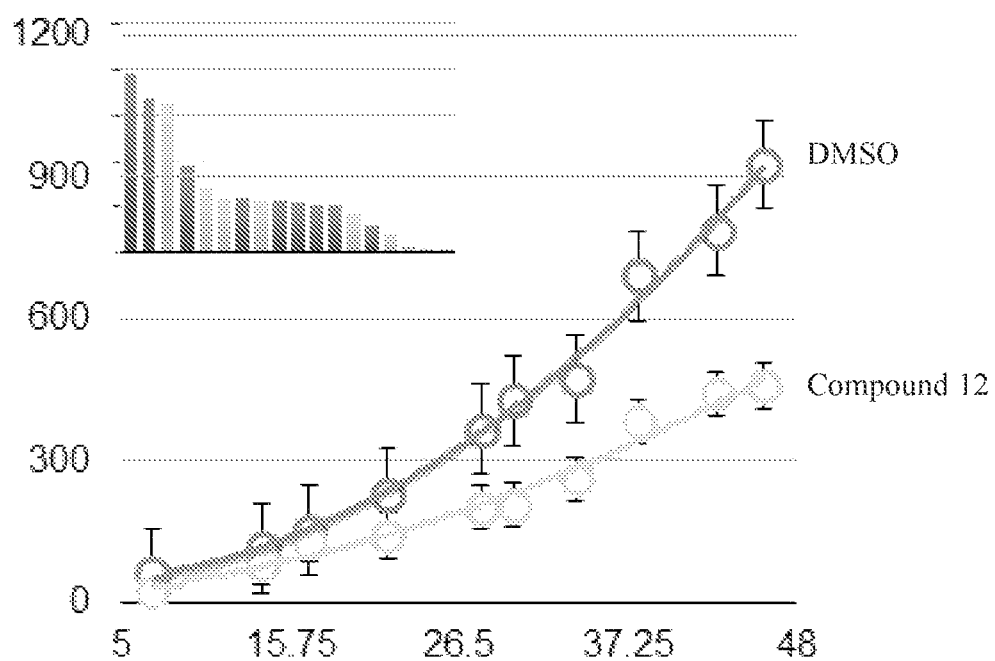
FIG. 11 is a graph which demonstrates the effect of compound 12 to inhibit the growth of human triple negative breast invasive ductal carcinoma (MDA-MB-436) at the tumor transplant site.

Example 202: Effect of Compound 12 in Triple Negative Breast Invasive Ductal Carcinoma Model 4 tested the effect of compounds of the application to inhibit the growth of tumour cells at the transplantation site. MDA-MB-436 cells were injected subcutaneously into recipient mice, followed 2 days later by single daily intraperitoneal injections of compound 12 (3.5 mg/kg in 1% DMSO) for the entire course of the experiment. Tumour burden was monitored longitudinally for up to 12 weeks in vivo by palpation and caliper measurements of tumour volume, and subsequently histology performed on tumours at the end of the experiment. FIG. 11 shows the effect of compound 12 in triple negative breast invasive ductal carcinoma. The data show significant reductions in average tumour growth for both cell lines. The inserted waterfall plot demonstrates the extent of the biological variability between individual xenograft tumours, and they highlight the distribution of tumour sizes between treated (light grey) and untreated (dark grey) tumours.

EQUIVALENTS

Those skilled in the art will recognize, or be able to ascertain using no more than routine experimentation, many equivalents to the specific embodiments and methods described herein. Such equivalents are intended to be encompassed by the scope of the present application.

INCORPORATION BY REFERENCE

All patents, patent applications, and literature references cited herein are hereby expressly incorporated by reference for all purposes.

The invention claimed is:
1. A compound of the following structure:

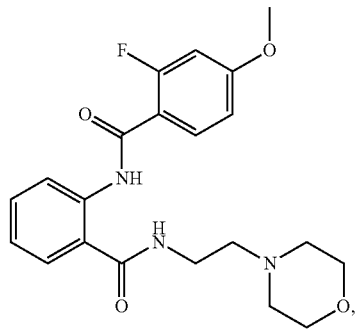 [SMILES: COc1ccc(C(=O)Nc2ccccc2C(=O)NCCN2CCOCC2)c(F)c1]

or a pharmaceutically acceptable salt thereof.

2. A pharmaceutical composition comprising the compound according to claim 1 and a pharmaceutically or veterinarily acceptable excipient or carrier.

* * * * *